United States Patent
Mori et al.

(10) Patent No.: US 10,662,378 B2
(45) Date of Patent: May 26, 2020

(54) COMPOUND HAVING FLUORODIBENZOFURAN RING, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Ayako Mori, Ichihara (JP); Hiroyuki Tanaka, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 162 days.

(21) Appl. No.: 15/918,778

(22) Filed: Mar. 12, 2018

(65) Prior Publication Data

US 2018/0258347 A1 Sep. 13, 2018

(30) Foreign Application Priority Data

Mar. 13, 2017 (JP) ................. 2017-047338

(51) Int. Cl.
| | |
|---|---|
| *C09K 19/34* | (2006.01) |
| *C07D 307/91* | (2006.01) |
| *C07D 407/12* | (2006.01) |
| *C07D 407/10* | (2006.01) |
| *C07D 403/10* | (2006.01) |
| *C07D 401/10* | (2006.01) |

(52) U.S. Cl.
CPC ........ *C09K 19/3405* (2013.01); *C07D 307/91* (2013.01); *C07D 401/10* (2013.01); *C07D 403/10* (2013.01); *C07D 407/10* (2013.01); *C07D 407/12* (2013.01); *C09K 2019/3408* (2013.01); *C09K 2019/3422* (2013.01); *C09K 2019/3425* (2013.01)

(58) Field of Classification Search
CPC .................................................... C09K 19/34
See application file for complete search history.

(56) References Cited

U.S. PATENT DOCUMENTS

| | | | | |
|---|---|---|---|---|
| 2004/0124399 A1* | 7/2004 | Schmidt | ................. | C07C 25/22 252/299.62 |
| 2015/0259602 A1* | 9/2015 | Reiffenrath | ........ | C09K 19/3405 252/299.61 |
| 2016/0376503 A1* | 12/2016 | Tanaka | ................... | C09K 19/32 252/299.61 |

FOREIGN PATENT DOCUMENTS

| | | | |
|---|---|---|---|
| CN | 106699710 A | * | 5/2017 |
| EP | 1223210 A1 | | 2/2018 |
| JP | 2015174864 A | | 10/2015 |
| JP | H10236992 A | | 2/2018 |
| WO | WO-2002055463 A1 | | 7/2002 |
| WO | WO-2015129412 A1 | | 9/2015 |

OTHER PUBLICATIONS

Zeng et al. ( The OH-initiated atmospheric chemical reactions of polyfluorinated dibenzofurans and polychlorinated dibenzofurans: A comparative theoretical study ; Journal of Chemosphere 168 (2017) 10-17) (Year: 2017).*

* cited by examiner

*Primary Examiner* — Chanceity N Robinson
(74) *Attorney, Agent, or Firm* — Hogan Lovells US LLP

(57) ABSTRACT

Provided are liquid crystal compounds satisfying at least one of physical properties such as high stability to heat or light, a high clearing point (or high maximum temperature), low minimum temperature of a liquid crystal phase, small viscosity, large optical anisotropy, large negative dielectric anisotropy, a suitable elastic constant and good compatibility with other liquid crystal compounds, a liquid crystal composition containing the compound and a liquid crystal display device including the composition. The compound is represented by formula (1):

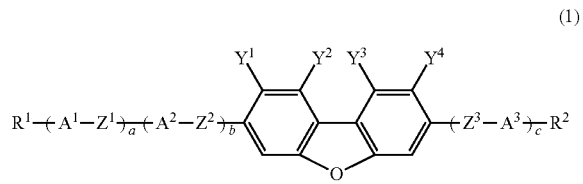

wherein $R^1$ and $R^2$ are independently hydrogen or alkyl having 1 to 15 carbons; and $A^1$, $A^2$ and $A^3$ are independently 1,4-cyclohexylene or 1,4-phenylene;

$Z^1$, $Z^2$ and $Z^3$ are independently a single bond;

$Y^1$, $Y^2$, $Y^3$ and $Y^4$ are independently hydrogen, fluorine or the like; and a, b and c are independently 0 or 1, and a sum of a, b and c is 0 to 3.

14 Claims, No Drawings

COMPOUND HAVING FLUORODIBENZOFURAN RING, LIQUID CRYSTAL COMPOSITION AND LIQUID CRYSTAL DISPLAY DEVICE

TECHNICAL FIELD

The invention relates to a liquid crystal compound, a liquid crystal composition and a liquid crystal display device. More specifically, the invention relates to a liquid crystal compound having a fluorodibenzofuran ring and negative dielectric anisotropy, a liquid crystal composition containing the liquid crystal compound, and a liquid crystal display device including the composition.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field-induced photo-reactive alignment (FPA) mode. A classification based on a driving mode in the device includes a passive matrix (PM) and an active matrix (AM). The PM is classified into static, multiplex and so forth, and the AM is classified into a thin film transistor (TFT), a metal insulator metal (MIM) and so forth.

The device is sealed with a liquid crystal composition. Physical properties of the composition relate to characteristics in the device. Specific examples of the physical properties in the composition include stability to heat or light, a temperature range of a nematic phase, viscosity, optical anisotropy, dielectric anisotropy, specific resistance and an elastic constant. The composition is prepared by mixing many liquid crystal compounds. Physical properties required for a compound include high stability to environment such as water, air, heat and light, a wide temperature range of a liquid crystal phase, small viscosity, large optical anisotropy, large dielectric anisotropy, a suitable elastic constant and good compatibility with other liquid crystal compounds. A compound having high maximum temperature of the nematic phase is preferred. A compound having low minimum temperature in the liquid crystal phase such as the nematic phase and a smectic phase is preferred. A compound having small viscosity can shorten a response time in the device. A compound having large optical anisotropy can decrease cell thickness in the device, and therefore can shorten the response time. A compound having large positive or negative dielectric anisotropy is preferred for driving the device at low voltage. A compound having good compatibility with other liquid crystal compounds is preferred for preparing the composition. The device may be occasionally used at a temperature below freezing point, and therefore a compound having good compatibility at low temperature is preferred.

Many liquid crystal compounds have been so far prepared. Development of a new liquid crystal compound has been still continued. The reason is that good physical properties that are not found in conventional compounds are expected from a new compound. The reason is that the new compound may be occasionally provided with a suitable balance regarding at least two physical properties in the composition. Compounds as described below are reported. However, in compounds (A) and (B), a melting point is high, and the compatibility with other liquid crystal compounds is not sufficiently high. Moreover, compounds (C), (D) and (E) do not exhibit sufficiently large negative dielectric anisotropy.

JP H10-236992 A discloses compound (A) on page 36.

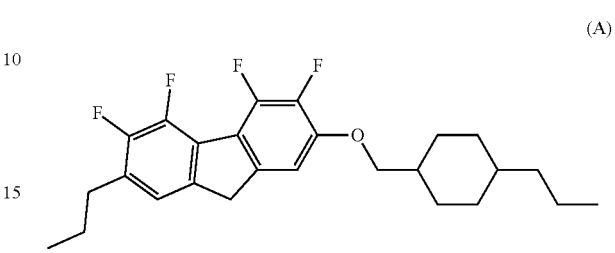

(A)

WO 2015/129412 A discloses compounds (B-1) and (B-2) on page 71 and page 73, respectively.

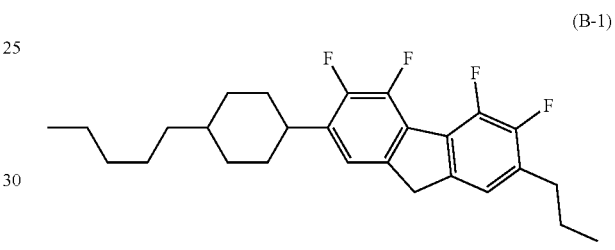

(B-1)

(B-2)

WO 2002/055463 A discloses compound (C-1) on page 27.

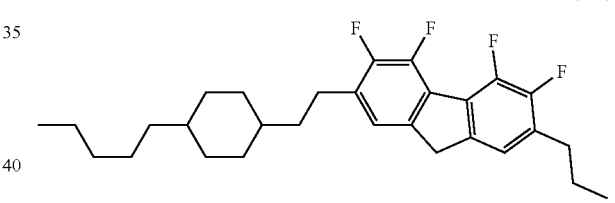

(C)

JP 2015-174864 A discloses compound (D) on page 26.

(D)

EP 1223210 A discloses compound (E) on page 16.

(E)

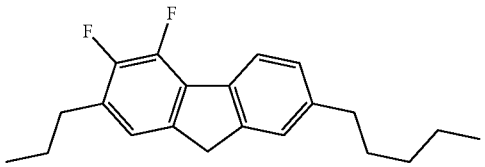

CITATION LIST

Patent Literature

Patent literature No. 1: JP H10-236992 A.
Patent literature No. 2: WO 2015/129412 A.
Patent literature No. 3: WO 2002/055463 A.
Patent literature No. 4: JP 2015-174864 A.
Patent literature No. 5: EP 1223210 A.

SUMMARY OF INVENTION

Technical Problem

A first object is to provide a liquid crystal compound satisfying at least one of physical properties such as high stability to heat or light, a high clearing point (or high maximum temperature of a nematic phase), low minimum temperature of a liquid crystal phase, small viscosity, large optical anisotropy, large negative dielectric anisotropy, a suitable elastic constant and good compatibility with other liquid crystal compounds. In particular, the object is to provide a compound having larger optical anisotropy and larger negative dielectric anisotropy in comparison with a similar compound. A second object is to provide a liquid crystal composition that contains the compound and satisfies at least one of physical properties such as high stability to heat or light, high maximum temperature of a nematic phase, low minimum temperature of the nematic phase, small viscosity, large optical anisotropy, large negative dielectric anisotropy, large specific resistance and a suitable elastic constant. The object is to provide a liquid crystal composition having a suitable balance regarding at least two of the physical properties. A third object is to provide a liquid crystal display device including the composition, and having a wide temperature range in which the device can be used, a short response time, a large voltage holding ratio, low threshold voltage, a large contrast ratio, a small flicker rate and a long service life.

Solution to Problem

The invention concerns a compound represented by formula (1), a liquid crystal composition containing the compound, and a liquid crystal display device including the composition:

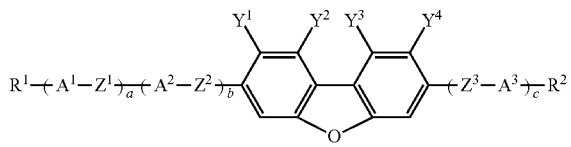

(1)

wherein, in formula (1), $R^1$ and $R^2$ are independently hydrogen or alkyl having 1 to 15 carbons, and in the alkyl, at least one piece of —$CH_2$— may be replaced by —O—, —S—, —CO— or —$SiH_2$—, and at least one piece of —$CH_2CH_2$— may be replaced by —CH=CH— or —C≡C—, and in the groups, at least one hydrogen may be replaced by fluorine or chlorine;

$A^1$, $A^2$ and $A^3$ are independently 1,2-cyclopropylene, 1,3-cyclobutylene, 1,3-cyclopentylene, 1,4-cyclohexylene, 1,4-cycloheptylene, 1,4-phenylene, decahydronaphthalene-2,6-diyl, 1,2,3,4-tetrahydronaphthalene-2,6-diyl, naphthalene-2,6-diyl, 9,10-dihydrophenanthrene-2,7-diyl, 9H-xanthene-2,6-diyl or 9H-fluorene-2,7-diyl, and in the groups, at least one piece of —$CH_2$— may be replaced by —O—, —S—, —CO— or —$SiH_2$—, and at least one piece of —$CH_2CH_2$— may be replaced by —CH=CH— or —CH=N—, and in the divalent groups, at least one hydrogen may be replaced by fluorine, chlorine, —C≡N, —$CF_3$, —$CHF_2$, —$CH_2F$, —$OCF_3$, —$OCHF_2$ or —$OCH_2F$;

$Z^1$, $Z^2$ and $Z^3$ are independently a single bond or alkylene having 1 to 6 carbons, and in the alkylene, at least one piece of —$CH_2$— may be replaced by —O—, —S—, —CO— or —$SiH_2$—, and one or two pieces of —$CH_2CH_2$— may be replaced by —CH=CH— or —C≡C—, and in the divalent groups, at least one hydrogen may be replaced by fluorine or chlorine;

$Y^1$, $Y^2$, $Y^3$ and $Y^4$ are independently hydrogen, fluorine, chlorine, —$CF^3$ or —$CHF^2$, and at least two of $Y^1$, $Y^2$, $Y^3$ and $Y^4$ is fluorine, chlorine, —$CF_3$ or —$CHF_2$; and a, b and c are independently 0 or 1, and a sum of a, b and c is 0 to 3.

Advantageous Effects of Invention

A first advantage is to provide a liquid crystal compound satisfying at least one of physical properties such as high stability to heat or light, a high clearing point (or high maximum temperature of a nematic phase), low minimum temperature of a liquid crystal phase, small viscosity, large optical anisotropy, large negative dielectric anisotropy, a suitable elastic constant and good compatibility with other liquid crystal compounds. In particular, the advantage is to provide a compound having larger optical anisotropy, larger negative dielectric anisotropy and better compatibility with other liquid crystal compounds in comparison with a similar compound (Comparative Examples 1 and 2). A second advantage is to provide a liquid crystal composition that contains the compound and satisfies at least one of physical properties such as high stability to heat or light, high maximum temperature of a nematic phase, low minimum temperature of the nematic phase, small viscosity, large optical anisotropy, large negative dielectric anisotropy, large specific resistance and a suitable elastic constant. The advantage is to provide a liquid crystal composition having a suitable balance regarding at least two of the physical properties. A third advantage is to provide a liquid crystal display device including the composition, and having a wide temperature range in which the device can be used, a short response time, a large voltage holding ratio, low threshold voltage, a large contrast ratio, a small flicker rate and a long service life.

DESCRIPTION OF EMBODIMENTS

Usage of terms herein is as described below. Terms "liquid crystal compound," "liquid crystal composition" and "liquid crystal display device" may be occasionally abbreviated as "compound," "composition" and "device," respectively. "Liquid crystal compound" is a generic term for a compound having a liquid crystal phase such as a nematic phase and a smectic phase, and a compound having no liquid crystal phase but to be added for the purpose of adjusting physical properties of a composition such as maximum temperature, minimum temperature, viscosity and dielectric anisotropy. The compound has a six-membered ring such as 1,4-cyclohexylene and 1,4-phenylene, and has rod-like molecular structure. "Liquid crystal display device" is a generic term for a liquid crystal display panel and a liquid crystal display module. "Polymerizable compound" is a compound to be added for the purpose of forming a polymer in the composition.

The liquid crystal composition is prepared by mixing a plurality of liquid crystal compounds. An additive is added to the composition for the purpose of further adjusting the physical properties. The additive such as the polymerizable compound, a polymerization initiator, a polymerization inhibitor, an optically active compound, an antioxidant, an ultraviolet light absorber, a light stabilizer, a heat stabilizer, a dye and an antifoaming agent is added thereto when necessary. The liquid crystal compound and the additive are mixed in such a procedure. A proportion (content) of the liquid crystal compound is expressed in terms of weight percent (% by weight) based on the weight of the liquid crystal composition containing no additive, even after the additive has been added. A proportion (amount of addition) of the additive is expressed in terms of weight percent (% by weight) based on the weight of the liquid crystal composition containing no additive. Weight parts per million (ppm) may be occasionally used. A proportion of the polymerization initiator and the polymerization inhibitor is exceptionally expressed based on the weight of the polymerizable compound.

"Clearing point" is a transition temperature between the liquid crystal phase and an isotropic phase in the liquid crystal compound. "Minimum temperature of the liquid crystal phase" is a transition temperature between a solid and the liquid crystal phase (the smectic phase, the nematic phase or the like) in the liquid crystal compound. "Maximum temperature of the nematic phase" is a transition temperature between the nematic phase and the isotropic phase in a mixture of the liquid crystal compound and a base liquid crystal or in the liquid crystal composition, and may be occasionally abbreviated as "maximum temperature." "Minimum temperature of the nematic phase" may be occasionally abbreviated as "minimum temperature." An expression "increase the dielectric anisotropy" means that a value of dielectric anisotropy positively increases in a composition having positive dielectric anisotropy, and the value of dielectric anisotropy negatively increases in a composition having negative dielectric anisotropy. An expression "having a large voltage holding ratio" means that the device has a large voltage holding ratio at room temperature and also at a temperature close to the maximum temperature in an initial stage, and the device has the large voltage holding ratio at room temperature and also at a temperature close to the maximum temperature even after the device has been used for a long period of time. In the composition or the device, the characteristics may be occasionally examined before and after an aging test (including an acceleration deterioration test).

A compound represented by formula (1) may be occasionally abbreviated as compound (1). At least one compound selected from the group of compounds represented by formula (1) may be occasionally abbreviated as compound (1). "Compound (1)" means one compound, a mixture of two compounds or a mixture of three or more compounds represented by formula (1). A same rule applies also to any other compound represented by any other formula. In formulas (1) to (15), a symbol of $A^1$, $B^1$, $C^1$ or the like surrounded by a hexagonal shape correspond to a ring such as ring $A^1$, ring $B^1$ and ring $C^1$, respectively. The hexagonal shape represents a six-membered ring such as cyclohexane or benzene. The hexagonal shape may occasionally represents a fused ring such as naphthalene or a bridged ring such as adamantane.

A symbol of terminal group $R^{11}$ is used in a plurality of compounds in chemical formulas of component compounds. In the compounds, two groups represented by two pieces of arbitrary $R^{11}$ may be identical or different. For example, in one case, $R^{11}$ of compound (2) is ethyl and $R^{11}$ of compound (3) is ethyl. In another case, $R^{11}$ of compound (2) is ethyl and $R^{11}$ of compound (3) is propyl. A same rule applies also to a symbol of $R^{12}$, $R^{13}$, $Z^{11}$ or the like. In compound (15), when i is 2, two of ring $E^1$ exists. In the compound, two groups represented by two of ring $E^1$ may be identical or different. A same rule applies also to two of arbitrary ring $E^1$ when i is larger than 2. A same rule applies also to other symbols.

An expression "at least one piece of 'A'" means that the number of 'A' is arbitrary. An expression "at least one piece of 'A' may be replaced by 'B'" means that, when the number of 'A' is 1, a position of 'A' is arbitrary, and also when the number of 'A' is 2 or more, positions thereof can be selected without restriction. A same rule applies also to an expression "at least one piece of 'A' is replaced by 'B'." An expression "at least one piece of 'A' may be replaced by 'B', 'C' or 'D'" includes a case where arbitrary 'A' is replaced by 'B', a case where arbitrary 'A' is replaced by 'C', and a case where arbitrary 'A' is replaced by 'D', and also a case where a plurality of pieces of 'A' are replaced by at least two pieces of 'B', 'C' and/or 'D'. For example, "alkyl in which at least one piece of —$CH_2$— may be replaced by —O— or —CH=CH—" includes alkyl, alkoxy, alkoxyalkyl, alkenyl, alkoxyalkenyl and alkenyloxyalkyl. In addition, a case where two pieces of consecutive —$CH_2$— are replaced by —O— to form —O—O— is not preferred. In alkyl or the like, a case where —$CH_2$— of a methyl part (—$CH_2$—H) is replaced by —O— to form —O—H is not preferred, either.

An expression "$R^{11}$ and $R^{12}$ are independently alkyl having 1 to 10 carbons or alkenyl having 2 to 10 carbons, and in the alkyl and the alkenyl, at least one piece of —$CH_2$— may be replaced by —O—, and in the groups, at least one hydrogen may be replaced by fluorine" may be occasionally used. In the expression, "in the groups" may be interpreted according to wording. In the expression, "the groups" means alkyl, alkenyl, alkoxy, alkenyloxy or the like. More specifically, "the groups" represents all of the groups described before the term "in the groups." The common interpretation is applied also to terms of "in the monovalent groups" or "in the divalent groups." For example, "the monovalent groups" represents all of the groups described before the term "in the monovalent groups."

Halogen means fluorine, chlorine, bromine and iodine. Preferred halogen is fluorine and chlorine. Further preferred halogen is fluorine. Alkyl of the liquid crystal compound is straight-chain alkyl or branched-chain alkyl, but includes no cyclic alkyl. In general, straight-chain alkyl is preferred to branched-chain alkyl. A same rule applies also to a terminal group such as alkoxy and alkenyl. With regard to a configuration of 1,4-cyclohexylene, trans is preferred to cis for increasing the maximum temperature. Then, 2-fluoro-1,4- phenylene means two divalent groups described below. In a chemical formula, fluorine may be leftward (L) or rightward (R). A same rule applies also to an asymmetrical divalent group formed by removing two hydrogens from a ring, such as tetrahydropyran-2,5-diyl.

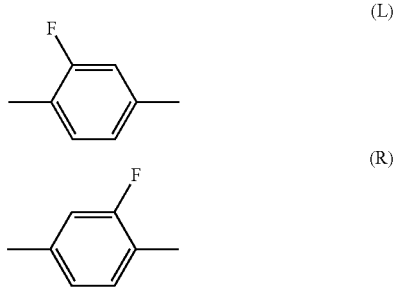

The invention includes items described below.

Item 1. A compound, represented by formula (1):

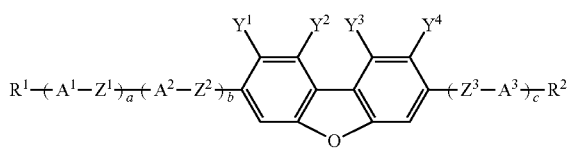

wherein, in formula (1), $R^1$ and $R^2$ are independently hydrogen or alkyl having 1 to 15 carbons, and in the alkyl, at least one piece of —$CH_2$— may be replaced by —O—, —S—, —CO— or —$SiH_2$—, and at least one piece of —$CH_2CH_2$— may be replaced by —CH=CH— or —C≡C—, and in the groups, at least one hydrogen may be replaced by fluorine or chlorine;

$A^1$, $A^2$ and $A^3$ are independently 1,2-cyclopropylene, 1,3-cyclobutylene, 1,3-cyclopentylene, 1,4-cyclohexylene, 1,4-cycloheptylene, 1,4-phenylene, decahydronaphthalene-2,6-diyl, 1,2,3,4-tetrahydronaphthalene-2,6-diyl, naphthalene-2,6-diyl, 9,10-dihydrophenanthrene-2,7-diyl, 9H-xanthene-2,6-diyl or 9H-fluorene-2,7-diyl, and in the groups, at least one piece of —$CH_2$— may be replaced by —O—, —S—, —CO— or —$SiH_2$—, and at least one piece of —$CH_2CH_2$— may be replaced by —CH=CH— or —CH=N—, and in the divalent groups, at least one hydrogen may be replaced by fluorine, chlorine, —C≡N, —$CF_3$, —$CHF_2$, —$CH_2F$, —$OCF_3$, —$OCHF_2$ or —$OCH_2F$;

$Z^1$, $Z^2$ and $Z^3$ are independently a single bond or alkylene having 1 to 6 carbons, and in the alkylene, at least one piece of —$CH_2$— may be replaced by —O—, —S—, —CO— or —$SiH_2$—, and one or two pieces of —$CH_2CH_2$— may be replaced by —CH=CH— or —C≡C—, and in the divalent groups, at least one hydrogen may be replaced by fluorine or chlorine;

$Y^1$, $Y^2$, $Y^3$ and $Y^4$ are independently hydrogen, fluorine, chlorine, —$CF^3$ or —$CHF^2$, and at least two of $Y^1$, $Y^2$, $Y^3$ and $Y^4$ is fluorine, chlorine, —$CF_3$ or —$CHF_2$; and a, b and c are independently 0 or 1, and a sum of a, b and c is 0 to 3.

Item 2. The compound according to item 1, wherein, in formula (1), $A^1$, $A^2$ and $A^3$ are independently 1,4-cyclohexylene, 1,4-cycloheptylene, 1,4-cyclohexenylene, 1,4-phenylene, 2-fluoro-1,4-phenylene, 2,3-difluoro-1,4-phenylene, tetrahydropyran-2,5-diyl, 1,3-dioxane-2,5-diyl, pyridine-2,5-diyl, pyrimidine-2,5-diyl, decahydronaphthalene-2,6-diyl, 1,2,3,4-tetrahydronaphthalene-2,6-diyl or naphthalene-2,6-diyl.

Item 3. The compound according to item 1, wherein, in formula (1), $Z^1$, $Z^2$ and $Z^3$ are independently a single bond, —$(CH_2)_2$—, —CH=CH—, —C≡C—, —COO—, —OCO—, —$CF_2O$—, —$OCF_2$—, —$CH_2O$—, —$OCH_2$— or —CF=CF—.

Item 4. The compound according to any one of items 1 to 3, represented by any one of formulas (1-1) to (1-5):

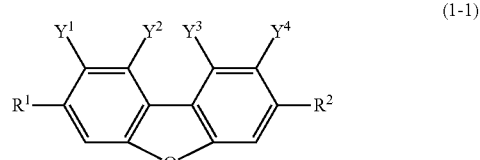

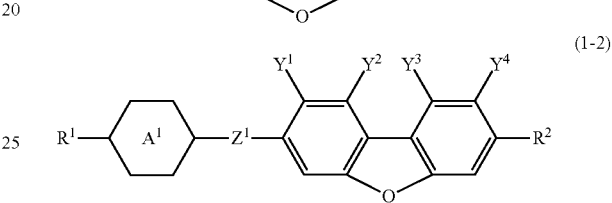

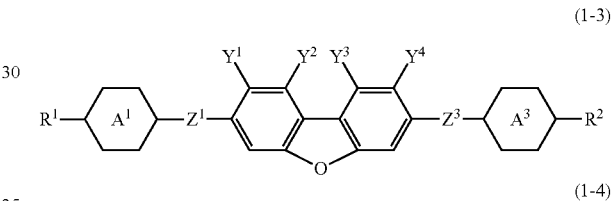

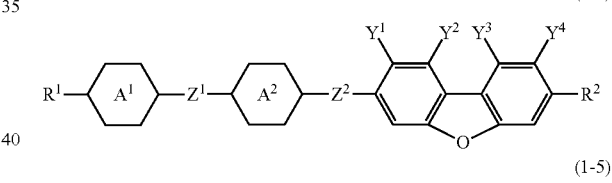

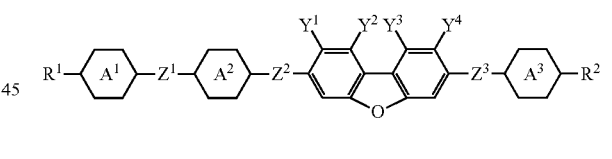

wherein, in formulas (1-1) to (1-5), $R^1$ and $R^2$ are independently hydrogen, alkyl having 1 to 10 carbons, alkenyl having 2 to 10 carbons, alkoxy having 1 to 10 carbons or alkenyloxy having 2 to 10 carbons, and in the groups, at least one hydrogen may be replaced by fluorine;

ring $A^1$, ring $A^2$ and ring $A^3$ are independently 1,4-cyclohexylene, 1,4-cyclohexenylene, 1,4-phenylene, 2-fluoro-1,4-phenylene, 2,3-difluoro-1,4-phenylene or tetrahydropyran-2,5-diyl;

$Z^1$, $Z^2$ and $Z^3$ are independently a single bond, —$(CH_2)_2$—, —C≡C—, —$CF_2O$—, —$OCF_2$—, —$CH_2O$— or —$OCH_2$—; and $Y^1$, $Y^2$, $Y^3$ and $Y^4$ are independently hydrogen, fluorine, chlorine, —$CF_3$ or —$CHF_2$, and at least two of $Y^1$, $Y^2$, $Y^3$ and $Y^4$ is fluorine, chlorine, —$CF_3$ or —$CHF_2$.

Item 5. The compound according to item 1, represented by any one of formulas (1-6) to (1-11):

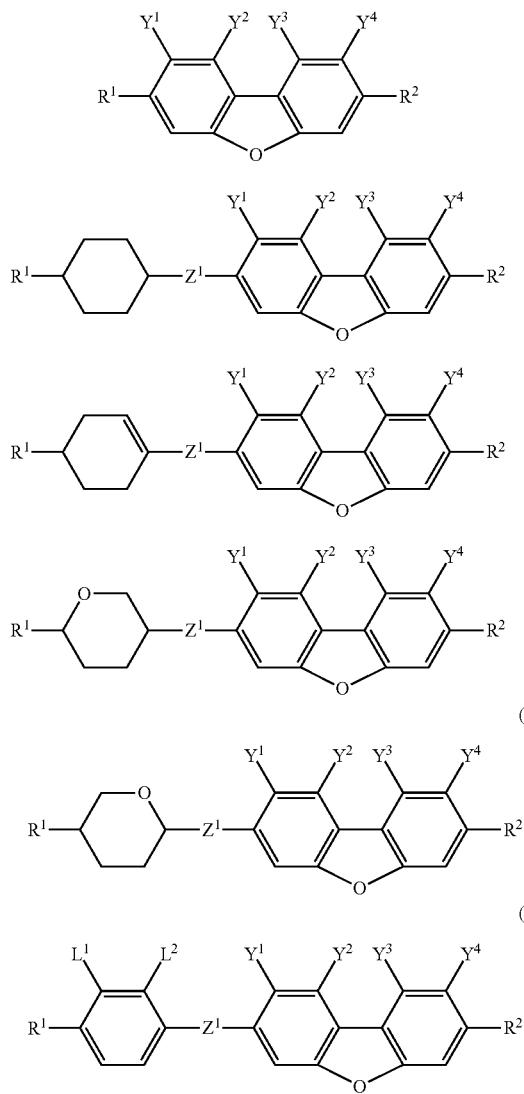

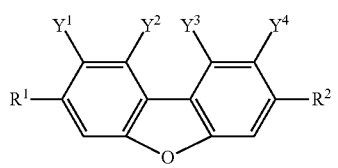

wherein, in formulas (1-6) to (1-11),
$R^1$ and $R^2$ are independently alkyl having 1 to 10 carbons, alkenyl having 2 to 10 carbons, alkoxy having 1 to 10 carbons or alkenyloxy having 2 to 10 carbons, and in the groups, at least one hydrogen may be replaced by fluorine;
$Z^1$ is a single bond, —(CH$_2$)$_2$—, —CH$_2$O— or —OCH$_2$—;
$Y^1$, $Y^2$, $Y^3$ and $Y^4$ are independently hydrogen or fluorine, and at least two of $Y^1$, $Y^2$, $Y^3$ and $Y^4$ is fluorine; and
$L^1$ and $L^2$ are independently hydrogen or fluorine.

Item 6. The compound according to item 1, represented by any one of formulas (1-12) to (1-14):

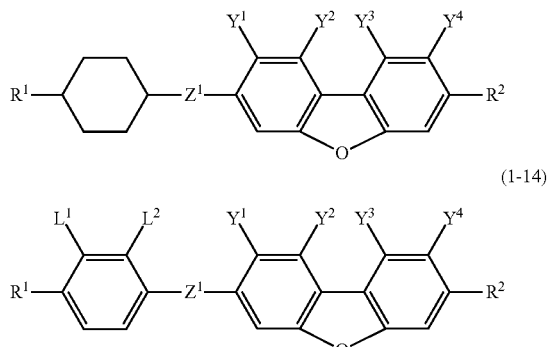

wherein, in formulas (1-12) to (1-14),
$R^1$ and $R^2$ are independently alkyl having 1 to 10 carbons, alkenyl having 2 to 10 carbons or alkoxy having 1 to 10 carbons;
$Z^1$ is a single bond, —(CH$_2$)$_2$—, —CH$_2$O— or —OCH$_2$—;
$Y^1$, $Y^2$, $Y^3$ and $Y^4$ are independently hydrogen or fluorine, and at least two of $Y^1$, $Y^2$, $Y^3$ and $Y^4$ is fluorine; and
$L^1$ and $L^2$ are independently hydrogen or fluorine.

Item 7. The compound according to item 1, represented by any one of formulas (1-15) to (1-32):

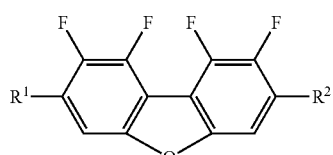

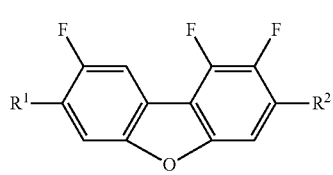

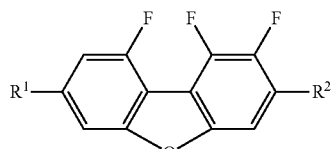

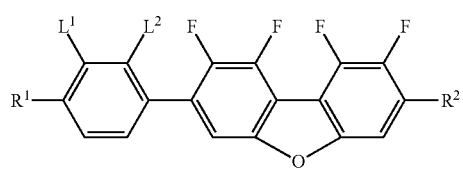

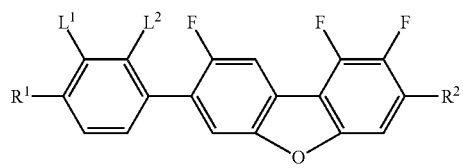

-continued
(1-20)
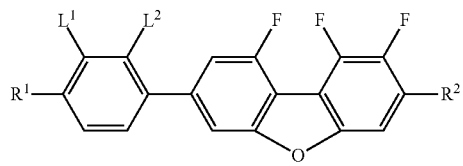
(1-21)
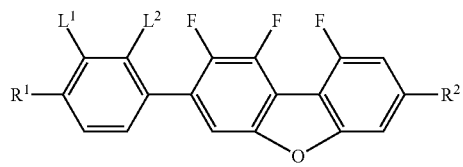
(1-22)
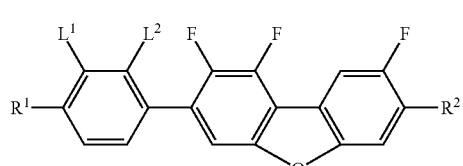
(1-23)
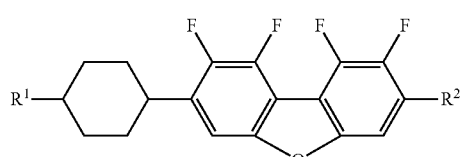
(1-24)
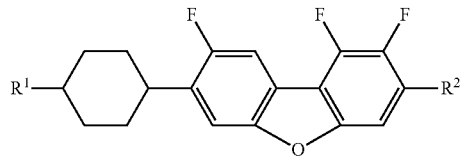
(1-25)
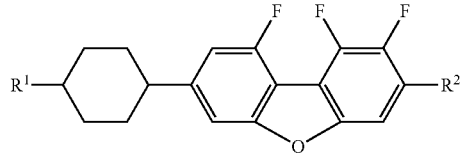
(1-26)
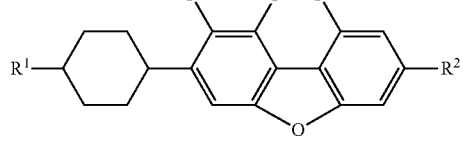
(1-27)
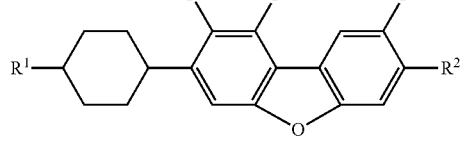
(1-28)
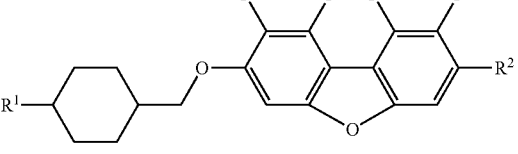
-continued
(1-29)
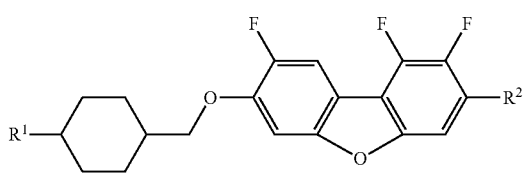
(1-30)
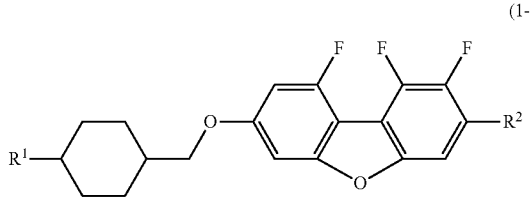
(1-31)
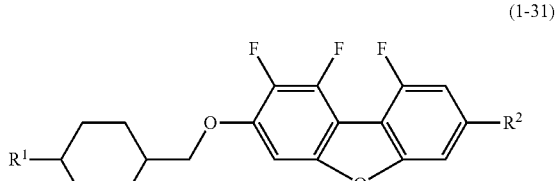
(1-32)
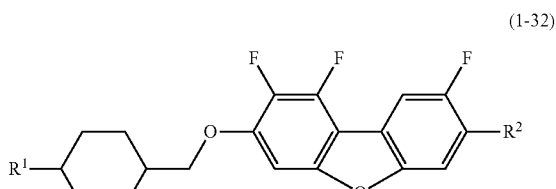
wherein, in formulas (1-15) to formula (1-32),
$R^1$ and $R^2$ are independently alkyl having 1 to 10 carbons, alkenyl having 2 to 10 carbons or alkoxy having 1 to 10 carbons; and
$L^1$ and $L^2$ are independently hydrogen or fluorine.
Item 8. The compound according to item 1, represented by any one of formulas (1-33) to (1-36):
(1-33)
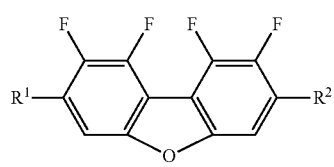
(1-34)
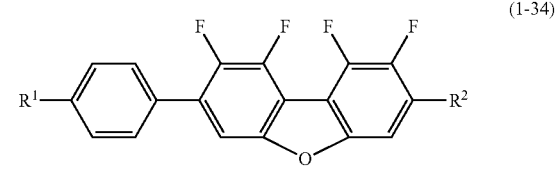
(1-35)
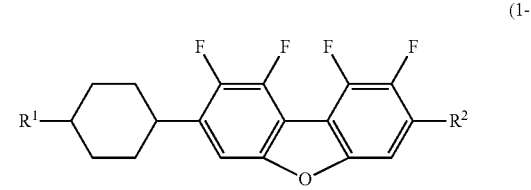

-continued (1-36)

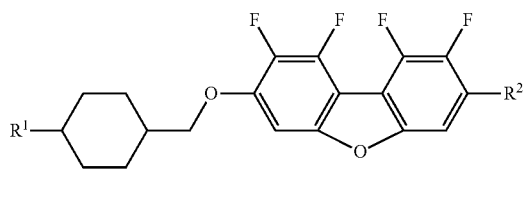

wherein, in formulas (1-33) to (1-36), $R^1$ and $R^2$ are independently alkyl having 1 to 10 carbons or alkoxy 1 to 10 carbons.

Item 9. A liquid crystal composition, containing at least one compound according to any one of items 1 to 8.

Item 10. The liquid crystal composition according to item 9, further containing at least one compound selected from the group of compounds represented by formulas (2) to (4):

(2)

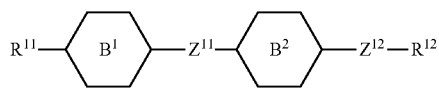

-continued (3)

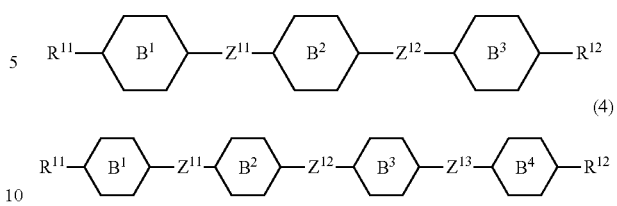

(4)

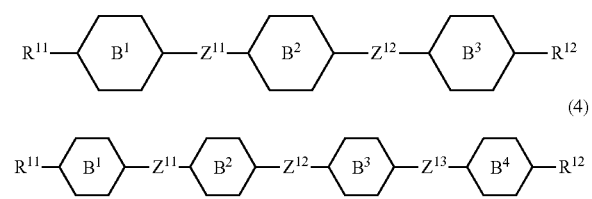

wherein, in formulas (2) to (4), $R^{11}$ and $R^{12}$ are independently alkyl having 1 to 10 carbons or alkenyl having 2 to 10 carbons, and in the alkyl and the alkenyl, at least one piece of —$CH_2$— may be replaced by —O—, and in the groups, at least one hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —COO—, —$CH_2CH_2$—, —CH=CH— or —C≡C—.

Item 11. The liquid crystal composition according to item 9 or 10, further containing at least one compound selected from the group of compounds represented by formulas (5) to (11):

(5)

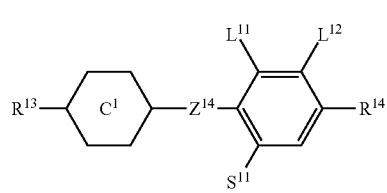

(6)

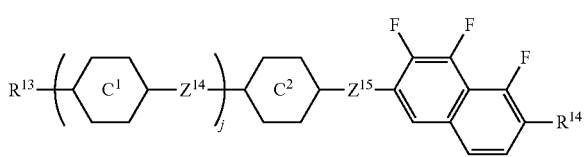

(7)

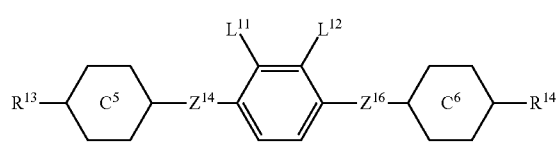

(8)

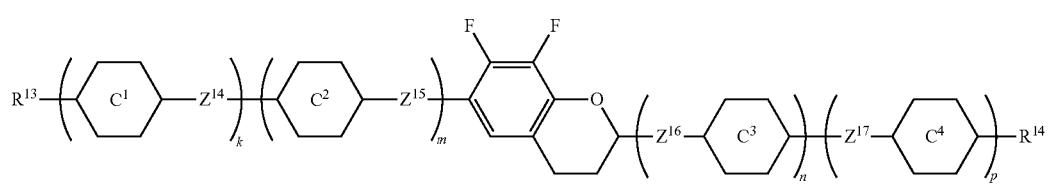

(9)

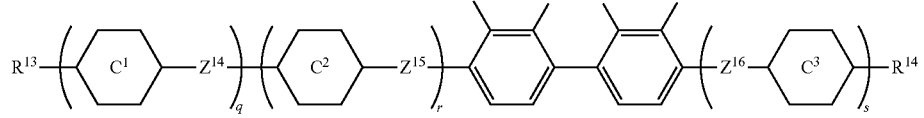

(10)

wherein, in formulas (5) to (11), $R^{13}$, $R^{14}$ and $R^{15}$ are independently alkyl having 1 to 10 carbons or alkenyl having 2 to 10 carbons, and in the alkyl and the alkenyl, at least one piece of —CH$_2$— may be replaced by —O—, and in the groups, at least one hydrogen may be replaced by fluorine, and $R^{15}$ may be hydrogen or fluorine;

ring $C^1$, ring $C^2$, ring $C^3$ and ring $C^4$ are independently 1,4-cyclohexylene, 1,4-cyclohexenylene, 1,4-phenylene in which at least one hydrogen may be replaced by fluorine, tetrahydropyran-2,5-diyl, or decahydronaphthalene-2,6-diyl;

ring $C^5$ and ring $C^6$ are independently 1,4-cyclohexylene, 1,4-cyclohexenylene, 1,4-phenylene, tetrahydropyran-2,5-diyl or decahydronaphthalene-2,6-diy;

$Z^{14}$, $Z^{is}$, $Z^{16}$ and $Z^{17}$ are independently a single bond, —COO—, —CH$_2$O—, —OCF$_2$—, —CH$_2$CH$_2$— or —OCF$_2$CH$_2$CH$_2$—;

$L^{11}$ and $L^{12}$ are independently fluorine or chlorine;

$S^{11}$ is hydrogen or methyl;

X is —CHF— or —CF$_2$—; and j, k, m, n, p, q, r and s are independently 0 or 1, a sum of k, m, n and p is 1 or 2, a sum of q, r and s is 0, 1, 2 or 3, and t is 1, 2 or 3.

Item 12. The liquid crystal composition according to item 8 or 9, further containing at least one compound selected from the group of compounds represented by formulas (12) to (14):

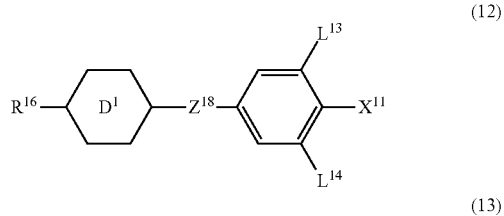

(12)

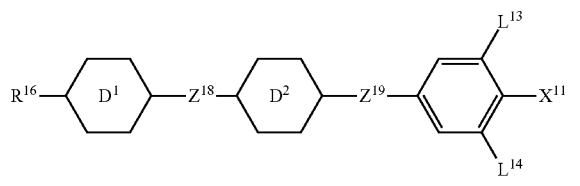

(13)

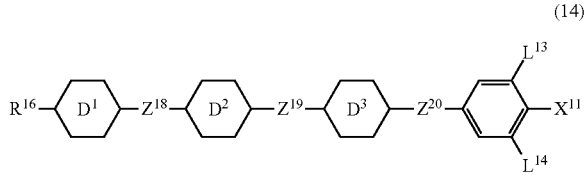

(14)

wherein, in formulas (12) to (14), $R^{16}$ is alkyl having 1 to 10 carbons or alkenyl having 2 to 10 carbons, and in the alkyl and the alkenyl, at least one piece of —CH$_2$— may be replaced by —O—, and in the groups, at least one hydrogen may be replaced by fluorine;

$X^{11}$ is fluorine, chlorine, —CF$_3$, —CHF$_2$, —CH$_2$F, —OCF$_3$, —OCHF$_2$, —OCF$_2$CHF$_2$ or —OCF$_2$CHFCF$_3$;

ring $D^1$, ring $D^2$ and ring $D^3$ are independently 1,4-cyclohexylene, 1,4-phenylene in which at least one hydrogen may be replaced by fluorine, tetrahydropyran-2,5-diyl, 1,3-dioxane-2,5-diyl, or pyrimidine-2,5-diyl;

$Z^{18}$, $Z^{19}$ and $Z^{20}$ are independently a single bond, —COO—, —CH$_2$O—, —CF$_2$O—, —OCF$_2$—, —CH$_2$CH$_2$—, —CH=CH—, —C≡C— or —(CH$_2$)$_4$—; and $L^{13}$ and $L^{14}$ are independently hydrogen or fluorine.

Item 13. The liquid crystal composition according to any one of items 9 to 12, further containing at least one compound selected from the group of compounds represented by formula (15):

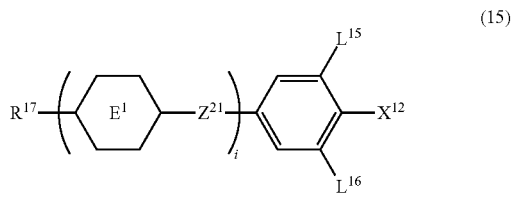

(15)

wherein, in formula (15), $R^{17}$ is alkyl having 1 to 10 carbons or alkenyl having 2 to 10 carbons, and in the alkyl and the alkenyl, at least one piece of —CH$_2$— may be replaced by —O—, and in the groups, at least one hydrogen may be replaced by fluorine;

$X^{12}$ is —C≡N or —C≡C—C≡N;

ring $E^1$ is 1,4-cyclohexylene, 1,4-phenylene in which at least one hydrogen may be replaced by fluorine, tetrahydropyran-2,5-diyl, 1,3-dioxane-2,5-diyl, or pyrimidine-2,5-diyl;

$Z^{21}$ is a single bond, —COO—, —CH$_2$O—, —CF$_2$O—, —OCF$_2$—, —CH$_2$CH$_2$— or —C≡C—;

$L^{15}$ and $L^{16}$ are independently hydrogen or fluorine; and i is 1, 2, 3 or 4.

Item 14. A liquid crystal display device, including the liquid crystal composition according to any one of items 9 to 13.

The invention further includes the following items: (a) the composition, further containing at least one optically active compound and/or at least one polymerizable compound; and (b) the composition, further containing at least one antioxidant and/or at least one ultraviolet light absorber.

The invention still further includes the following items: (c) the composition, further containing one, two or at least three additives selected from the group of a polymerizable compound, a polymerization initiator, a polymerization inhibitor, an optically active compound, an antioxidant, an ultraviolet light absorber, a light stabilizer, a heat stabilizer, a dye and an antifoaming agent; and (d) the composition, wherein a maximum temperature of a nematic phase is 70° C. or higher, an optical anisotropy (measured at 25° C.) at a wavelength of 589 nanometers is 0.08 or more and a dielectric anisotropy (measured at 25° C.) at a frequency of 1 kHz is −2 or less.

The invention still further includes the following items: (e) a device including the composition and having a PC mode, a TN mode, an STN mode, an ECB mode, an OCB mode, an IPS mode, a VA mode, an FFS mode, an FPA mode or a PSA mode; (f) an AM device including the composition; (g) a transmissive device including the composition; (h) use of the composition as the composition having the nematic phase; and (i) use as an optically active composition by adding the optically active compound to the composition.

An aspect of compound (1), synthesis of compound (1), the liquid crystal composition and the liquid crystal display device will be described in the order.

1. Aspect of Compound (1)

Compound (1) has features of having a fluorodibenzofuran ring. The compound is physically and chemically significantly stable under conditions in which the device is ordinarily used, and has large optical anisotropy, large negative dielectric anisotropy and good compatibility with other liquid crystal compounds. A composition containing the compound is stable under conditions in which the device is ordinarily used. When the composition is stored at low temperature, the compound has small tendency of precipitation as a crystal (or a smectic phase). The compound has general physical properties required for a component of the composition, such as large optical anisotropy and large negative dielectric anisotropy.

Preferred examples of terminal groups $R^1$ and $R^2$, $A^1$, $A^2$, $A^3$ and $A^4$, bonding groups $Z^1$, $Z^2$, $Z^3$ and $Z^4$, lateral groups $Y^1$, $Y^2$ and $Y^3$, and a, b, c and d in compound (1) are as described below. In compound (1), physical properties can be arbitrarily adjusted by suitably combining the groups. Compound (1) may contain a larger amount of isotope such as $^2H$ (deuterium) and $^{13}C$ than the amount of natural abundance because no significant difference exists in the physical properties of the compound. In addition, definitions of symbols of compound (1) are as described in item 1.

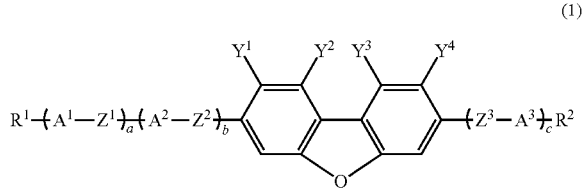

(1)

In formula (1), $R^1$ and $R^2$ are independently hydrogen or alkyl having 1 to 15 carbons, and in the alkyl, at least one piece of —$CH_2$— may be replaced by —O—, —S—, —CO— or —$SiH_2$—, and at least one piece of —$CH_2CH_2$— may be replaced by —CH=CH— or —C≡C—, and in the groups, at least one hydrogen may be replaced by fluorine or chlorine.

Preferred $R^1$ or $R^2$ is hydrogen, alkyl, alkoxy, alkoxyalkyl, alkoxyalkoxy, alkylthio, alkylthioalkoxy, acyl, acylalkyl, acyloxy, acyloxyalkyl, alkoxycarbonyl, alkoxycarbonylalkyl, alkenyl, alkenyloxy, alkenyloxyalkyl, alkoxyalkenyl, alkynyl, alkynyloxy, silaalkyl and disilaalkyl. In the groups, at least one hydrogen may be replaced by fluorine or chlorine. The example includes a group in which at least two hydrogens are replaced by both fluorine and chlorine. A group in which at least one hydrogen is replaced by fluorine only is further preferred. In the groups, a straight chain is preferred to a branched chain. However, if $R^1$ or $R^2$ has the branched chain, the group is preferred when the group has optical activity. Further preferred $R^1$ or $R^2$ is alkyl, alkoxy, alkoxyalkyl, alkenyl, monofluoroalkyl, polyfluoroalkyl, monofluoroalkoxy, polyfluoroalkoxy, monofluoroalkenyl and polyfluoroalkenyl.

A preferred configuration of —CH=CH— in the alkenyl depends on a position of a double bond. A trans configuration is preferred in the alkenyl such as 1-propenyl, 1-butenyl, 1-pentenyl, 1-hexenyl, 3-pentenyl and 3-hexenyl. A cis configuration is preferred in the alkenyl such as 2-butenyl, 2-pentenyl and 2-hexenyl.

Specific $R^1$ or $R^2$ is hydrogen, methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, 1-propynyl and 1-pentenyl.

Specific $R^1$ or $R^2$ is 2-fluoroethyl, 3-fluoropropyl, 2,2,2-trifluoroethyl, 2-fluorovinyl, 2,2-difluorovinyl, 2-fluoro-2-vinyl, 3-fluoro-1-propenyl, 3,3,3-trifluoro-1-propenyl, 4-fluoro-1-propenyl and 4,4-difluoro-3-butenyl.

Further preferred $R^1$ or $R^2$ is methyl, ethyl, propyl, butyl, pentyl, hexyl, heptyl, methoxy, ethoxy, propoxy, butoxy, pentyloxy, hexyloxy, methoxymethyl, ethoxymethyl, propoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy and 2-pentenyloxy. Most preferred $R^1$ or $R^2$ is methyl, ethyl, propyl, butyl, pentyl, methoxy, ethoxy, propoxy, butoxy, pentyloxy, vinyl, 1-propenyl, 3-butenyl and 3-pentenyl.

In formula (1), $A^1$, $A^2$ and $A^3$ are independently 1,2-cyclopropylene, 1,3-cyclobutylene, 1,3-cyclopentylene, 1,4-cyclohexylene, 1,4-cycloheptylene, 1,4-phenylene, decahydronaphthalene-2,6-diyl, 1,2,3,4-tetrahydronaphthalene-2,6-diyl, naphthalene-2,6-diyl, 9,10-dihydrophenanthrene-2,7-diyl, 9H-xanthene-2,6-diyl or 9H-fluorene-2,7-diyl, and in the groups, at least one piece of —$CH_2$— may be replaced by —O—, —S—, —CO— or —$SiH_2$—, and at least one piece of —$CH_2CH_2$— may be replaced by —CH=CH— or —CH=N—, and in the divalent groups, at least one hydrogen may be replaced by fluorine, chlorine, —C≡N, —$CF_3$, —$CHF_2$, —$CH_2F$, —$OCF_3$, —$OCHF_2$ or —$OCH_2F$.

Preferred examples of "in the groups, at least one piece of —$CH_2$— may be replaced by —O—, —S—, —CO— or —$SiH_2$—, and at least one piece of —$CH_2CH_2$— may be replaced by —CH=CH— or —CH=N—" include a divalent group represented by formulas (16-1) to (16-50) described below. Further preferred examples include the divalent group represented by formulas (16-1) to (16-4), formula (16-15), formula (16-23), formulas (16-27) to (16-29), formula (16-36), formula (16-39) and formula (16-45).

(16-1)

(16-2)

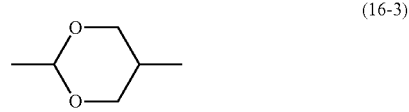

(16-3)

(16-4)

(16-5)

(16-6)

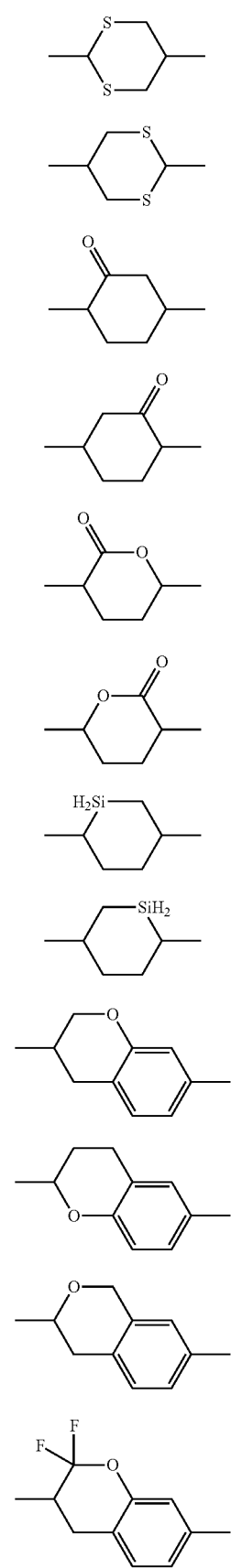
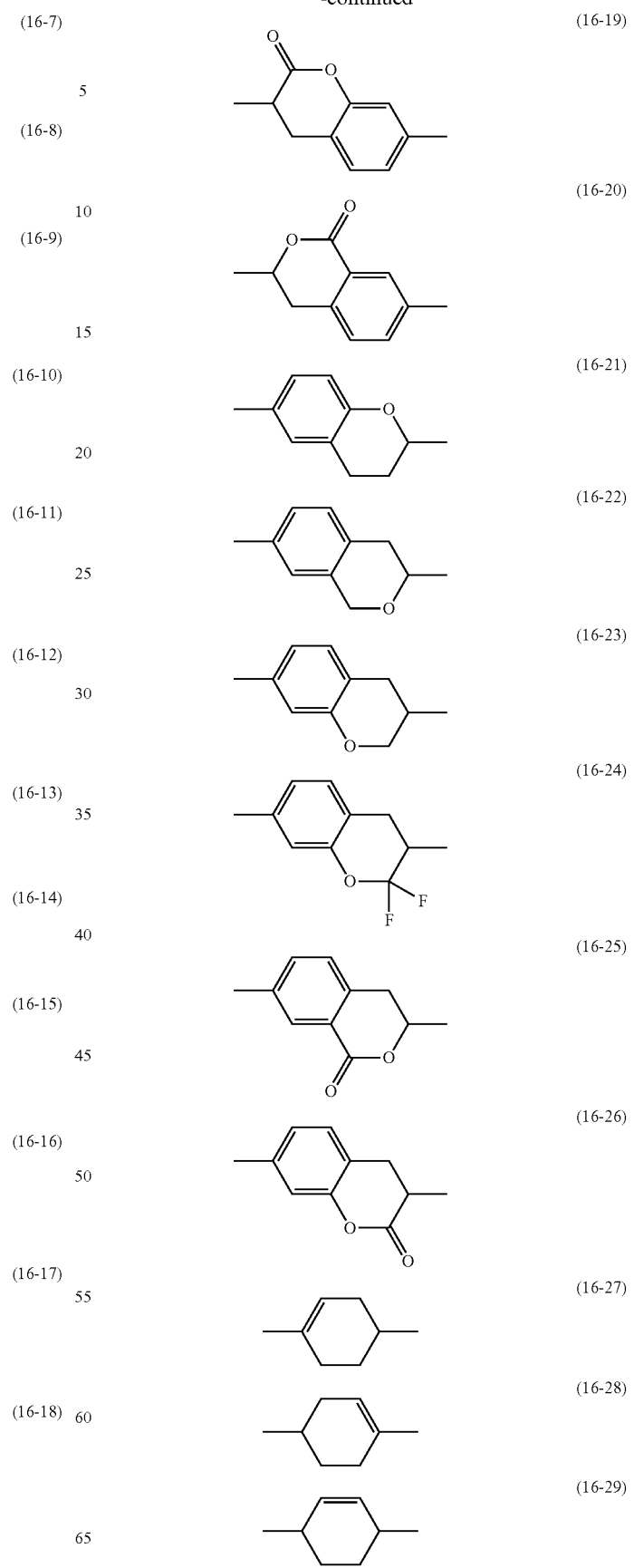

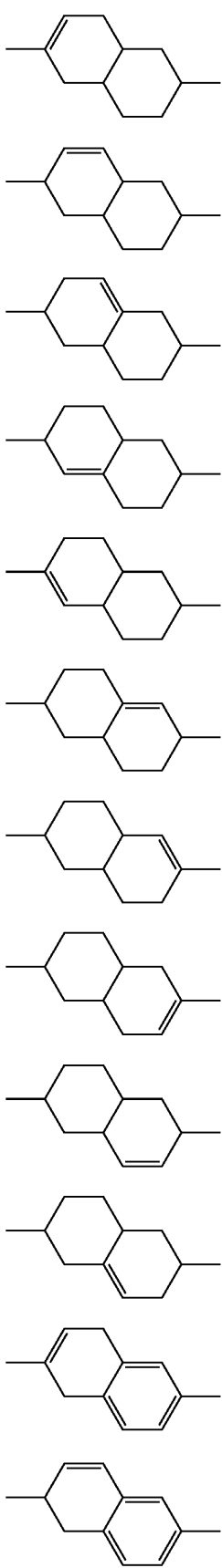
(16-30)
(16-31)
(16-32)
(16-33)
(16-34)
(16-35)
(16-36)
(16-37)
(16-38)
(16-39)
(16-40)
(16-41)
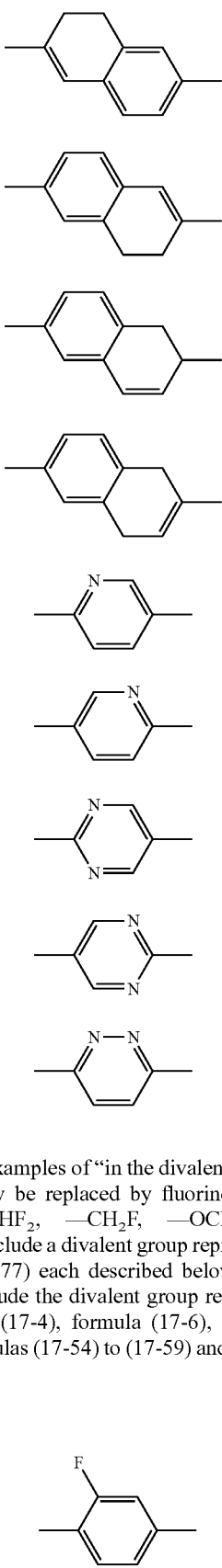
(16-42)
(16-43)
(16-44)
(16-45)
(16-46)
(16-47)
(16-48)
(16-49)
(16-50)
Preferred examples of "in the divalent groups, at least one hydrogen may be replaced by fluorine, chlorine, —C≡N, —CF$_3$, —CHF$_2$, —CH$_2$F, —OCF$_3$, —OCHF$_2$ or —OCH$_2$F" include a divalent group represented by formulas (17-1) to (17-77) each described below. Further preferred examples include the divalent group represented by formulas (17-1) to (17-4), formula (17-6), formulas (17-10) to (17-15), formulas (17-54) to (17-59) and formulas (17-72) to (17-76).
(17-1)

-continued
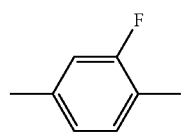 (17-2)
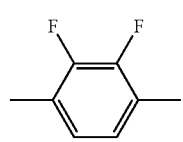 (17-3)
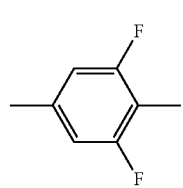 (17-4)
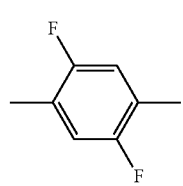 (17-5)
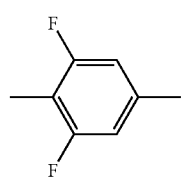 (17-6)
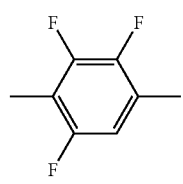 (17-7)
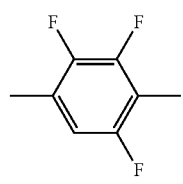 (17-8)
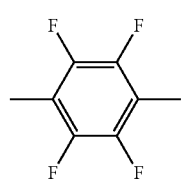 (17-9)
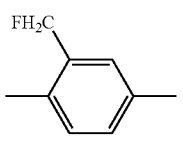 (17-10)
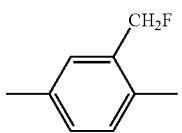 (17-11)
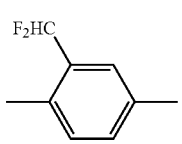 (17-12)
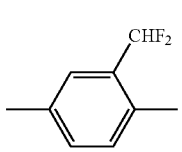 (17-13)
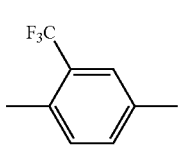 (17-14)
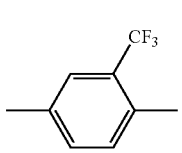 (17-15)
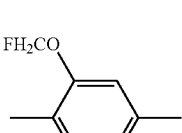 (17-16)
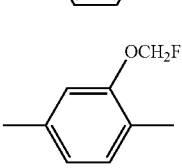 (17-17)
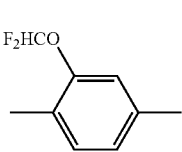 (17-18)
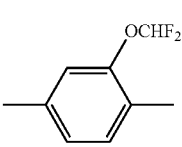 (17-19)
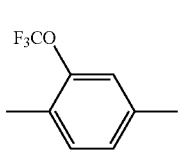 (17-20)
(17-21)

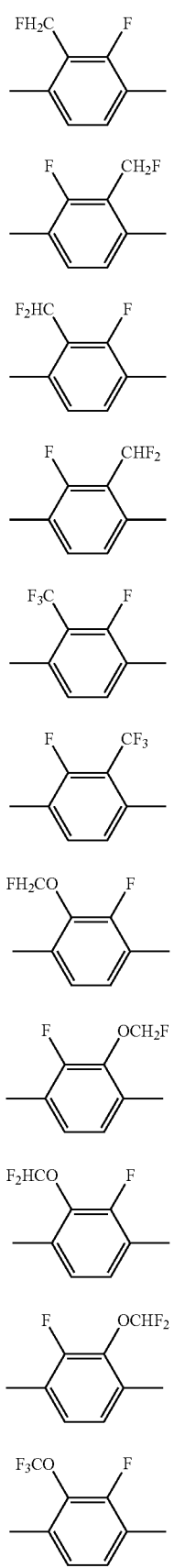
(17-22)
(17-23)
(17-24)
(17-25)
(17-26)
(17-27)
(17-28)
(17-29)
(17-30)
(17-31)
(17-32)
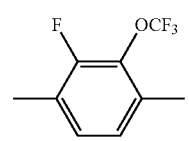 (17-33)
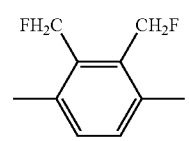 (17-34)
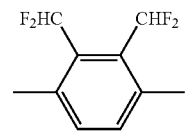 (17-35)
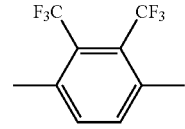 (17-36)
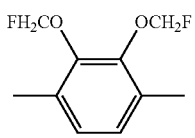 (17-37)
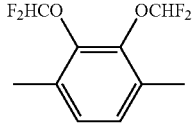 (17-38)
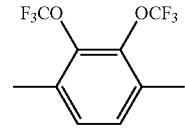 (17-39)
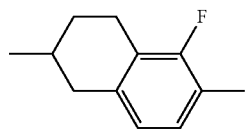 (17-40)
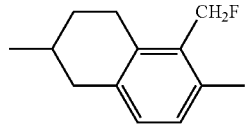 (17-41)
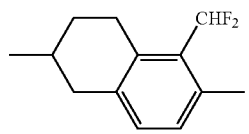 (17-42)
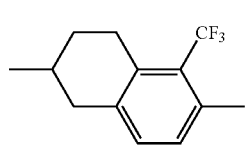 (17-43)

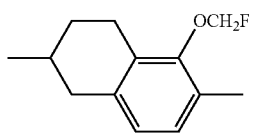
(17-44)
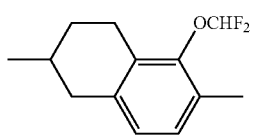
(17-45)
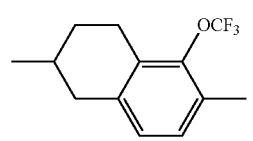
(17-46)
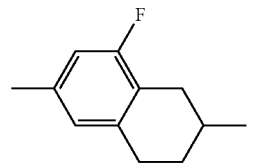
(17-47)
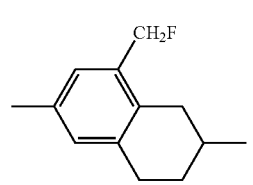
(17-48)
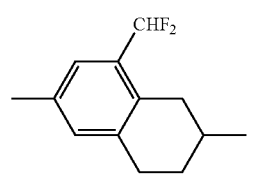
(17-49)
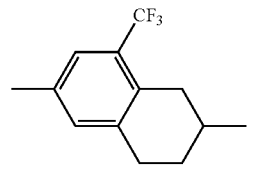
(17-50)
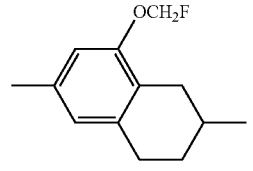
(17-51)
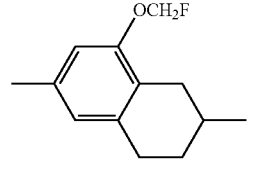
(17-52)
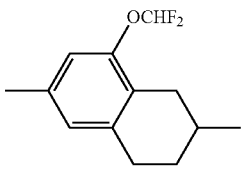
(17-53)
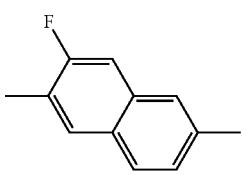
(17-54)
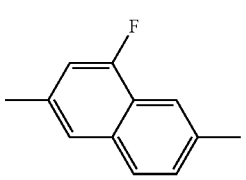
(17-55)
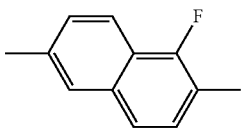
(17-56)
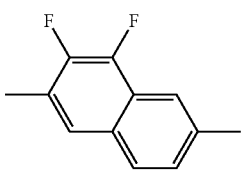
(17-57)
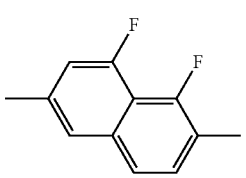
(17-58)
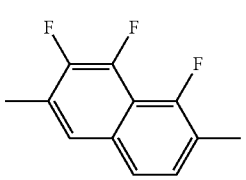
(17-59)
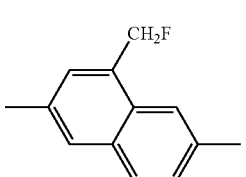
(17-60)
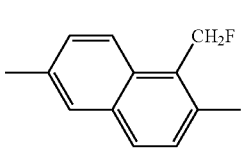
(17-61)

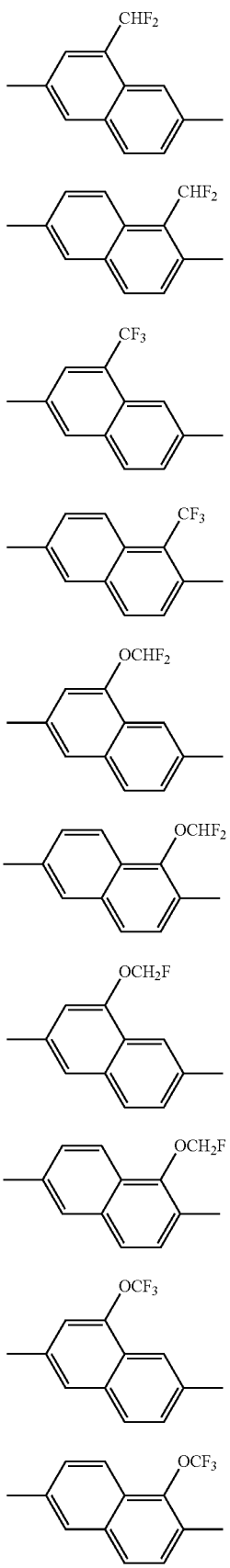
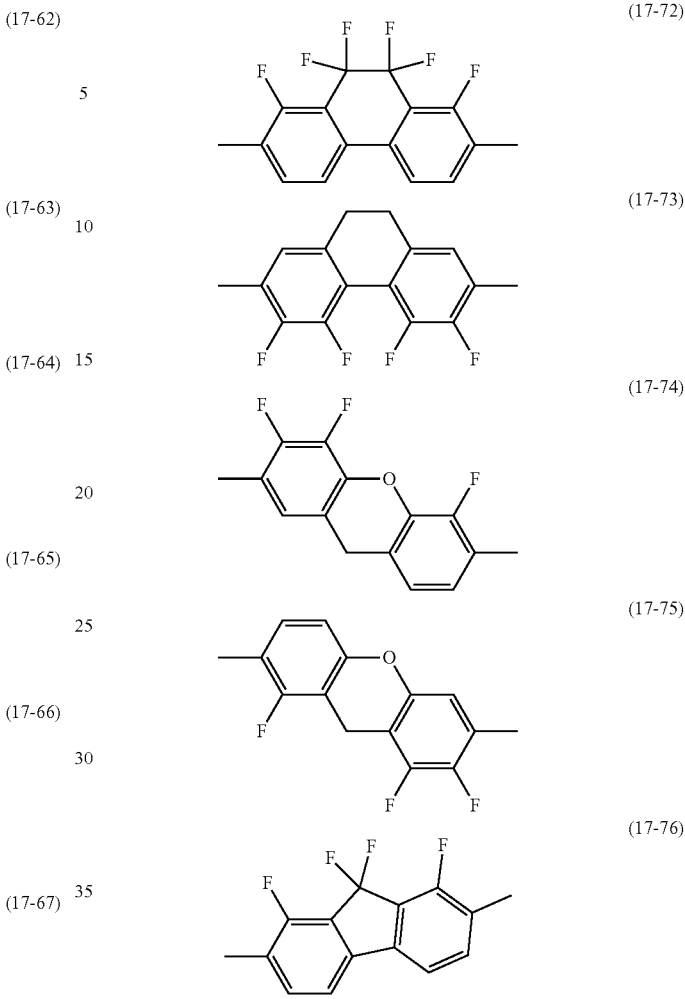

Further preferred $A^1$, $A^2$ or $A^3$ is 1,4-cyclohexylene, 1,4-cyclohexenylene, tetrahydropyran-2,5-diyl, 1,3-dioxane-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2,3,5-trifluoro-1,4-phenylene, pyridine-2,5-diyl, 3-fluoropyridine-2,5-diyl, pyrimidine-2,5-diyl, pyridazine-2,5-diyl, decahydronaphthalene-2,6-diyl, 1,2,3,4-tetrahydronaphthalene-2,6-diyl and naphthalene-2,6-diyl. With regard to a configuration of 1,4-cyclohexylene, tetrahydropyran-2,5-diyl and 1,3-dioxane-2,5-diyl, trans is preferred to cis.

Particularly preferred $A^1$, $A^2$ or $A^3$ is 1,4-cyclohexylene, 1,4-cyclohexenylene, tetrahydropyran-2,5-diyl, 1,4-phenylene, 2-fluoro-1,4-phenylene and 2,3-difluoro-1,4-phenylene. Most preferred $A^1$, $A^2$ or $A^3$ is 1,4-cyclohexylene, 1,4-phenylene, 2-fluoro-1,4-phenylene and 2,3-difluoro-1,4-phenylene.

In formula (1), $Z^1$, $Z^2$ and $Z^3$ are independently a single bond or alkylene having 1 to 6 carbons, and in the alkylene, at least one piece of —$CH_2$— may be replaced by —O—, —S—, —CO— or —$SiH_2$—, and one or two pieces of —$CH_2CH_2$— may be replaced by —CH=CH— or —C≡C—, and in the divalent groups, at least one hydrogen may be replaced by fluorine or chlorine.

Specific examples of $Z^1$, $Z^2$ or $Z^3$ include a single bond, —COO—, —OCO—, —$CH_2$O—, —O$CH_2$—, —$CF_2$O—, —OC$F_2$—, —$CH_2CH_2$—, —CH=CH—, —CF=CH—, —CH=CF—, —CF=CF—, —C≡C—, —CH$_2$CO—, —COCH$_2$—, —CH$_2$SiH$_2$—, —SiH$_2$CH$_2$—, —(CH$_2$)$_4$—, —(CH$_2$)$_2$COO—, —(CH$_2$)$_2$OCO—, —OCO(CH$_2$)$_2$—, —COO(CH$_2$)$_2$—, —(CH$_2$)$_2$CF$_2$O—, —(CH$_2$)$_2$OCF$_2$—, —OCF$_2$(CH$_2$)$_2$—, —CF$_2$O(CH$_2$)$_2$—, —(CH$_2$)$_3$O— or —O(CH$_2$)$_3$—. With regard to a configuration of a double bond of a bonding group such as —CH=CH—, —CF=CF—, —CH=CH—CH$_2$O— and —OCH$_2$—CH=CH—, trans is preferred to cis.

Preferred $Z^1$, $Z^2$ or $Z^3$ is a single bond, —(CH$_2$)$_2$—, —CH=CH—, —C≡C—, —COO—, —OCO—, —CF$_2$O—, —OCF$_2$—, —CH$_2$O—, —OCH$_2$— and —CF=CF—. Further preferred $Z_1$, $Z_2$ or $Z_3$ is a single bond, —(CH$_2$)$_2$—, —CH=CH—, —C≡C—, —CH$_2$O—, and —OCH$_2$—. Most preferred $Z^1$, $Z^2$ or $Z^3$ is a single bond, —(CH$_2$)$_2$—, —CH$_2$O— and —OCH$_2$—.

In formula (1), $Y^1$, $Y^2$, $Y^3$ and $Y^4$ are independently fluorine, chlorine, —CF$_3$ or —CHF$_2$. Preferred $Y^1$, $Y^2$, $Y^3$ and $Y^4$ are fluorine.

In formula (1), a, b and c are independently 0 or 1, and a sum of a, b and c is 0 to 3. Compound (1) has zero to three rings in addition to the fluorodibenzofuran ring. The rings also include a fused ring or a bridged six-membered ring in addition to an ordinary six-membered ring.

Physical properties such as optical anisotropy and dielectric anisotropy can be arbitrarily adjusted by suitably selecting a terminal group, a ring and a bonding group in compound (1). An effect of kinds of terminal groups $R^1$ and $R^2$, rings $A^1$, $A^2$ and $A^3$ and bonding groups $Z^1$, $Z^2$ and $Z^3$ on physical properties of compound (1) will be described below.

In compound (1), when $R^1$ or $R^2$ has the straight chain, a temperature range of the liquid crystal phase is wide, and the viscosity is small. When $R^1$ or $R^2$ has the branched chain, the compatibility with other liquid crystal compounds is good. A compound in which $R^1$ or $R^2$ is an optically active group is useful as a chiral dopant. A reverse twisted domain to be generated in the device can be prevented by adding the compound to the composition. A compound in which $R^1$ or $R^2$ is not the optically active group is useful as a component of the composition. When $R^1$ or $R^2$ is alkenyl, a preferred configuration depends on a position of a double bond. An alkenyl compound having the preferred configuration has high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327.

When ring $A^1$, $A^2$ or $A^3$ is 1,4-phenylene in which at least one hydrogen may be replaced by fluorine or chlorine, pyridine-2,5-diyl, pyrimidine-2,5-diyl, 1,2,3,4-tetrahydronaphthalene-2,6-diyl, naphthalene-2,6-diyl, 9,10-dihydrophenanthrene-2,7-diyl, 9H-xanthene-2,6-diyl or 9H-fluorene-2,7-diyl, the optical anisotropy is large. When ring $A^1$, $A^2$ or $A^3$ is 1,4-cyclohexylene, 1,4-cyclohexenylene, decahydronaphthalene-2,6-diyl, tetrahydropyran-2,5-diyl or 1,3-dioxane-2,5-diyl, the optical anisotropy is small. When ring $A^1$, $A^2$ or $A^3$ is 2-fluoro-1,4-phenylene, 2,3-difluoro-1,4-phenylene or tetrahydropyran-2,5-diyl, the dielectric anisotropy is negatively large. When ring $A^1$, $A^2$ or $A^3$ is 1,4-cyclohexenylene, 2-fluoro-1,4-phenylene or tetrahydropyran-2,5-diyl, the compatibility with other liquid crystal compounds is good.

When at least two rings are 1,4-cyclohexylene, the maximum temperature is high, the optical anisotropy is small, and the viscosity is small. When at least one ring is 1,4-phenylene, the optical anisotropy is comparatively large and an orientational order parameter is large. When at least two rings are 1,4-phenylene, the optical anisotropy is large, the temperature range of the liquid crystal phase is wide, and the maximum temperature is high.

When bonding group $Z^1$, $Z^2$ or $Z^3$ is a single bond, —(CH$_2$)$_2$—, —CH=CH—, —CF$_2$O—, —OCF$_2$—, —CH$_2$O—, —OCH$_2$— or —CF=CF—, the viscosity is small. When the bonding group is a single bond, —CH$_2$CH$_2$—, —CH=CH—, —OCF$_2$— or —CF$_2$O—, the viscosity is further smaller. When the bonding group is —(CH$_2$)$_2$—, —CH=CH—, —CH$_2$O— or —OCH$_2$—, the temperature range of the liquid crystal phase is wide, and an elastic constant ratio $K_{33}/K_{11}$ ($K_{33}$: a bend elastic constant, $K_{11}$: a splay elastic constant) is large. When the bonding group is —C≡C—, the optical anisotropy is large.

When $Y^1$, $Y^2$, $Y^3$ or $Y^4$ is composed of hydrogen and fluorine, the clearing point is high and the compatibility with other liquid crystal compounds is good. When $Y^1$, $Y^2$, $Y^3$ or $Y^4$ consists essentially of fluorine, the clearing point is high, the dielectric anisotropy is negatively large and the viscosity is small. When $Y^1$, $Y^2$, $Y^3$ or $Y^4$ is composed of fluorine and —CF$_3$, the dielectric anisotropy is negatively large and chemical stability is high. When at least one of $Y^1$, $Y^2$, $Y^3$ or $Y^4$ is —OCF$_3$, —OCHF$_2$ or —OCH$_2$F, the compatibility with other liquid crystal compounds is good.

When compound (1) consists essentially of the fluorodibenzofuran ring, the viscosity is small. When compound (1) has one ring in addition to the fluorodibenzofuran ring, the clearing point is high, the viscosity is small and the compatibility with other liquid crystal compounds is good. When compound (1) has two or three rings in addition to the fluorodibenzofuran ring, the clearing point is particularly high. As described above, a compound having required physical properties can be obtained by suitably selecting a kind of the terminal group, the ring and the bonding group, and the number of the rings. Accordingly, compound (1) is useful as a component of a composition used in a device having a mode such as the PC mode, the TN mode, the STN mode, the ECB mode, the OCB mode, the IPS mode and the VA mode.

Preferred examples of compound (1) include compound (1-6) to compound (1-11) described in item 5. Further preferred examples include compound (1-12) to compound (1-14) described in item 6. Still further preferred examples include compound (1-15) to compound (1-32) described in item 7. Most preferred examples include compound (1-33) to compound (1-36) described in item 8. Compound (1) is suitable for a device having a mode such as the VA mode, the IPS mode and the PSA mode.

2. Synthesis of Compound (1)

A synthetic method of compound (1) will be described. Compound (1) can be prepared by suitably combining methods in synthetic organic chemistry. A method for introducing a required terminal group, ring and bonding group into a starting material is described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza in Japanese)" (Maruzen Co., Ltd.).

2-1. Formation of Bonding Group Z

First, a scheme is shown with regard to a method for forming bonding groups $Z^1$ to $Z^3$. Next, reactions described in the scheme in methods (1) to (11) will be described. In the scheme, MSG¹ (or MSG²) is a monovalent organic group having at least one ring. The monovalent organic groups represented by a plurality of MSG¹ (or MSG²) used in the scheme may be identical or different. Compounds (1A) to (1J) correspond to compound (1).

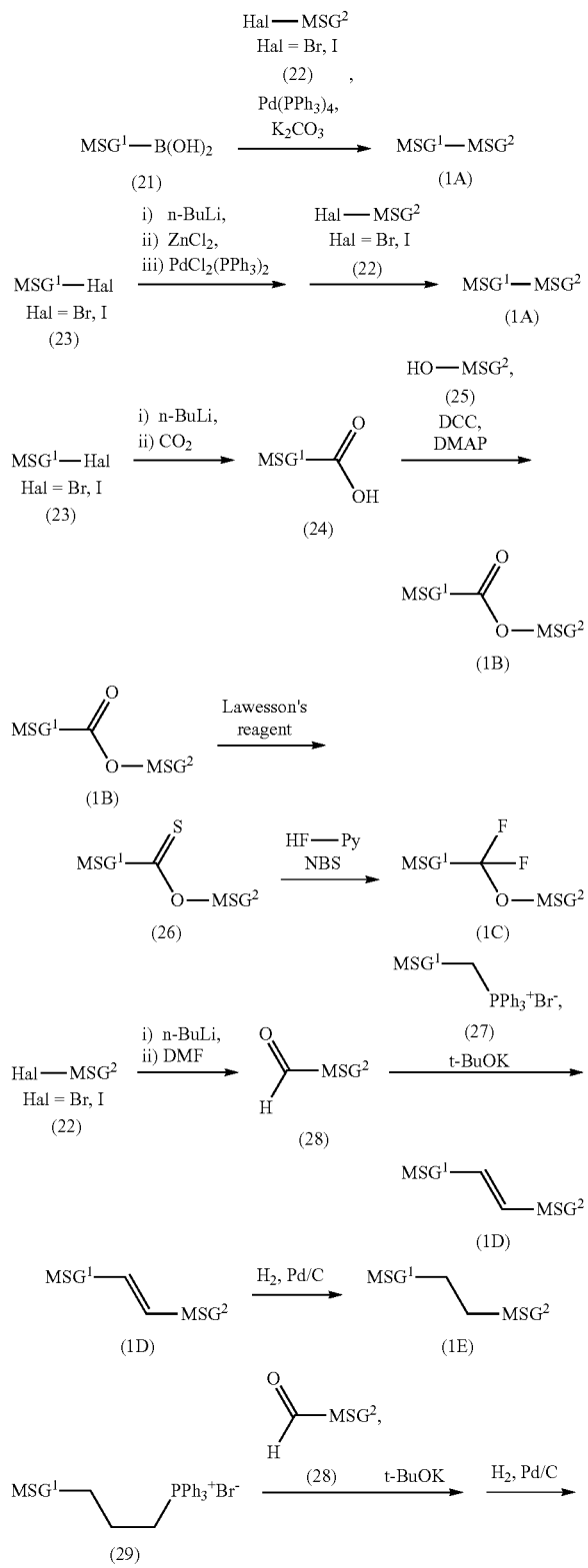

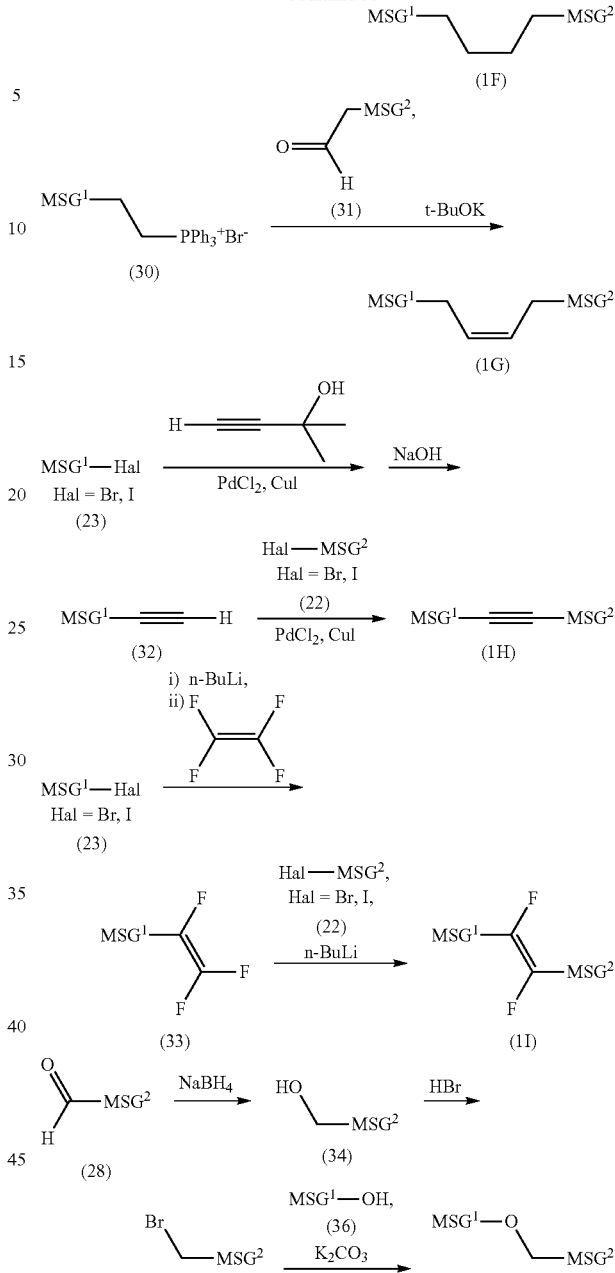

(1) Formation of a Single Bond

Compound (1A) is prepared by allowing aryl boronic acid (21) prepared according to a publicly known method to react with halide (22), in the presence of carbonate and a catalyst such as tetrakis(triphenylphosphine)palladium. Compound (1A) is also prepared by allowing halide (23) prepared according to a publicly known method to react with n-butyllithium and subsequently with zinc chloride, and further with halide (22) in the presence of a catalyst such as dichlorobis(triphenylphosphine)palladium.

(2) Formation of —COO—

Carboxylic acid (24) is obtained by allowing halide (23) to react with n-butyllithium and subsequently with carbon dioxide. Compound (1B) is prepared by dehydration of compound (25) prepared according to a publicly known method and carboxylic acid (24) in the presence of 1,3-dicyclohexylcarbodiimide (DCC) and 4-dimethylaminopyridine (DMAP).

(3) Formation of —CF$_2$O—

Thionoester (26) is obtained by treating compound (1B) with a thiation reagent such as Lawesson's reagent. Compound (1C) is prepared by fluorinating thionoester (26) with a hydrogen fluoride-pyridine complex and N-bromosuccinimide (NBS). Refer to M. Kuroboshi et al., Chem. Lett., 1992, 827. Compound (1C) is also prepared by fluorinating thionoester (26) with (diethylamino) sulfur trifluoride (DAST). Refer to W. H. Bunnelle et al., J. Org. Chem. 1990, 55, 768. The bonding group can also be formed according to the method described in Peer. Kirsch et al., Angew. Chem. Int. Ed. 2001, 40, 1480.

(4) Formation of —CH=CH—

Aldehyde (28) is obtained by treating halide (22) with n-butyllithium and then allowing the treated halide to react with N,N-dimethylformamide (DMF). Phosphorus ylide is generated by treating phosphonium salt (27) prepared according to a publicly known method with a base such as potassium t-butoxide. Compound (1D) is prepared by allowing the phosphorus ylide to react with aldehyde (28). A cis isomer may be generated depending on reaction conditions, and therefore the cis isomer is isomerized into a trans isomer according to a publicly known method when necessary.

(5) Formation of —(CH$_2$)$_2$—

Compound (1E) is prepared by hydrogenating compound (1D) in the presence of a catalyst such as palladium on carbon.

(6) Formation of —(CH$_2$)$_4$—

A compound having —(CH$_2$)$_2$—CH=CH— is obtained by using phosphonium salt (29) in place of phosphonium salt (27) according to the method in method (4). Compound (1F) is prepared by performing catalytic hydrogenation of the compound obtained.

(7) Formation of —CH$_2$CH=CHCH$_2$—

Compound (1G) is prepared by using phosphonium salt (30) in place of phosphonium salt (27) and aldehyde (31) in place of aldehyde (28) according to the method of method (4). A trans isomer may be generated depending on reaction conditions, and therefore the trans isomer is isomerized to a cis isomer according to a publicly known method when necessary.

(8) Formation of —C≡C—

Compound (32) is obtained by allowing halide (23) to react with 2-methyl-3-butyn-2-ol in the presence of a catalyst of dichloropalladium and copper halide, and then performing deprotection under basic conditions. Compound (1H) is prepared by allowing compound (32) to react with halide (22) in the presence of the catalyst of dichloropalladium and copper halide.

(9) Formation of —CF=CF—

Compound (33) is obtained by treating halide (23) with n-butyllithium and then allowing the treated halide to react with tetrafluoroethylene. Compound (1I) is prepared by treating halide (22) with n-butyllithium, and then allowing the treated halide to react with compound (33).

(10) Formation of —OCH$_2$—

Compound (34) is obtained by reducing aldehyde (28) with a reducing agent such as sodium borohydride. Bromide (35) is obtained by brominating compound (34) with hydrobromic acid or the like. Compound (1J) is prepared by allowing bromide (35) to react with compound (36) in the presence of a base such as potassium carbonate.

(11) Formation of —(CF$_2$)$_2$—

A compound having —(CF$_2$)$_2$— is obtained by fluorinating diketone (—COCO—) with sulfur tetrafluoride, in the presence of a hydrogen fluoride catalyst, according to a method described in J. Am. Chem. Soc., 2001, 123, 5414.

2-2. Formation of Rings A$^1$ to A$^3$

Next, a formation method with regard to rings A$^1$ to A$^3$ will be described. A starting material is commercially available or the formation method is well known with regard to a ring such as 1,4-cyclohexylene, 1,3-dioxane-2,5-diyl, 1,4-phenylene, 2-fluoro-1,4-phenylene, 2,3-difluoro-1,4-phenylene, pyridine-2,5-diyl and pyrimidine-2,5-diyl. Then, compounds (64), (67) and (71) described below will be described.

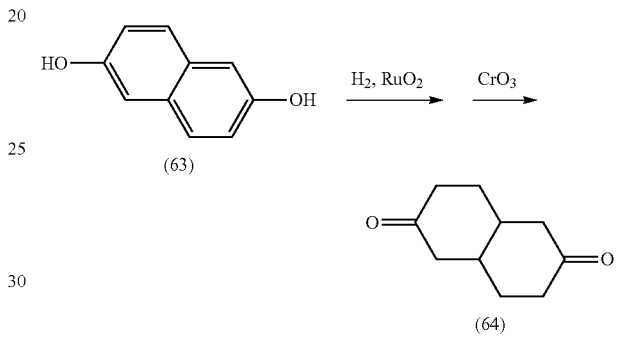

Decahydronaphthalene-2,6-dione (64) is a starting material of a compound having decahydronaphthalene-2,6-diyl. The compound (64) is obtained by performing catalytic hydrogenation with diol (63) in the presence of ruthenium oxide according to a method described in JP 2000-239564 A, and further oxidizing the resulting material with chromium oxide. The compound obtained is converted into compound (1) according to an ordinary method.

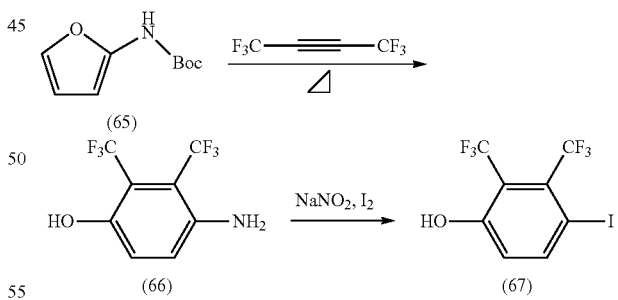

A structural unit of 2,3-(bistrifluoromethyl)phenylene is prepared according to a method described in Org. Lett., 2000, 2 (21), 3345. Aniline (66) is prepared by allowing furan (65) to perform Diels Alder reaction with 1,1,1,4,4,4-hexafluoro-2-butyne at high temperature. Iodide (67) is obtained by performing a Sandmeyer reaction to the compound obtained according to a method described in Org. Synth. Coll., Vol. 2, 1943, 355. The compound obtained is converted into compound (1) according to an ordinary method.

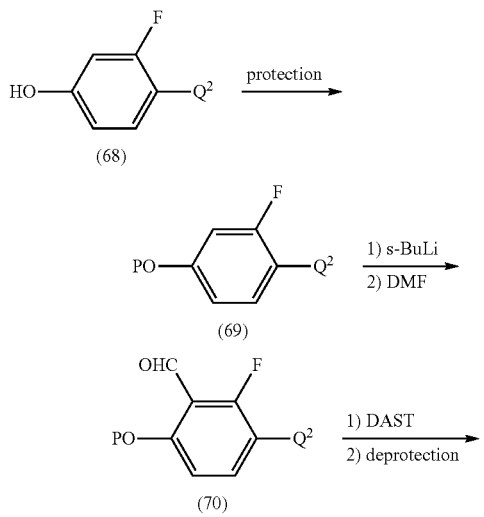

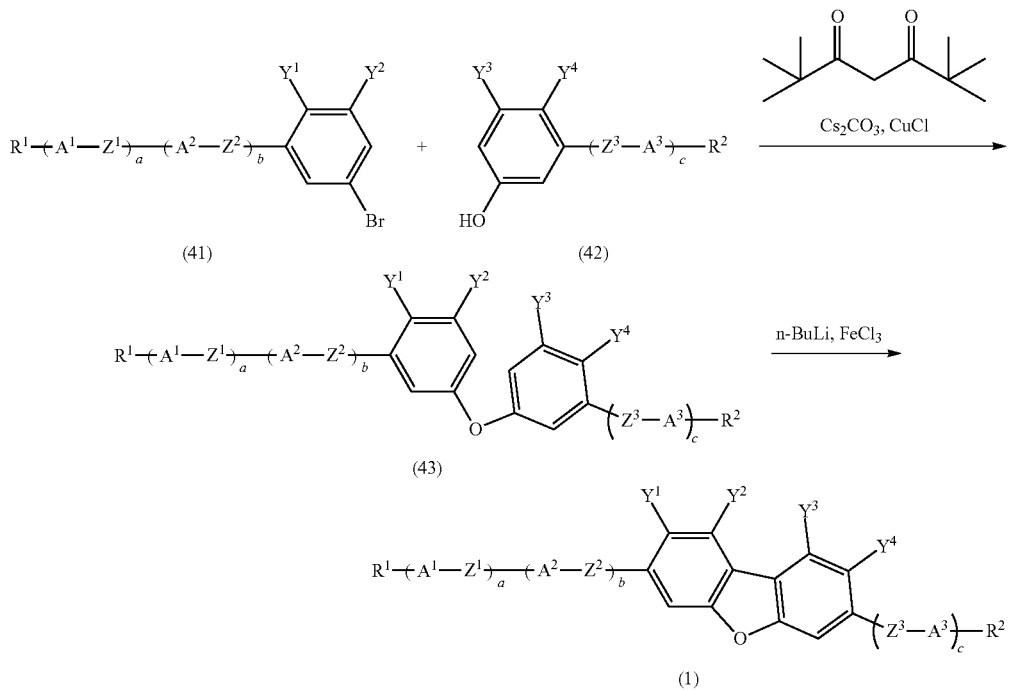

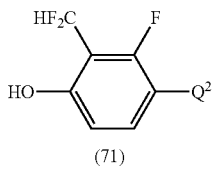

A structural unit of 2-difluoromethyl-3-fluorophenylene is prepared according to a method as described below. Compound (69) is obtained by protecting a hydroxyl group of compound (68) with a suitable protective group. P means the protective group. Aldehyde (70) is obtained by allowing s-butyllithium to act on compound (69), and subsequently allowing the obtained material to react with N,N-dimethylformamide (DMF). Phenol (71) is obtained by fluorinating the compound obtained with diethylaminosulfur trifluoride (DAST), and subsequently deprotecting the resulting material. The compound obtained is converted into compound (1) according to an ordinary method.

2-3. Synthesis Example

An example of a method for preparing compound (1) is as described below. In the compounds, $R^1$, $R^2$, $A^1$, $A^2$, $A^3$, $Z^1$, $Z^2$, $Z^3$, $Y^1$, $Y^2$, $Y^3$, $Y^4$, a, b and c are defined in a manner identical with the definitions in item 1.

An example of a method for preparing compound (1) is as described below. Compound (43) is obtained by sequentially adding copper(I) chloride, cesium carbonate and 2,2,6,6-tetramethylheptane-3,5-dione to compound (41) and compound (42) prepared according to a publicly known method, and the resulting material was stirred and heated. Next, compound (1) can be prepared by allowing n-butyllithium to act on compound (43), and then adding iron(III) chloride thereto.

3. Liquid Crystal Composition 3-1. Component Compound

A liquid crystal composition of the invention will be described. The composition contains at least one compound (1) as component (a). The composition may contain two, three or more compounds (1). A component in the composition may be only compound (1). The composition preferably contains at least one of compounds (1) in a range of about 1% by weight to about 99% by weight in order to develop good physical properties. In a composition having negative dielectric anisotropy, a preferred content of compound (1) is in a range of about 5% by weight to about 60% by weight. In a composition having positive dielectric anisotropy, a preferred content of compound (1) is about 30% by weight or less.

TABLE 1

| Component | Component compound | Dielectric anisotropy |
|---|---|---|
| Component (a) | Compound (1) | Negatively large |
| Component (b) | Compound (2) to compound (4) | Small |
| Component (c) | Compound (5) to compound (11) | Negatively large |
| Component (d) | Compound (12) to compound (14) | Positively large |
| Component (e) | Compound (15) | Positively large |

The composition contains compound (1) as component (a). The composition further preferably contains a liquid crystal compound selected from components (b) to (e) described in Table 1. When the composition is prepared, components (b) to (e) are preferably selected by taking into account the positive or negative dielectric anisotropy and magnitude of the dielectric anisotropy. The composition may contain a liquid crystal compound different from compounds (1) to (15). The composition may not contain such a liquid crystal compound.

Component (b) includes a compound in which two terminal groups are alkyl or the like. Specific examples of preferred component (b) include compounds (2-1) to (2-11), compounds (3-1) to (3-19) and compounds (4-1) to (4-7). In the compounds, $R^{11}$ and $R^{12}$ are independently alkyl having 1 to 10 carbons or alkenyl having 2 to 10 carbons, and in the alkyl and the alkenyl, at least one piece of —$CH_2$— may be replaced by —O—, and in the groups, at least one hydrogen may be replaced by fluorine.

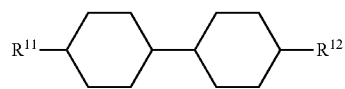

(2-1)

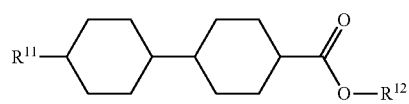

(2-2)

(2-3)

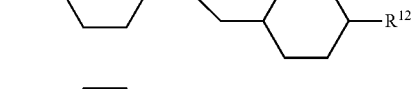

(2-4)

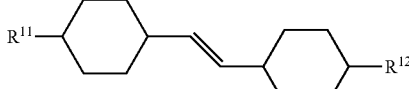

(2-5)

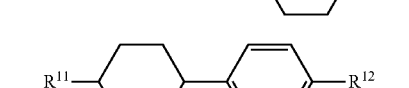

(2-6)

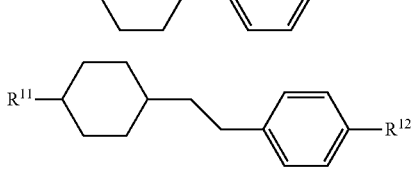

-continued

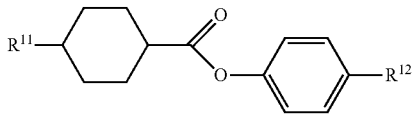

(2-7)

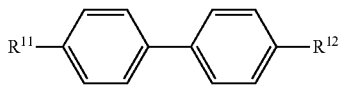

(2-8)

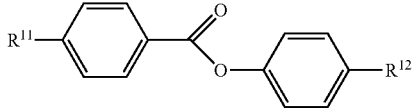

(2-9)

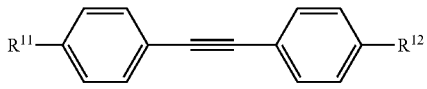

(2-10)

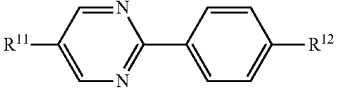

(2-11)

(3-1)

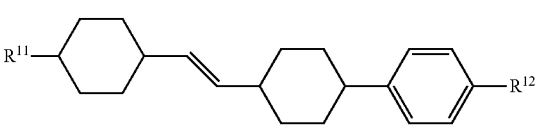

(3-2)

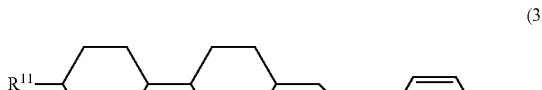

(3-3)

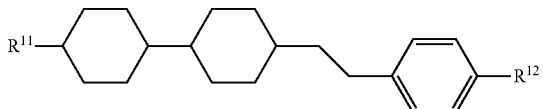

(3-4)

(3-5)

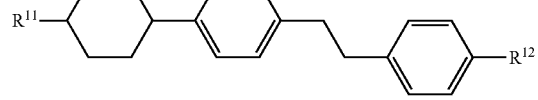

(3-6)

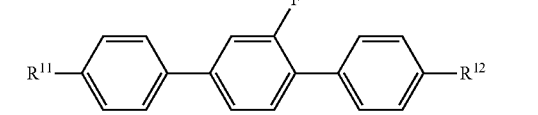

(3-7)

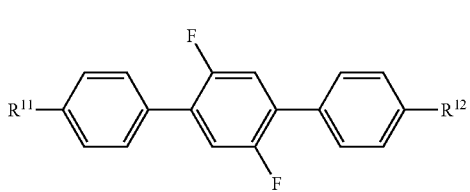

(3-8)
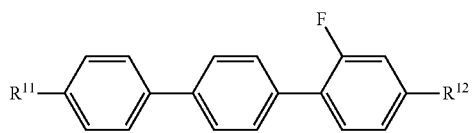

(3-9)
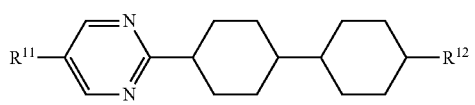

(3-10)
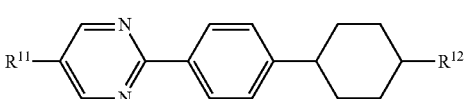

(3-11)
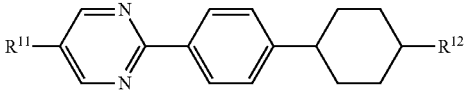

(3-12)
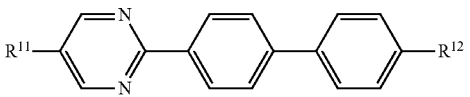

(3-13)
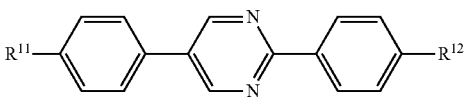

(3-14)
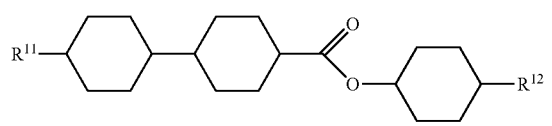

(3-15)
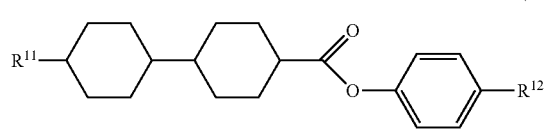

(3-16)
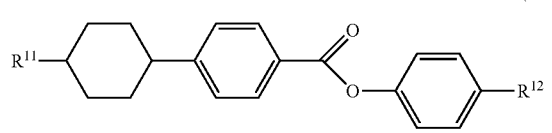

(3-17)
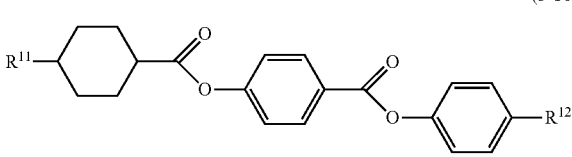

(3-18)
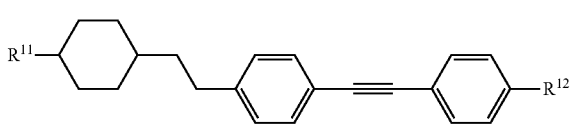

(3-19)
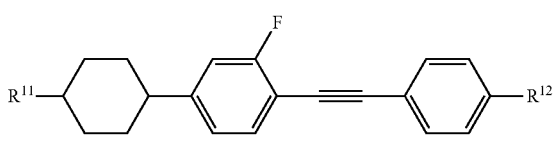

(4-1)
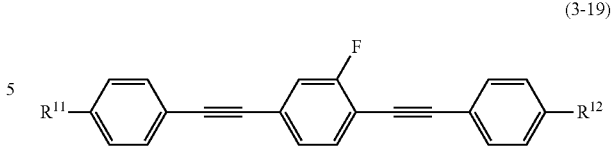

(4-2)
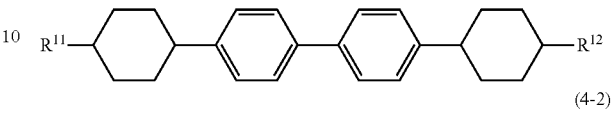

(4-3)
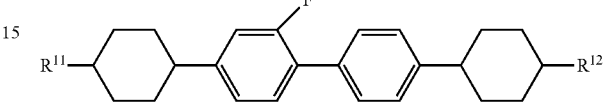

(4-4)
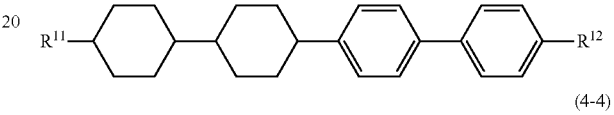

(4-5)
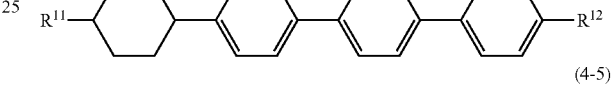

(4-6)
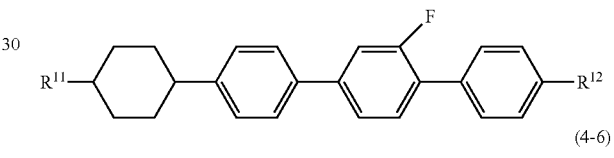

(4-7)
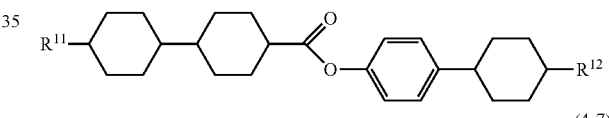

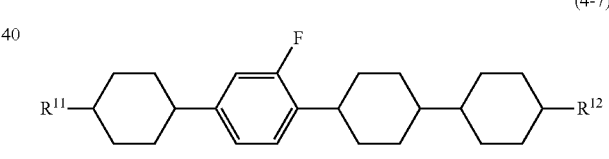

Component (b) has small dielectric anisotropy. Component (b) is close to neutrality. Compound (2) is effective in decreasing the viscosity or adjusting the optical anisotropy. Compounds (3) and (4) are effective in extending the temperature range of the nematic phase by increasing the maximum temperature, or in adjusting the optical anisotropy.

As a content of component (b) is increased, the viscosity of the composition is decreased, but the dielectric anisotropy is decreased. Thus, as long as a desired value of threshold voltage of a device is met, the content is preferably as large as possible. When a composition for the IPS mode, the VA mode or the like is prepared, the content of component (b) is preferably about 30% by weight or more, and further preferably about 40% by weight or more, based on the weight of the liquid crystal composition.

Component (c) includes compounds (5) to (11). The compounds have phenylene in which hydrogen in lateral positions are replaced by two halogens, such as 2,3-difluoro-1,4-phenylene. Specific examples of preferred component (c) include compounds (5-1) to (5-8), compounds (6-1) to (6-18), compound (7-1), compounds (8-1) to (8-3), compounds (9-1) to (9-11), compounds (10-1) to (10-3) and compounds (11-1) to (11-3). In the compounds, $R^{13}$, $R^{14}$ and $R^{15}$ are independently alkyl having 1 to 10 carbons or alkenyl having 2 to 10 carbons, and in the alkyl and the alkenyl, at least one piece of —CH$_2$— may be replaced by —O—, and in the groups, at least one hydrogen may be replaced by fluorine, and $R^{15}$ may be hydrogen or fluorine.
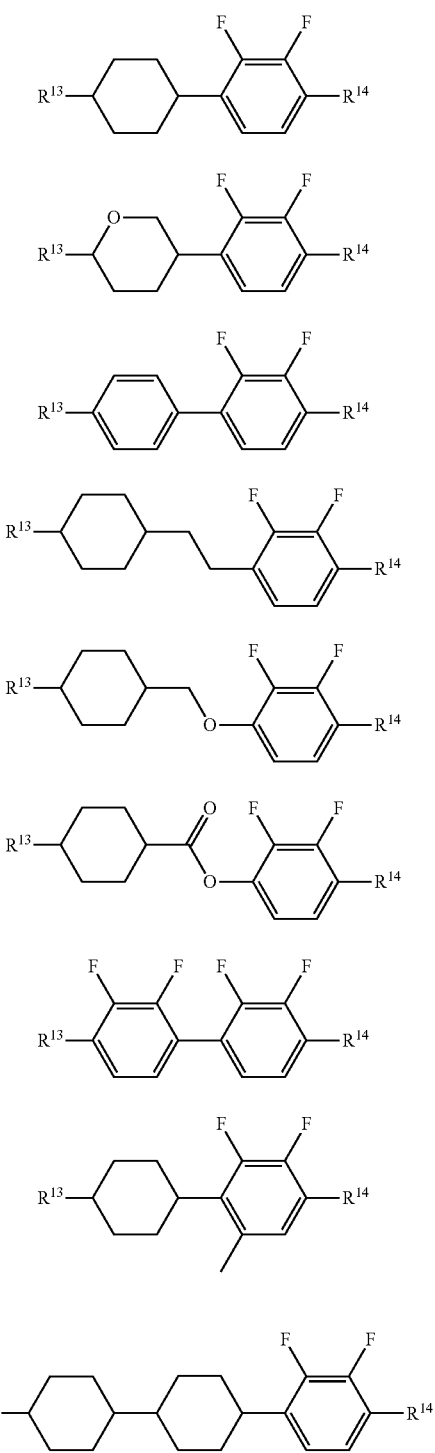
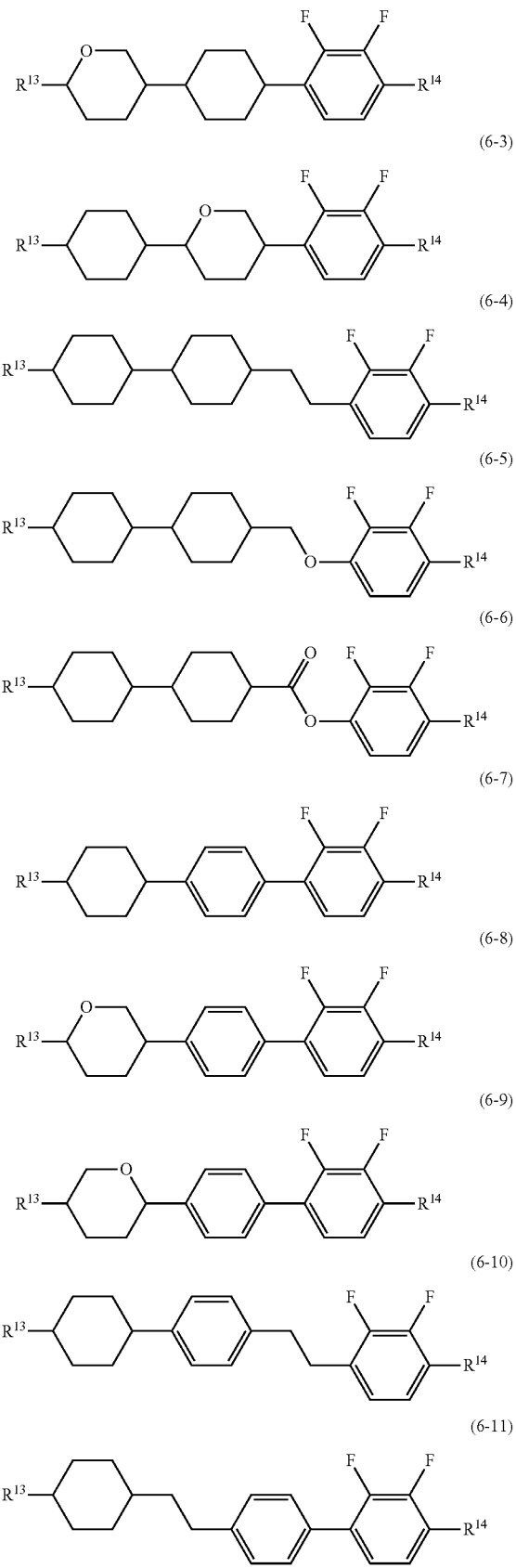

(6-12) 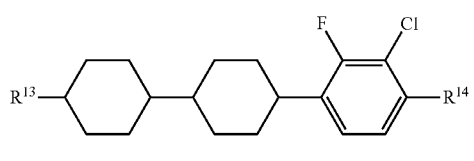
(6-13) 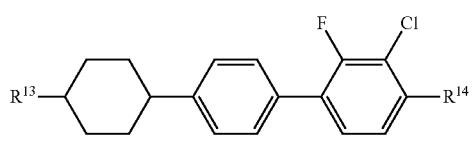
(6-14) 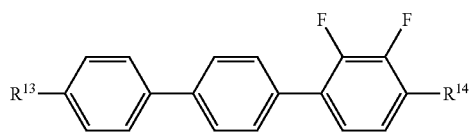
(6-15) 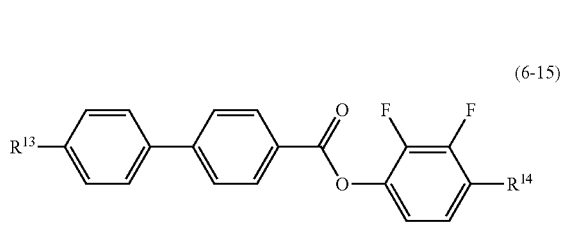
(6-16) 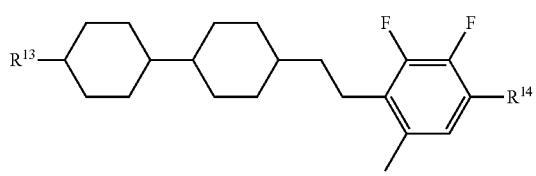
(6-17) 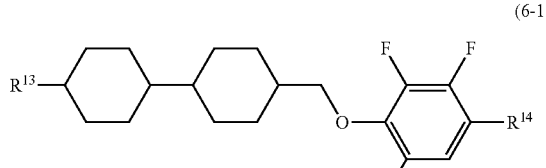
(6-18) 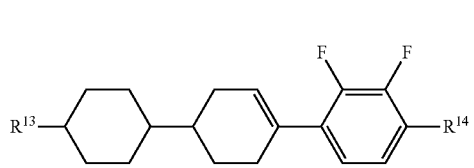
(7-1) 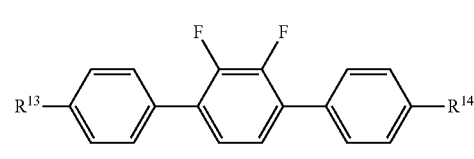
(8-1) 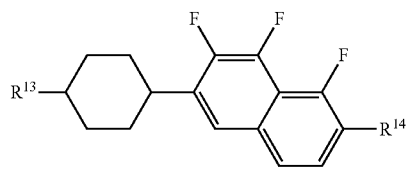
(8-2) 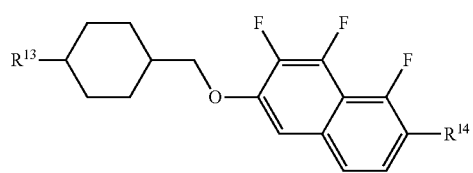
(8-3) 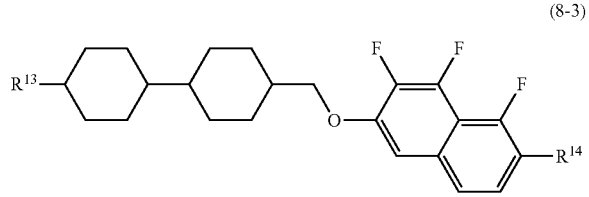
(9-1) 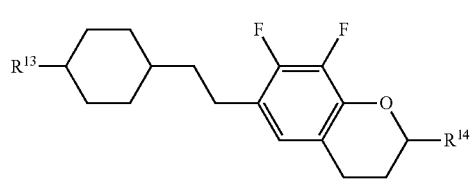
(9-2) 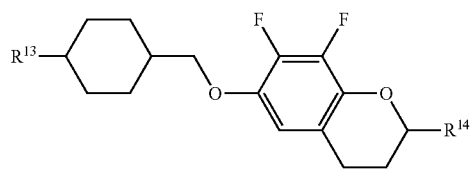
(9-3) 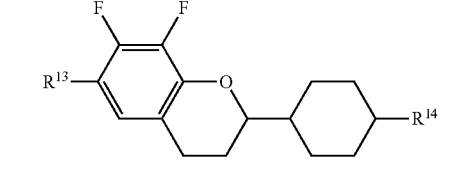
(9-4) 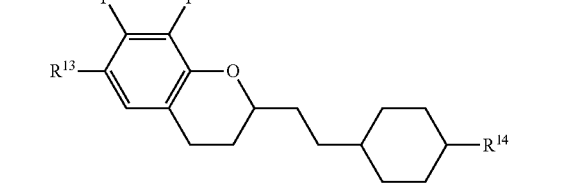
(9-5) 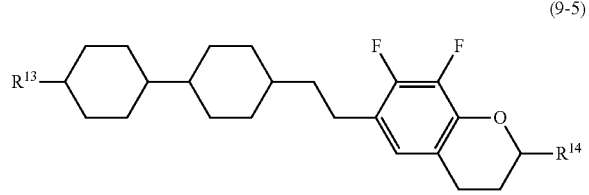
(9-6) 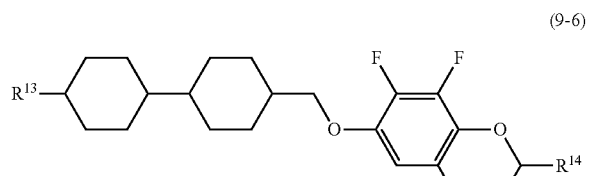

(9-7)
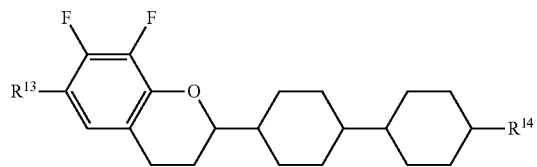

(9-8)
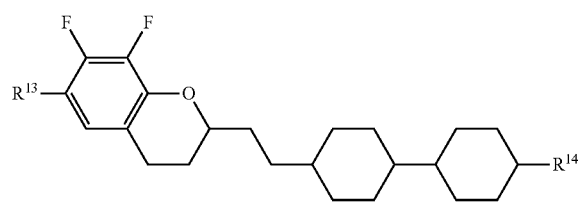

(9-9)
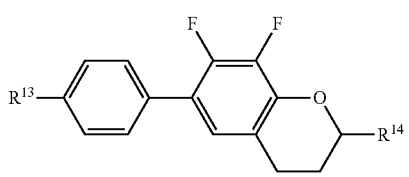

(9-10)
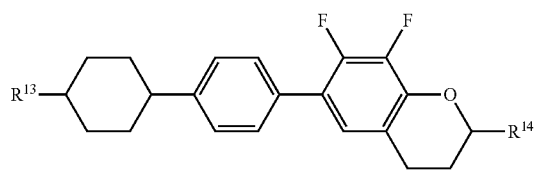

(9-11)
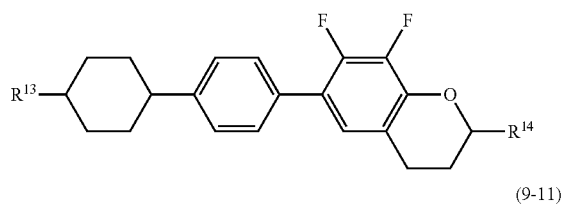

(10-1)
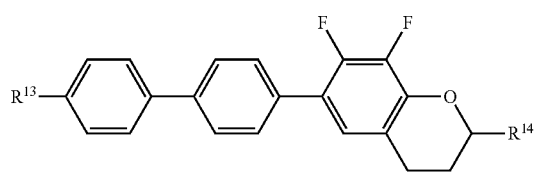

(10-2)
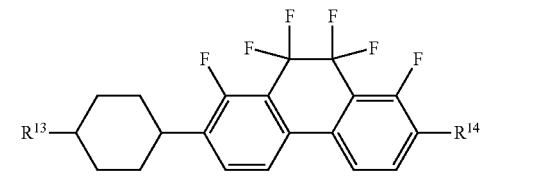

(10-3)
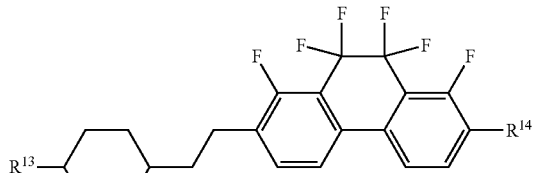

(11-1)
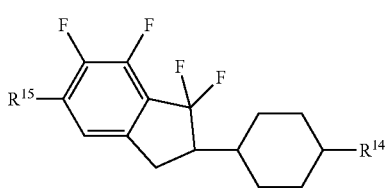

(11-2)
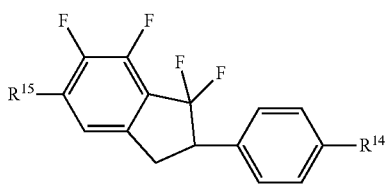

(11-3)
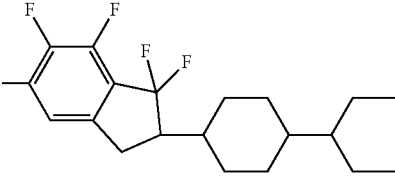

Component (c) has negatively large dielectric anisotropy. Component (c) is used when a composition for the IPS mode, the VA mode, the PSA mode or the like is prepared. As a content of component (c) is increased, the dielectric anisotropy of the composition is negatively increased, but the viscosity is increased. Thus, as long as a desired value of threshold voltage of the device is met, the content is preferably as small as possible. When the dielectric anisotropy at a degree of −5 is taken into account, the content is preferably about 40% by weight or more in order to allow a sufficient voltage driving.

Among types of component (c), compound (5) is a bicyclic compound, and therefore is effective in decreasing the viscosity, adjusting the optical anisotropy or increasing the dielectric anisotropy. Compounds (5) and (6) are a tricyclic compound, and therefore are effective in increasing the maximum temperature, the optical anisotropy or the dielectric anisotropy. Compounds (8) to (11) are effective in increasing the dielectric anisotropy.

When a composition for the IPS mode, the VA mode, the PSA mode or the like is prepared, the content of component (c) is preferably about 40% by weight or more, and further preferably in the range of about 50% by weight to about 95% by weight, based on the weight of the liquid crystal composition. When component (c) is added to the composition having positive dielectric anisotropy, the content of component (c) is preferably about 30% by weight or less. Addition of component (c) allows adjustment of the elastic constant of the composition and adjustment of a voltage-transmittance curve of the device.

Component (d) is a compound having a halogen-containing group or a fluorine-containing group at a right terminal.

Specific examples of preferred component (d) include compounds (12-1) to (12-16), compounds (13-1) to (13-113) and compounds (14-1) to (14-58). In the compounds, $R^{16}$ is alkyl having 1 to 10 carbons or alkenyl having 2 to 10 carbons, and in the alkyl and the alkenyl, at least one piece of —$CH_2$— may be replaced by —O—, and in the groups, at least one hydrogen may be replaced by fluorine. $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$.

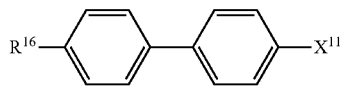
(12-1)

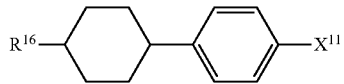
(12-2)

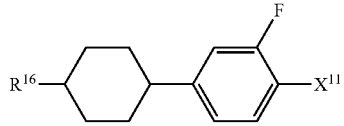
(12-3)

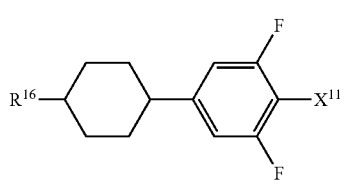
(12-4)

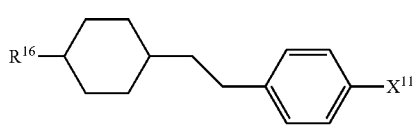
(12-5)

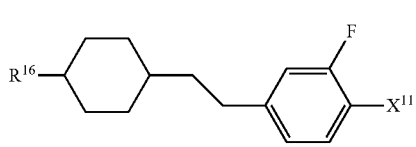
(12-6)

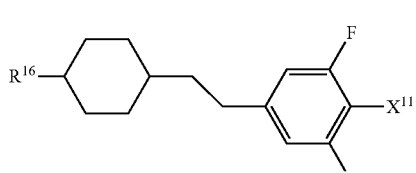
(12-7)

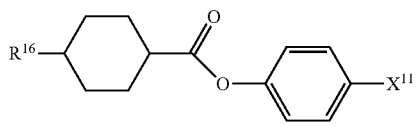
(12-8)

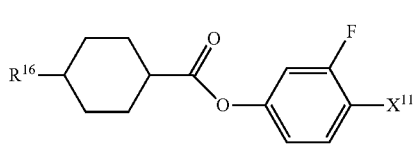
(12-9)

-continued

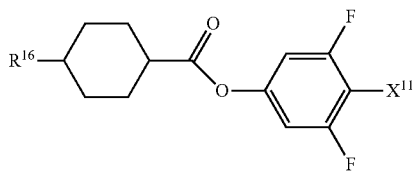
(12-10)

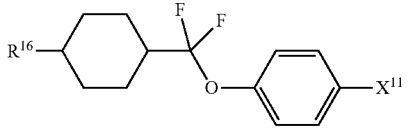
(12-11)

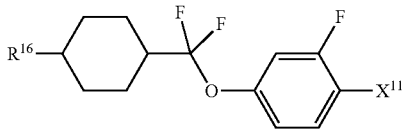
(12-12)

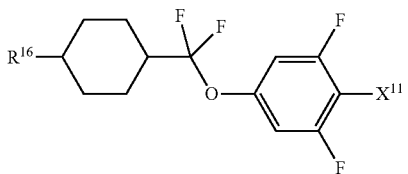
(12-13)

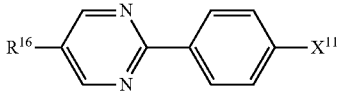
(12-14)

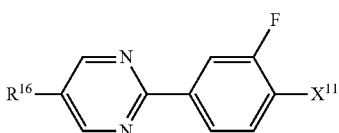
(12-15)

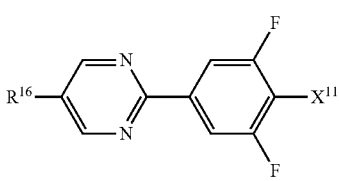
(12-16)

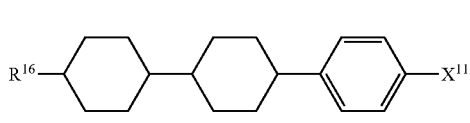
(13-1)

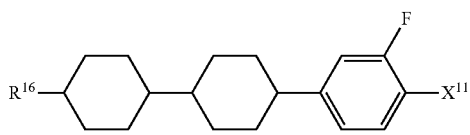
(13-2)

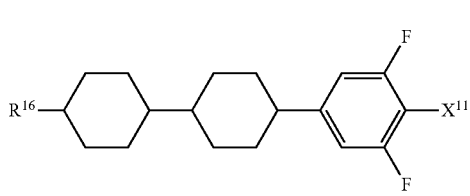
(13-3)

(13-4) through (13-23): chemical structure formulas (13-24)
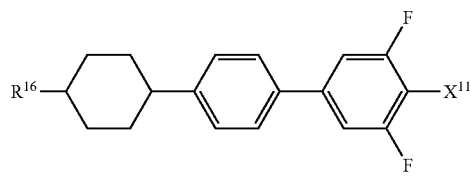
(13-25)
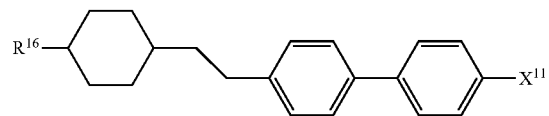
(13-26)
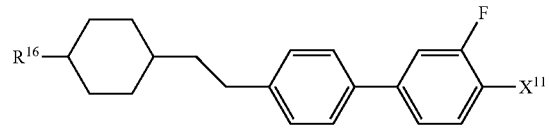
(13-27)
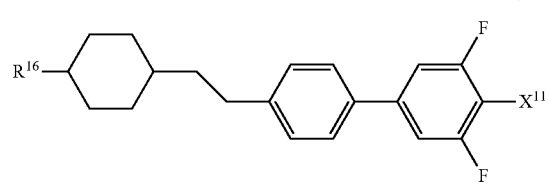
(13-28)
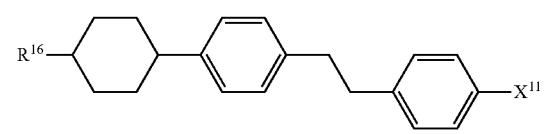
(13-29)
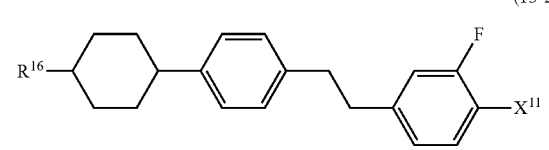
(13-30)
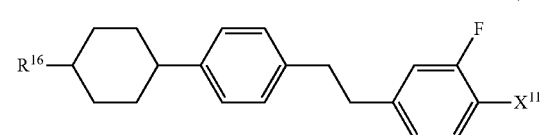
(13-31)
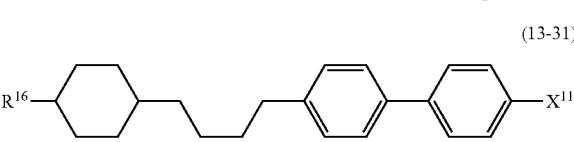
(13-32)
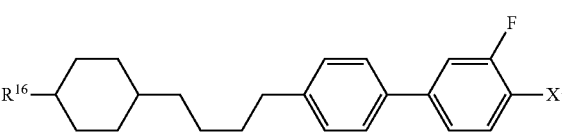
(13-33)
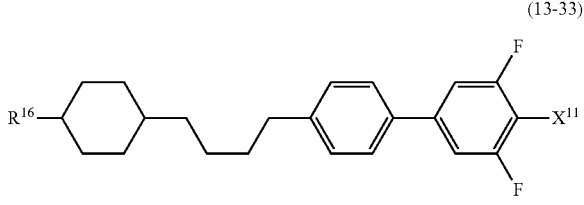
(13-34)
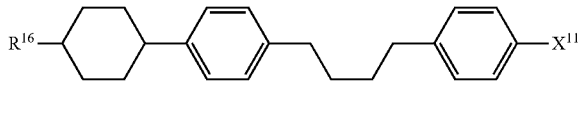
(13-35)
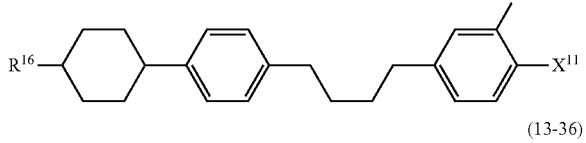
(13-36)
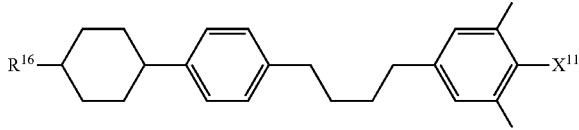
(13-37)
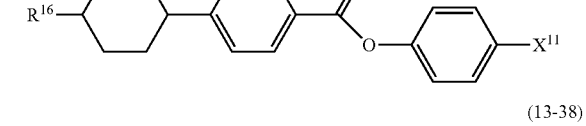
(13-38)
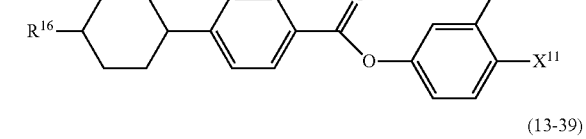
(13-39)
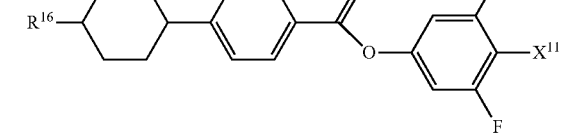
(13-40)
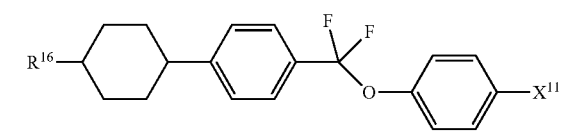
(13-41)
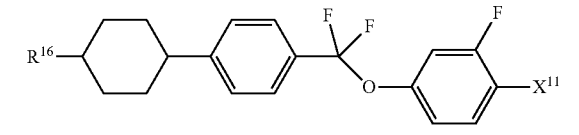

(13-42)
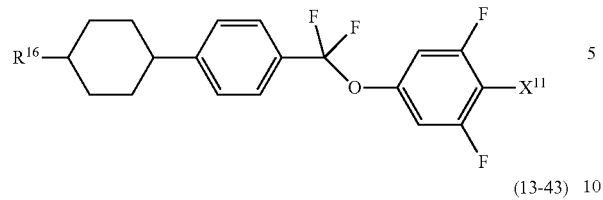
(13-51)
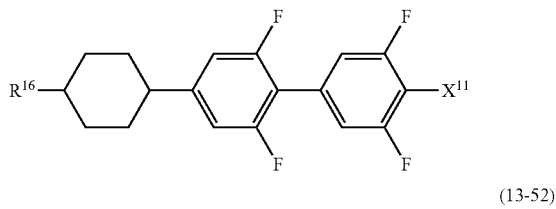
(13-43)
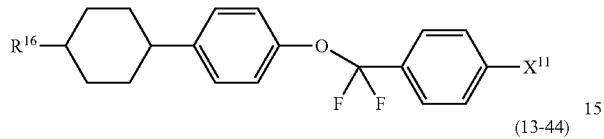
(13-52)
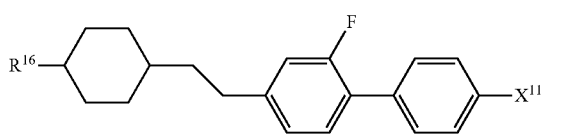
(13-44)
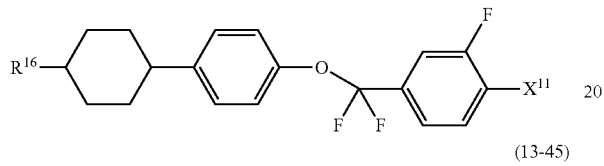
(13-53)
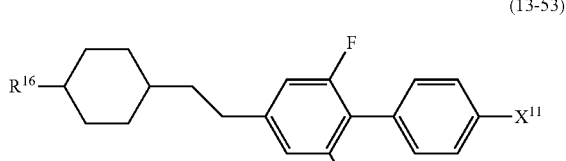
(13-45)
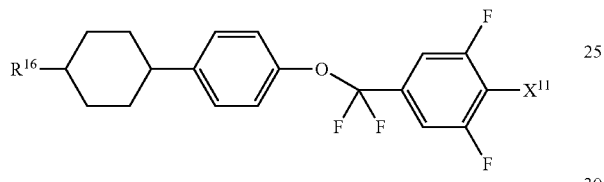
(13-54)
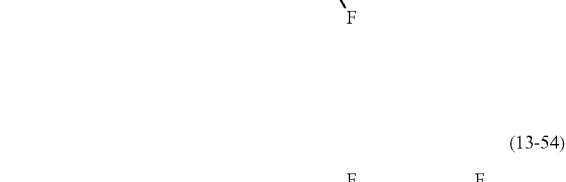
(13-46)
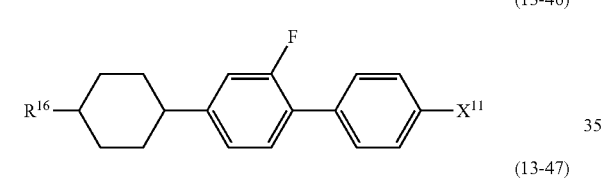
(13-55)
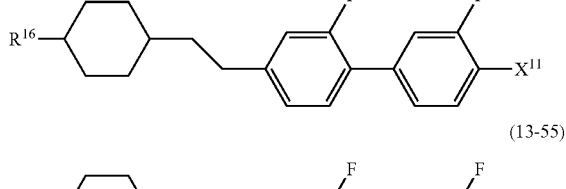
(13-47)
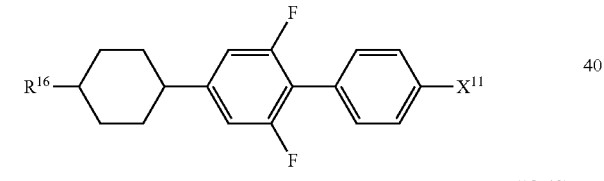
(13-56)
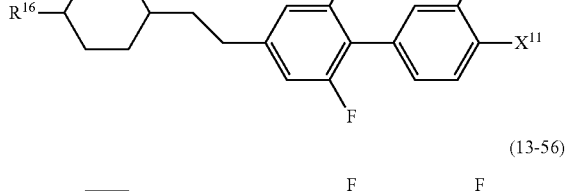
(13-48)
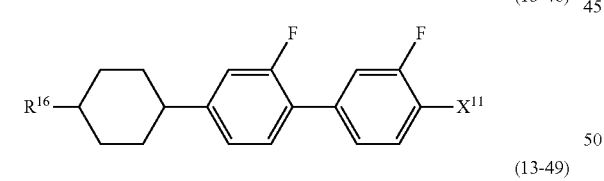
(13-57)
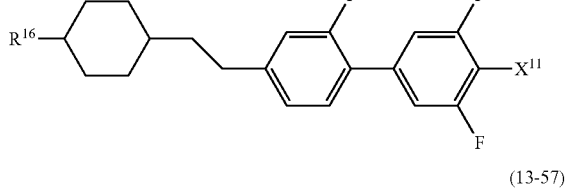
(13-49)
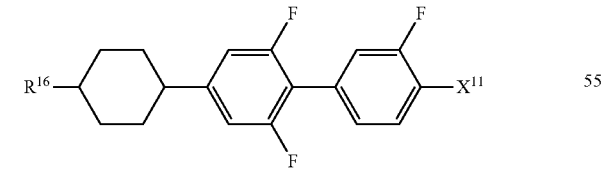
(13-58)
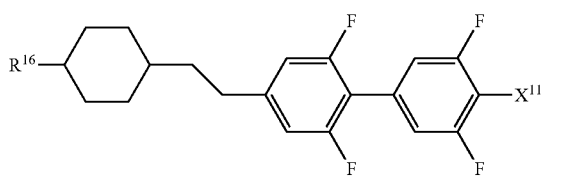
(13-50)
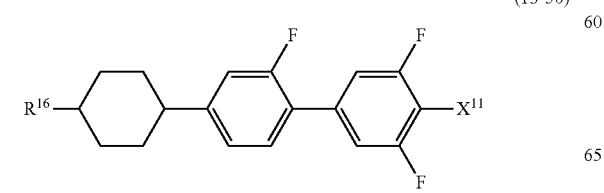

(13-59) 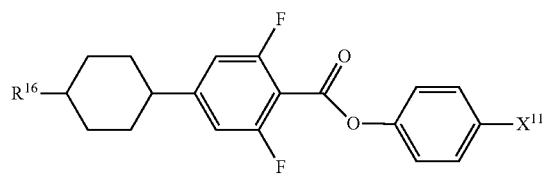
(13-60) 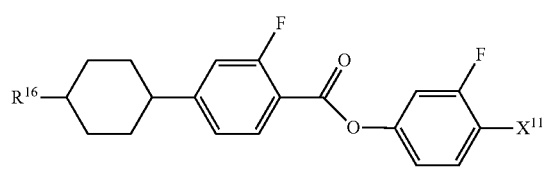
(13-61) 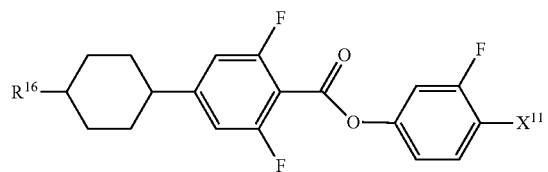
(13-62) 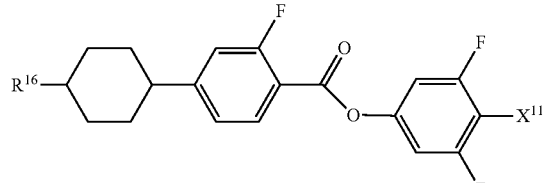
(13-63) 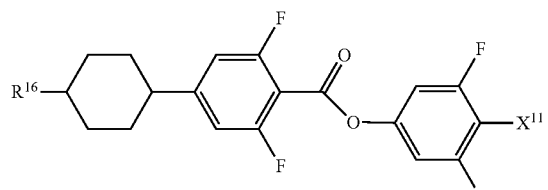
(13-64) 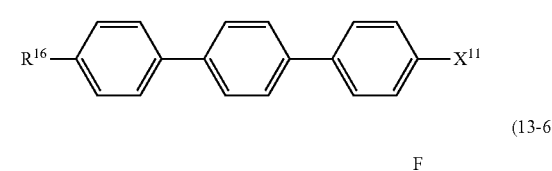
(13-65) 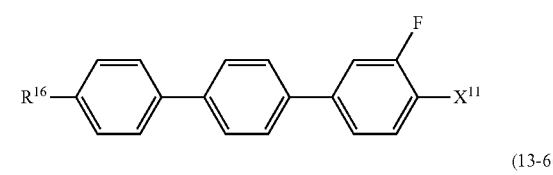
(13-66) 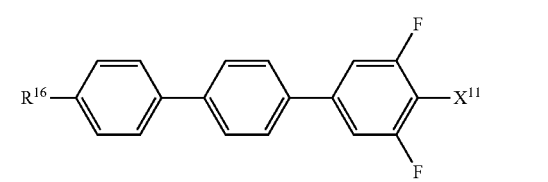
(13-67) 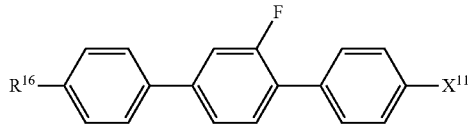
(13-68) 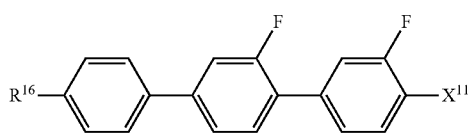
(13-69) 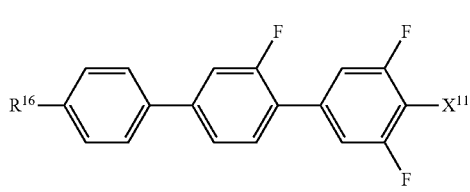
(13-70) 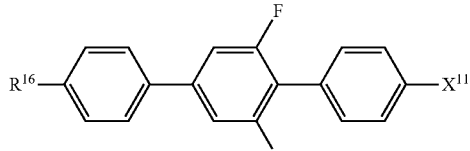
(13-71) 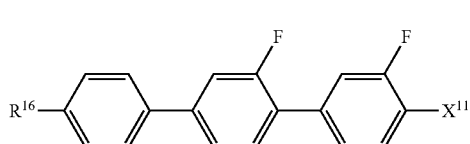
(13-72) 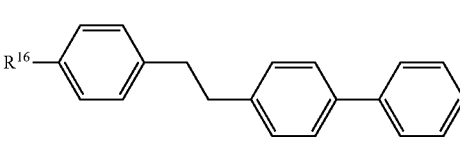
(13-73) 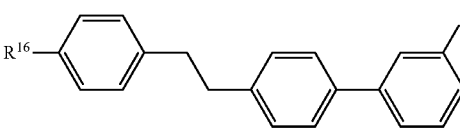
(13-74) 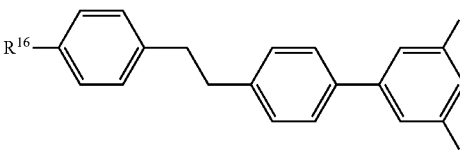
(13-75) 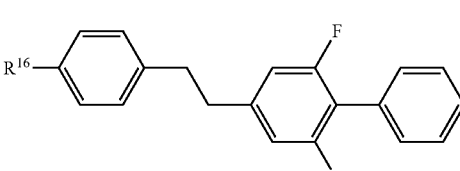

(13-76)
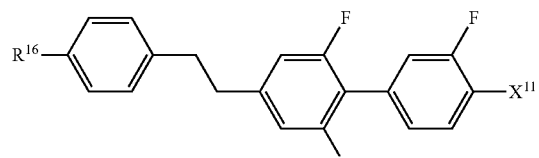
(13-77)
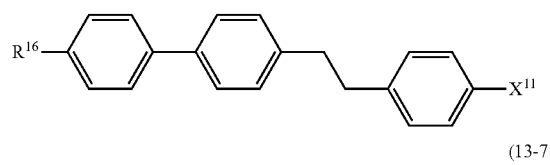
(13-78)
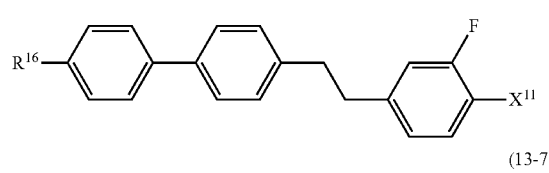
(13-79)
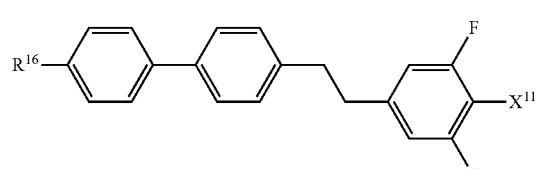
(13-80)
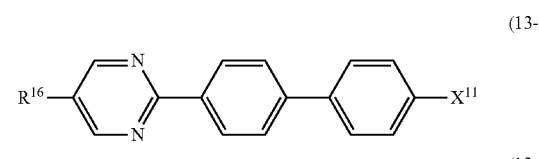
(13-81)
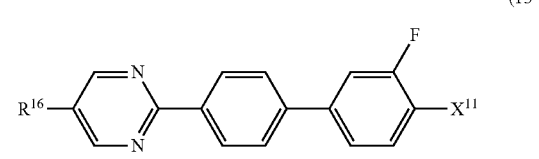
(13-82)
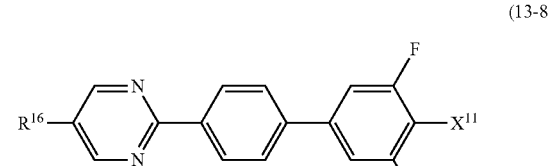
(13-83)
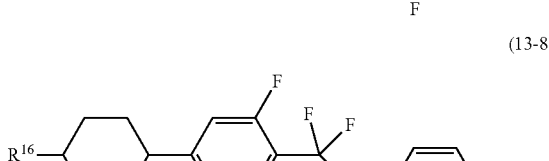
(13-84)
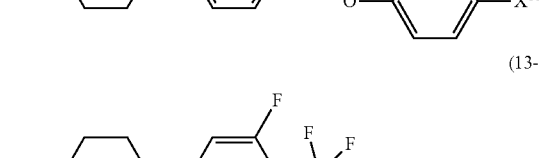
(13-85)
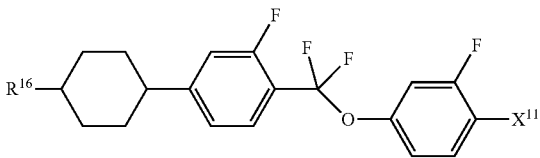
(13-86)
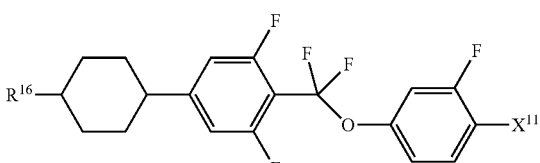
(13-87)
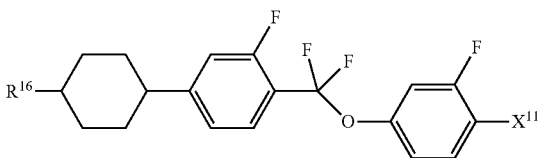
(13-88)
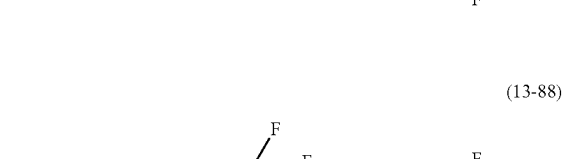
(13-89)
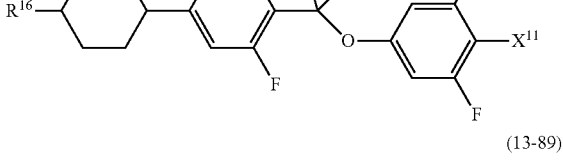
(13-90)
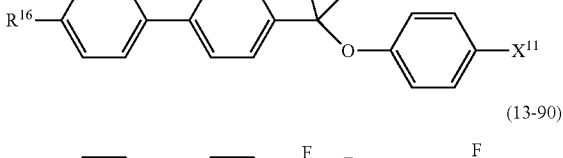
(13-91)
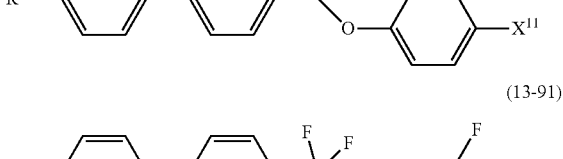
(13-92)
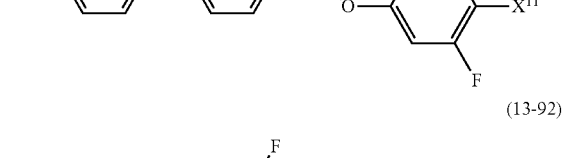

(13-93) 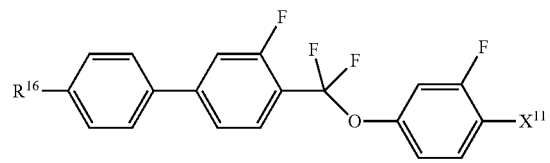
(13-94) 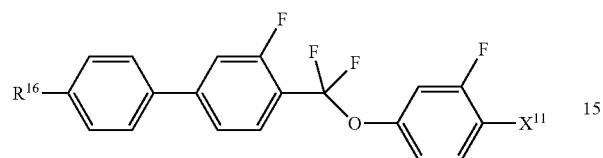
(13-95) 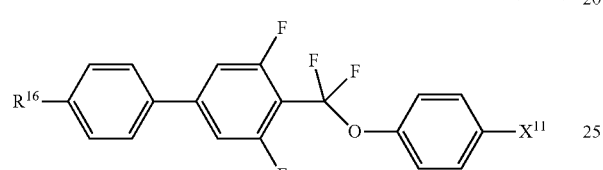
(13-96) 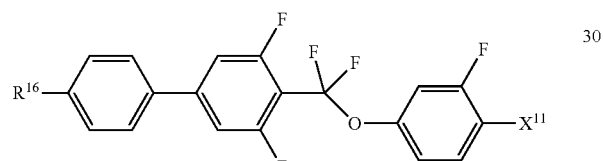
(13-97) 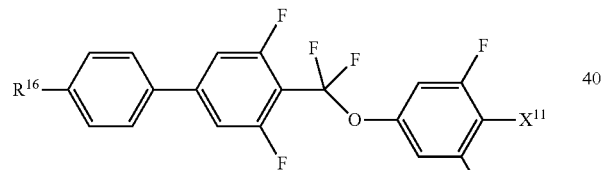
(13-98) 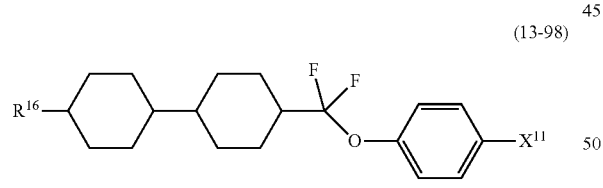
(13-99) 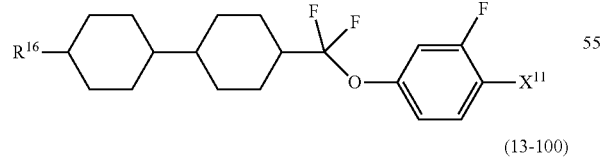
(13-100) 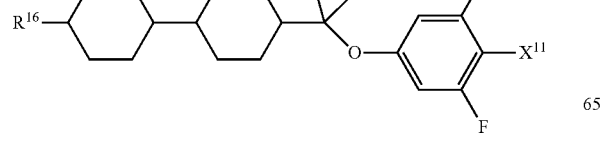
(13-101) 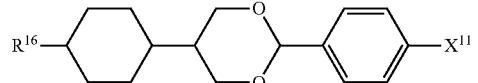
(13-102) 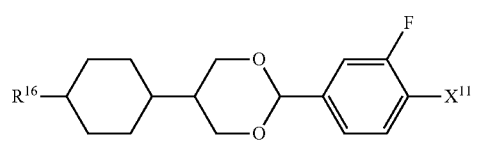
(13-103) 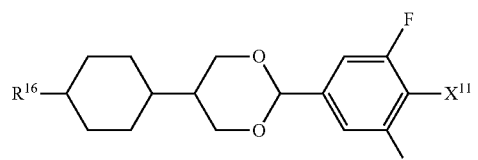
(13-104) 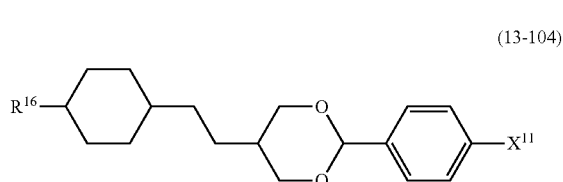
(13-105) 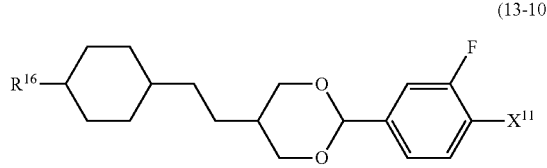
(13-106) 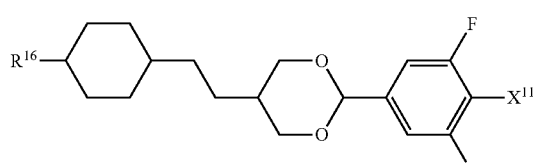
(13-107) 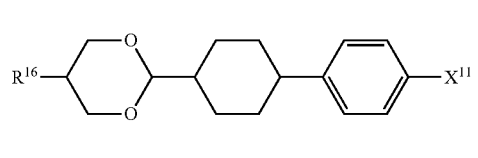
(13-108) 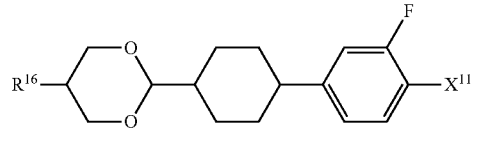
(13-109) 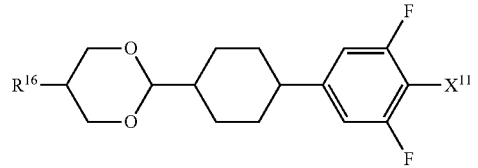

(13-110)
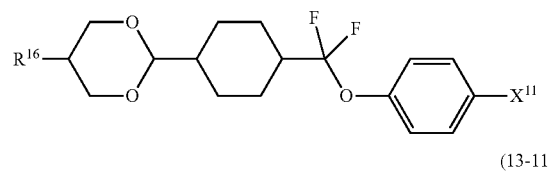
(13-111)
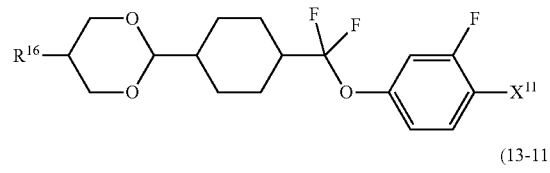
(13-112)
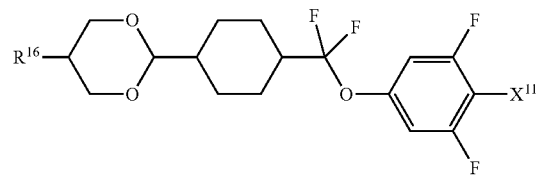
(13-113)
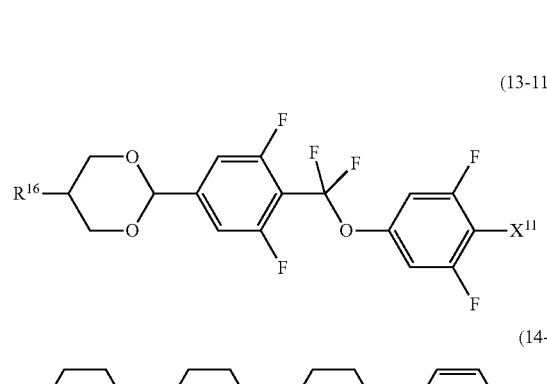
(14-1)
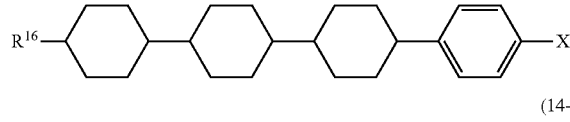
(14-2)
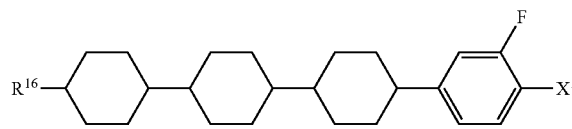
(14-3)
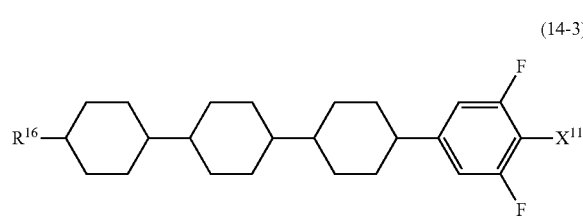
(14-4)
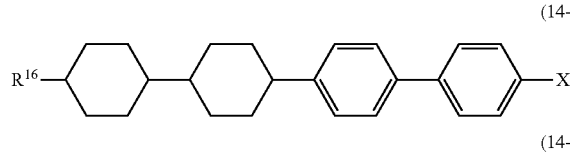
(14-5)
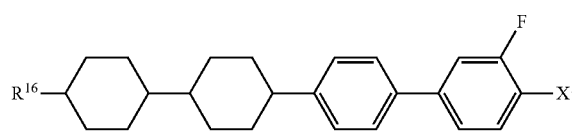
(14-6)
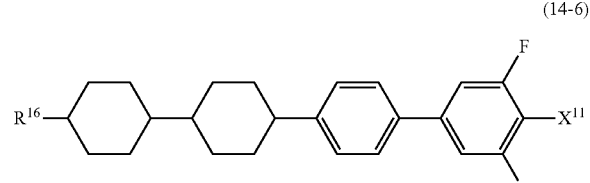
(14-7)
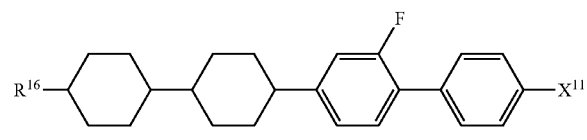
(14-8)
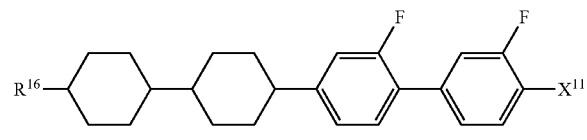
(14-9)
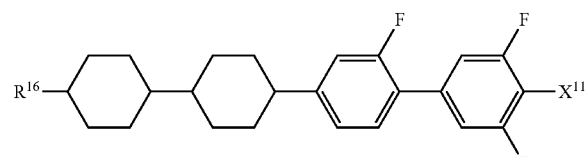
(14-10)
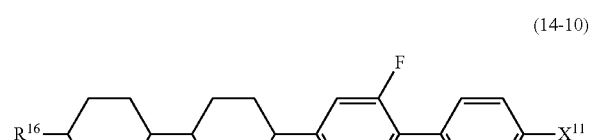
(14-11)
(14-12)
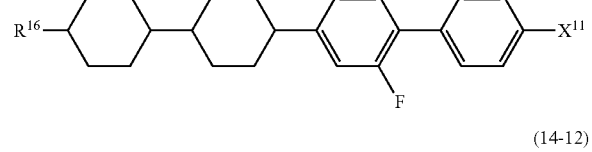
(14-13)
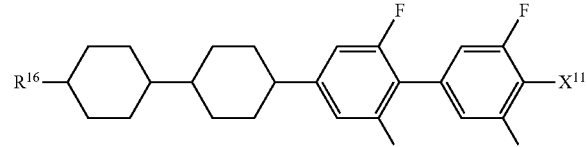
(14-14)
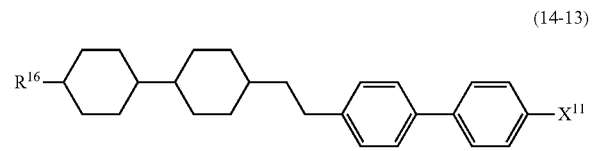

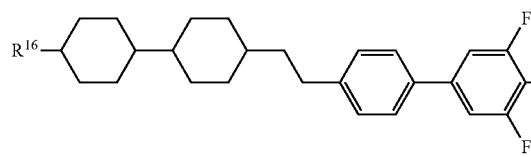
(14-15)
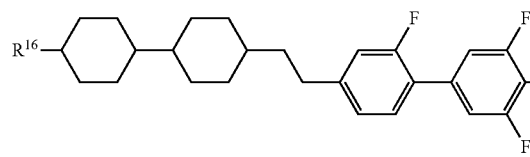
(14-16)
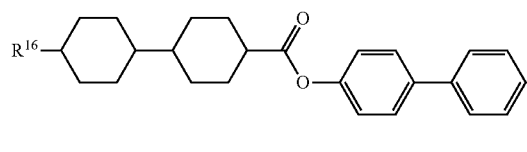
(14-17)
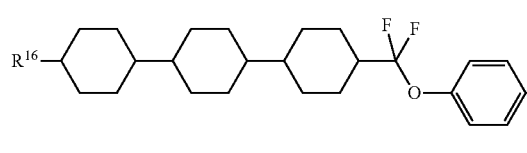
(14-18)
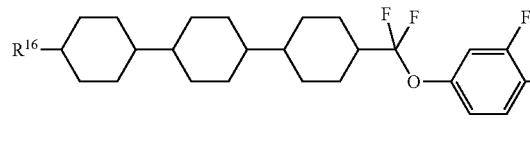
(14-19)
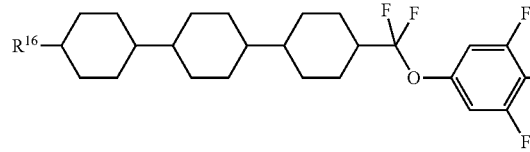
(14-20)
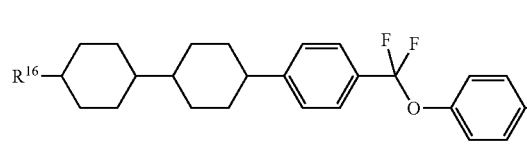
(14-21)
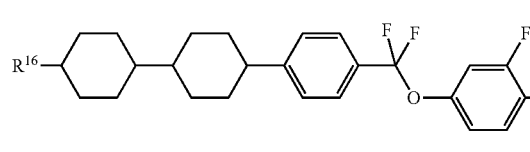
(14-22)
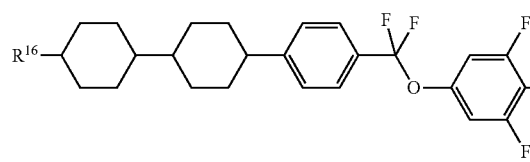
(14-23)
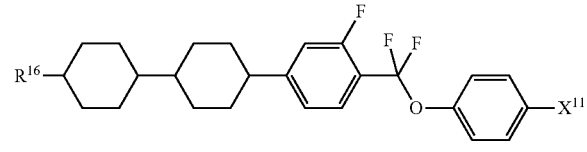
(14-24)
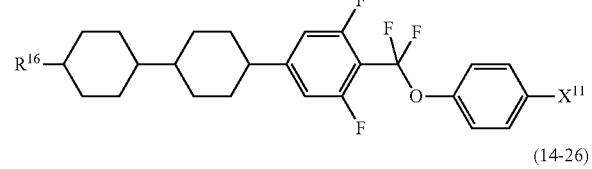
(14-25)
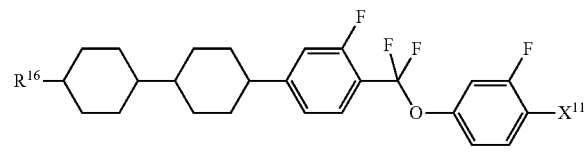
(14-26)
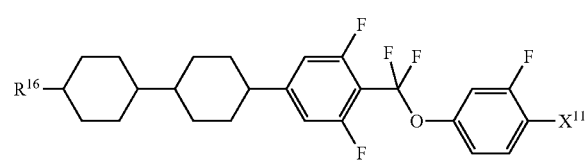
(14-27)
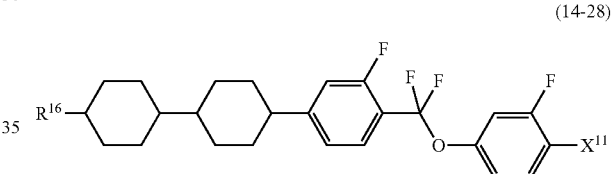
(14-28)
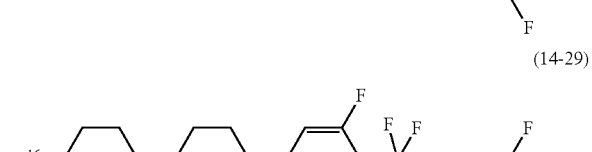
(14-29)
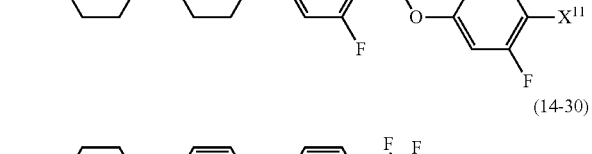
(14-30)
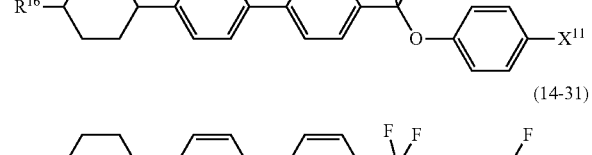
(14-31)
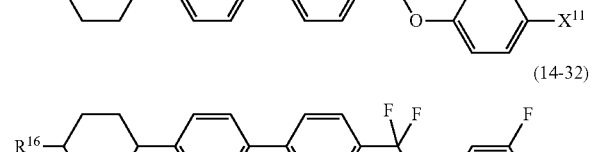
(14-32)

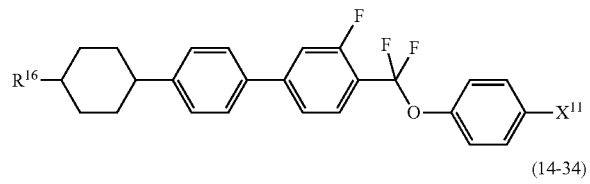
(14-33)
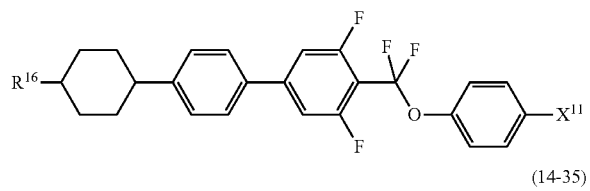
(14-34)
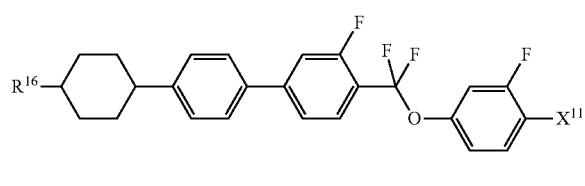
(14-35)
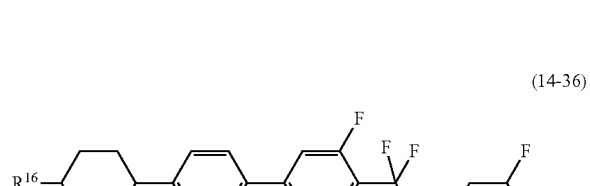
(14-36)
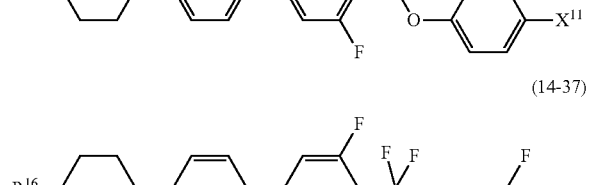
(14-37)
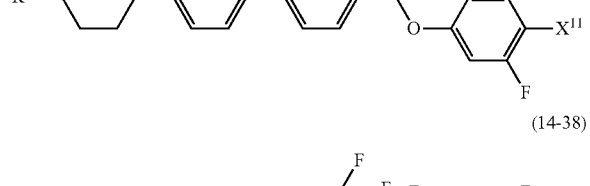
(14-38)
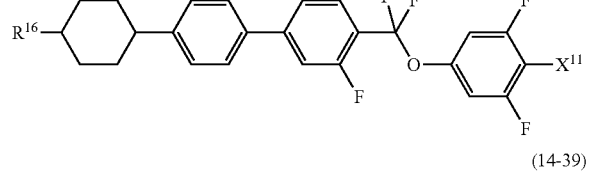
(14-39)
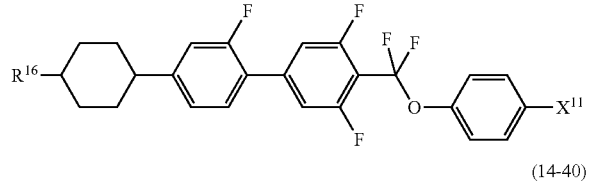
(14-40)
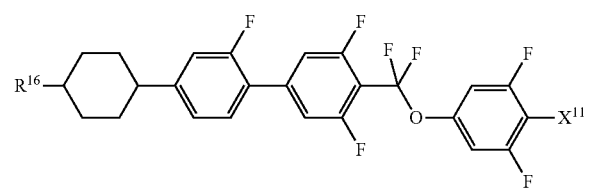
(14-41)
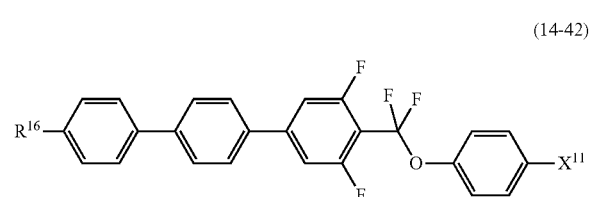
(14-42)
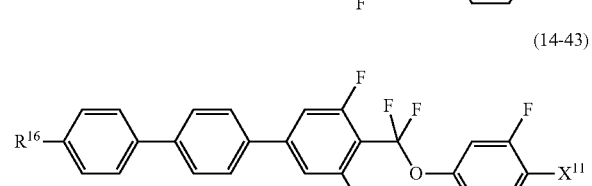
(14-43)
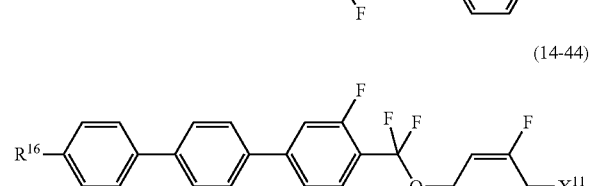
(14-44)
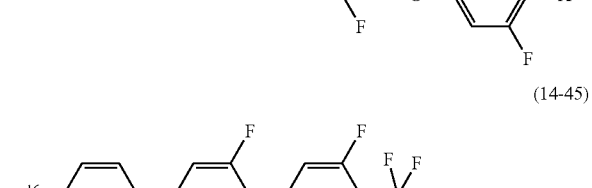
(14-45)
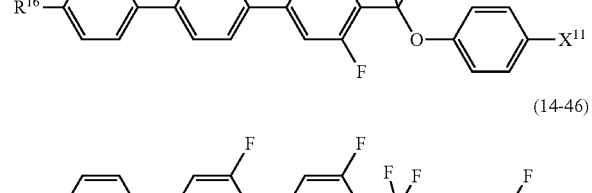
(14-46)
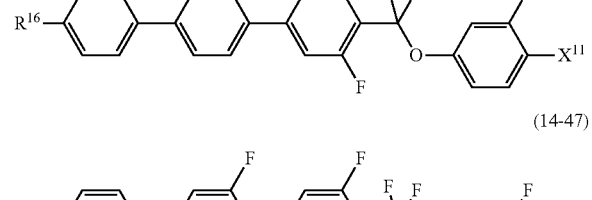
(14-47)
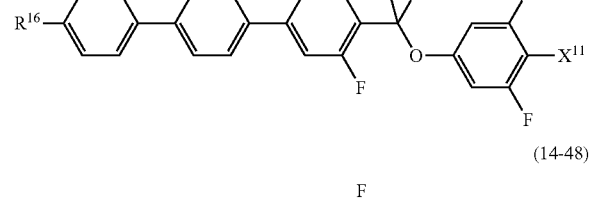
(14-48)

(14-49)
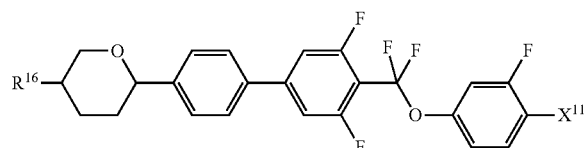

(14-50)
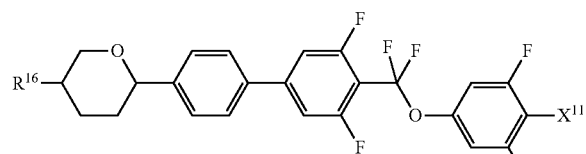

(14-51)
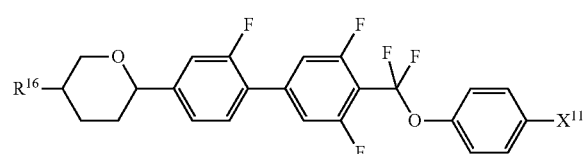

(14-52)
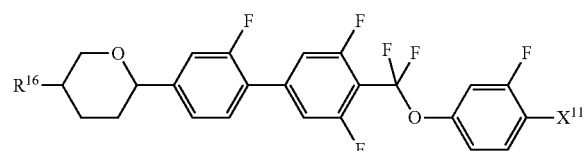

(14-53)
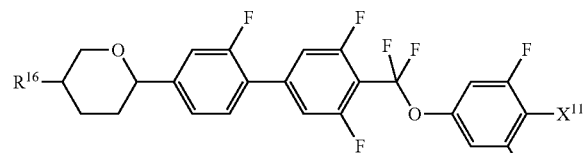

(14-54)
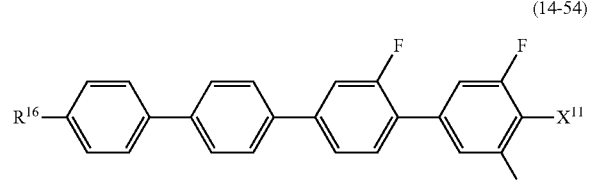

(14-55)
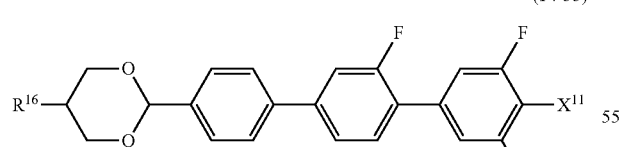

(14-56)
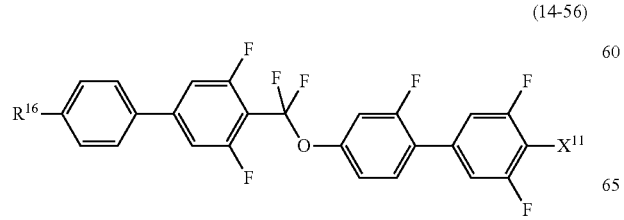

(14-57)
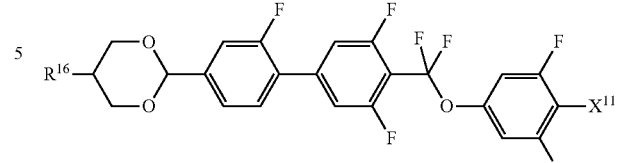

(14-58)
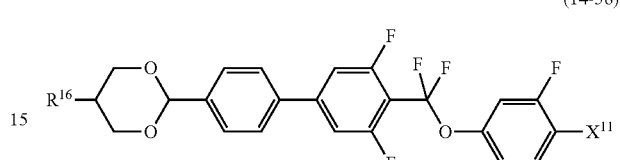

Component (d) has positive dielectric anisotropy, and significantly satisfactory stability to heat or light, and therefore is used when a composition for the IPS mode, the FFS mode, the OCB mode or the like is prepared. A content of component (d) is suitably in the range of about 1% by weight to about 99% by weight, preferably in the range of about 10% by weight to about 97% by weight, and further preferably in the range of about 40% by weight to about 95% by weight, based on the weight of the liquid crystal composition. When component (d) is added to the composition having negative dielectric anisotropy, the content of component (d) is preferably about 30% by weight or less. Addition of component (d) allows adjustment of the elastic constant of the composition and adjustment of the voltage-transmittance curve of the device.

Component (e) is compound (15) in which a right-terminal group is —C≡N or —C≡C—C≡N. Specific examples of preferred component (e) include compounds (15-1) to (15-64). In the compounds, $R^{17}$ is alkyl having 1 to 10 carbons or alkenyl having 2 to 10 carbons, and in the alkyl and the alkenyl, at least one piece of —CH$_2$— may be replaced by —O—, and in the groups, at least one hydrogen may be replaced by fluorine. $X^{12}$ is —C≡N or —C≡C—C≡N.

(15-1)
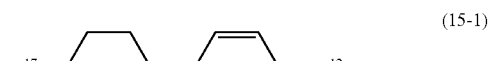

(15-2)
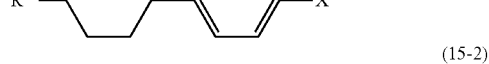

(15-3)
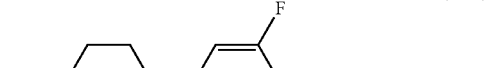

(15-4)
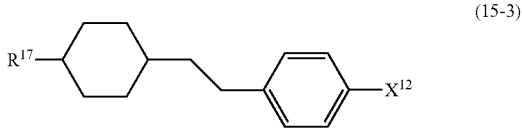

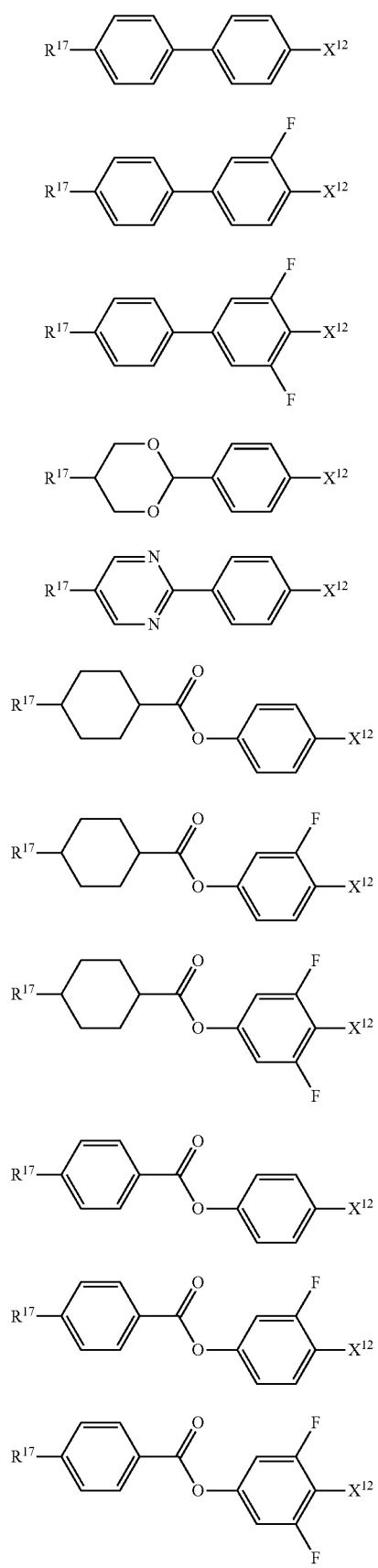
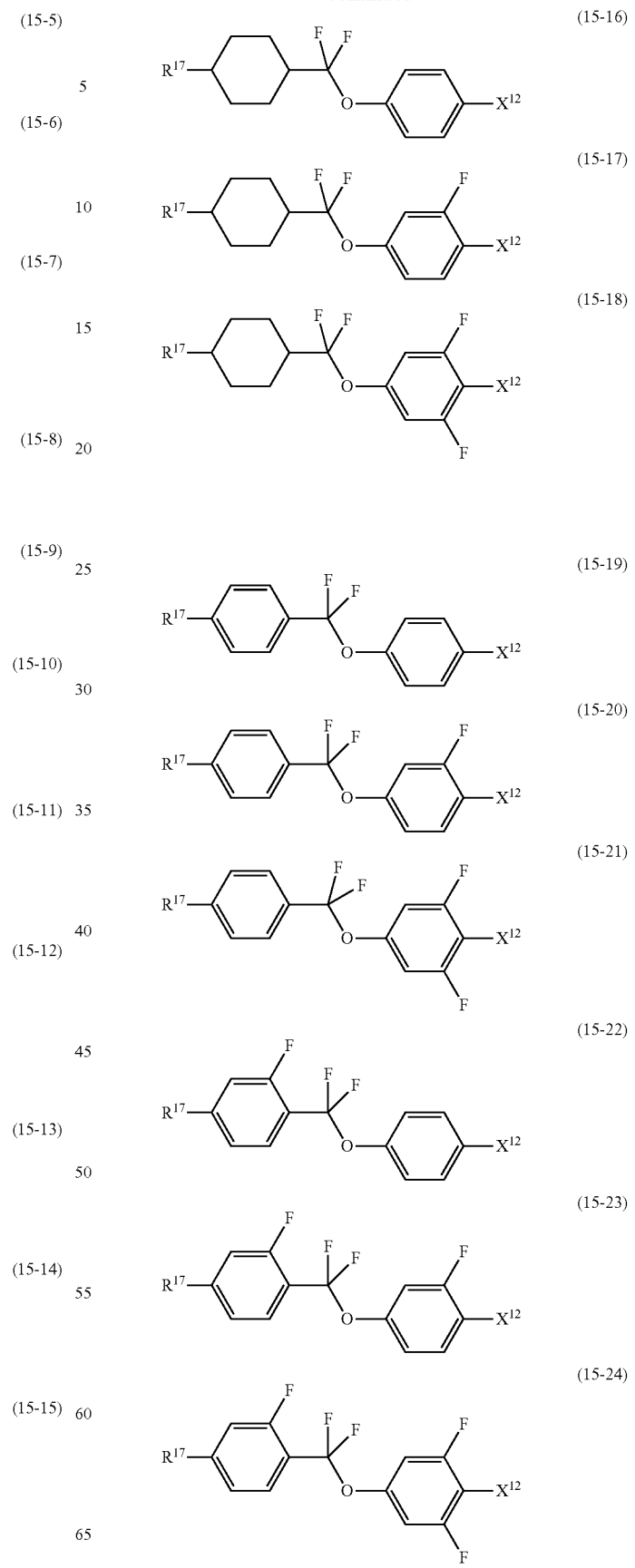

(15-25)
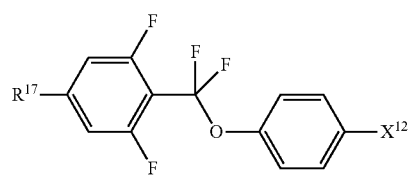
(15-26)
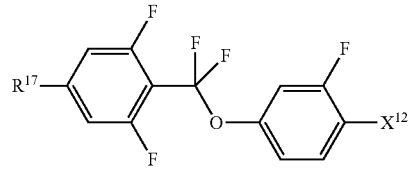
(15-27)
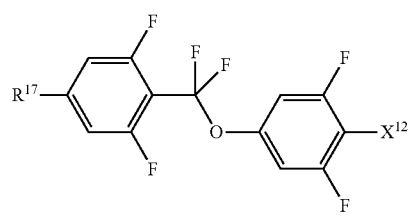
(15-28)
(15-29)
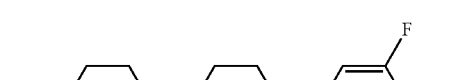
(15-30)
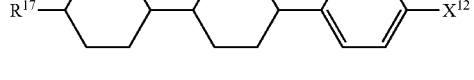
(15-31)
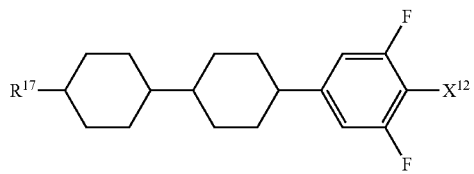
(15-32)
(15-33)
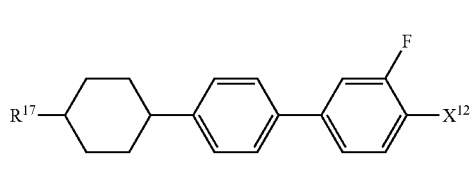
(15-34)
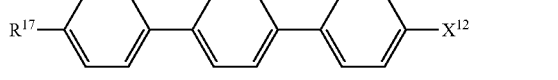
(15-35)
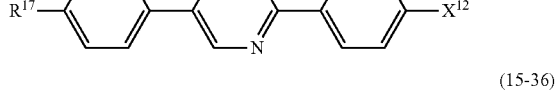
(15-36)
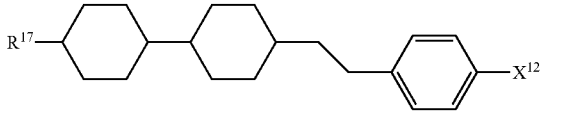
(15-37)
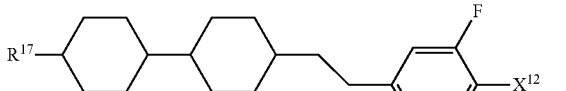
(15-38)
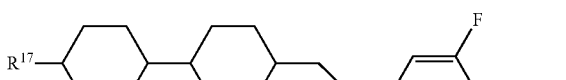
(15-39)
(15-40)
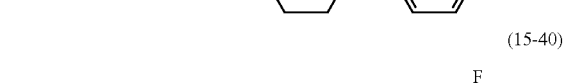
(15-41)
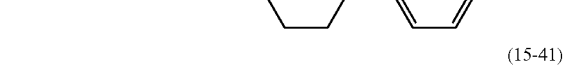
(15-42)
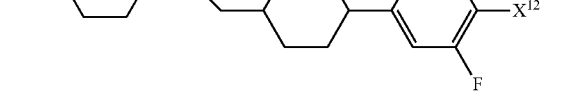
(15-43)
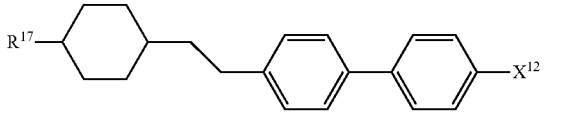
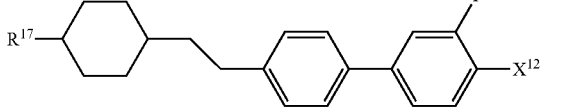

(15-44)
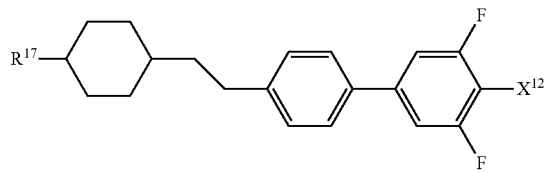
(15-45)
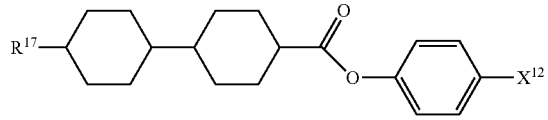
(15-46)
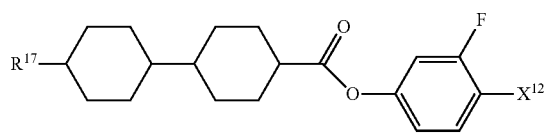
(15-47)
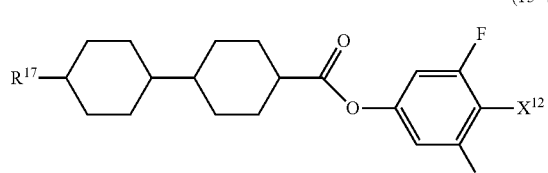
(15-48)
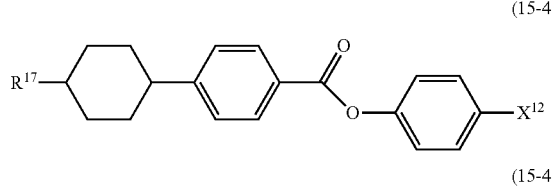
(15-49)
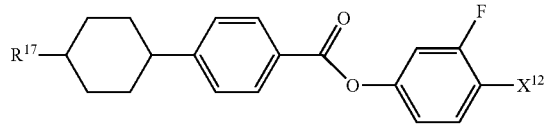
(15-50)
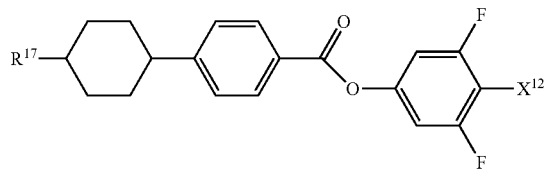
(15-51)
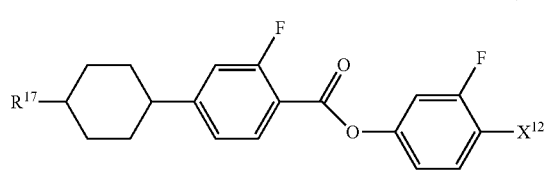
(15-52)
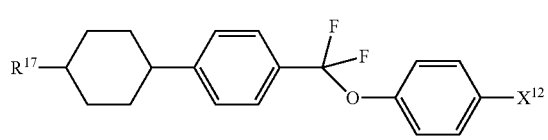
(15-53)
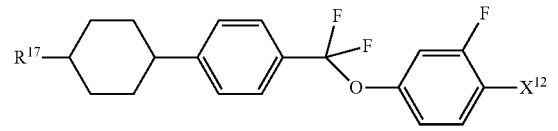
(15-54)
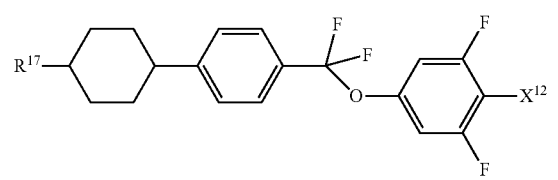
(15-55)
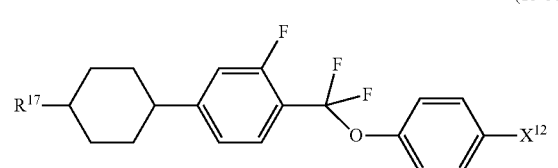
(15-56)
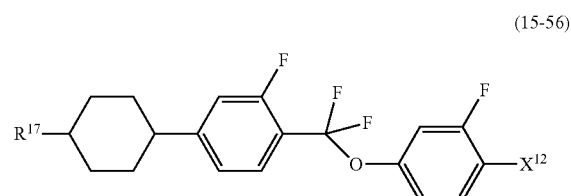
(15-57)
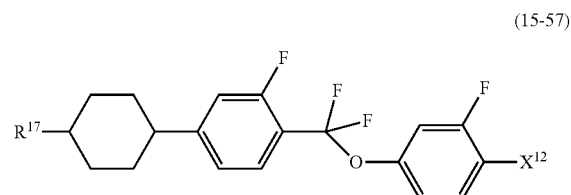
(15-58)
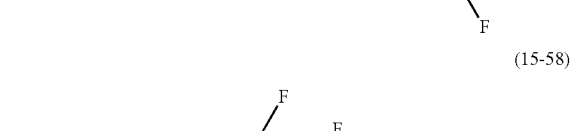
(15-59)
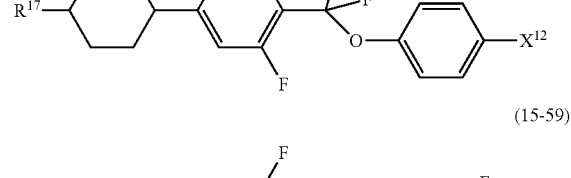
(15-60)
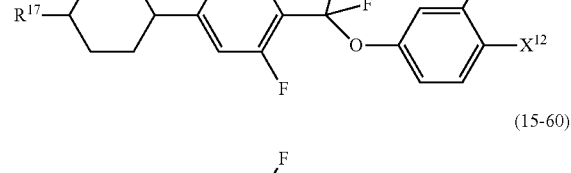

-continued

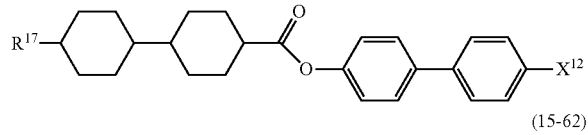
(15-61)

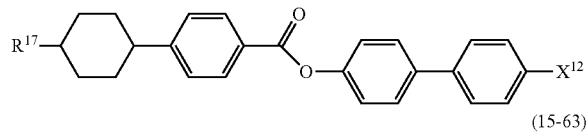
(15-62)

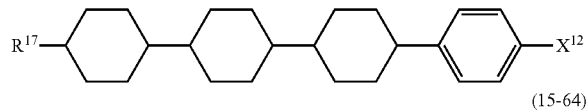
(15-63)

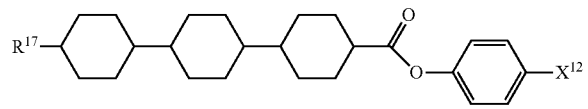
(15-64)

Component (e) has positive dielectric anisotropy and a value thereof is large, and therefore component (e) is used when a composition for the TN mode or the like is prepared. Addition of component (e) can increase the dielectric anisotropy of the composition. Component (e) is effective in extending the temperature range of the liquid crystal phase, adjusting the viscosity or adjusting the optical anisotropy. Component (e) is also useful for adjustment of the voltage-transmittance curve of the device.

When the composition for the TN mode or the like is prepared, a content of component (e) is suitably in the range of about 1% by weight to about 99% by weight, preferably in the range of about 10% by weight to about 97% by weight, and further preferably in the range of about 40% by weight to about 95% by weight, based on the weight of the liquid crystal composition. When component (e) is added to a composition having negative dielectric anisotropy, the content of component (e) is preferably about 30% by weight or less. Addition of component (e) allows adjustment of the elastic constant of the composition and adjustment of the voltage-transmittance curve of the device.

A liquid crystal composition satisfying at least one of physical properties such as high stability to heat or light, high maximum temperature, low minimum temperature, small viscosity, suitable optical anisotropy (more specifically, large optical anisotropy or small optical anisotropy), large positive or negative dielectric anisotropy, large specific resistance and a suitable elastic constant (more specifically, a large elastic constant or a small elastic constant) can be prepared by combining a compound suitably selected from components (b) to (e) described above with compound (1). A device including such a composition has a wide temperature range in which the device can be used, a short response time, a large voltage holding ratio, low threshold voltage, a large contrast ratio, a small flicker rate and a long service life.

If the device is used for a long period of time, a flicker may be occasionally generated on a display screen. The flicker rate (%) can be represented by a formula (luminance when applying positive voltage−luminance when applying negative voltage|/average luminance)×100. In a device having the flicker rate in the range of about 0% to about 1%, a flicker is hardly generated on the display screen even if the device is used for a long period of time. The flicker is associated with image persistence, and is presumed to be generated according to a difference in electric potential between a positive frame and a negative frame in driving at alternating current. The composition containing compound (1) is also useful for a decrease in generation of the flicker.

3-2. Additive

A liquid crystal composition is prepared according to a publicly known method. For example, the component compounds are mixed and dissolved in each other by heating. According to an application, an additive may be added to the composition. Specific examples of the additives include the polymerizable compound, the polymerization initiator, the polymerization inhibitor, the optically active compound, the antioxidant, the ultraviolet light absorber, the light stabilizer, the heat stabilizer, the dye and the antifoaming agent. Such additives are well known to those skilled in the art, and described in literature.

In a liquid crystal display device having the polymer sustained alignment (PSA) mode, the composition contains a polymer. The polymerizable compound is added for the purpose of forming the polymer in the composition. The polymerizable compound is polymerized by irradiation with ultraviolet light while voltage is applied between electrodes, and thus the polymer is formed in the composition. A suitable pretilt is achieved by the method, and therefore the device in which a response time is shortened and the image persistence is improved is prepared.

Preferred examples of the polymerizable compound include acrylate, methacrylate, a vinyl compound, a vinyloxy compound, propenyl ether, an epoxy compound (oxirane, oxetane) and vinyl ketone. Further preferred examples include a compound having at least one acryloyloxy, and a compound having at least one methacryloyloxy. Still further preferred examples also include a compound having both acryloyloxy and methacryloyloxy.

Still further preferred examples include compounds (M-1) to (M-18). In the compounds, $R^{25}$ to $R^{31}$ are independently hydrogen or methyl; $R^{32}$, $R^{33}$ and $R^{34}$ are independently hydrogen or alkyl having 1 to 5 carbons, and at least one of $R^{32}$, $R^{33}$ and $R^{34}$ is alkyl having 1 to 5 carbons; v, w and x are independently 0 or 1; and u and y are independently an integer from 1 to 10. $L^{21}$ to $L^{26}$ are independently hydrogen or fluorine; and $L^{27}$ and $L^{28}$ are independently hydrogen, fluorine or methyl.

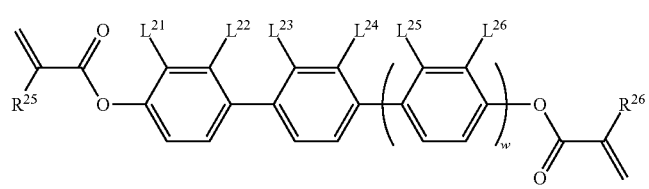
(M-1)

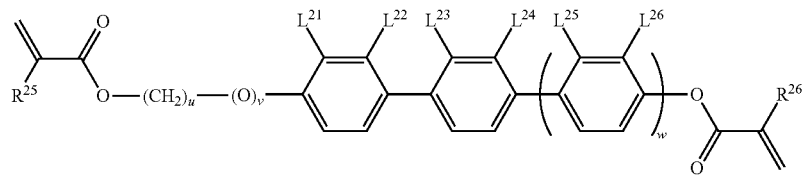
(M-2)
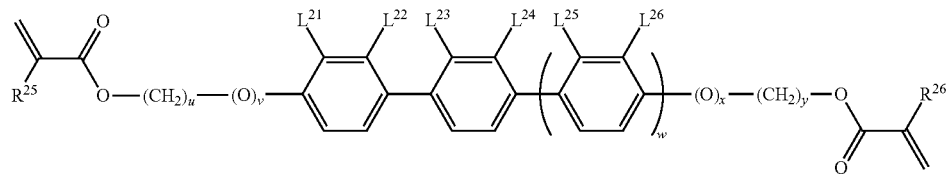
(M-3)
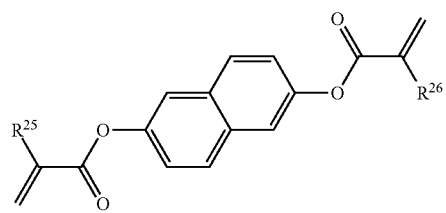
(M-4)
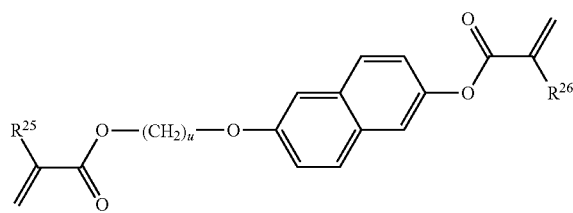
(M-5)
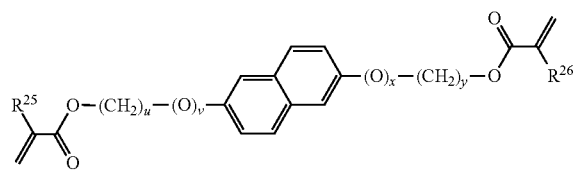
(M-6)
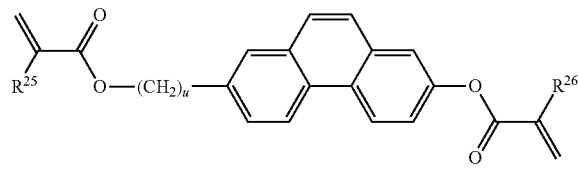
(M-7)
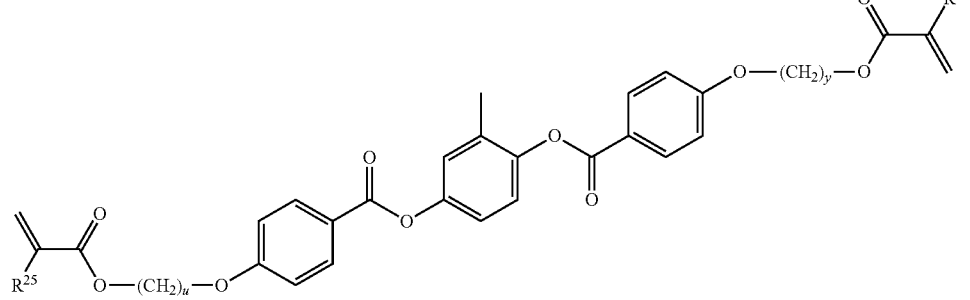
(M-9)
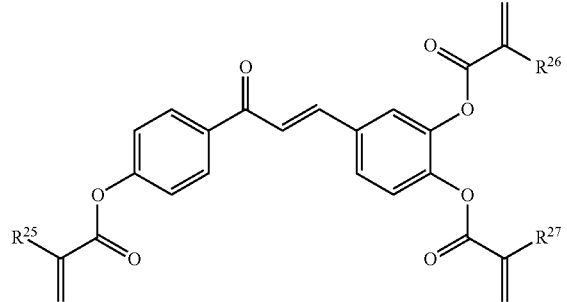
(M-10)

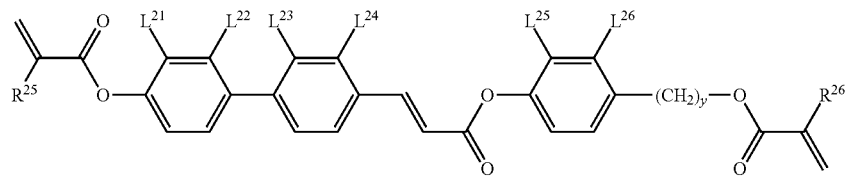
(M-11)
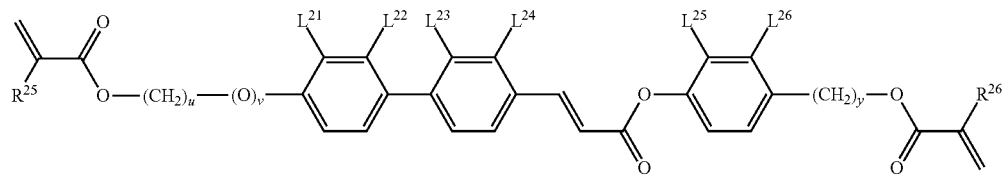
(M-12)
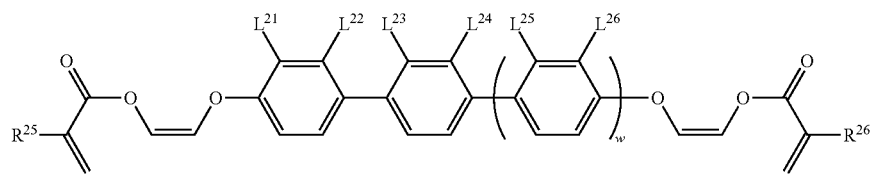
(M-13)
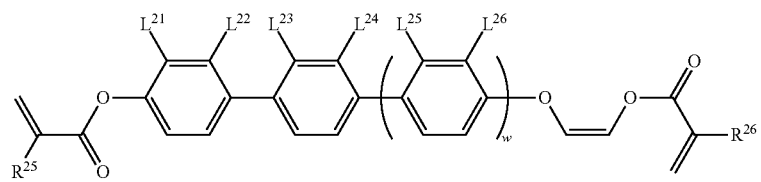
(M-14)
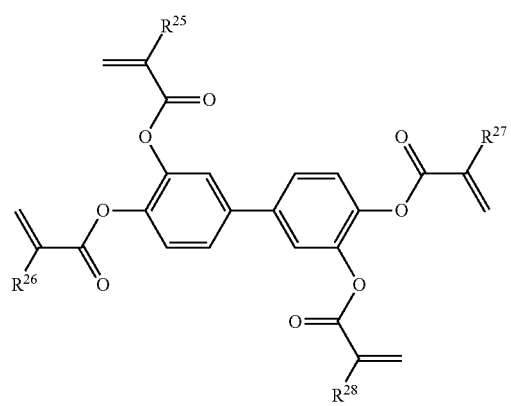
(M-15)
(M-16)
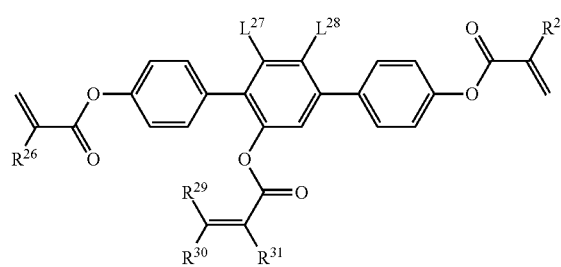
(M-17)
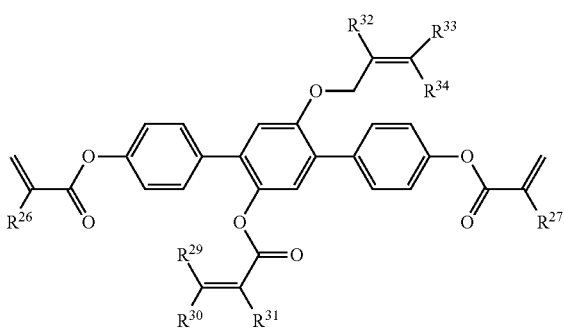
(M-18)

The polymerizable compound can be rapidly polymerized by adding the polymerization initiator. An amount of a remaining polymerizable compound can be reduced by optimizing reaction conditions. Examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series thereof.

Additional examples of the photoradical polymerization initiator include 4-methoxyphenyl-2,4-bis(trichloromethyl)triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a mixture of 2,4-diethylxanthone and methyl p-dimethylaminobenzoate, and a mixture of benzophenone and methyltriethanolamine.

After the photoradical polymerization initiator is added to the liquid crystal composition, polymerization can be performed by irradiation with ultraviolet light while an electric field is applied. However, an unreacted polymerization initiator or a decomposition product of the polymerization initiator may cause poor display such as image persistence in the device. In order to prevent such an event, photopolymerization may be performed with no addition of the polymerization initiator. A preferred wavelength of irradiation light is in the range of about 150 nanometers to about 500 nanometers. A further preferred wavelength is in the range of about 250 nanometers to about 450 nanometers, and a most preferred wavelength is in the range of about 300 nanometers to about 400 nanometers.

Upon storing the polymerizable compound, the polymerization inhibitor may be added thereto for preventing polymerization. The polymerizable compound is ordinarily added to the composition without removing the polymerization inhibitor. Examples of the polymerization inhibitor include hydroquinone, a hydroquinone derivative such as methylhydroquinone, 4-t-butylcatechol, 4-methoxyphenol and phenothiazine.

The optically active compound is effective in inducing helical structure in liquid crystal molecules to give a required twist angle, and thereby preventing a reverse twist. A helical pitch can be adjusted by adding the optically active compound thereto. Two or more optically active compounds may be added for the purpose of adjusting temperature dependence of the helical pitch. Specific examples of a preferred optically active compound include compounds (Op-1) to (Op-18) described below. In compound (Op-18), ring J is 1,4-cyclohexylene or 1,4-phenylene, and $R^{28}$ is alkyl having 1 to 10 carbons. Asterisk mark (*) represents asymmetrical carbon.

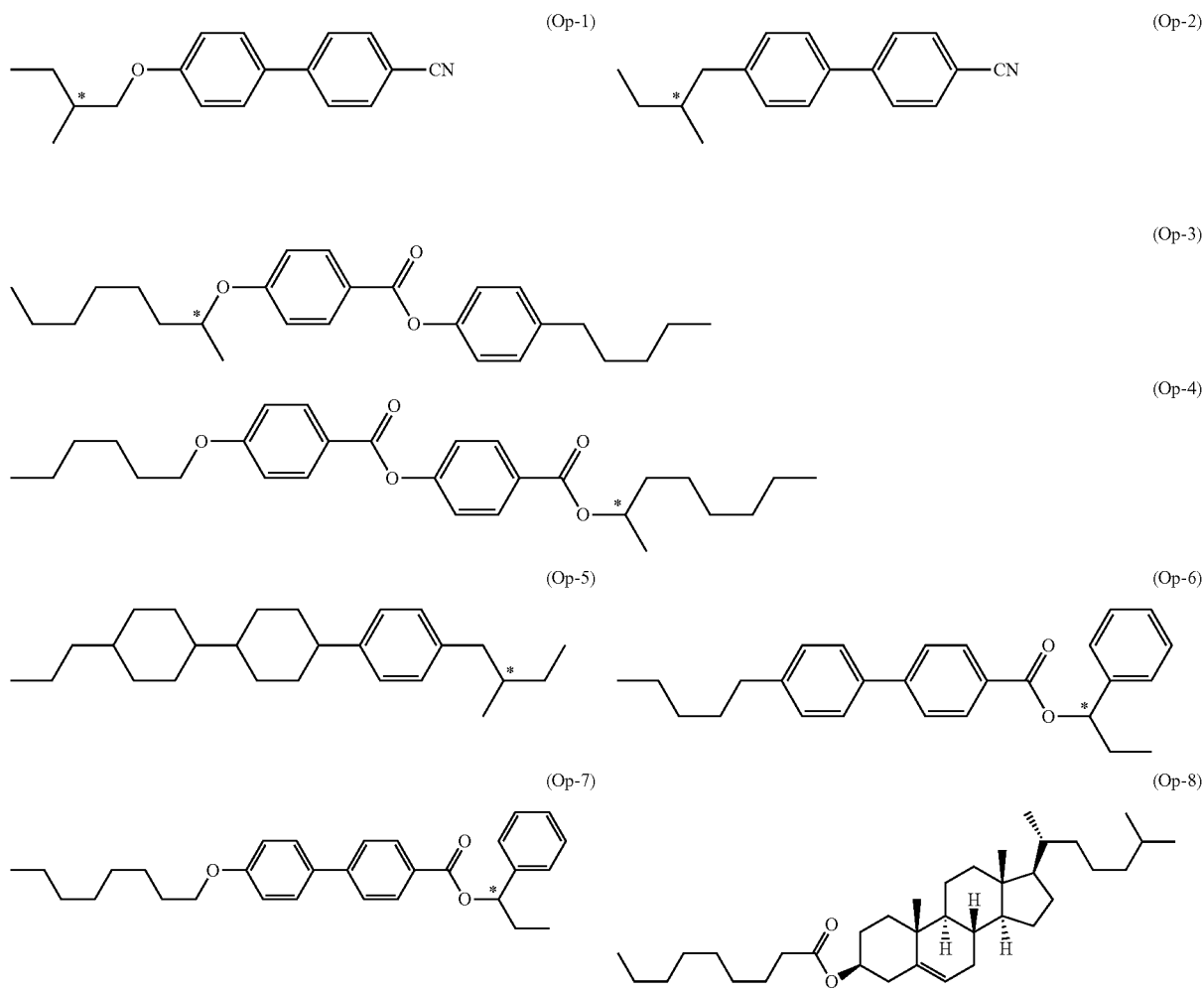

-continued
(Op-9)
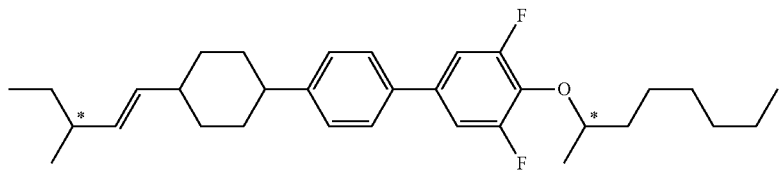
(Op-10)
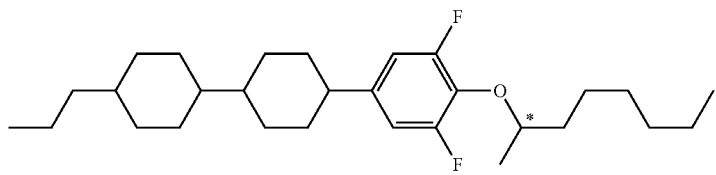
(Op-11)
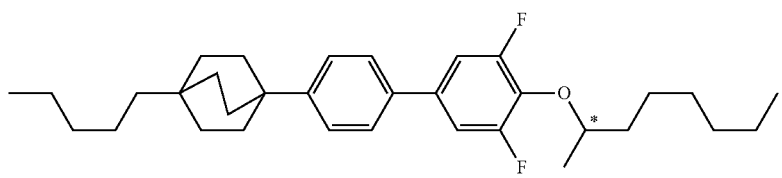
(Op-12)
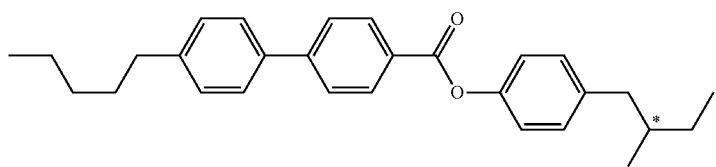
(Op-13)
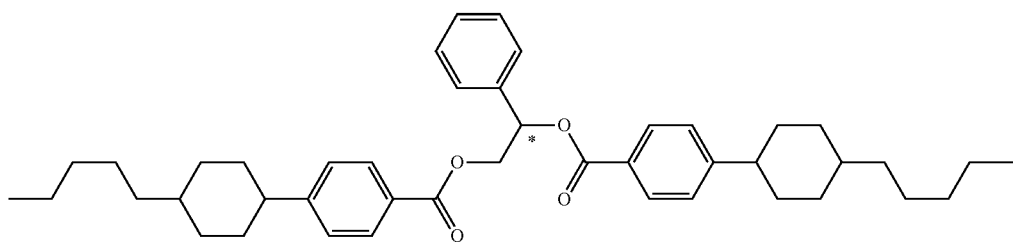
(Op-14)
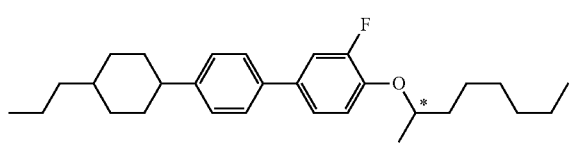
(Op-15)
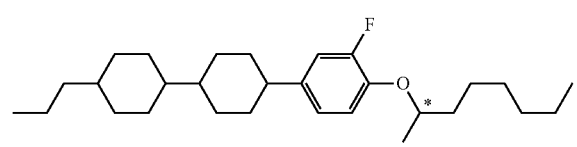
(Op-16)
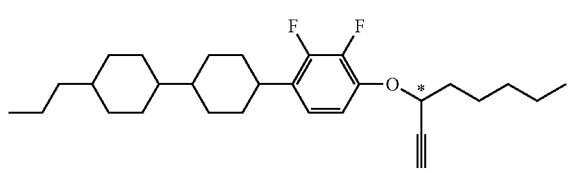
(Op-17)
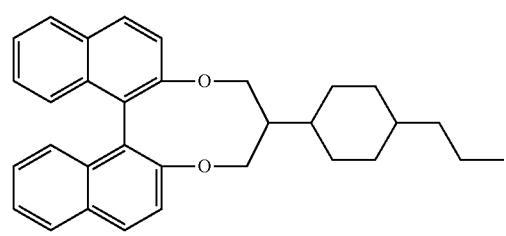

(Op-18)

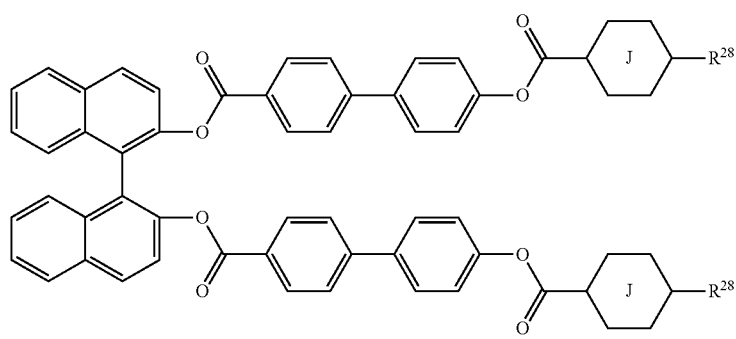

The antioxidant is effective for maintaining the large voltage holding ratio. Specific examples of a preferred antioxidant include compounds (AO-1) and (AO-2) described below; and Irganox 415, Irganox 565, Irganox 1010, Irganox 1035, Irganox 3114 and Irganox 1098 (trade names; BASF SE). The ultraviolet light absorber is effective for preventing a decrease of the maximum temperature. Preferred examples of the ultraviolet light absorber include a benzophenone derivative, a benzoate derivative and a triazole derivative, and specific examples include compounds (AO-3) and (AO-4) described below; Tinuvin 329, Tinuvin P, Tinuvin 326, Tinuvin 234, Tinuvin 213, Tinuvin 400, Tinuvin 328 and Tinuvin 99-2 (trade names; BASF SE); and 1,4-diazabicyclo[2.2.2]octane (DABCO).

The light stabilizer such as an amine having steric hindrance is preferred for maintaining the large voltage holding ratio. Specific examples of a preferred light stabilizer include compounds (AO-5), (AO-6) and (AO-7) described below; Tinuvin 144, Tinuvin 765 and Tinuvin 770DF (trade names; BASF SE); and LA-77Y and LA-77G (trade names; ADEKA Corporation). The heat stabilizer is also effective for maintaining the large voltage holding ratio, and specific preferred examples include Irgafos 168 (trade name; BASF SE). A dichroic dye such as an azo dye or an anthraquinone dye is added to the composition to be adapted for a device having a guest host (GH) mode. The antifoaming agent is effective for preventing foam formation. Preferred examples of the antifoaming agent include dimethyl silicone oil and methylphenyl silicone oil.

(AO-1)

(AO-2)

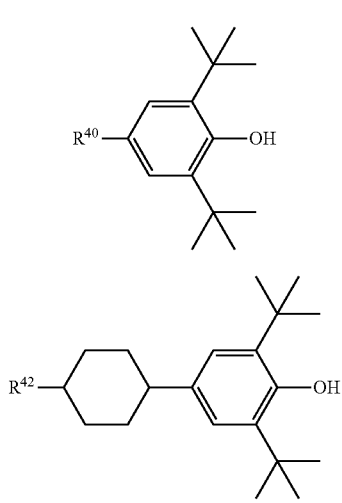

(AO-3)

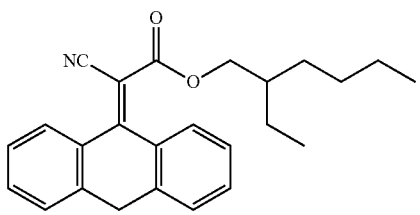

(AO-4)

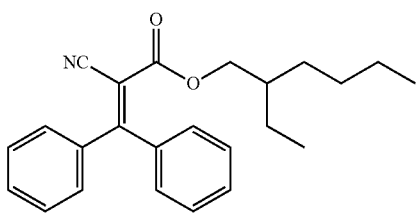

(AO-5)

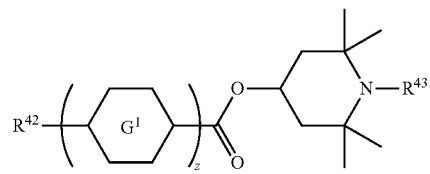

(AO-6)

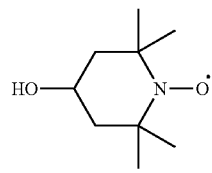

(AO-7)

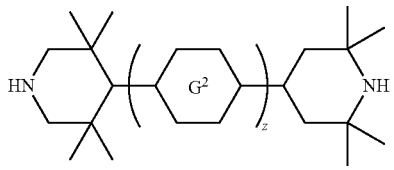

In compound (AO-1), $R^{40}$ is alkyl having 1 to 20 carbons, alkoxy having 1 to 20 carbons, —COOR$^{41}$ or —CH$_2$CH$_2$COOR$^{41}$, in which $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O. (oxygen radical); and ring $G^1$ is 1,4-cyclohexylene or 1,4-phenylene; in compound (AO-7), ring $G^2$ is 1,4-cyclohexylene, 1,4-phenylene, or 1,4-phenylene in which at least one hydrogen is replaced by fluorine; and in compounds (AO-5) and (AO-7), z is 1, 2 or 3.

4. Liquid Crystal Display Device

The liquid crystal composition can be used in a liquid crystal display device having an operating mode such as the PC mode, the TN mode, the STN mode, the OCB mode and the PSA mode, and driven by an active matrix mode. The composition can also be used in a liquid crystal display device having the operating mode such as the PC mode, the TN mode, the STN mode, the OCB mode, the VA mode and the IPS mode, and driven by a passive matrix mode. The devices can be applied to any of a reflective type, a transmissive type and a transflective type.

The composition is also suitable for a nematic curvilinear aligned phase (NCAP) device, and the composition is microencapsulated herein. The composition can also be used in a polymer dispersed liquid crystal display device (PDLCD) or a polymer network liquid crystal display device (PNLCD). In the compositions, a large amount of polymerizable compound is added. On the other hand, when a proportion of the polymerizable compound is about 10% by weight or less based on the weight of the liquid crystal composition, the liquid crystal display device having the PSA mode is prepared. A preferred proportion is in the range of about 0.1% by weight to about 2% by weight based thereon. A further preferred proportion is in the range of about 0.2% by weight to about 1.0% by weight based thereon. The device having the PSA mode can be driven by the driving mode such as the active matrix mode and the passive matrix mode. Such devices can be applied to any of the reflective type, the transmissive type and the transflective type.

EXAMPLES

1. Example of Compound (1)

The invention will be described in greater detail by way of Examples. The Examples include a typical example, and therefore the invention is not limited by the Examples. Compound (1) was prepared according to procedures described below. The thus prepared compound was identified by methods such as an NMR analysis. Physical properties of the compound and the composition, and characteristics of a device were measured by methods described below.

NMR analysis: For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, $CFCl_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Gas chromatographic analysis: For measurement, GC-2010 Gas Chromatograph made by Shimadzu Corporation was used. As a column, a capillary column DB-1 (length 60 m, bore 0.25 mm, film thickness 0.25 μm) made by Agilent Technologies, Inc. was used. As a carrier gas, helium (1 mL/minute) was used. A temperature of a sample vaporizing chamber and a temperature of a detector (FID) were set to 300° C. and 300° C., respectively. A sample was dissolved in acetone and prepared to be a 1 weight % solution, and then 1 microliter of the solution obtained was injected into the sample vaporizing chamber. As a recorder, GC Solution System made by Shimadzu Corporation or the like was used.

Gas chromatography mass analysis: For measurement, QP-2010 Ultra Gas Chromatograph Mass Spectrometer made by Shimadzu Corporation was used. As a column, a capillary column DB-1 (length 60 m, bore 0.25 mm, film thickness 0.25 μm) made by Agilent Technologies, Inc. was used. As a carrier gas, helium (1 mL/minute) was used. A temperature of a sample vaporizing chamber, a temperature of an ion source, ionizing voltage and emission current were set to 300° C., 200° C., 70 eV and 150 uA, respectively. A sample was dissolved in acetone and prepared to be a 1 weight % solution, and then 1 microliter of the solution obtained was injected into the sample vaporizing chamber. As a recorder, GCMS solution system made by Shimadzu Corporation was used.

HPLC Analysis: For measurement, Prominence (LC-20AD; SPD-20A) made by Shimadzu Corporation was used. As a column, YMC-Pack ODS-A (length 150 mm, bore 4.6 mm, particle diameter 5 μm) made by YMC Co., Ltd. was used. As an eluate, acetonitrile and water were appropriately mixed and used. As a detector, a UV detector, an RI detector, a CORONA detector or the like was appropriately used. When the UV detector was used, a detection wavelength was set to 254 nanometers. A sample was dissolved in acetonitrile and prepared to be a 0.1 weight % solution, and then 1 microliter of the solution was introduced into a sample chamber. As a recorder, C-R7Aplus made by Shimadzu Corporation was used.

Ultraviolet-Visible spectrophotometry: For measurement, PharmaSpec UV-1700 made by Shimadzu Corporation was used. A detection wavelength was adjusted in the range of 190 nanometers to 700 nanometers. A sample was dissolved in acetonitrile and prepared to be a 0.01 mmol/L solution, and measurement was carried out by putting the solution in a quartz cell (optical path length: 1 cm).

Sample for measurement: Upon measuring phase structure and a transition temperature (a clearing point, a melting point, a polymerization starting temperature or the like), the compound itself was used as a sample. Upon measuring physical properties such as maximum temperature of a nematic phase, viscosity, optical anisotropy and dielectric anisotropy, a mixture of the compound and a base liquid crystal was used as a sample.

When the sample prepared by mixing the compound with the base liquid crystal was used, measurement was carried out as described below. The sample was prepared by mixing 15% by weight of the compound and 85% by weight of the base liquid crystal. From a measured value of the sample, an extrapolated value was calculated according to the following equation, and the calculated value was described: [extrapolated value]=(100×[measured value of a sample]−[% by weight of a base liquid crystal]×[measured value of the base liquid crystal])/[% by weight of a compound].

When crystals (or a smectic phase) precipitated at 25° C. at the ratio, a ratio of the compound to the base liquid crystal was changed in the order of (10% by weight:90% by weight), (5% by weight:95% by weight), and (1% by weight:99% by weight), and the physical properties of the sample were measured at a ratio at which no crystal (or no smectic phase) precipitated at 25° C. In addition, unless otherwise noted, the ratio of the compound to the base liquid crystal was (15% by weight:85% by weight)

When the dielectric anisotropy of the compound was zero or positive, base liquid crystal (A) described below was used. A proportion of each component was expressed in terms of weight percent (% by weight).

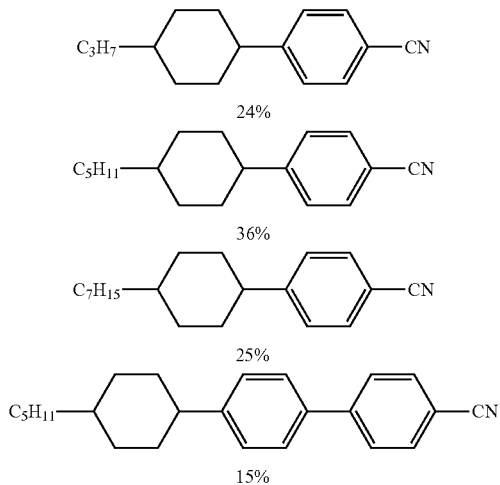

When the dielectric anisotropy of the compound was zero or negative, base liquid crystal (B) described below was used. A proportion of each component was expressed in terms of weight percent (% by weight).

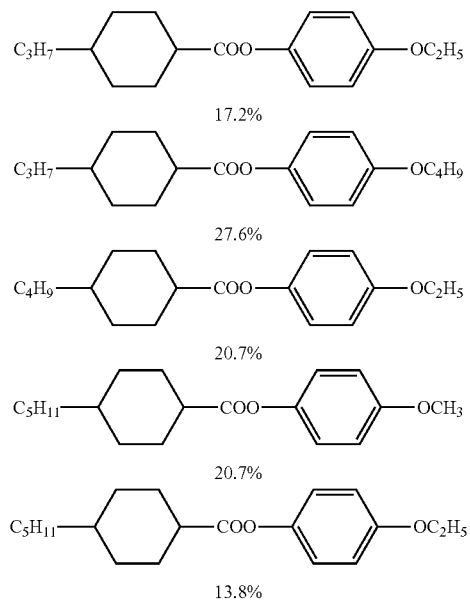

Measuring method: Physical properties were measured according to methods described below. Most of the methods are described in the Standard of Japan Electronics and Information Technology Industries Association (JEITA) discussed and established in JEITA (JEITA ED-2521B). A modification of the methods were also used. No thin film transistor (TFT) was attached to a TN device used for measurement.

(1) Phase structure: A sample was placed on a hot plate in a melting point apparatus (FP-52 Hot Stage made by Mettler-Toledo International Inc.) equipped with a polarizing microscope. A state of phase and a change thereof were observed with the polarizing microscope while the sample was heated at a rate of 3° C. per minute, and a kind of the phase was specified.

(2) Transition temperature (° C.): For measurement, a differential scanning calorimeter, Diamond DSC System, made by PerkinElmer, Inc., or a high sensitivity differential scanning calorimeter, X-DSC7000, made by SII NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. A melting point and a polymerization starting temperature of a compound were also measured using the apparatus. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to liquid may be occasionally abbreviated as "clearing point."

A crystal was expressed as C. When the crystals were distinguishable into two kinds, each of the crystals was expressed as $C_1$ or $C_2$. The smectic phase or the nematic phase was expressed as S or N. When a phase was distinguishable such as smectic A phase, smectic B phase, smectic C phase and smectic F, the phase was expressed as $S_A$, $S_B$, $S_C$ and $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Compatibility of compound: Samples in which the base liquid crystal and the compound were mixed for proportions of the compounds to be 20% by weight, 15% by weight, 10% by weight, 5% by weight, 3% by weight or 1% by weight were prepared. The samples were put in a glass vials, and kept in freezers at −10° C. or −20° C. for a predetermined period of time. Whether a nematic phase of the samples was maintained or crystals (or a smectic phase) precipitated was observed. Conditions on which the nematic phase was maintained were used as a measure of the compatibility. Proportions of the compounds and each temperature in the freezers may be occasionally changed when necessary.

(4) Maximum temperature of nematic phase ($T_{NI}$ or NI; ° C.): A sample was placed on a hot plate in a melting point apparatus equipped with a polarizing microscope, and heated at a rate of 1° C. per minute. Temperature when part of the sample began to change from a nematic phase to an isotropic liquid was measured. When the sample was a mixture of compound (1) and the base liquid crystal, the maximum temperature was expressed in terms of a symbol $T_{NI}$. When the sample was a mixture of compound (1) and a compound selected from compounds (2) to (15), the maximum temperature was expressed in terms of a symbol NI. A maximum temperature of the nematic phase may be occasionally abbreviated as "maximum temperature."

(5) Minimum temperature of nematic phase ($T_C$; ° C.): Samples each having a nematic phase were put in glass vials and kept in freezers at temperatures of 0° C., −10° C., −20° C., −30° C. and −40° C. for 10 days, and then liquid crystal phases were observed. For example, when the sample was maintained in the nematic phase at −20° C. and changed to crystals or a smectic phase at −30° C., $T_C$ was expressed as $T_C$<−20° C. A minimum temperature of the nematic phase may be occasionally abbreviated as "minimum temperature."

(6) Viscosity (bulk viscosity; η; measured at 20° C.; mPa·s): For measurement, a cone-plate (E type) rotational viscometer made by Tokyo Keiki Inc. was used.

(7) Optical anisotropy (refractive index anisotropy; measured at 25° C.; Δn): Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when the direction of polarized light was perpendicular to the direction of rubbing. A value of optical anisotropy (Δn) was calculated from an equation: Δn=n∥−n⊥.

(8) Specific resistance (ρ; measured at 25° C.; Ωcm): Into a vessel equipped with electrodes, 1.0 milliliter of sample was injected. A direct current voltage (10 V) was applied to the vessel, and a direct current after 10 seconds was measured. Specific resistance was calculated from the following equation:

(specific resistance)={(voltage)×(electric capacity of a vessel)}/{(direct current)×(dielectric constant of vacuum)}.

(9) Voltage holding ratio (VHR-1; measured at 25° C.; %): A TN device used for measurement had a polyimide alignment film, and a distance (cell gap) between two glass substrates was 5 micrometers. A sample was put in the device, and then the device was sealed with an ultraviolet-curable adhesive. The device was charged by applying a pulse voltage (60 microseconds at 5 V). A decaying voltage was measured for 16.7 milliseconds with a high-speed voltmeter, and area A between a voltage curve and a horizontal axis in a unit cycle was determined. Area B is an area without decay. A voltage holding ratio is expressed in terms of a percentage of area A to area B.

(10) Voltage holding ratio (VHR-2; measured at 80° C.; %): A voltage holding ratio was measured according to the method described above except that the voltage holding ratio was measured at 80° C. in place of 25° C. The results obtained were expressed in terms of a symbol VHR-2.

(11) Flicker rate (measured at 25° C.; %): For measurement, 3298F Multimedia Display Tester made by Yokogawa Electric Corporation was used. A light source was LED. A sample was put in a normally black mode FFS device in which a distance (cell gap) between two glass substrates was 3.5 micrometers, and a rubbing direction was anti-parallel. The device was sealed with an ultraviolet-curable adhesive. Voltage was applied to the device, and a voltage having a maximum amount of light transmitted through the device was measured. A sensor part was brought close to the device while the voltage was applied, and a flicker rate displayed thereon was read.

The measuring method of the physical properties may be different between a sample having positive dielectric anisotropy and a sample having negative dielectric anisotropy. When the dielectric anisotropy was positive, the measuring method was described in measurement (12a) to measurement (16a). When the dielectric anisotropy was negative, the measuring method was described in measurement (12b) to measurement (16b).

(12a) Viscosity (rotational viscosity; γ1; measured at 25° C.; mPa·s; for a sample having positive dielectric anisotropy): Measurement was carried out according to a method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device from 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and equation (8) on page 40 of the paper presented by M. Imai et al. A value of dielectric anisotropy required for the calculation was determined using the device by which the rotational viscosity was measured and by a method described below.

(12b) Viscosity (rotational viscosity; γ1; measured at 25° C.; mPa·s; for a sample having negative dielectric anisotropy): Measurement was carried out according to the method described in M. Imai et al., Molecular Crystals and Liquid Crystals, Vol. 259, p. 37 (1995). A sample was put in a VA device in which a distance (cell gap) between two glass substrates was 20 micrometers. Voltage was applied stepwise to the device from 39 V to 50 V at an increment of 1 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and equation (8) on page 40 of the paper presented by M. Imai et al. Dielectric anisotropy required for the calculation was measured in a section of dielectric anisotropy described below.

(13a) Dielectric anisotropy (Δε; measured at 25° C.; for a sample having positive dielectric anisotropy): A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (ε∥) of liquid crystal molecules in a major axis direction was measured. Sine waves (0.5 V, 1 kHz) were applied to the device, and after 2 seconds, a dielectric constant (ε⊥) of liquid crystal molecules in a minor axis direction was measured. A value of dielectric anisotropy was calculated from an equation: Δε=ε∥−ε⊥.

(13b) Dielectric anisotropy (Δε; measured at 25° C.; for a sample having negative dielectric anisotropy): A value of dielectric anisotropy was calculated from the equation: Δε=ε∥−ε⊥. A dielectric constant (εv and ε⊥) was measured as described below.

(1) Measurement of dielectric constant (ε∥): An ethanol (20 mL) solution of octadecyltriethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (ε∥) of liquid crystal molecules in a major axis direction was measured.

(2) Measurement of dielectric constant (ε⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant ($\varepsilon\perp$) of liquid crystal molecules in a minor axis direction was measured.

(14a) Elastic constant (K; measured at 25° C.; pN; for a sample having positive dielectric anisotropy): For measurement, HP4284A LCR Meter made by Yokogawa-Hewlett-Packard Co. was used. A sample was put in a horizontal alignment device in which a distance (cell gap) between two glass substrates was 20 micrometers. An electric charge from 0 V to 20 V was applied to the device, and electrostatic capacity (C) and applied voltage (V) were measured. The measured values were fitted to equation (2.98) and equation (2.101) on page 75 of "Liquid Crystal Device Handbook (Ekisho Debaisu Handobukku in Japanese; Nikkan Kogyo Shimbun, Ltd.)," and values of $K_{11}$ and $K_{33}$ were obtained from equation (2.99). Next, $K_{22}$ was calculated using the previously determined values of $K_{11}$ and $K_{33}$ in equation (3.18) on page 171. Elastic constant K was expressed in terms of a mean value of the thus determined $K_{11}$, $K_{22}$ and $K_{33}$.

(14b) Elastic constant ($K_{11}$ and $K_{33}$; measured at 25° C.; pN; for a sample having negative dielectric anisotropy): For measurement, Elastic Constant Measurement System Model EC-1 made by TOYO Corporation was used. A sample was put in a vertical alignment device in which a distance (cell gap) between two glass substrates was 20 micrometers. An electric charge from 20 V to 0 V was applied to the device, and electrostatic capacity (C) and applied voltage (V) were measured. The measured values were fitted to equation (2.98) and equation (2.101) on page 75 of "Liquid Crystal Device Handbook (Ekisho Debaisu Handobukku in Japanese; Nikkan Kogyo Shimbun, Ltd.)," and values of elastic constants were obtained from equation (2.100).

(15a) Threshold voltage (Vth; measured at 25° C.; V; for a sample having positive dielectric anisotropy): For measurement, an LCD-5100 luminance meter made by Otsuka Electronics Co., Ltd. was used. A light source was a halogen lamp. A sample was put in a normally white mode TN device in which a distance (cell gap) between two glass substrates was 0.45/$\Delta$n ($\mu$m) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of voltage at 90% transmittance.

(15b) Threshold voltage (Vth; measured at 25° C.; V; for a sample having negative dielectric anisotropy): For measurement, an LCD-5100 luminance meter made by Otsuka Electronics Co., Ltd. was used. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of voltage at 10% transmittance.

(16a) Response time ($\tau$; measured at 25° C.; ms; for a sample having positive dielectric anisotropy): For measurement, an LCD-5100 luminance meter made by Otsuka Electronics Co., Ltd. was used. A light source was a halogen lamp. A low-pass filter was set to 5 kHz. A sample was put in a normally white mode TN device in which a distance (cell gap) between two glass substrates was 5.0 micrometers and a twist angle was 80 degrees. A voltage (rectangular waves; 60 Hz, 5 V, 0.5 second) was applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. Arise time ($\tau r$; millisecond) was expressed in terms of time required for a change from 90% transmittance to 10% transmittance. A fall time ($\tau f$; millisecond) was expressed in terms of time required for a change from 10% transmittance to 90% transmittance. A response time was expressed by a sum of the rise time and the fall time thus determined.

(16b) Response time ($\tau$; measured at 25° C.; ms; for a sample having negative dielectric anisotropy): For measurement, an LCD-5100 luminance meter made by Otsuka Electronics Co., Ltd. was used. A light source was a halogen lamp. A low-pass filter was set to 5 kHz. A sample was put in a normally black mode PVA device in which a distance (cell gap) between two glass substrates was 3.2 micrometers, and a rubbing direction was anti-parallel. The device was sealed with an ultraviolet-curable adhesive. The device was applied with a voltage of a little exceeding a threshold voltage for 1 minute, and then was irradiated with ultraviolet light of 23.5 mW/cm$^2$ for 8 minutes, while applying a voltage of 5.6 V. A voltage (rectangular waves; 60 Hz, 10 V, 0.5 second) was applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A response time was expressed in terms of time required for a change from 90% transmittance to 10% transmittance (fall time; millisecond).

Synthesis Example 1

Synthesis of Compound (1-1-7)

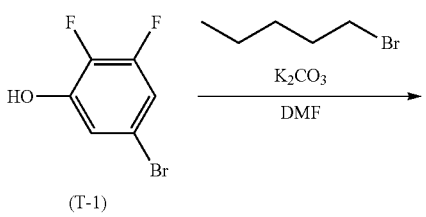

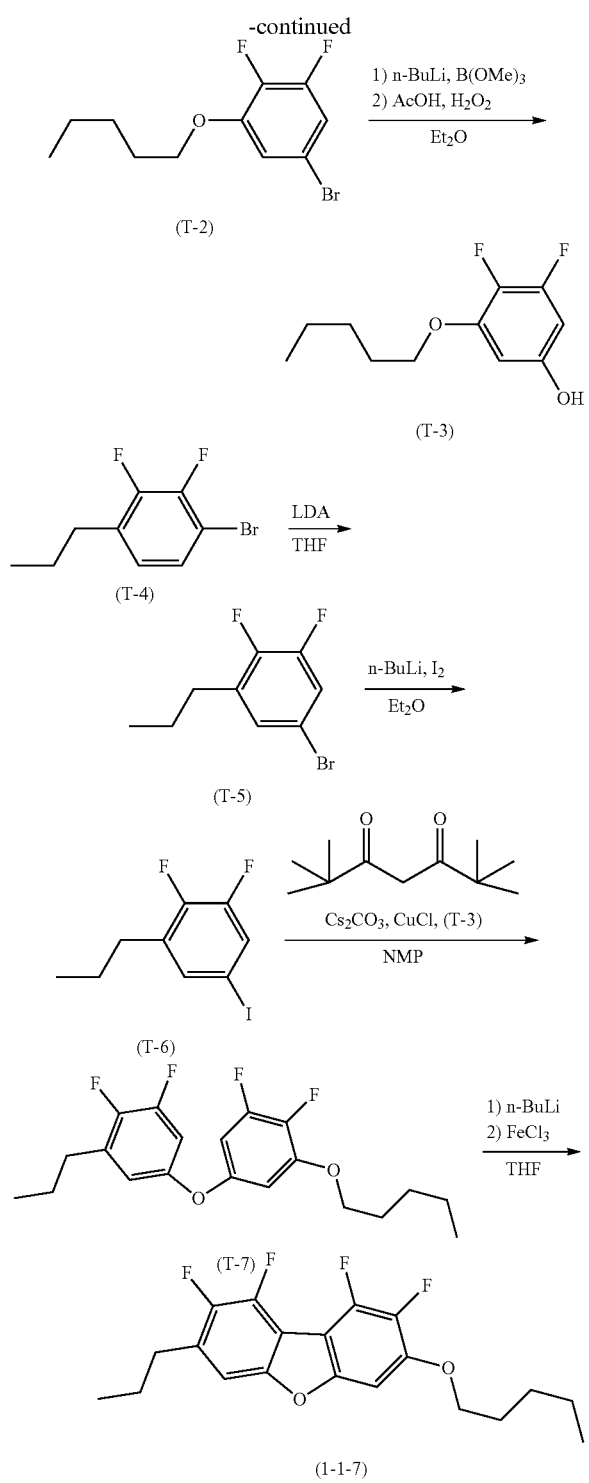

centrated under reduced pressure, and the residue was purified by silica gel chromatography (heptane) to obtain compound (T-2) (45.1 g, yield: 96%).

Second Step: Synthesis of Compound (T-3)

Under a nitrogen atmosphere, a diethyl ether solution (100 mL) of compound (T-2) (20.0 g) was cooled down to −40° C. Then, n-butyllithium (1.64 M; hexane solution; 48.4 mL) was slowly added, and stirred at −40° C. for 1 hour. Thereto, a diethyl ether solution (50 mL) of trimethyl borate (9.6 mL) was added dropwise, and the resulting solution was returned to room temperature while stirring. The resulting reaction mixture was cooled down to −5° C. Thereto, a diethyl ether solution (50 mL) of acetic acid (8.2 mL) was added dropwise, and the resulting mixture was stirred for 30 minutes. Next, hydrogen peroxide (30% solution; 4.9 g) was added dropwise thereto. The resulting reaction mixture was poured into water, and an ordinary post-treatment was applied thereto, and the resulting solution was purified by silica gel chromatography (heptane:ethyl acetate=4:1 in a volume ratio) to obtain compound (T-3) (13.0 g, yield: 83%).

Third Step: Synthesis of Compound (T-5)

Under a nitrogen atmosphere, a THF (240 mL) solution of compound (T-4) (24.0 g) was cooled down to −70° C. Then, lithium diisopropylamide (LDA; 1.01 M; THF solution; 204.1 mL) was slowly added thereto, and the resulting solution was stirred for 2 hours while maintaining −70° C. Thereto, methanol (100 mL) was added, and the resulting solution was poured into water. An ordinary post-treatment was applied thereto, and the resulting solution was purified by silica gel chromatography (heptane) to obtain compound (T-5) (19.8 g, yield: 78%).

Fourth Step: Synthesis of Compound (T-6)

Under a nitrogen atmosphere, a diethyl ether solution (50 mL) of compound (T-5) (5.0 g) was cooled down to −40° C. Then, n-butyllithium (1.64 M; hexane solution; 14.4 mL) was slowly added, and the resulting solution was stirred at −40° C. for 1 hour. Thereto, a diethyl ether solution (50 mL) of iodine (6.5 g) was added dropwise, and the resulting solution was returned to room temperature while stirring. The resulting reaction mixture was poured into water, and an ordinary post-treatment was applied thereto, and the resulting solution was purified by silica gel chromatography (heptane) to obtain compound (T-6) (4.35 g, yield: 61%).

Fifth Step: Synthesis of Compound (T-7)

Under a nitrogen atmosphere, compound (T-3) (6.1 g), copper(I) chloride (0.7 g), cesium carbonate (9.2 g), 2,2,6,6-tetramethyl-3,5-heptanedione (0.3 g) and N-methyl-2-pyrrolidone (80 mL) were added to compound (T-6) (4.0 g), and the resulting solution was stirred and heated at 120° C. for 6 hours. The resulting reaction mixture was poured into 1 N hydrochloric acid, and an ordinary post-treatment was applied thereto, and the resulting solution was purified by silica gel chromatography (heptane) to obtain compound (T-7) (2.1 g, yield: 34%).

Sixth Step: Synthesis of Compound (1-1-7)

Under a synthetic nitrogen atmosphere, a THF (20 mL) solution of compound (T-7) (2.1 g) was cooled down to −70° C. Then, n-butyllithium (1.64 M; hexane solution; 8.0 mL) was slowly added, and the resulting solution was stirred at −70° C. for 3 hours. Thereto, iron(III) chloride dried under First Step: Synthesis of Compound (T-2)

Under a nitrogen atmosphere, compound (T-1) (35.0 g), potassium carbonate (27.7 g), DMF (350 mL) and bromopentane (30.4 g) were put in a reaction vessel, and the resulting mixture was stirred at 90° C. for 2 hours. The resulting reaction mixture was poured into ice water, and an aqueous layer was subjected to extraction with toluene. Combined organic layers were washed with water, and dried over anhydrous magnesium sulfate. The solution was conreduced pressure for 3 hours at 100° C. was added, and the resulting solution was returned to room temperature while stirring. The resulting reaction mixture was poured into 1 N hydrochloric acid, and an ordinary post-treatment was applied thereto, and the resulting solution was purified by silica gel chromatography (heptane) and recrystallization to obtain compound (1-1-7) (0.43 g, yield: 20%).

$^1$H-NMR (CDCl$_3$; δ ppm): 7.11-7.09 (m, 1H), 6.93-6.11 (m, 1H), 4.10 (t, J=6.5 Hz, 2H), 2.80-2.77 (m, 2H), 1.89-1.88 (m, 2H), 1.72-1.70 (m, 2H), 1.55-1.38 (m, 4H), 1.00-0.95 (m, 6H).

Phase transition temperature: C 81.8 I.

Maximum temperature (NI)=−15.7° C.; optical anisotropy (Δn)=0.140; dielectric anisotropy (Δε)=−7.2; viscosity (η)=98.5 mPa·s.

Synthesis Example 2

Synthesis of Compound (1-2-22)

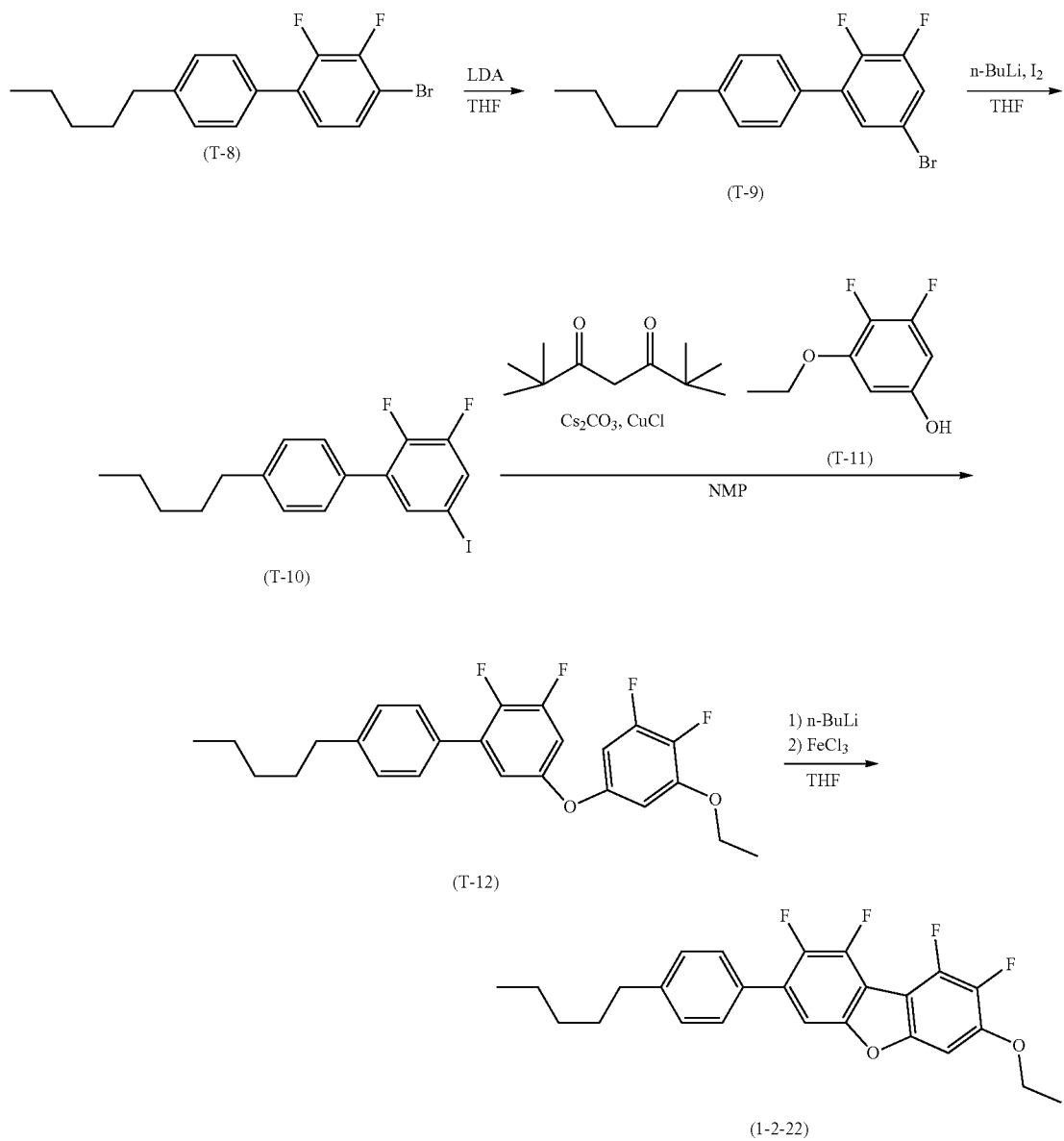

First Step: Synthesis of Compound (T-9)

Compound (T-9) (9.76 g, yield: 63%) was obtained by using compound (T-8) (15.0 g) as a raw material in a manner similar to the technique in the third step in Synthesis Example 1.

Second Step: Synthesis of Compound (T-10)

Compound (T-10) (8.87 g, yield: 66%) was obtained in a manner similar to the technique in the fourth step in Synthesis Example 1.

Third Step: Synthesis of Compound (T-12)

Compound (T-12) (3.8 g, yield: 28%) was obtained by using compound (T-10) (8.87 g) and compound (T-11) (8.0 g) as a raw material in a manner similar to the technique in the fifth step in Synthesis Example 1.

Fourth Step: Synthesis of Compound (1-2-22)

Compound (1-2-22) (1.05 g, yield: 34%) was obtained by using compound (T-12) (3.1 g) as a raw material in a manner similar to the technique in the sixth step in Synthesis Example 1.

$^1$H-NMR (CDCl$_3$; δ ppm): 7.54-7.51 (m, 2H), 7.36-7.29 (m, 3H), 6.94-6.97 (m, 1H), 4.20 (q, J=7.0 Hz, 2H), 2.67 (t, J=7.9 Hz, 2H), 1.70-1.63 (m, 2H), 1.55-1.52 (m, 4H), 1.38-1.35 (m, 3H), 0.93-0.90 (m, 3H).

Phase transition temperature: C 123.5 I.

Maximum temperature (NI)=114.3° C.; optical anisotropy (Δn)=0.254; dielectric anisotropy (Δε)=−10.1; viscosity (η)=82.7 mPa·s.

In addition, a sample having a ratio of the compound to a base liquid crystal (3% by weight:97% by weight) was used for measurement of the maximum temperature, the optical anisotropy, the dielectric anisotropy and the viscosity.

Synthesis Example 3

Synthesis of Compound (1-2-43)

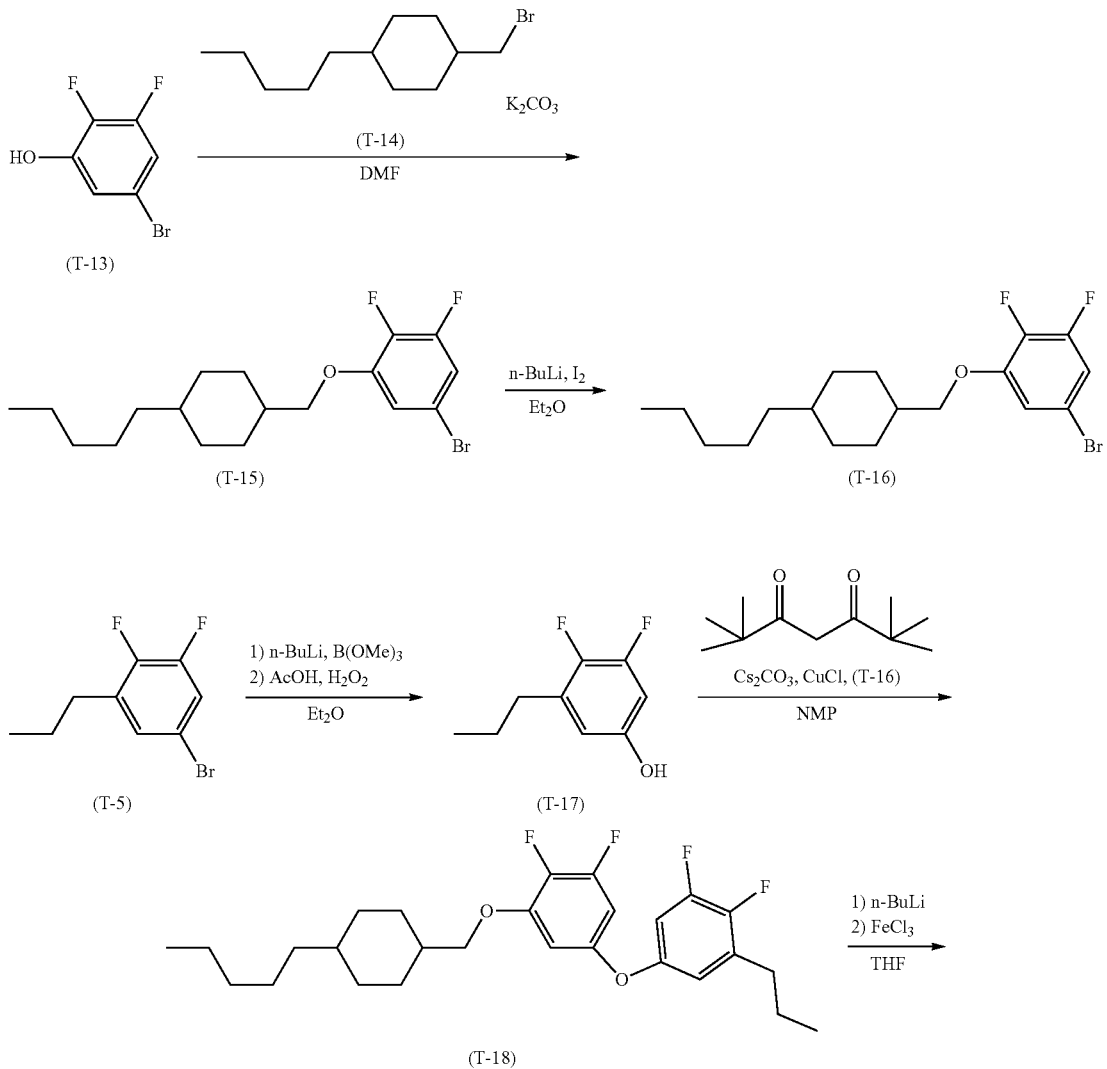

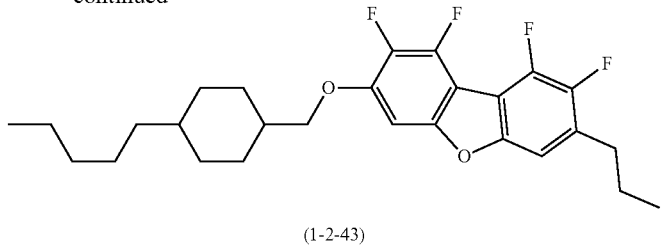

(1-2-43)

First Step: Synthesis of Compound (T-15)

Compound (T-15) (22.5 g, yield: 71%) was obtained by using compound (T-14) (22.0 g) prepared according to a publicly known method in place of bromopentane in a manner similar to the technique in the first step in Synthesis Example 1.

Second Step: Synthesis of Compound (T-16)

Compound (T-16) (19.8 g, yield: 71%) was obtained in a manner similar to the technique in the fourth step in Synthesis Example 1.

Third Step: Synthesis of Compound (T-17)

Compound (T-17) (11.2 g, yield: 80%) was obtained by using compound (T-5) (19.0 g) as a raw material in a manner similar to the technique in the second step in Synthesis Example 1.

Fourth Step: Synthesis of Compound (T-18)

Compound (T-18) (8.3 g, yield: 35%) was obtained by using compound (T-16) (12.1 g) and compound (T-17) (9.9 g) as a raw material in a manner similar to the technique in the fifth step in Synthesis Example 1.

Fifth Step: Synthesis of Compound (1-2-43)

Compound (1-2-43) (2.86 g, yield: 35%) was obtained by using compound (T-18) (8.3 g) as a raw material in a manner similar to the technique in the sixth step in Synthesis Example 1.

$^1$H-NMR (CDCl$_3$; δ ppm): 7.10 (d, J=4.3 Hz, 1H), 6.90 (dd, J=5.6 Hz, 1.0 Hz, 1H), 3.89 (d, J=6.4 Hz, 2H), 2.77 (t, J=7.5 Hz, 2H), 1.95-1.82 (m, 5H), 1.73-1.69 (m, 2H), 1.33-1.18 (m, 9H), 1.14-1.06 (m, 2H), 1.01-0.89 (m, 8H)

Phase transition temperature: C 84.2 S$_A$ 95.9 N 101.2 I.

Maximum temperature (NI)=89.0° C.; optical anisotropy (Δn)=0.167; dielectric anisotropy (Δε)=−8.24; viscosity (η)=117.8 mPa·s.

Synthesis Example 4

Synthesis of Compound (1-2-49)

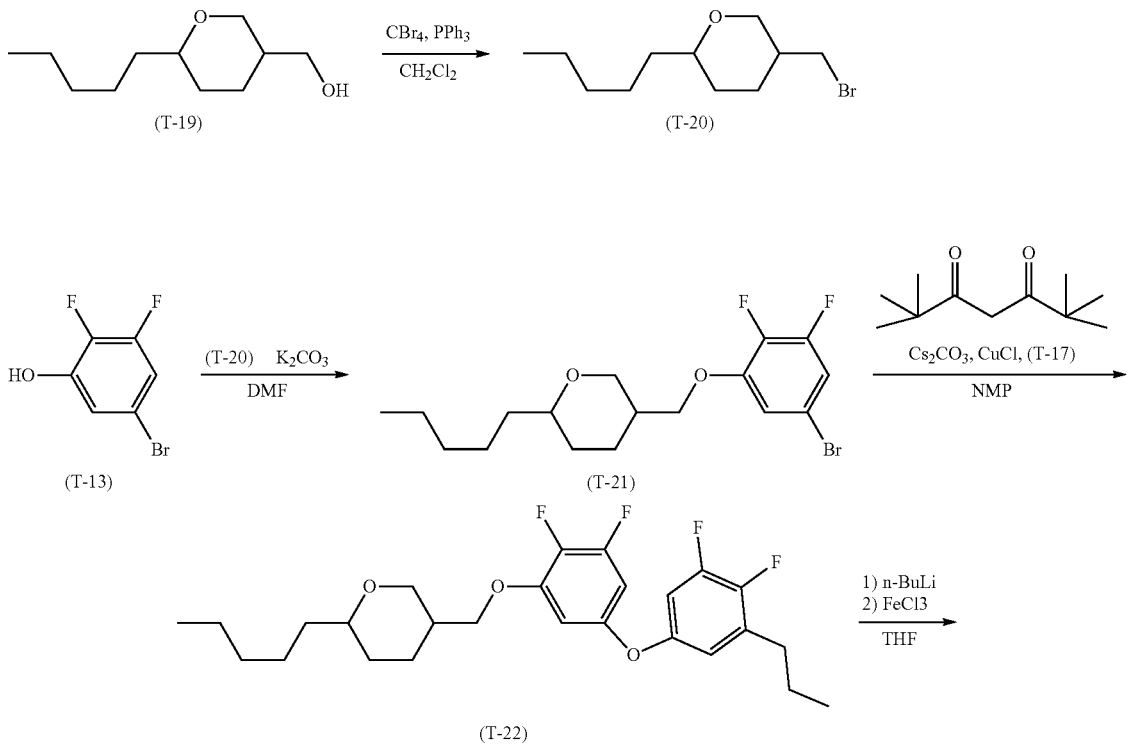

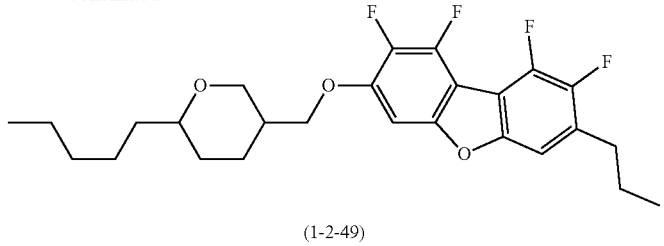

(1-2-49)

First Step: Synthesis of Compound (T-20)

A dichloromethane (100 mL) solution of compound (T-19) (35.0 g) prepared according to a publicly known method and carbon tetrabromide (93.5 g) was cooled down to 0° C. Thereto, a dichloromethane (75 mL) solution of triphenyl phosphine (98.6 g) was added dropwise, and the resulting solution was returned to room temperature while stirring. An ordinary post-treatment was applied thereto, and the resulting solution was purified by silica gel chromatography (toluene) to obtain compound (T-20) (38.6 g, 145.9 mmol; 78%).

Second Step: Synthesis of Compound (T-21)

Compound (T-21) (22.0 g, yield: 38%) was obtained by using compound (T-20) (38.6 g) in place of iodoethane in a manner similar to the technique in the first step in Synthesis Example 1.

Third Step: Synthesis of Compound (T-22)

Compound (T-22) (5.2 g, yield: 66%) was obtained by using compound (T-21) (5.5 g) and compound (T-17) (5.0 g) as a raw material in a manner similar to the technique in the fifth step in Synthesis Example 1.

Fourth Step: Synthesis of Compound (1-2-49)

Compound (1-2-49) (2.52 g, yield: 55%) was obtained by using compound (T-22) (4.2 g) as a raw material in a manner similar to the technique in the sixth step in Synthesis Example 1.

$^1$H-NMR (CDCl$_3$; δ ppm): 7.10 (d, J=4.3 Hz, 1H), 6.90 (dd, J=5.6 Hz, 1.0 Hz, 1H), 4.22-4.18 (m, 1H), 3.95-3.87 (m, 2H), 3.33-3.23 (m, 52H), 2.23-2.19 (m, 1H), 2.01-1.98 (m, 1H), 1.74-1.67 (m, 3H), 1.56-1.51 (m, 2H), 1.45-1.26 (m, 10H), 1.01-0.98 (m, 3H), 0.99-0.86 (m, 3H).

Phase transition temperature: C 89.0 S$_A$ 99.6 I.

Maximum temperature (NI)=77.6° C.; optical anisotropy (Δn)=0.160; dielectric anisotropy (Δε)=−10.52; viscosity (η)=151.7 mPa·s.

Synthesis Example 5

Synthesis of Compound (1-2-29)

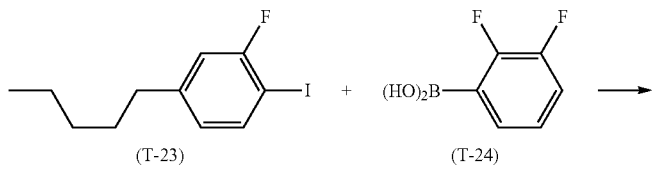

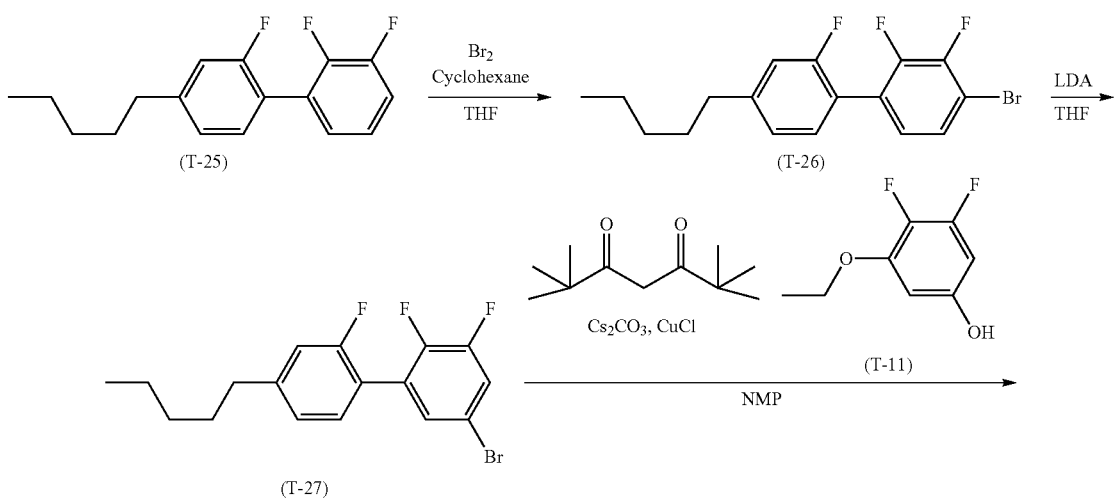

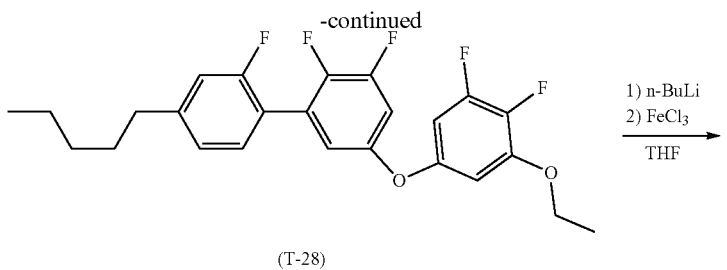

(T-28)

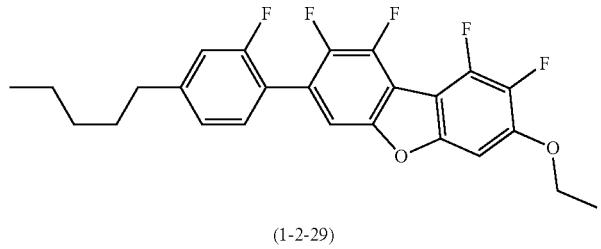

(1-2-29)

First Step: Synthesis of Compound (T-25)

Under a nitrogen atmosphere, Solmix (120 mL) and water (24 mL) were added to a toluene (120 mL) solution of compound (T-23) (12.0 g), compound (T-24) (7.8 g), potassium carbonate (11.4 g), tetrabutylammonium bromide (TBAB; 3.3 g) and tetrakis(triphenylphosphine)palladium (0) (2.4 g), and the resulting solution was stirred and heated for 2 hours. The resulting reaction mixture was poured into water, and an ordinary post-treatment was applied thereto, and the resulting solution was purified by silica gel chromatography (heptane) to obtain compound (T-25) (6.61 g, yield: 55%).

Second Step: Synthesis of Compound (T-26)

Under a nitrogen atmosphere, a THF solution (100 mL) of compound (T-25) (6.61 g) was cooled down to −70° C. Then, sec-butyllithium (1.05 M; hexane solution; 27.1 mL) was slowly added, and the resulting solution was stirred at −70° C. for 3 hours. Thereto, a cyclohexane solution (10 mL) of bromine (1.47 mL) was added dropwise, and the resulting solution was returned to room temperature while stirring. The resulting reaction mixture was poured into water, and an ordinary post-treatment was applied thereto, and the resulting solution was purified by silica gel chromatography (heptane) to obtain compound (T-26) (6.15 g, yield: 71%).

Third Step: Synthesis of Compound (T-27)

Compound (T-27) (5.54 g, yield: 90%) was obtained by using compound (T-26) (6.15 g) as a raw material in a manner similar to the technique in the third step in Synthesis Example 1.

Fourth Step: Synthesis of Compound (T-28)

Compound (T-28) (2.0 g, yield: 60%) was obtained by using compound (T-27) (3.89 g) as a raw material in a manner similar to the technique in the fifth step in Synthesis Example 1.

Fifth Step: Synthesis of Compound (1-2-29)

Compound (1-2-29) (0.27 g, yield: 15%) was obtained by using compound (T-12) (1.8 g) as a raw material in a manner similar to the technique in the sixth step in Synthesis Example 1.

$^1$H-NMR (CDCl$_3$; δ ppm): 7.37-7.31 (m, 2H), 7.09-7.02 (m, 2H), 6.97-6.94 (m, 1H), 4.21 (q, J=7.0 Hz, 2H), 3.69-3.61 (m, 2H), 1.71-1.64 (m, 2H), 1.56-1.52 (m, 3H), 1.39-1.35 (m, 4H), 0.94-0.90 (m, 3H).

Phase transition temperature: C 94.5 I.

Maximum temperature (NI)=70.3° C.; optical anisotropy (Δn)=0.227; dielectric anisotropy (Δε)=−9.2.

Comparative Example 1

As a comparative compound, compound (S-1) described below disclosed in JP H10-236992 A was selected. The compound was prepared according to a publicly known method.

(S-1)

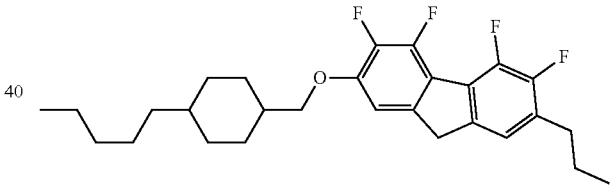

$^1$H-NMR (CDCl$_3$; δ ppm): 7.03 (d, J=5.6 Hz, 1H), 6.89 (d, J=6.2 Hz, 1H), 3.87 (d, J=6.4 Hz, 2H), 3.84 (s, 2H), 2.67 (t, J=7.3 Hz, 2H), 1.97-1.90 (m, 2H), 1.88-1.77 (m, 3H), 1.72-1.63 (m, 2H), 1.36-1.16 (m, 9H), 1.15-1.02 (m, 2H), 1.01-0.86 (m, 8H).

Physical properties of compound (S-1) were as described below. In addition, a sample having a ratio of the compound to the base liquid crystal (3% by weight:97% by weight) was used for measurement of the maximum temperature, the optical anisotropy, the dielectric anisotropy and the viscosity.

Transition temperature: C 157 I.

Maximum temperature (T$_{NI}$)=97.9° C.; optical anisotropy (Δn)=0.147; dielectric anisotropy (Δε)=−13.1; viscosity (η)=98.9 mPa·s.

The results obtained by measuring the compatibility with regard to compound (1-2-43), compound (1-2-49) and compound (S-1) are summarized in Table 2. Samples for measurement were prepared according to the "extrapolation method" described above. Then, 15% by weight of compound (1-2-43) and compound (1-2-49) each was mixed with 85% by weight of liquid crystal (B), and dissolved therein by heating the mixture. The mixture was returned to room temperature, but no crystals precipitated. In contrast, when compound (S-1) was dissolved in liquid crystal (B) in an identical proportion and the resulting solution was returned to room temperature, crystals precipitated. The proportion of the compound (S-1) was changed to 10% by weight or 5% by weight, but crystals precipitated. When the proportion was 3% by weight, no crystals precipitated. The results show that compound (1-2-43) and compound (1-2-49) were excellent in the compatibility because an oxygen atom of a fluorodibenzofuran ring has an effect of degrading crystallinity. When the refractive index anisotropy (Δn) of the samples was measured, compound (1-2-43) and compound (1-2-49) had a larger value. The results show that compound (1-2-43) and compound (1-2-49) having the fluorodibenzofuran ring are superior to comparative compound (S-1).

TABLE 2

Compatibility and refractive index anisotropy of compound

| Compound | Structural formula | Compatibility (ratio of compound) | Refractive index anisotropy (Δn) |
|---|---|---|---|
| Compound (1-2-43) | | 15% by weight: 85% by weight | 0.167 |
| Compound (1-2-49) | | 15% by weight: 85% by weight | 0.160 |
| Compound (S-1) | | 3% by weight: 97% by weight | 0.147 |

Comparative Example 2

As a comparative compound, compound (S-2) described below disclosed in JP 2015-174864 A was selected. The compound was prepared according to a publicly known method.

(S-2)

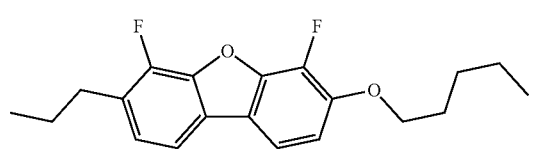 [SMILES: CCCCCOc1ccc2c(oc3c(F)c(CCC)ccc32)c1F]

$^1$H-NMR (CDCl$_3$; δ ppm): 7.52-7.51 (m, 2H), 7.14-7.11 (m, 1H), 7.02-6.98 (m, 1H), 4.14 (t, J=6.7 Hz, 2H), 2.78 (t, J=7.5 Hz, 2H), 1.90-1.84 (m, 2H), 1.73-1.69 (m, 2H), 1.52-1.39 (m, 4H), 1.00-0.94 (m, 6H).

Physical properties of compound (S-2) were as described below.

Transition temperature: C 54.8 I.

Maximum temperature (T$_{NI}$)=−12.4° C.; optical anisotropy (Δn)=0.16; dielectric anisotropy (Δε)=−6.9; viscosity (η)=55.8 mPa·s.

The results obtained by measuring the dielectric anisotropy of compound (1-1-7) and compound (S-2) are summarized in Table 3. Samples for measurement were prepared according to the "extrapolation method" described above. Compound (1-1-7) had negatively larger value. The results show that compound (1-1-7) having a fluorine group in a position on a side reverse to an oxygen atom of a fluorodibenzofuran ring is superb in comparison with comparative compound (S-2)

TABLE 3

Dielectric anisotropy of compound

| Compound | Structural formula | Dielectric anisotropy (Δε) |
|---|---|---|
| Compound (1-1-7) | | −7.2 |
| Compound (S-2) | | −6.9 |

Compounds shown below can be prepared with reference to the method described in Synthesis Examples and the section "2. Synthesis of compound (1)."

| No. |  |
|---|---|
| 1-1-1 | |
| 1-1-2 | |
| 1-1-3 | |
| 1-1-4 | |
| 1-1-5 | |

-continued
| No. | |
|---|---|
| 1-1-6 | 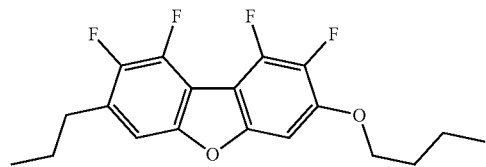 [SMILES: CCCCOc1cc2oc3cc(CCC)c(F)c(F)c3c2c(F)c1F] |
| 1-1-7 | 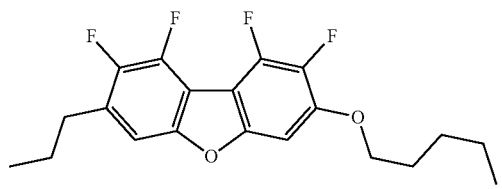<br>C 81.8 I<br>$T_{NI}$; -15.7, Δε; -7.2, Δn; 0.140, η; 98.5. |
| 1-1-8 | 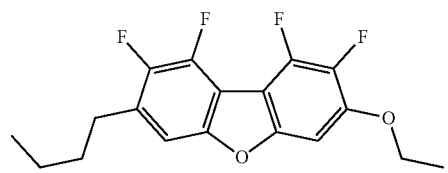 [SMILES: CCCCc1cc2oc3cc(OCC)c(F)c(F)c3c2c(F)c1F] |
| 1-1-9 | 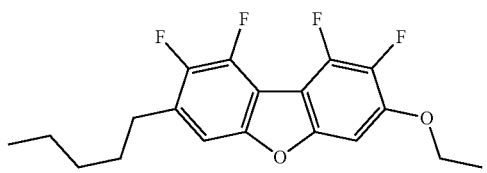 [SMILES: CCCCCc1cc2oc3cc(OCC)c(F)c(F)c3c2c(F)c1F] |
| 1-1-10 | 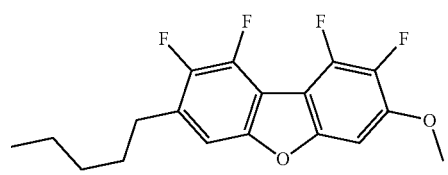 [SMILES: CCCCCc1cc2oc3cc(OC)c(F)c(F)c3c2c(F)c1F] |
| 1-1-11 | 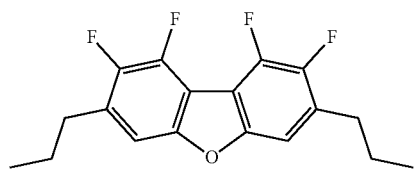 |
| 1-1-12 | 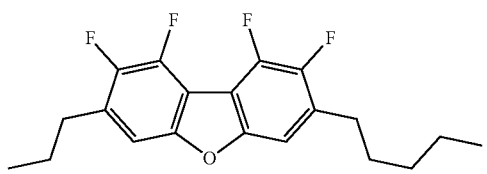 [SMILES: CCCCCc1cc2oc3cc(CCC)c(F)c(F)c3c2c(F)c1F] |
| 1-1-13 | 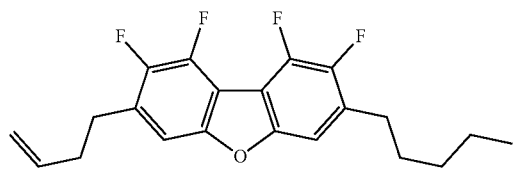 [SMILES: C=CCCc1cc2oc3cc(CCCCC)c(F)c(F)c3c2c(F)c1F] |

-continued
| No. | |
|---|---|
| 1-1-14 | 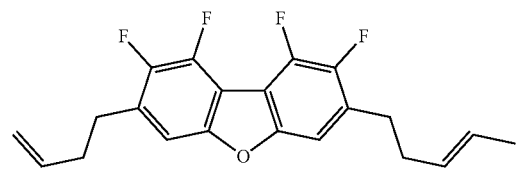 [SMILES: C=CCCc1cc2oc3cc(CC/C=C/C)c(F)c(F)c3c2c(F)c1F] |
| 1-1-15 | 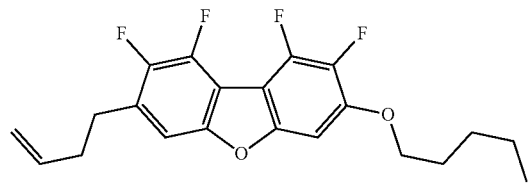 [SMILES: C=CCCc1cc2oc3cc(OCCCCC)c(F)c(F)c3c2c(F)c1F] |
| 1-1-16 | 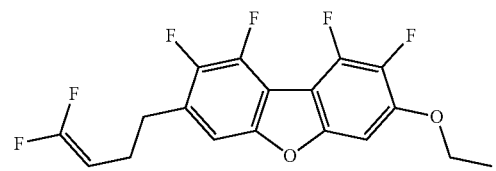 [SMILES: CCOc1cc2oc3cc(CCC=C(F)F)c(F)c(F)c3c2c(F)c1F] |
| 1-1-17 | 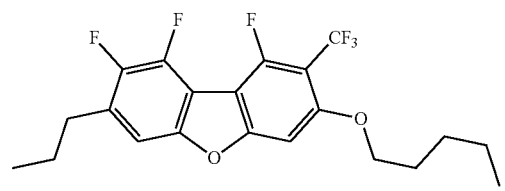 [SMILES: CCCCCOc1cc2oc3cc(CCC)c(F)c(F)c3c2c(F)c1C(F)(F)F] |
| 1-1-18 | 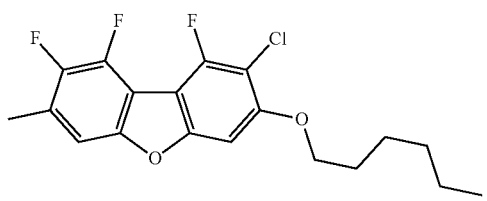 [SMILES: CCCCCCOc1cc2oc3cc(C)c(F)c(F)c3c2c(F)c1Cl] |
| 1-1-19 | 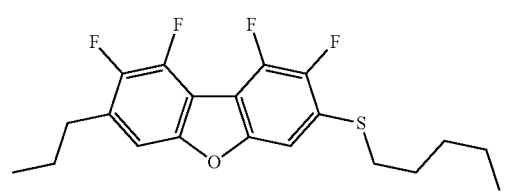 [SMILES: CCCCCSc1cc2oc3cc(CCC)c(F)c(F)c3c2c(F)c1F] |
| 1-1-20 | 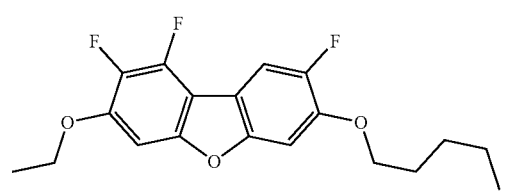 [SMILES: CCCCCOc1cc2oc3cc(OCC)c(F)c(F)c3c2cc1F] |
| 1-2-1 | 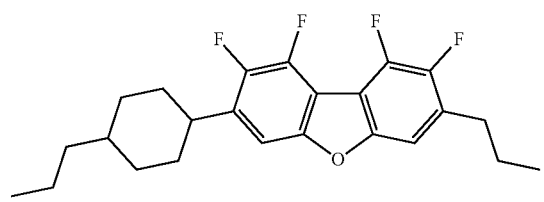 |

-continued
| No. | |
|---|---|
| 1-2-2 | 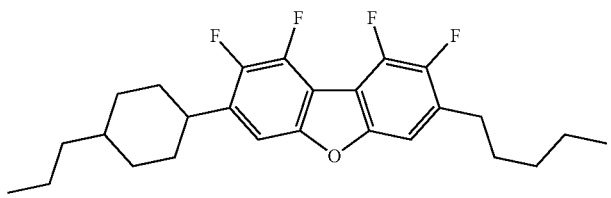 |
| 1-2-3 | 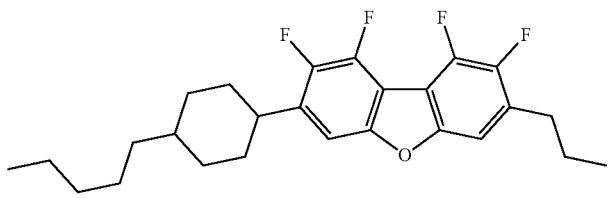 [SMILES: CCCCCC1CCC(c2cc3oc4cc(CCC)c(F)c(F)c4c3c(F)c2F)CC1] |
| 1-2-4 | 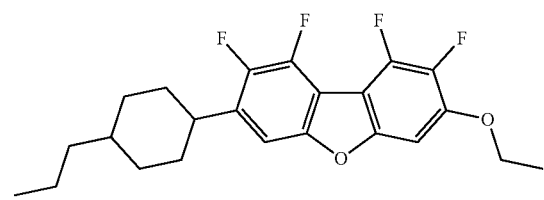 [SMILES: CCCC1CCC(c2cc3oc4cc(OCC)c(F)c(F)c4c3c(F)c2F)CC1] |
| 1-2-5 | 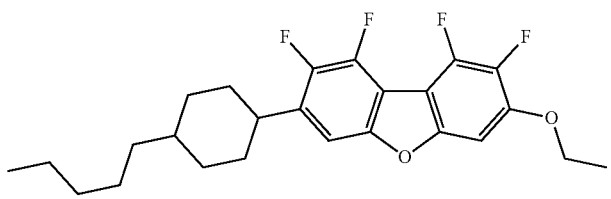 [SMILES: CCCCCC1CCC(c2cc3oc4cc(OCC)c(F)c(F)c4c3c(F)c2F)CC1] |
| 1-2-6 | 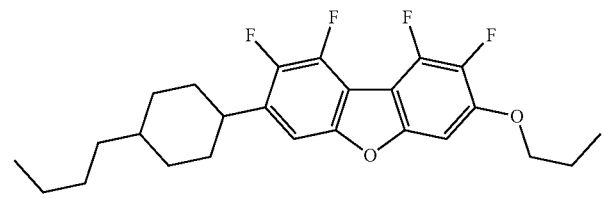 |
| 1-2-7 | 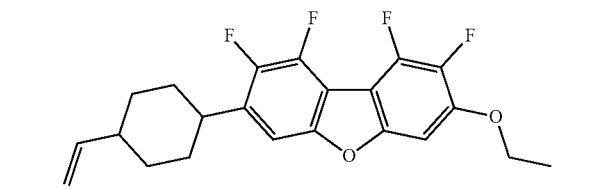 [SMILES: C=CC1CCC(c2cc3oc4cc(OCC)c(F)c(F)c4c3c(F)c2F)CC1] |
| 1-2-8 | 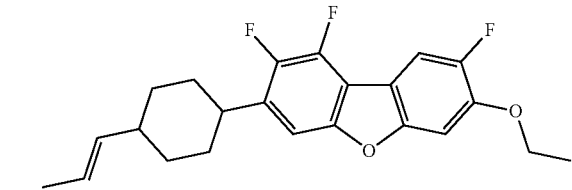 [SMILES: C/C=C/C1CCC(c2cc3oc4cc(OCC)c(F)cc4c3c(F)c2F)CC1] |
| 1-2-9 | 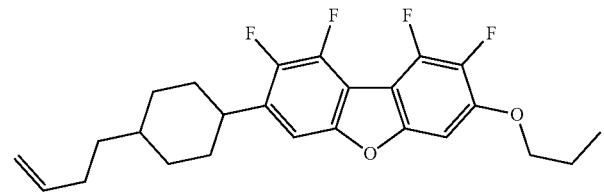 [SMILES: C=CCCC1CCC(c2cc3oc4cc(OCCC)c(F)c(F)c4c3c(F)c2F)CC1] |

| No. | |
|---|---|
| 1-2-10 | 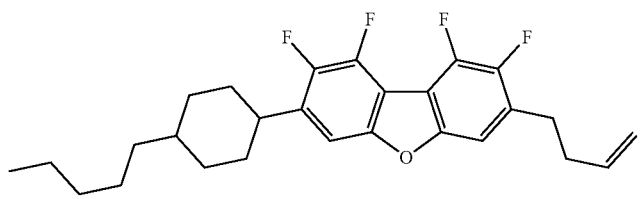 [SMILES: C=CCCc1cc2oc3cc(C4CCC(CCCCC)CC4)c(F)c(F)c3c2c(F)c1F] |
| 1-2-11 | 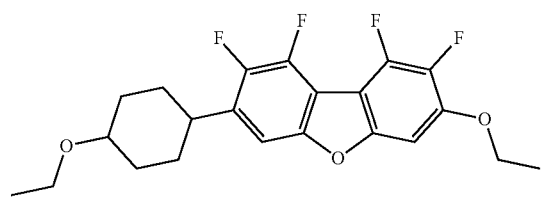 |
| 1-2-12 | 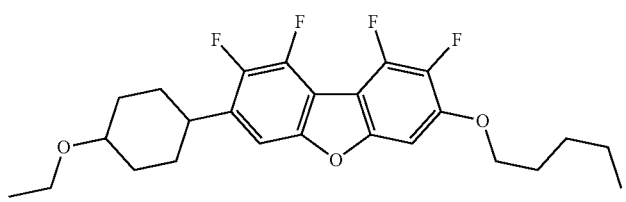 [SMILES: CCCCCOc1cc2oc3cc(C4CCC(OCC)CC4)c(F)c(F)c3c2c(F)c1F] |
| 1-2-13 | 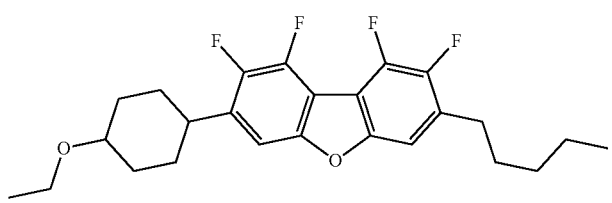 [SMILES: CCCCCc1cc2oc3cc(C4CCC(OCC)CC4)c(F)c(F)c3c2c(F)c1F] |
| 1-2-14 | 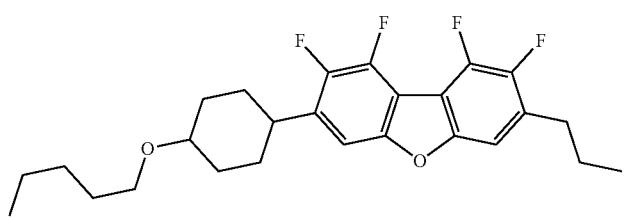 [SMILES: CCCCCOC1CCC(c2cc3oc4cc(CCC)c(F)c(F)c4c3c(F)c2F)CC1] |
| 1-2-15 | 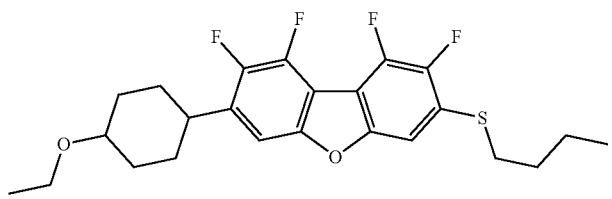 |
| 1-2-16 | 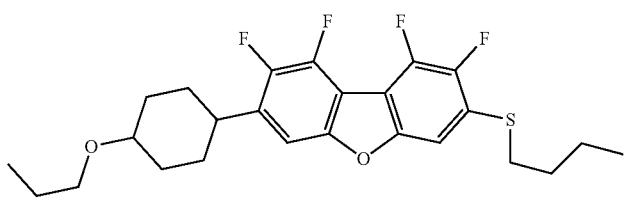 [SMILES: CCCCSc1cc2oc3cc(C4CCC(OCCC)CC4)c(F)c(F)c3c2c(F)c1F] |

| No. | |
|---|---|
| 1-2-17 | 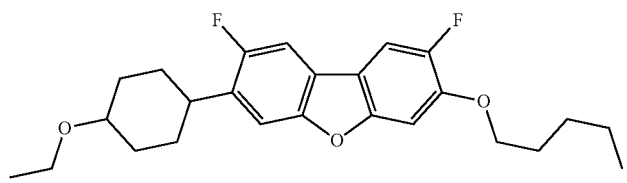 [SMILES: CCCCCOc1cc2oc3cc(C4CCC(OCC)CC4)c(F)cc3c2cc1F] |
| 1-2-18 | 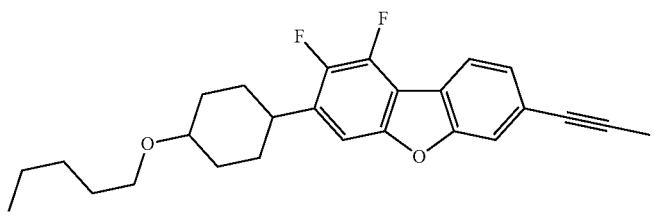 [SMILES: CC#Cc1ccc2c(c1)oc1cc(C3CCC(OCCCCC)CC3)c(F)c(F)c12] |
| 1-2-19 | 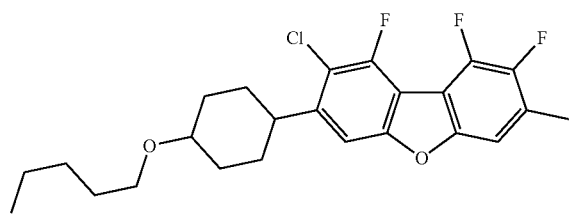 [SMILES: CCCCCOC1CCC(c2cc3oc4cc(C)c(F)c(F)c4c3c(F)c2Cl)CC1] |
| 1-2-20 | 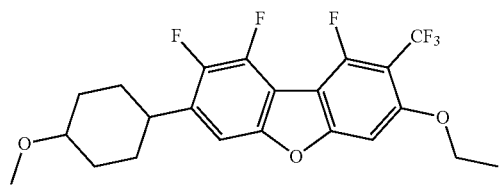 [SMILES: CCOc1cc2oc3cc(C4CCC(OC)CC4)c(F)c(F)c3c2c(F)c1C(F)(F)F] |
| 1-2-21 | 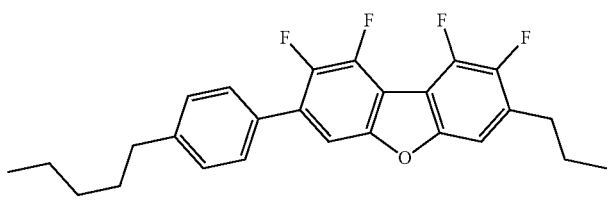 |
| 1-2-22 | 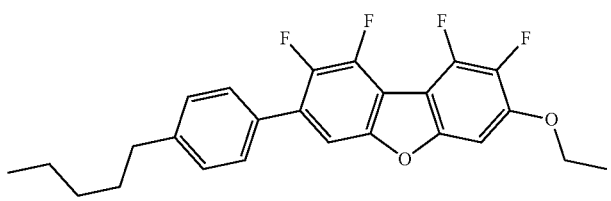 [SMILES: CCCCCc1ccc(-c2cc3oc4cc(CCC)c(F)c(F)c4c3c(F)c2F)cc1]<br>C 123.5 I<br>$T_{NI}$; 114.3, Δε; -10.1, Δn; 0.254, η; 82.7. |
| 1-2-23 | 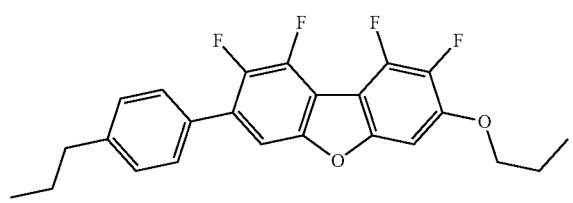 [SMILES: CCCOc1cc2oc3cc(-c4ccc(CCC)cc4)c(F)c(F)c3c2c(F)c1F] |

-continued
| No. | |
|---|---|
| 1-2-24 | 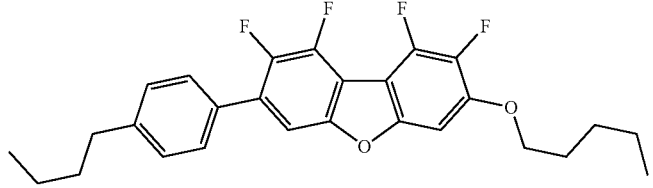 [SMILES: CCCCCOc1cc2oc3cc(-c4ccc(CCCC)cc4)c(F)c(F)c3c2c(F)c1F] |
| 1-2-25 | 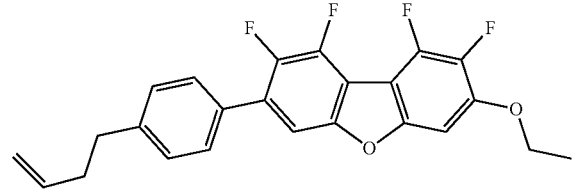 [SMILES: C=CCCc1ccc(-c2cc3oc4cc(OCC)c(F)c(F)c4c3c(F)c2F)cc1] |
| 1-2-26 | 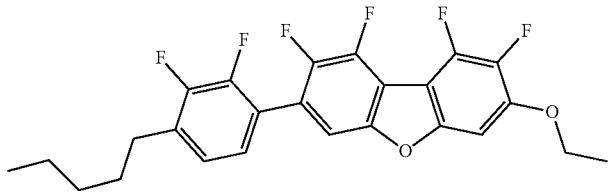 [SMILES: CCCCCc1ccc(-c2cc3oc4cc(OCC)c(F)c(F)c4c3c(F)c2F)c(F)c1F] |
| 1-2-27 | 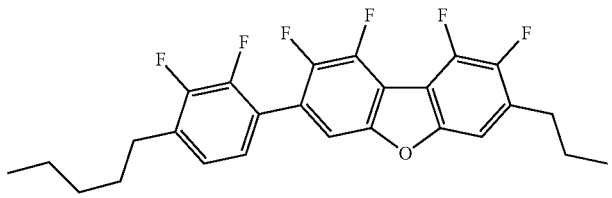 [SMILES: CCCCCc1ccc(-c2cc3oc4cc(CCC)c(F)c(F)c4c3c(F)c2F)c(F)c1F] |
| 1-2-28 | 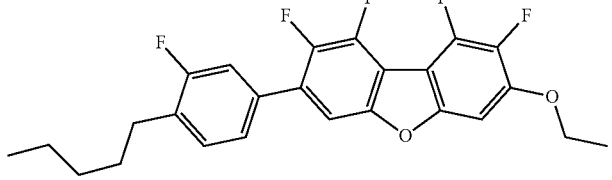 |
| 1-2-29 | 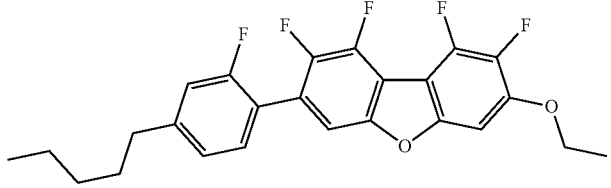<br>C 94.5 I<br>$T_{NI}$; 70.3, $\Delta\varepsilon$; -9.2, $\Delta n$; 0.227. |
| 1-2-30 | 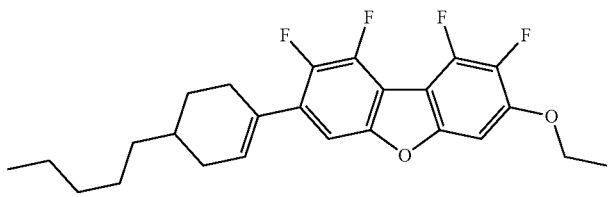 [SMILES: CCCCCC1CC=C(c2cc3oc4cc(OCC)c(F)c(F)c4c3c(F)c2F)CC1] |

| No. | |
|---|---|
| 1-2-31 | 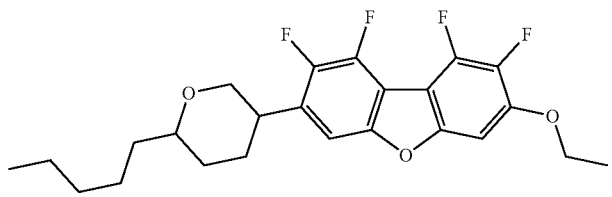 [SMILES: CCCCCC1CCC(c2cc3oc4cc(OCC)c(F)c(F)c4c3c(F)c2F)CO1] |
| 1-2-32 | 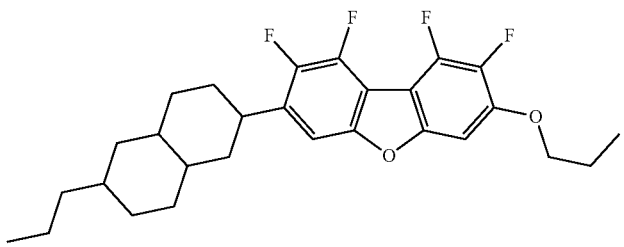 [SMILES: CCCOc1cc2oc3cc(C4CCC5CC(CCC)CCC5C4)c(F)c(F)c3c2c(F)c1F] |
| 1-2-33 | 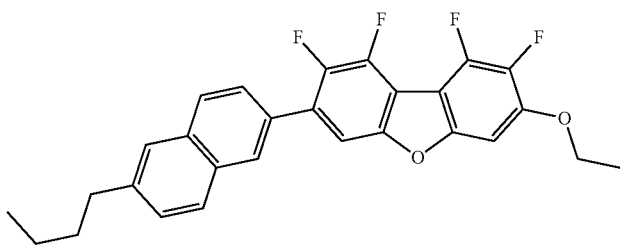 [SMILES: CCCCc1ccc2cc(-c3cc4oc5cc(OCC)c(F)c(F)c5c4c(F)c3F)ccc2c1] |
| 1-2-34 | 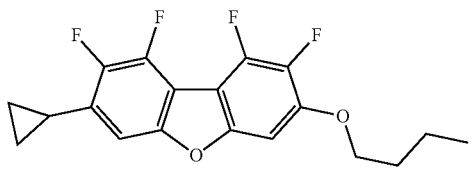 [SMILES: CCCCOc1cc2oc3cc(C4CC4)c(F)c(F)c3c2c(F)c1F] |
| 1-2-35 | 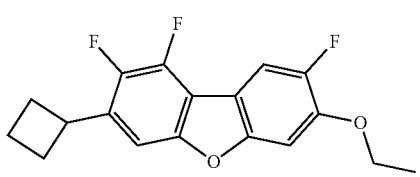 [SMILES: CCOc1cc2oc3cc(C4CCC4)c(F)c(F)c3c2cc1F] |
| 1-2-36 | 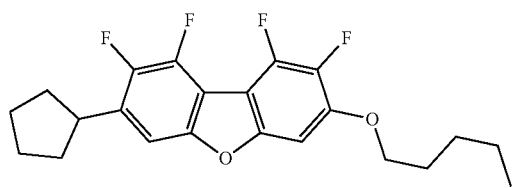 [SMILES: CCCCCOc1cc2oc3cc(C4CCCC4)c(F)c(F)c3c2c(F)c1F] |
| 1-2-37 | 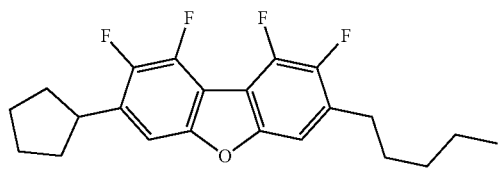 [SMILES: CCCCCc1cc2oc3cc(C4CCCC4)c(F)c(F)c3c2c(F)c1F] |
| 1-2-38 | 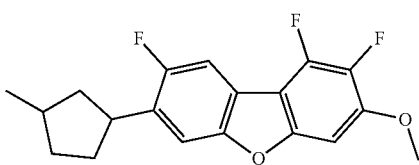 |

| No. | |
|---|---|
| 1-2-39 | 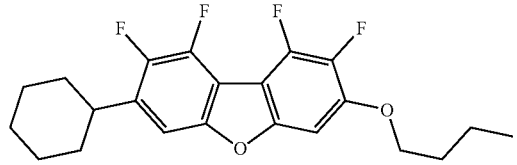 [SMILES: CCCCOc1cc2oc3cc(C4CCCCC4)c(F)c(F)c3c2c(F)c1F] |
| 1-2-40 | 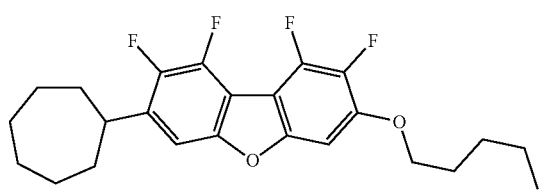 [SMILES: CCCCCOc1cc2oc3cc(C4CCCCCC4)c(F)c(F)c3c2c(F)c1F] |
| 1-2-41 | 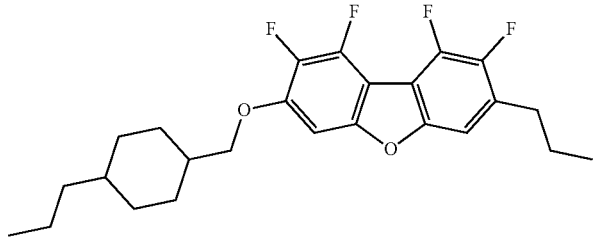 [SMILES: CCCc1cc2oc3cc(OCC4CCC(CCC)CC4)c(F)c(F)c3c2c(F)c1F] |
| 1-2-42 | 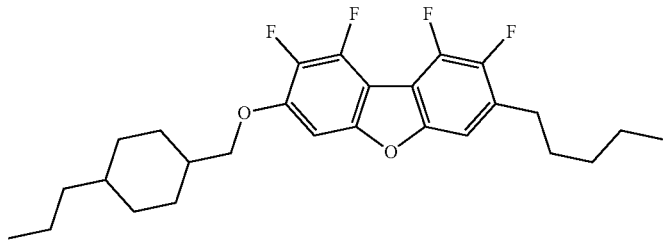 |
| 1-2-43 | 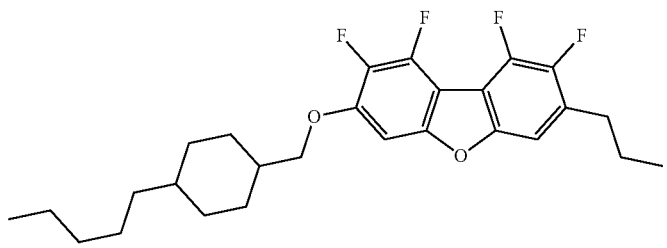 C 64.9 $S_A$ 96.1 N 101.1 I<br>$T_{NI}$; 89.0, $\Delta\epsilon$; -8.2, $\Delta n$; 0.167, $\eta$; 117.8. |
| 1-2-44 | 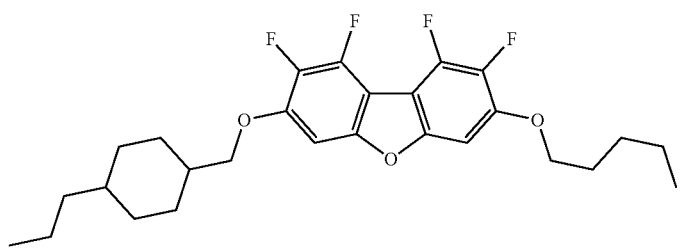 [SMILES: CCCCCOc1cc2oc3cc(OCC4CCC(CCC)CC4)c(F)c(F)c3c2c(F)c1F] |

| No. | |
|---|---|
| 1-2-45 | 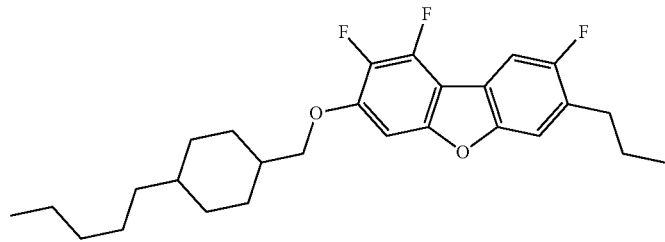 [SMILES: CCCCCC1CCC(COc2cc3oc4cc(CCC)c(F)cc4c3c(F)c2F)CC1] |
| 1-2-46 | 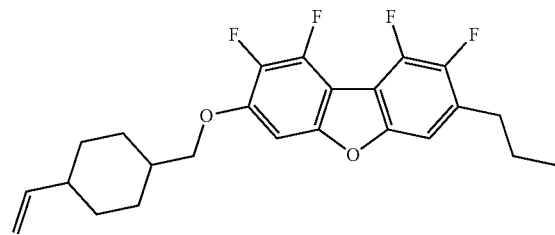 [SMILES: C=CC1CCC(COc2cc3oc4cc(CCC)c(F)c(F)c4c3c(F)c2F)CC1] |
| 1-2-47 | 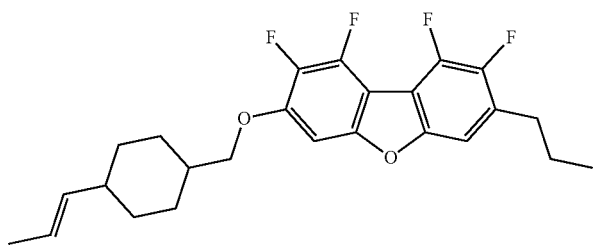 [SMILES: C/C=C/C1CCC(COc2cc3oc4cc(CCC)c(F)c(F)c4c3c(F)c2F)CC1] |
| 1-2-48 | 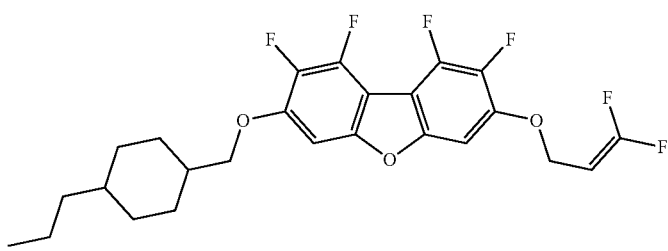 [SMILES: CCCC1CCC(COc2cc3oc4cc(OCC=C(F)F)c(F)c(F)c4c3c(F)c2F)CC1] |
| 1-2-49 | 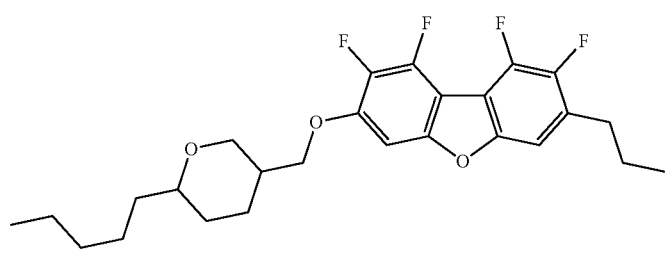 [SMILES: CCCCCC1CCC(COc2cc3oc4cc(OCC)c(F)c(F)c4c3c(F)c2F)CO1]<br>C 93.1 S$_A$ 99.4 N I<br>T$_{NI}$; 77.6, Δε; -10.5, Δn; 0.160, η; 151.7. |
| 1-2-50 | 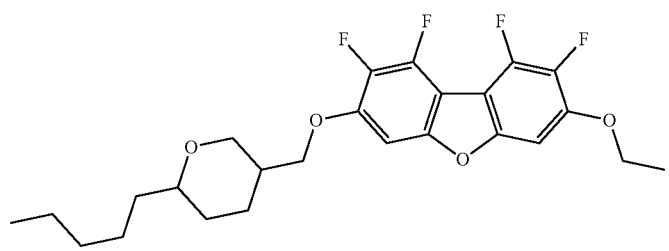 |

| No. | |
|---|---|
| 1-2-51 | 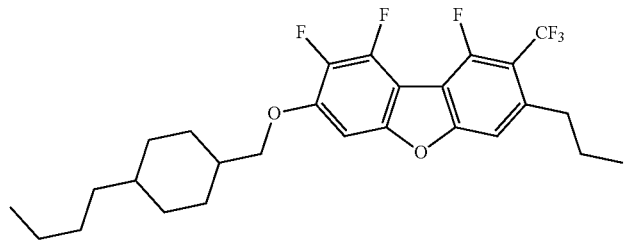 [SMILES: CCCCC1CCC(COc2cc3oc4cc(CCC)c(C(F)(F)F)c(F)c4c3c(F)c2F)CC1] |
| 1-2-52 | 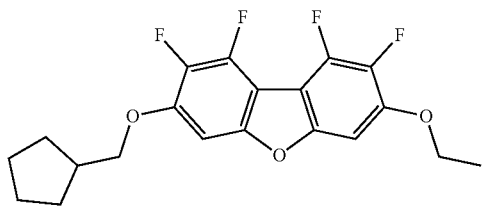 [SMILES: CCOc1cc2oc3cc(OCC4CCCC4)c(F)c(F)c3c2c(F)c1F] |
| 1-2-53 | 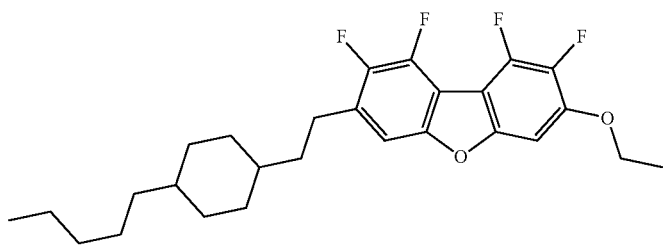 |
| 1-2-54 | 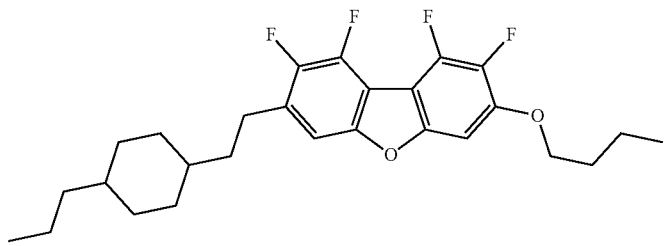 [SMILES: CCCCOc1cc2oc3cc(CCC4CCC(CCC)CC4)c(F)c(F)c3c2c(F)c1F] |
| 1-2-55 | 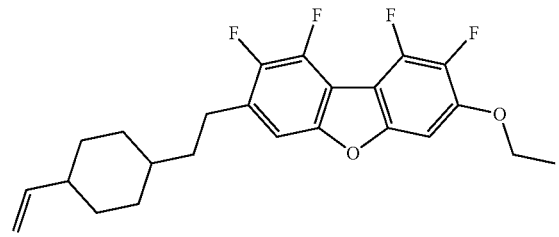 [SMILES: C=CC1CCC(CCc2cc3oc4cc(OCC)c(F)c(F)c4c3c(F)c2F)CC1] |
| 1-2-56 | 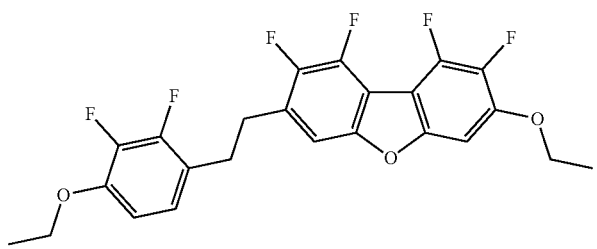 [SMILES: CCOc1ccc(CCc2cc3oc4cc(OCC)c(F)c(F)c4c3c(F)c2F)c(F)c1F] |

| No. | |
|---|---|
| 1-2-57 | 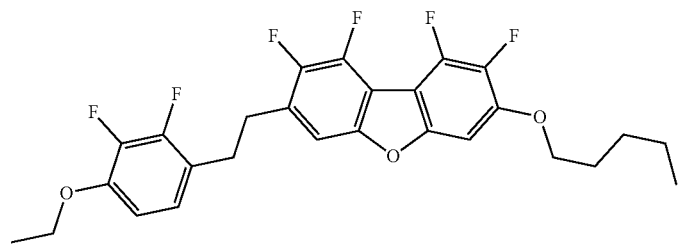 [SMILES: CCCCCOc1cc2oc3cc(CCc4ccc(OCC)c(F)c4F)c(F)c(F)c3c2c(F)c1F] |
| 1-2-58 | 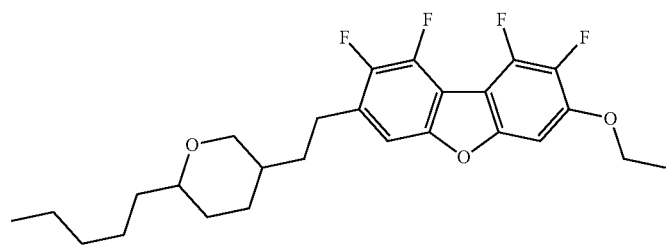 [SMILES: CCCCCC1CCC(CCc2cc3oc4cc(OCC)c(F)c(F)c4c3c(F)c2F)CO1] |
| 1-2-59 | 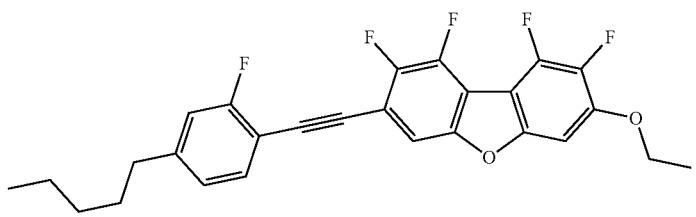 [SMILES: CCCCCc1ccc(C#Cc2cc3oc4cc(OCC)c(F)c(F)c4c3c(F)c2F)c(F)c1] |
| 1-2-60 | 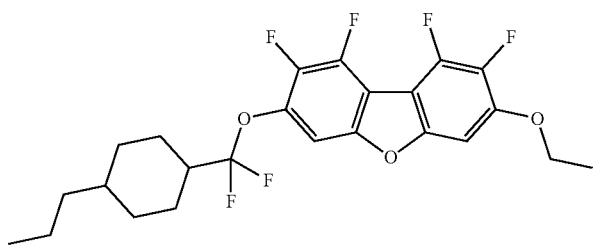 [SMILES: CCCC1CCC(C(F)(F)Oc2cc3oc4cc(OCC)c(F)c(F)c4c3c(F)c2F)CC1] |
| 1-2-61 | 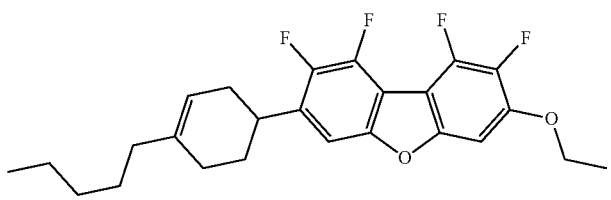 [SMILES: CCCCCC1=CCC(c2cc3oc4cc(OCC)c(F)c(F)c4c3c(F)c2F)CC1] |
| 1-2-62 | 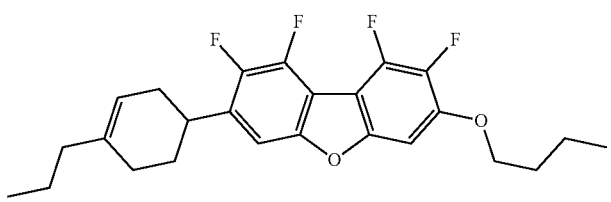 [SMILES: CCCCOc1cc2oc3cc(C4CC=C(CCC)CC4)c(F)c(F)c3c2c(F)c1F] |
| 1-2-63 | 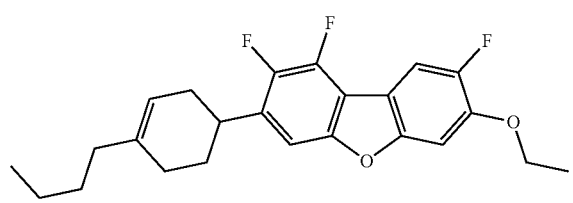 [SMILES: CCCCC1=CCC(c2cc3oc4cc(OCC)c(F)cc4c3c(F)c2F)CC1] |

| No. |  |
|---|---|
| 1-2-64 | 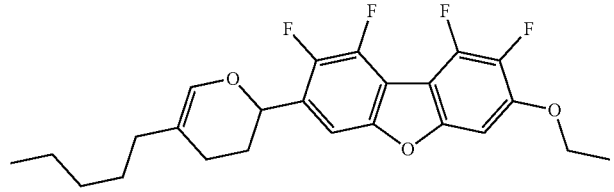 |
| 1-2-65 | 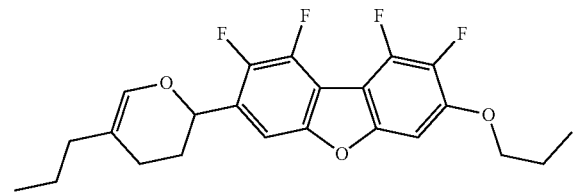 [SMILES: CCCOc1cc2oc3cc(C4CCC(CCC)=CO4)c(F)c(F)c3c2c(F)c1F] |
| 1-2-66 | 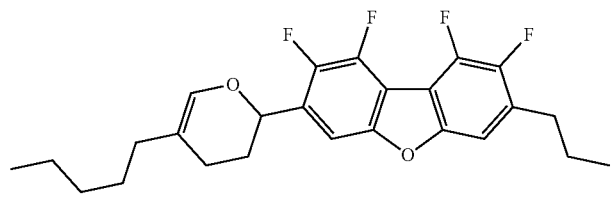 |
| 1-2-67 | 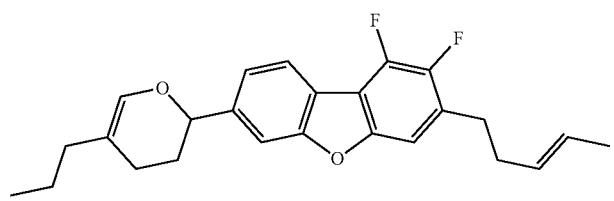 [SMILES: C/C=C/CCc1cc2oc3cc(C4CCC(CCC)=CO4)ccc3c2c(F)c1F] |
| 1-2-68 | 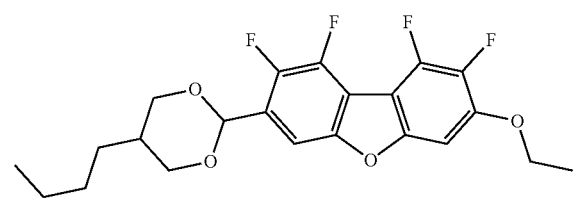 [SMILES: CCCCC1COC(c2cc3oc4cc(OCC)c(F)c(F)c4c3c(F)c2F)OC1] |
| 1-2-69 | 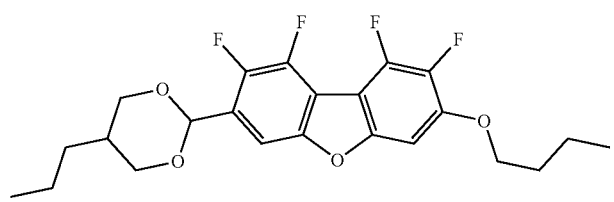 [SMILES: CCCCOc1cc2oc3cc(C4OCC(CCC)CO4)c(F)c(F)c3c2c(F)c1F] |
| 1-2-70 | 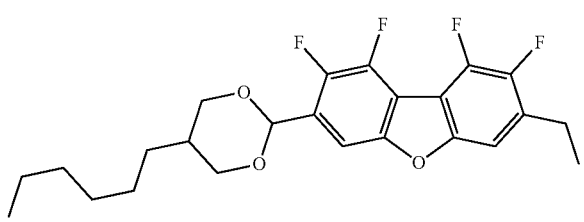 [SMILES: CCCCCCC1COC(c2cc3oc4cc(CC)c(F)c(F)c4c3c(F)c2F)OC1] |

| No. | |
|---|---|
| 1-2-71 | 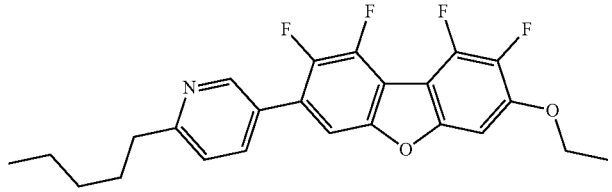 |
| 1-2-72 | 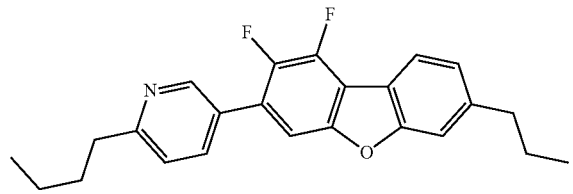 [SMILES: CCCCc1ccc(-c2cc3oc4cc(CCC)ccc4c3c(F)c2F)cn1] |
| 1-2-73 | 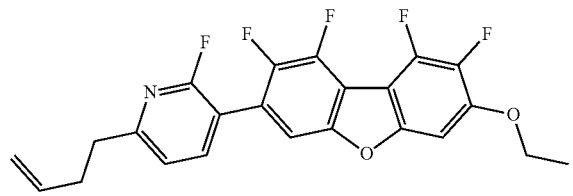 [SMILES: C=CCCc1ccc(-c2cc3oc4cc(OCC)c(F)c(F)c4c3c(F)c2F)c(F)n1] |
| 1-2-74 | 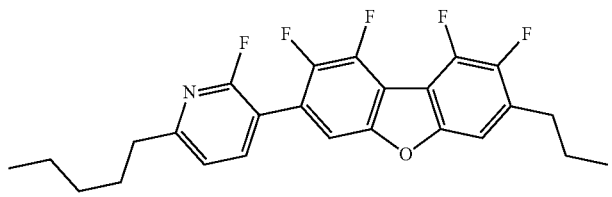 [SMILES: CCCCCc1ccc(-c2cc3oc4cc(CCC)c(F)c(F)c4c3c(F)c2F)c(F)n1] |
| 1-2-75 | 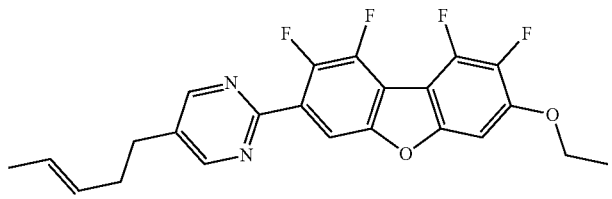 [SMILES: C/C=C/CCc1cnc(-c2cc3oc4cc(OCC)c(F)c(F)c4c3c(F)c2F)nc1] |
| 1-2-76 | 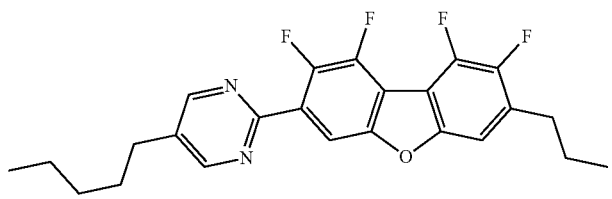 |
| 1-2-77 | 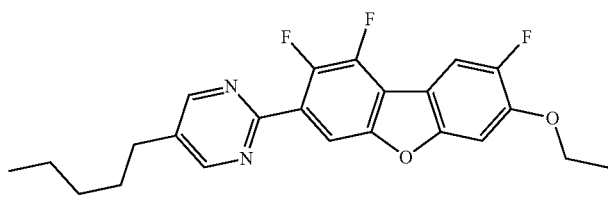 [SMILES: CCCCCc1cnc(-c2cc3oc4cc(OCC)c(F)cc4c3c(F)c2F)nc1] |

| No. |
|---|
| 1-2-78 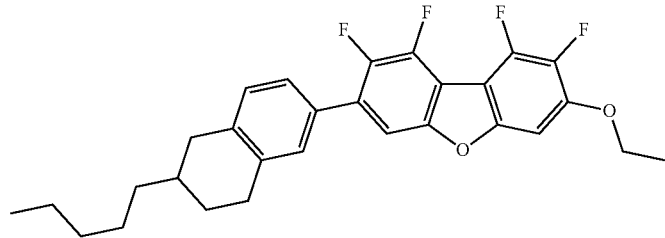 [SMILES: CCCCCC1CCc2cc(-c3cc4oc5cc(OCC)c(F)c(F)c5c4c(F)c3F)ccc2C1] |
| 1-2-79 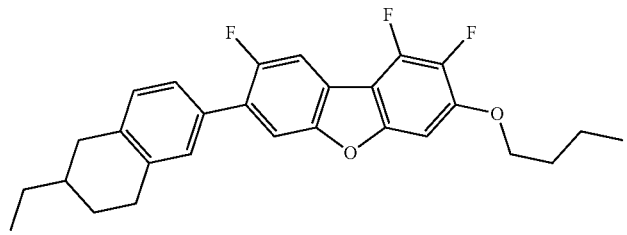 [SMILES: CCCCOc1cc2oc3cc(-c4ccc5c(c4)CCC(CC)C5)c(F)cc3c2c(F)c1F] |
| 1-2-80 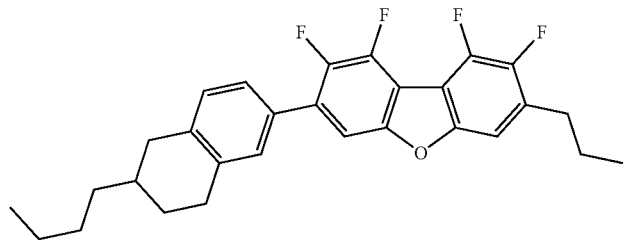 [SMILES: CCCCC1CCc2cc(-c3cc4oc5cc(CCC)c(F)c(F)c5c4c(F)c3F)ccc2C1] |
| 1-3-1 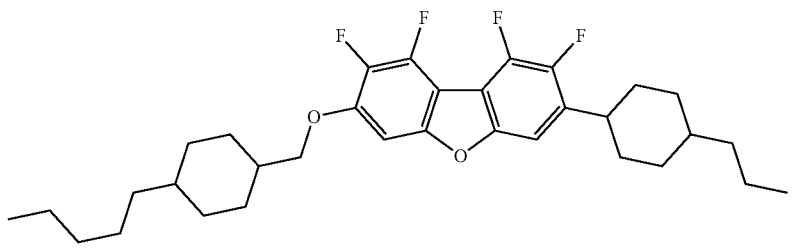 [SMILES: CCCCCC1CCC(COc2cc3oc4cc(C5CCC(CCC)CC5)c(F)c(F)c4c3c(F)c2F)CC1] |
| 1-3-2 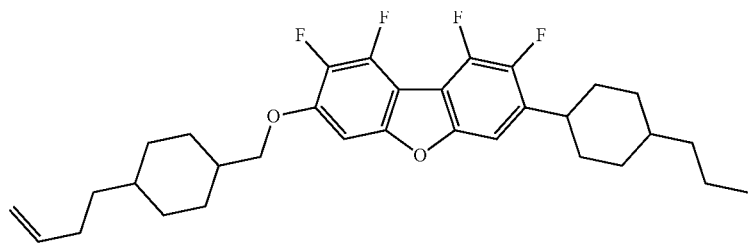 [SMILES: C=CCCC1CCC(COc2cc3oc4cc(C5CCC(CCC)CC5)c(F)c(F)c4c3c(F)c2F)CC1] |
| 1-3-3 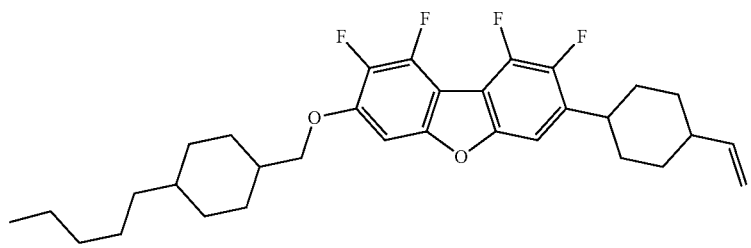 [SMILES: C=CC1CCC(c2cc3oc4cc(OCC5CCC(CCCCC)CC5)c(F)c(F)c4c3c(F)c2F)CC1] |

| No. | |
|---|---|
| 1-3-4 | 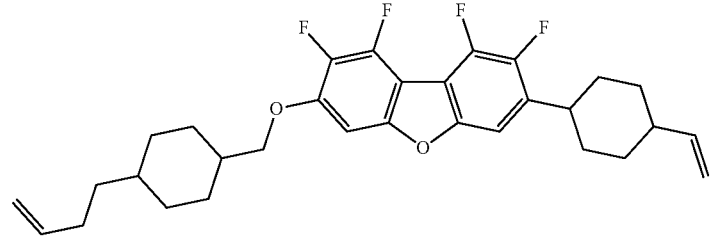 [SMILES: C=CCCC1CCC(COc2cc3oc4cc(C5CCC(C=C)CC5)c(F)c(F)c4c3c(F)c2F)CC1] |
| 1-3-5 | 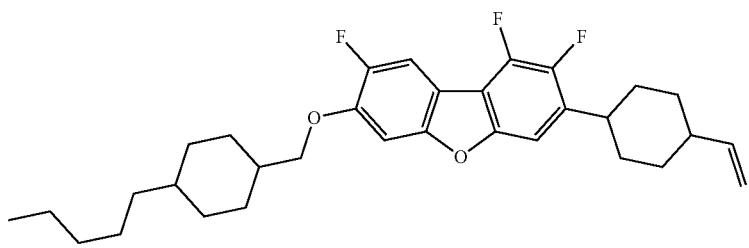 [SMILES: C=CC1CCC(c2cc3oc4cc(OCC5CCC(CCCCC)CC5)c(F)cc4c3c(F)c2F)CC1] |
| 1-3-6 | 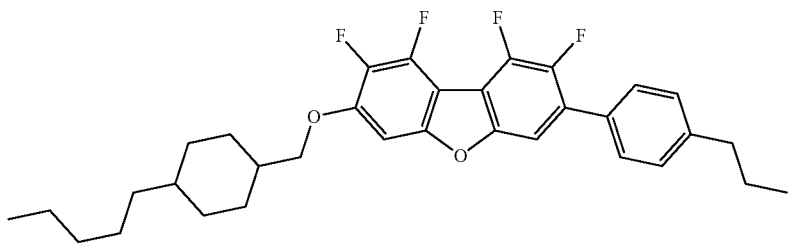 [SMILES: CCCCCC1CCC(COc2cc3oc4cc(-c5ccc(CCC)cc5)c(F)c(F)c4c3c(F)c2F)CC1] |
| 1-3-7 | 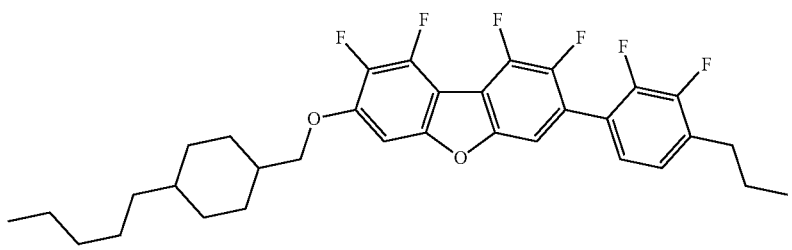 [SMILES: CCCCCC1CCC(COc2cc3oc4cc(-c5ccc(CCC)c(F)c5F)c(F)c(F)c4c3c(F)c2F)CC1] |
| 1-3-8 | 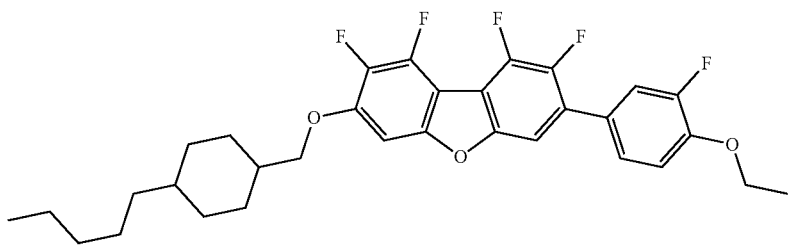 [SMILES: CCCCCC1CCC(COc2cc3oc4cc(-c5ccc(OCC)c(F)c5)c(F)c(F)c4c3c(F)c2F)CC1] |
| 1-3-9 | 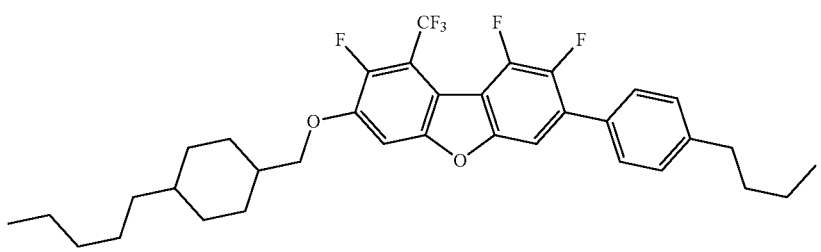 [SMILES: CCCCCC1CCC(COc2cc3oc4cc(-c5ccc(CCCC)cc5)c(F)c(F)c4c3c(C(F)(F)F)c2F)CC1] |

| No. | |
|---|---|
| 1-3-10 | 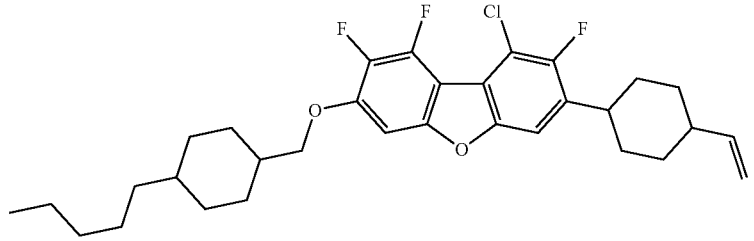 |
| 1-3-11 | 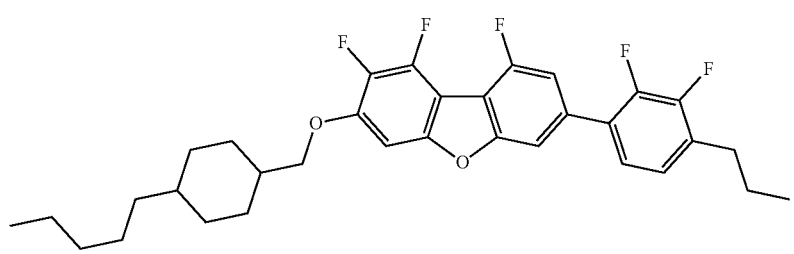 [SMILES: CCCCCC1CCC(COc2cc3oc4cc(-c5ccc(CCC)c(F)c5F)cc(F)c4c3c(F)c2F)CC1] |
| 1-3-12 | 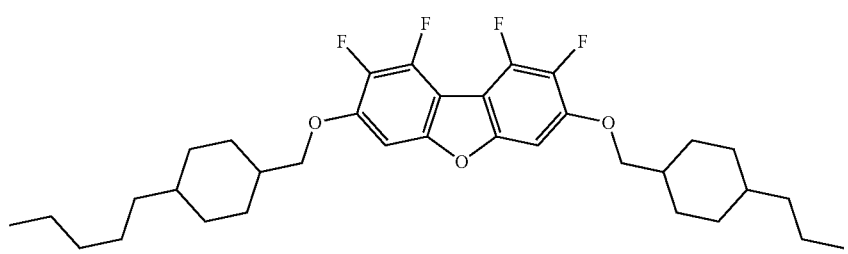 [SMILES: CCCCCC1CCC(COc2cc3oc4cc(OCC5CCC(CCC)CC5)c(F)c(F)c4c3c(F)c2F)CC1] |
| 1-3-13 | 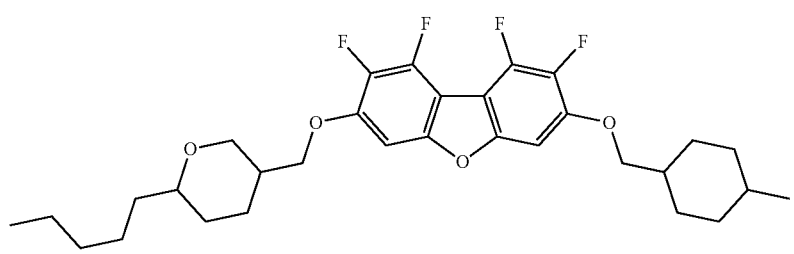 [SMILES: CCCCCC1CCC(COc2cc3oc4cc(OCC5CCC(C)CC5)c(F)c(F)c4c3c(F)c2F)CO1] |
| 1-3-14 | 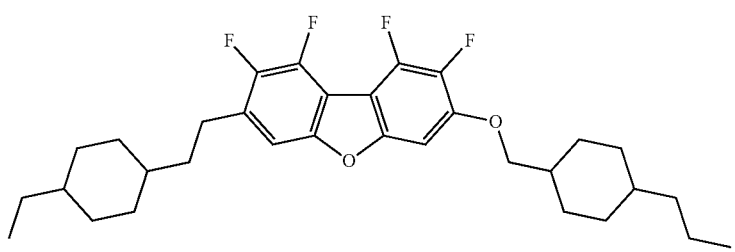 [SMILES: CCCC1CCC(COc2cc3oc4cc(CCC5CCC(CC)CC5)c(F)c(F)c4c3c(F)c2F)CC1] |
| 1-3-15 | 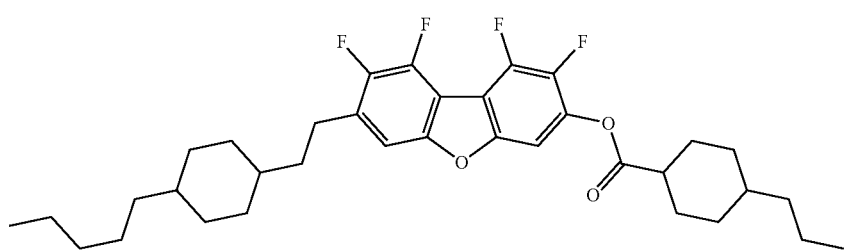 [SMILES: CCCCCC1CCC(CCc2cc3oc4cc(OC(=O)C5CCC(CCC)CC5)c(F)c(F)c4c3c(F)c2F)CC1] |

| No. |
|---|
1-3-16
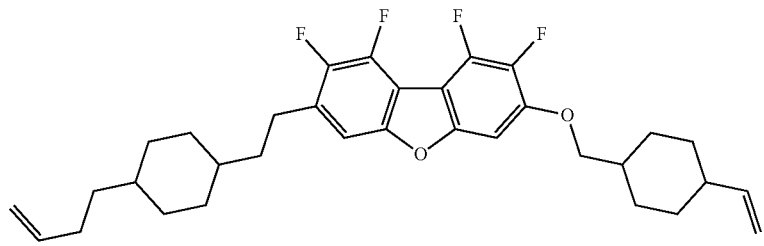 [SMILES: C=CCCC1CCC(CCc2cc3oc4cc(OCC5CCC(C=C)CC5)c(F)c(F)c4c3c(F)c2F)CC1]
1-3-17
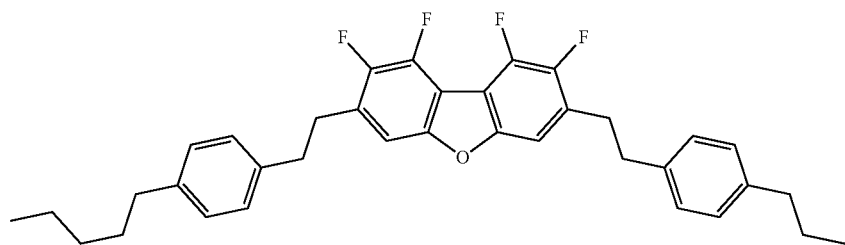 [SMILES: CCCCCc1ccc(CCc2cc3oc4cc(CCc5ccc(CCC)cc5)c(F)c(F)c4c3c(F)c2F)cc1]
1-3-18
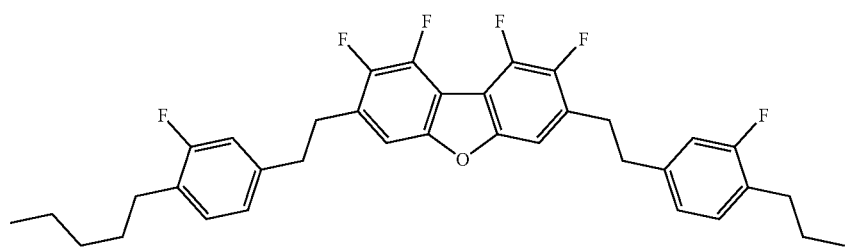 [SMILES: CCCCCc1ccc(CCc2cc3oc4cc(CCc5ccc(CCC)c(F)c5)c(F)c(F)c4c3c(F)c2F)cc1F]
1-3-19
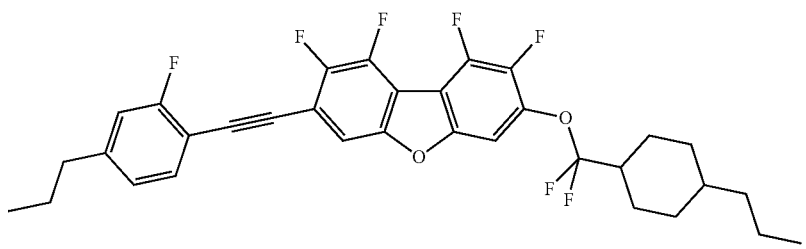 [SMILES: CCCc1ccc(C#Cc2cc3oc4cc(OC(F)(F)C5CCC(CCC)CC5)c(F)c(F)c4c3c(F)c2F)c(F)c1]
1-3-20
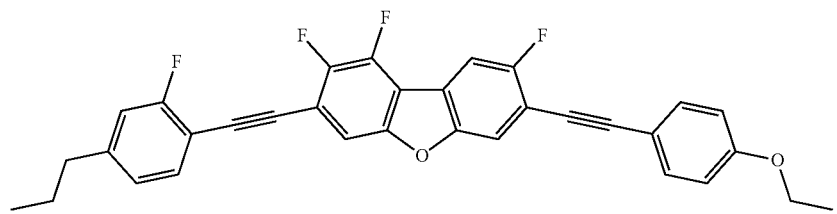 [SMILES: CCCc1ccc(C#Cc2cc3oc4cc(C#Cc5ccc(OCC)cc5)c(F)cc4c3c(F)c2F)c(F)c1]
1-4-1
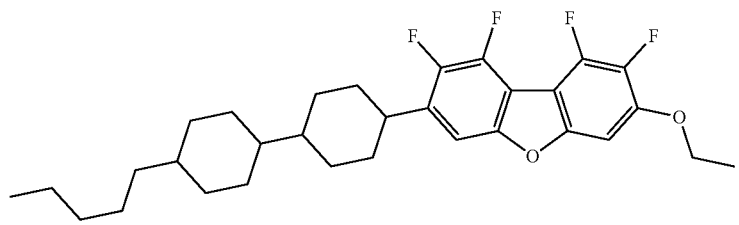 [SMILES: CCCCCC1CCC(C2CCC(c3cc4oc5cc(OCC)c(F)c(F)c5c4c(F)c3F)CC2)CC1]

| No. | |
|---|---|
| 1-4-2 | 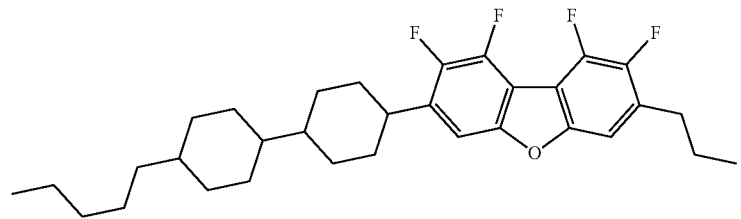 [SMILES: CCCCCC1CCC(C2CCC(c3cc4oc5cc(CCC)c(F)c(F)c5c4c(F)c3F)CC2)CC1] |
| 1-4-3 | 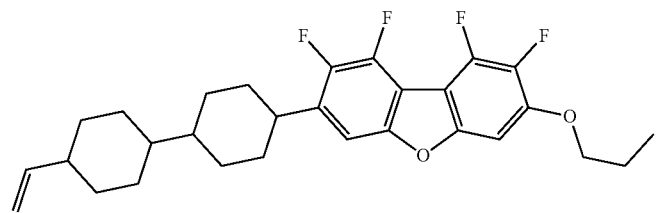 [SMILES: C=CC1CCC(C2CCC(c3cc4oc5cc(OCCC)c(F)c(F)c5c4c(F)c3F)CC2)CC1] |
| 1-4-4 | 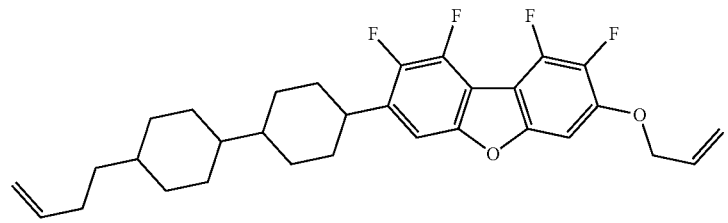 [SMILES: C=CCCC1CCC(C2CCC(c3cc4oc5cc(OCC=C)c(F)c(F)c5c4c(F)c3F)CC2)CC1] |
| 1-4-5 | 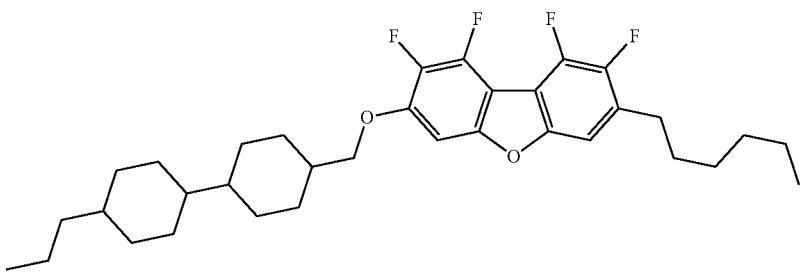 [SMILES: CCCCCCc1cc2oc3cc(OCC4CCC(C5CCC(CCC)CC5)CC4)c(F)c(F)c3c2c(F)c1F] |
| 1-4-6 | 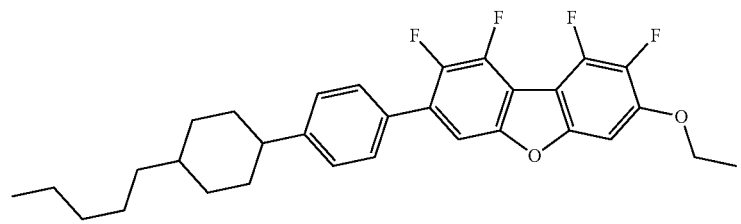 [SMILES: CCCCCC1CCC(c2ccc(-c3cc4oc5cc(OCC)c(F)c(F)c5c4c(F)c3F)cc2)CC1] |
| 1-4-7 | 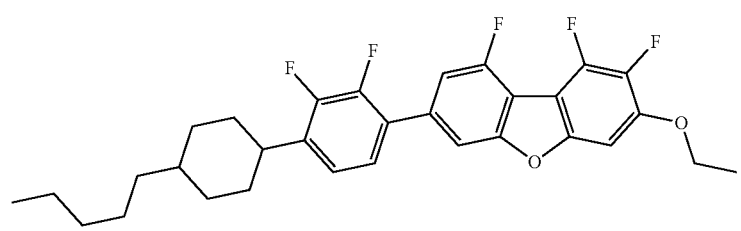 [SMILES: CCCCCC1CCC(c2ccc(-c3cc(F)c4c(c3)oc3cc(OCC)c(F)c(F)c34)c(F)c2F)CC1] |

| No. |
|---|
| 1-4-8 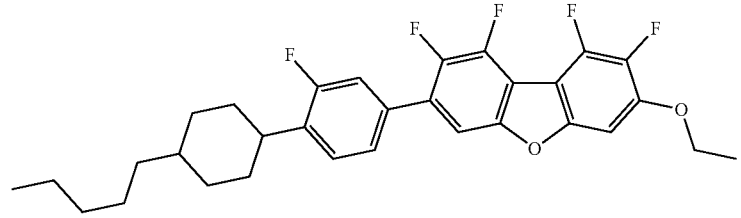 [SMILES: CCCCCC1CCC(c2ccc(-c3cc4oc5cc(OCC)c(F)c(F)c5c4c(F)c3F)cc2F)CC1] |
| 1-4-9 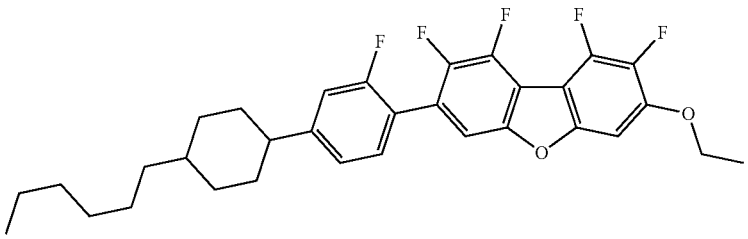 [SMILES: CCCCCCC1CCC(c2ccc(-c3cc4oc5cc(OCC)c(F)c(F)c5c4c(F)c3F)c(F)c2)CC1] |
| 1-4-10 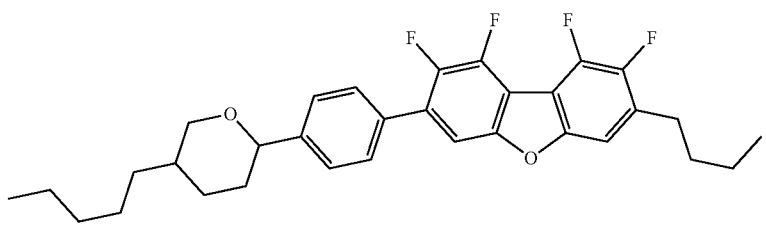 [SMILES: CCCCCC1CCC(c2ccc(-c3cc4oc5cc(CCCC)c(F)c(F)c5c4c(F)c3F)cc2)OC1] |
| 1-4-11 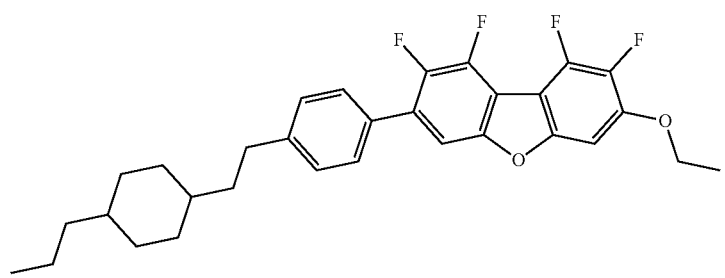 [SMILES: CCCC1CCC(CCc2ccc(-c3cc4oc5cc(OCC)c(F)c(F)c5c4c(F)c3F)cc2)CC1] |
| 1-4-12 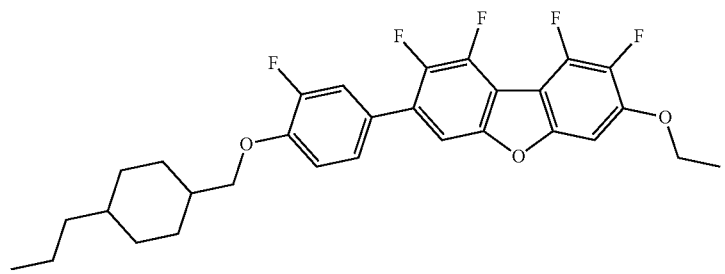 [SMILES: CCCC1CCC(COc2ccc(-c3cc4oc5cc(OCC)c(F)c(F)c5c4c(F)c3F)cc2F)CC1] |
| 1-4-13 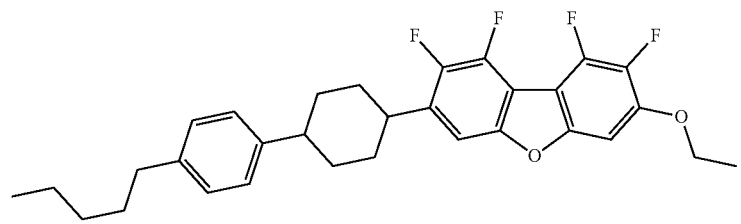 [SMILES: CCCCCc1ccc(C2CCC(c3cc4oc5cc(OCC)c(F)c(F)c5c4c(F)c3F)CC2)cc1] |

-continued
| No. | |
|---|---|
| 1-4-14 | 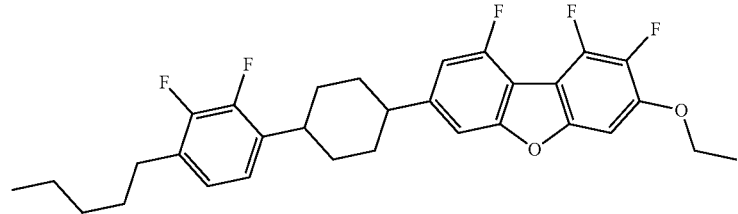 [SMILES: CCCCCc1ccc(C2CCC(c3cc(F)c4c(c3)oc3cc(OCC)c(F)c(F)c34)CC2)c(F)c1F] |
| 1-4-15 | 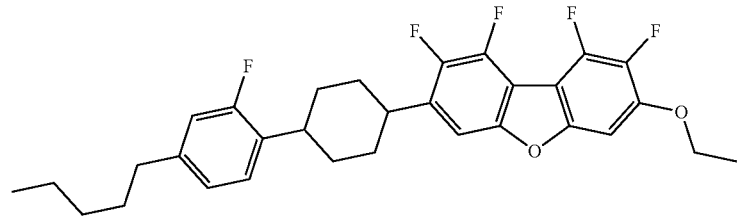 [SMILES: CCCCCc1ccc(C2CCC(c3cc4oc5cc(OCC)c(F)c(F)c5c4c(F)c3F)CC2)c(F)c1] |
| 1-4-16 | 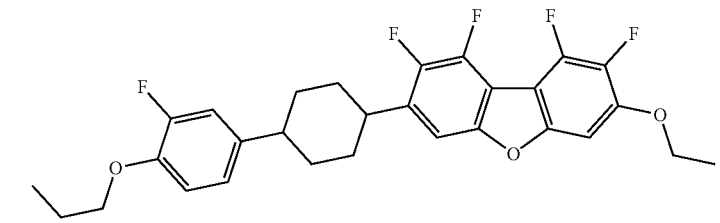 [SMILES: CCCOc1ccc(C2CCC(c3cc4oc5cc(OCC)c(F)c(F)c5c4c(F)c3F)CC2)cc1F] |
| 1-4-17 | 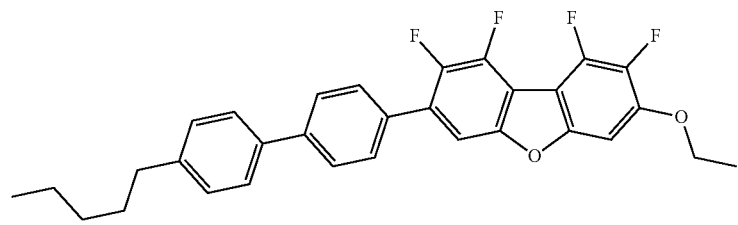 [SMILES: CCCCCc1ccc(-c2ccc(-c3cc4oc5cc(OCC)c(F)c(F)c5c4c(F)c3F)cc2)cc1] |
| 1-4-18 | 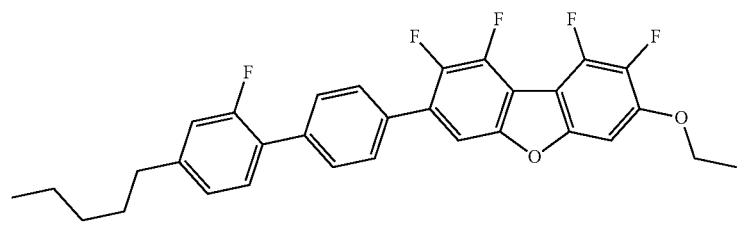 [SMILES: CCCCCc1ccc(-c2ccc(-c3cc4oc5cc(OCC)c(F)c(F)c5c4c(F)c3F)cc2)c(F)c1] |
| 1-4-19 | 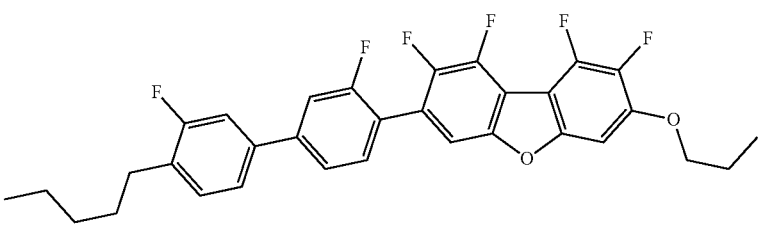 [SMILES: CCCCCc1ccc(-c2ccc(-c3cc4oc5cc(OCCC)c(F)c(F)c5c4c(F)c3F)c(F)c2)cc1F] |
| 1-4-20 | 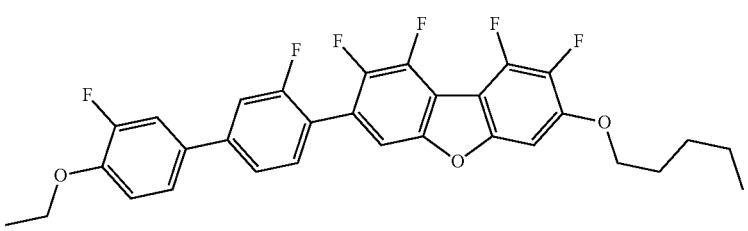 [SMILES: CCCCCOc1cc2oc3cc(-c4ccc(-c5ccc(OCC)c(F)c5)cc4F)c(F)c(F)c3c2c(F)c1F] |

-continued
| No. | |
|---|---|
| 1-5-1 | 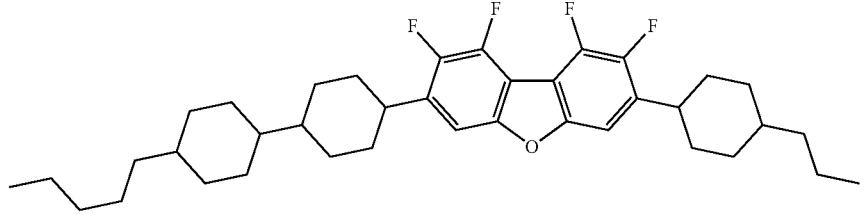 [SMILES: CCCCCC1CCC(C2CCC(c3cc4oc5cc(C6CCC(CCC)CC6)c(F)c(F)c5c4c(F)c3F)CC2)CC1] |
| 1-5-2 | 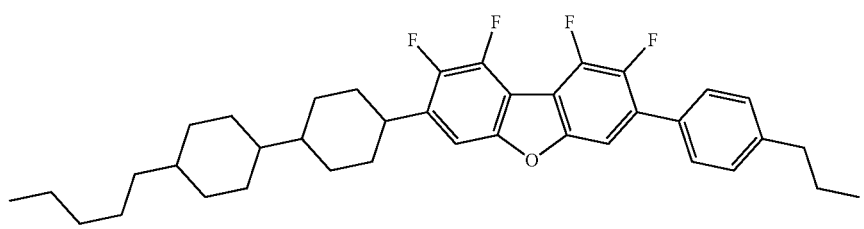 [SMILES: CCCCCC1CCC(C2CCC(c3cc4oc5cc(-c6ccc(CCC)cc6)c(F)c(F)c5c4c(F)c3F)CC2)CC1] |
| 1-5-3 | 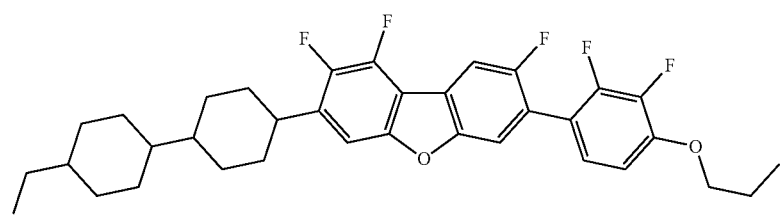 [SMILES: CCCOc1ccc(-c2cc3oc4cc(C5CCC(C6CCC(CC)CC6)CC5)c(F)c(F)c4c3cc2F)c(F)c1F] |
| 1-5-4 | 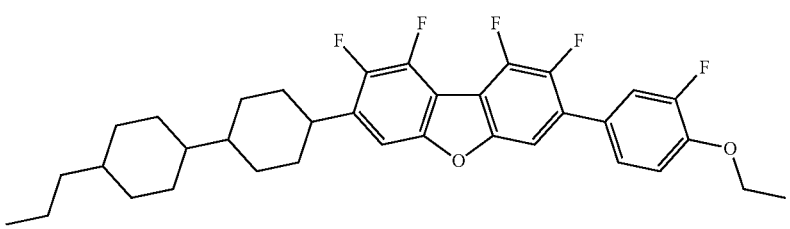 [SMILES: CCCC1CCC(C2CCC(c3cc4oc5cc(-c6ccc(OCC)c(F)c6)c(F)c(F)c5c4c(F)c3F)CC2)CC1] |
| 1-5-5 | 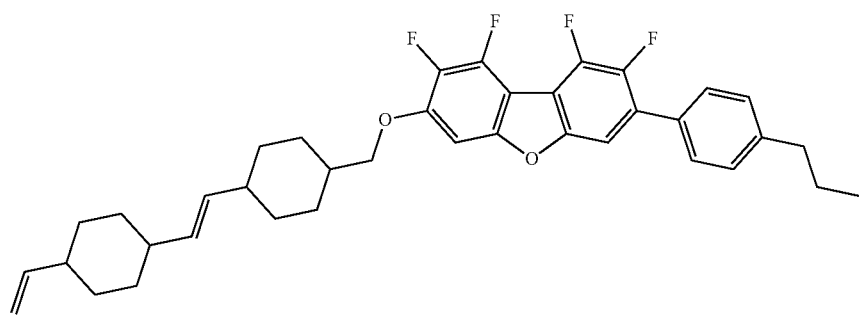 [SMILES: C=CC1CCC(/C=C/C2CCC(COc3cc4oc5cc(-c6ccc(CCC)cc6)c(F)c(F)c5c4c(F)c3F)CC2)CC1] |
| 1-5-6 | 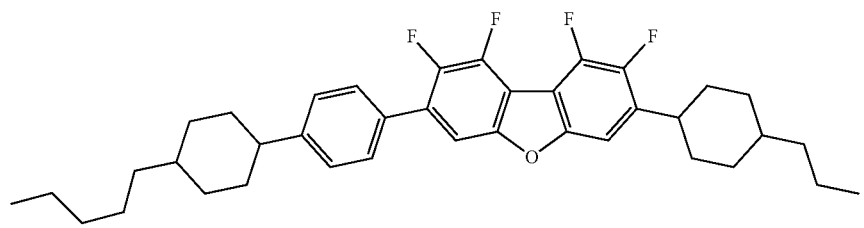 [SMILES: CCCCCC1CCC(c2ccc(-c3cc4oc5cc(C6CCC(CCC)CC6)c(F)c(F)c5c4c(F)c3F)cc2)CC1] |

| No. | |
|---|---|
| 1-5-7 | 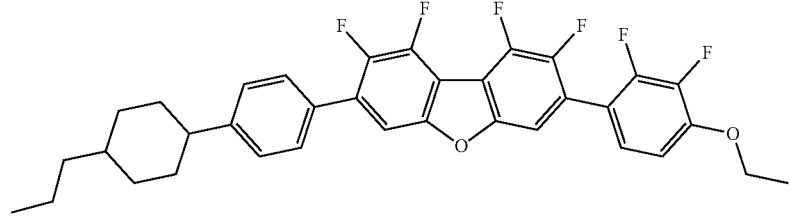 [SMILES: CCCC1CCC(c2ccc(-c3cc4oc5cc(-c6ccc(OCC)c(F)c6F)c(F)c(F)c5c4c(F)c3F)cc2)CC1] |
| 1-5-8 | 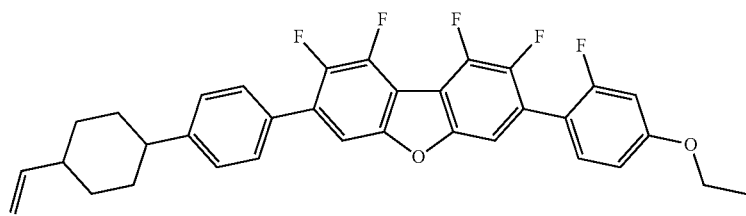 [SMILES: C=CC1CCC(c2ccc(-c3cc4oc5cc(-c6ccc(OCC)cc6F)c(F)c(F)c5c4c(F)c3F)cc2)CC1] |
| 1-5-9 | 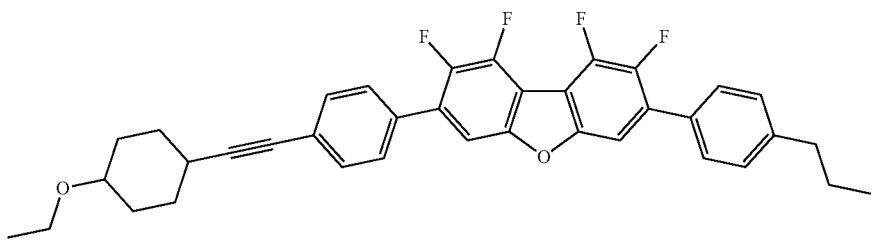 [SMILES: CCCc1ccc(-c2cc3oc4cc(-c5ccc(C#CC6CCC(OCC)CC6)cc5)c(F)c(F)c4c3c(F)c2F)cc1] |
| 1-5-10 | 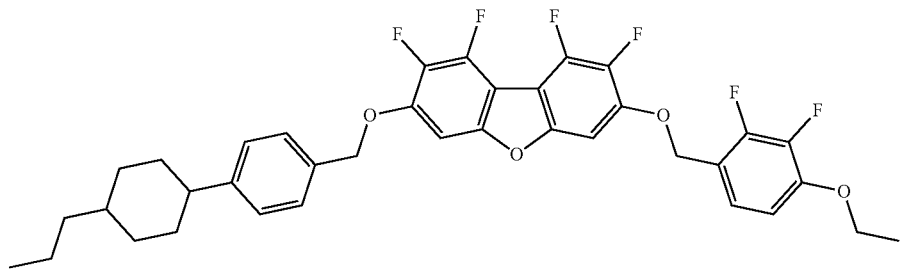 [SMILES: CCCC1CCC(c2ccc(COc3cc4oc5cc(OCc6ccc(OCC)c(F)c6F)c(F)c(F)c5c4c(F)c3F)cc2)CC1] |
| 1-5-11 | 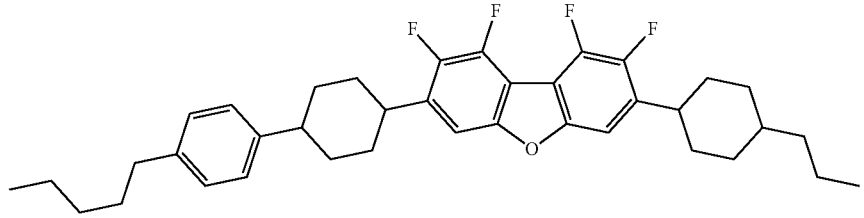 [SMILES: CCCCCc1ccc(C2CCC(c3cc4oc5cc(C6CCC(CCC)CC6)c(F)c(F)c5c4c(F)c3F)CC2)cc1] |
| 1-5-12 | 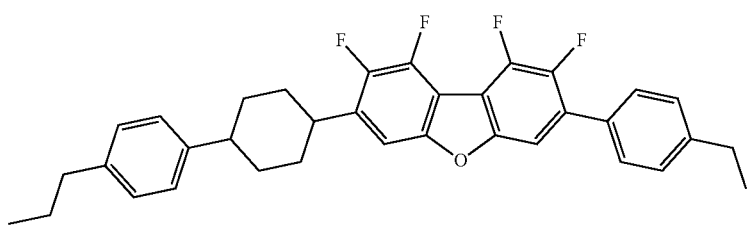 [SMILES: CCCc1ccc(C2CCC(c3cc4oc5cc(-c6ccc(CC)cc6)c(F)c(F)c5c4c(F)c3F)CC2)cc1] |

|No.|
|---|
| 1-5-13 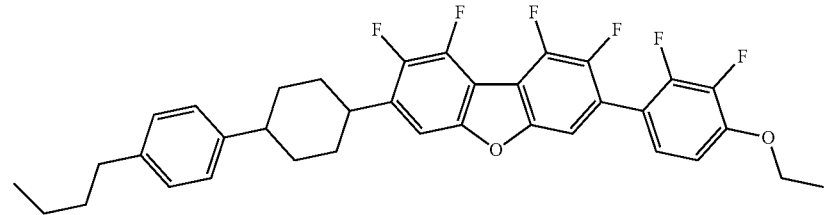 [SMILES: CCCCc1ccc(C2CCC(c3cc4oc5cc(-c6ccc(OCC)c(F)c6F)c(F)c(F)c5c4c(F)c3F)CC2)cc1] |
| 1-5-14 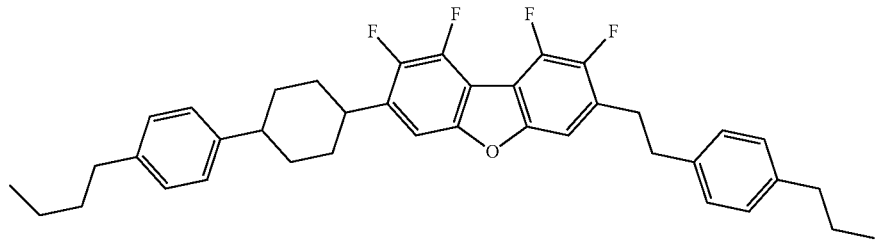 [SMILES: CCCCc1ccc(C2CCC(c3cc4oc5cc(CCc6ccc(CCC)cc6)c(F)c(F)c5c4c(F)c3F)CC2)cc1] |
| 1-5-15 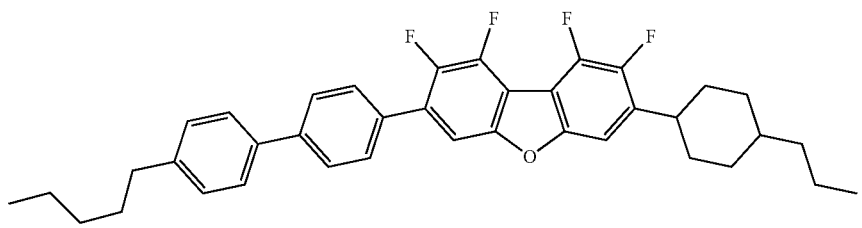 [SMILES: CCCCCc1ccc(-c2ccc(-c3cc4oc5cc(C6CCC(CCC)CC6)c(F)c(F)c5c4c(F)c3F)cc2)cc1] |
| 1-5-16 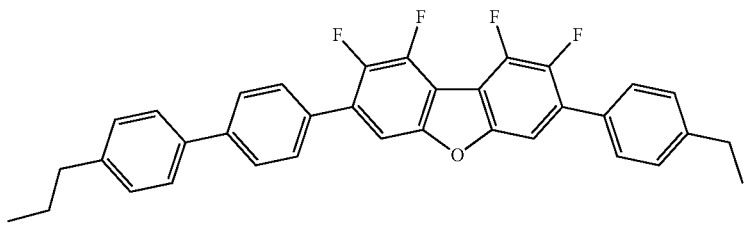 [SMILES: CCCc1ccc(-c2ccc(-c3cc4oc5cc(-c6ccc(CC)cc6)c(F)c(F)c5c4c(F)c3F)cc2)cc1] |
| 1-5-17 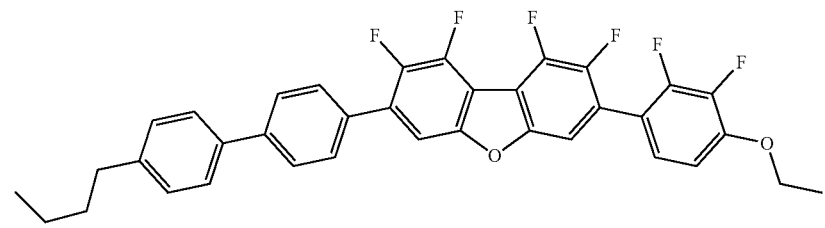 [SMILES: CCCCc1ccc(-c2ccc(-c3cc4oc5cc(-c6ccc(OCC)c(F)c6F)c(F)c(F)c5c4c(F)c3F)cc2)cc1] |
| 1-5-18 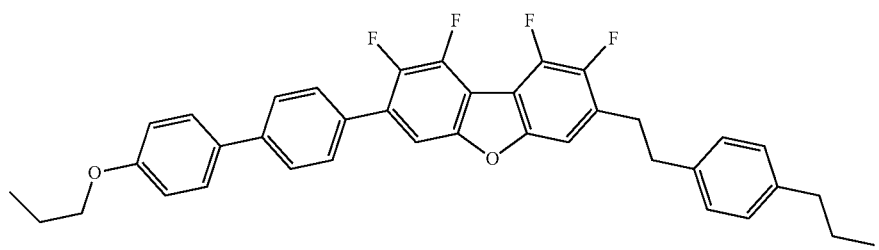 [SMILES: CCCOc1ccc(-c2ccc(-c3cc4oc5cc(CCc6ccc(CCC)cc6)c(F)c(F)c5c4c(F)c3F)cc2)cc1] |

| No. | |
|---|---|
| 1-5-19 | 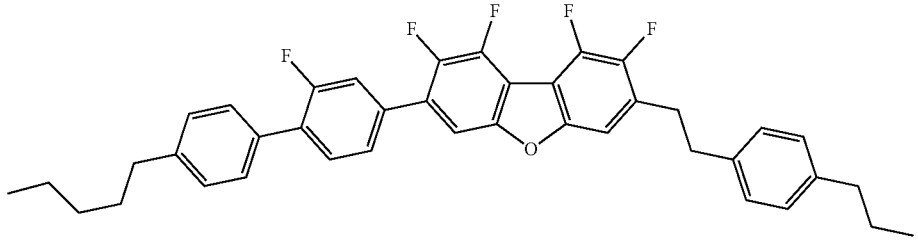 [SMILES: CCCCCc1ccc(-c2ccc(-c3cc4oc5cc(CCc6ccc(CCC)cc6)c(F)c(F)c5c4c(F)c3F)cc2F)cc1] |
| 1-5-20 | 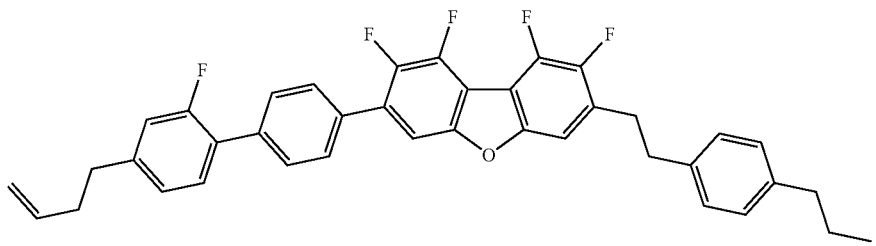 [SMILES: C=CCCc1ccc(-c2ccc(-c3cc4oc5cc(CCc6ccc(CCC)cc6)c(F)c(F)c5c4c(F)c3F)cc2)c(F)c1] |

2. Examples of Composition

The invention will be described in greater detail by way of Examples. The Examples include a typical example, and therefore the invention is not limited by the Examples. For example, in addition to compositions in Use Examples, the invention includes a mixture of a composition in Use Example 1 and a composition in Use Example 2. The invention also includes a mixture prepared by mixing at least two of the compositions in the Use Examples. Compounds in the Use Examples were represented using symbols according to definitions in Table 4 described below. In Table 4, the configuration of 1,4-cyclohexylene is trans. A parenthesized number next to a symbolized compound in the Use Examples represents a chemical formula to which the compound belongs. A symbol (-) means a liquid crystal compound different from compounds (1) to (15). A proportion (percentage) of the liquid crystal compound is expressed in terms of weight percent (% by weight) based on the weight of the liquid crystal composition containing no additives. Values of the physical properties of the composition are summarized in a last part. The physical properties were measured according to the methods described above, and measured values are directly described (without extrapolation).

TABLE 4

Method for description of compounds using symbols
R—($A_1$)—$Z_1$— . . . —$Z_n$—($A_n$)—R'

| 1) Left-terminal group R— | Symbol |
|---|---|
| $C_nH_{2n+1}$— | n- |
| $C_nH_{2n+1}O$— | nO— |
| $C_mH_{2m+1}OC_nH_{2n}$— | mOn— |
| $CH_2=CH$— | V— |
| $C_nH_{2n+1}$—CH=CH— | nV— |
| $CH_2=CH$—$C_nH_{2n}$— | Vn— |
| $C_mH_{2m+1}$—CH=CH—$C_nH_{2n}$— | mVn— |
| $CF_2=CH$— | VFF— |
| $CF_2=CH$—$C_nH_{2n}$— | VFFn— |

| 2) Right-terminal group —R' | Symbol |
|---|---|
| —$C_nH_{2n+1}$ | -n |
| —$OC_nH_{2n+1}$ | —On |
| —$COOCH_3$ | —EMe |
| —CH=$CH_2$ | —V |
| —CH=CH—$C_nH_{2n+1}$ | —Vn |
| —$C_nH_{2n}$—CH=$CH_2$ | —nV |
| —$C_mH_{2m}$—CH=CH—$C_nH_{2n+1}$ | —mVn |
| —CH=$CF_2$ | —VFF |
| —F | —F |
| —Cl | —CL |
| —$OCF_3$ | —OCF3 |
| —$OCF_2H$ | —OCF2H |
| —$CF_3$ | —CF3 |

TABLE 4-continued
| Method for description of compounds using symbols R—(A₁)—Z₁—...—Zₙ—(Aₙ)—R' | |
|---|---|
| —OCH=CH—CF₃ | —OVCF3 |
| —C≡N | —C |
| 3) Bonding group —Zₙ— | Symbol |
|---|---|
| —CₙH₂ₙ— | n |
| —COO— | E |
| —CH=CH— | V |
| —CH₂O-A50s | 1O |
| —OCH₂— | O1 |
| —CF₂O— | X |
| —C≡C— | T |
| 4) Ring structure —Aₙ— | Symbol |
|---|---|
| 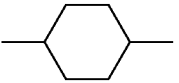 | H |
|  | B |
| 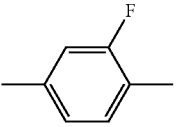 | B(F) |
| 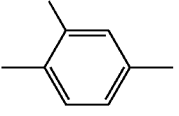 | B(2F) |
| 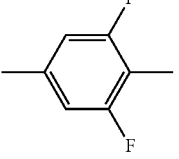 | B(F, F) |
| 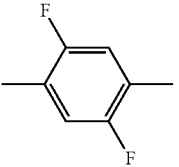 | B(2F, 5F) |
| 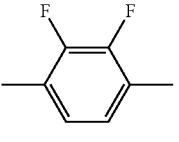 | B(2F, 3F) |
| 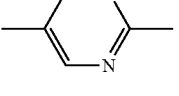 | Py |
| 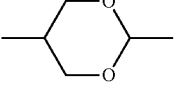 | G |

TABLE 4-continued
| Method for description of compounds using symbols |
| --- |
| R—(A$_1$)—Z$_1$—...—Z$_n$—(A$_n$)—R' |
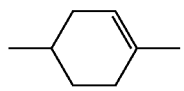 ch
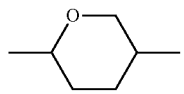 Dh
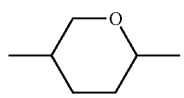 dh
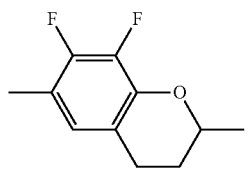 Cro(7F, 8F)
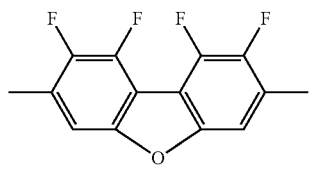 BF(1F, 2F, 8F, 9F)
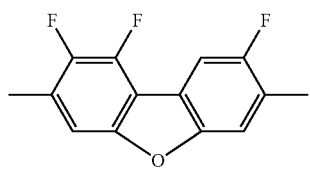 BF(1F, 2F, 8F)
5) Examples of description
Example 1. 5-H1OBF(1F,2F,8F,9F)-3
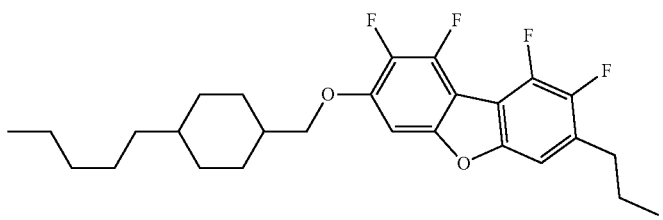 [SMILES: CCCCCC1CCC(COc2cc3oc4cc(CCC)c(F)c(F)c4c3c(F)c2F)CC1]
Example 2. 5-H1OBF(1F,2F,8F)-3
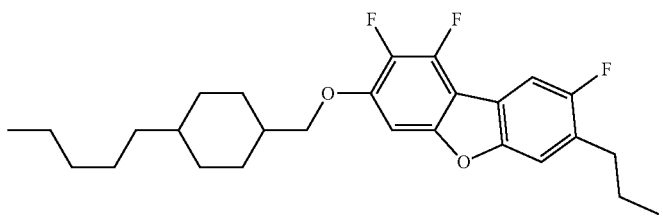

Use Example 1

| | | |
|---|---|---|
| 5-H1OBF(1F,2F,8F,9F)-3 | (1-2-43) | 5% |
| 3-HB-O2 | (2-5) | 15% |
| 2-BTB-1 | (2-10) | 3% |
| 3-HHB-1 | (3-1) | 8% |
| 3-HHB-O1 | (3-1) | 5% |
| 3-HHB-3 | (3-1) | 13% |
| 3-HHB-F | (13-1) | 4% |
| 2-HHB(F)-F | (13-2) | 6% |
| 3-HHB(F)-F | (13-2) | 8% |
| 5-HHB(F)-F | (13-2) | 6% |
| 3-HHB(F,F)-F | (13-3) | 4% |
| 3-HHEB-F | (13-10) | 4% |
| 5-HHEB-F | (13-10) | 5% |
| 2-HB-C | (15-1) | 5% |
| 3-HB-C | (15-1) | 9% |

NI = 103.0° C.; η = 23.5 mPa · s; Δn = 0.104; Δε = 3.7.

Use Example 2

| | | |
|---|---|---|
| 5O-BF(1F,2F,8F,9F)-3 | (1-1-7) | 3% |
| 3-HH-4 | (2-1) | 10% |
| 3-HB-O2 | (2-5) | 10% |
| 3-HB-CL | (12-2) | 10% |
| 3-HHB(F,F)-F | (13-3) | 5% |
| 3-HBB(F,F)-F | (13-24) | 25% |
| 5-HBB(F,F)-F | (13-24) | 23% |
| 5-HBB(F)B-2 | (4-5) | 7% |
| 5-HBB(F)B-3 | (4-5) | 7% |

NI = 77.3° C.; η = 23.0 mPa · s; Δn = 0.123; Δε = 4.8.

Use Example 3

| | | |
|---|---|---|
| 5-Dh1OBF(1F,2F,8F,9F)-O2 | (1-2-50) | 4% |
| 3-HB-O2 | (2-5) | 8% |
| 7-HB(F,F)-F | (12-4) | 4% |
| 2-HHB(F)-F | (13-2) | 8% |
| 3-HHB(F)-F | (13-2) | 8% |
| 5-HHB(F)-F | (13-2) | 8% |
| 2-HBB-F | (13-22) | 5% |
| 3-HBB-F | (13-22) | 5% |
| 5-HBB-F | (13-22) | 3% |
| 2-HBB(F)-F | (13-23) | 6% |
| 3-HBB(F)-F | (13-23) | 8% |
| 5-HBB(F)-F | (13-23) | 15% |
| 3-HBB(F,F)-F | (13-24) | 8% |
| 5-HBB(F,F)-F | (13-24) | 10% |

Use Example 4

| | | |
|---|---|---|
| 5-BBF(1F,2F,8F,9F)-O2 | (1-2-22) | 6% |
| 3-HH-4 | (2-1) | 10% |
| 3-HH-5 | (2-1) | 4% |
| 1O1-HBBH-5 | (4-1) | 4% |
| 5-HB-CL | (12-2) | 13% |
| 3-HHB-F | (13-1) | 4% |
| 3-HHB-CL | (13-1) | 4% |
| 4-HHB-CL | (13-1) | 4% |
| 3-HHB(F)-F | (13-2) | 8% |
| 4-HHB(F)-F | (13-2) | 8% |
| 5-HHB(F)-F | (13-2) | 8% |
| 7-HHB(F)-F | (13-2) | 6% |
| 5-HBB(F)-F | (13-23) | 4% |
| 3-HHBB(F,F)-F | (14-6) | 3% |
| 4-HHBB(F,F)-F | (14-6) | 3% |
| 5-HHBB(F,F)-F | (14-6) | 4% |
| 3-HH2BB(F,F)-F | (14-15) | 4% |
| 4-HH2BB(F,F)-F | (14-15) | 3% |

Use Example 5

| | | |
|---|---|---|
| 5-HBF(1F,2F,8F,9F)-O2 | (1-2-5) | 3% |
| 1O1-HBBH-4 | (4-1) | 4% |
| 1O1-HBBH-5 | (4-1) | 3% |
| 3-HHB(F,F)-F | (13-3) | 9% |
| 3-H2HB(F,F)-F | (13-15) | 8% |
| 4-H2HB(F,F)-F | (13-15) | 10% |
| 5-H2HB(F,F)-F | (13-15) | 8% |
| 3-HBB(F,F)-F | (13-24) | 17% |
| 5-HBB(F,F)-F | (13-24) | 19% |
| 3-H2BB(F,F)-F | (13-27) | 11% |
| 5-HHBB(F,F)-F | (14-6) | 3% |
| 3-HH2BB(F,F)-F | (14-15) | 3% |
| 5-HHEBB-F | (14-17) | 2% |

Use Example 6

| | | |
|---|---|---|
| 5O-BF(1F,2F,8F,9F)-O2 | (1-1-2) | 5% |
| 5-HBBH-3 | (4-1) | 3% |
| 3-HB(F)BH-3 | (4-2) | 3% |
| 5-HB-F | (12-2) | 12% |
| 6-HB-F | (12-2) | 9% |
| 7-HB-F | (12-2) | 7% |
| 2-HHB-OCF3 | (13-1) | 5% |
| 3-HHB-OCF3 | (13-1) | 5% |
| 4-HHB-OCF3 | (13-1) | 7% |
| 5-HHB-OCF3 | (13-1) | 4% |
| 3-HHB(F,F)-OCF2H | (13-3) | 5% |
| 3-HHB(F,F)-OCF3 | (13-3) | 6% |
| 3-HH2B-OCF3 | (13-4) | 3% |
| 5-HH2B-OCF3 | (13-4) | 4% |
| 3-HH2B(F)-F | (13-5) | 3% |
| 3-HBB(F)-F | (13-23) | 12% |
| 5-HBB(F)-F | (13-23) | 7% |

Use Example 7

| | | |
|---|---|---|
| V-H1OBF(1F,2F,8F,9F)-3 | (1-2-46) | 3% |
| 3-HH-4 | (2-1) | 8% |
| 3-HB-O2 | (2-5) | 4% |
| 3-HHB-1 | (3-1) | 3% |
| 5-HB-CL | (12-2) | 10% |
| 3-HHB(F,F)-F | (13-3) | 8% |
| 3-HHEB(F,F)-F | (13-12) | 8% |
| 4-HHEB(F,F)-F | (13-12) | 5% |
| 5-HHEB(F,F)-F | (13-12) | 5% |
| 3-HBB(F,F)-F | (13-24) | 15% |
| 5-HBB(F,F)-F | (13-24) | 13% |
| 2-HBEB(F,F)-F | (13-39) | 4% |
| 3-HBEB(F,F)-F | (13-39) | 4% |
| 5-HBEB(F,F)-F | (13-39) | 4% |
| 3-HHBB(F,F)-F | (14-6) | 6% |

Use Example 8

| | | |
|---|---|---|
| 5-H1OBF(1F,2F,8F)-3 | (1-2-45) | 5% |
| 3-HB-CL | (12-2) | 5% |
| 5-HB-CL | (12-2) | 4% |
| 3-HHB-OCF3 | (13-1) | 5% |
| V-HHB(F)-F | (13-2) | 5% |
| 3-HHB(F)-F | (13-2) | 3% |
| 5-HHB(F)-F | (13-2) | 4% |
| 3-H2HB-OCF3 | (13-13) | 3% |
| 5-H2HB(F,F)-F | (13-15) | 5% |
| 5-H4HB-OCF3 | (13-19) | 15% |
| 3-H4HB(F,F)-CF3 | (13-21) | 8% |
| 5-H4HB(F,F)-CF3 | (13-21) | 10% |
| 5-H4HB(F,F)-F | (13-21) | 7% |
| 2-H2BB(F)-F | (13-26) | 5% |
| 3-H2BB(F)-F | (13-26) | 8% |
| 3-HBEB(F,F)-F | (13-39) | 8% |

Use Example 9

| | | |
|---|---|---|
| 5-H1OBF(1F,2F,8F,9F)-3 | (1-2-43) | 4% |
| 3-HH-4 | (2-1) | 5% |
| 3-HH-5 | (2-1) | 10% |
| 3-HB-O2 | (2-5) | 13% |
| 3-HHB-1 | (3-1) | 8% |
| 3-HHB-O1 | (3-1) | 8% |
| 5-HB-CL | (12-2) | 15% |
| 7-HB(F,F)-F | (12-4) | 5% |
| 2-HHB(F)-F | (13-2) | 7% |
| 3-HHB(F)-F | (13-2) | 4% |
| 5-HHB(F)-F | (13-2) | 5% |
| 3-HHB(F,F)-F | (13-3) | 6% |
| 3-H2HB(F,F)-F | (13-15) | 5% |
| 4-H2HB(F,F)-F | (13-15) | 5% |

NI = 73.4° C.; η = 18.6 mPa · s; Δn = 0.077; Δε = 2.2.

Use Example 10

| | | |
|---|---|---|
| 5O-BF(1F,2F,8F,9F)-3 | (1-1-7) | 3% |
| 3-HH-4 | (2-1) | 9% |
| 3-HH-5 | (2-1) | 9% |
| 3-HB-O2 | (2-5) | 13% |
| 5-HB-CL | (12-2) | 4% |
| 7-HB(F)-F | (12-3) | 5% |
| 2-HHB(F,F)-F | (13-3) | 4% |
| 3-HHB(F,F)-F | (13-3) | 4% |
| 3-HHEB-F | (13-10) | 9% |
| 5-HHEB-F | (13-10) | 8% |
| 3-HHEB(F,F)-F | (13-12) | 8% |
| 4-HHEB(F,F)-F | (13-12) | 6% |
| 3-GHB(F,F)-F | (13-109) | 5% |
| 4-GHB(F,F)-F | (13-109) | 6% |
| 5-GHB(F,F)-F | (13-109) | 7% |

NI = 70.4° C.; η = 21.4 mPa · s; Δn = 0.071; Δε = 5.5.

Use Example 11

| | | |
|---|---|---|
| 5-Dh1OBF(1F,2F,8F,9F)-O2 | (1-2-50) | 6% |
| 3-HH-4 | (2-1) | 5% |
| 3-HH-V | (2-1) | 5% |
| 3-HB-O1 | (2-5) | 12% |
| 3-HB-O2 | (2-5) | 3% |
| 3-HHB-1 | (3-1) | 5% |
| 3-HB(2F,3F)-O2 | (5-1) | 10% |
| 5-HB(2F,3F)-O2 | (5-1) | 10% |
| 2-HHB(2F,3F)-1 | (6-1) | 8% |
| 3-HHB(2F,3F)-1 | (6-1) | 12% |
| 3-HHB(2F,3F)-O2 | (6-1) | 11% |
| 5-HHB(2F,3F)-O2 | (6-1) | 13% |

Use Example 12

| | | |
|---|---|---|
| 5-BBF(1F,2F,8F,9F)-O2 | (1-2-22) | 5% |
| 2-HH-5 | (2-1) | 3% |
| 3-HH-4 | (2-1) | 10% |
| 3-HH-5 | (2-1) | 5% |
| 3-HH-V | (2-1) | 10% |
| 3-HB-O2 | (2-5) | 8% |
| 3-HHB-1 | (3-1) | 3% |
| 3-HHB-3 | (3-1) | 4% |
| 3-HHB-O1 | (3-1) | 3% |
| 3-H2B(2F,3F)-O2 | (5-4) | 10% |
| 5-H2B(2F,3F)-O2 | (5-4) | 10% |
| 2-HBB(2F,3F)-O2 | (6-7) | 4% |
| 3-HBB(2F,3F)-O2 | (6-7) | 9% |
| 5-HBB(2F,3F)-O2 | (6-7) | 9% |
| 3-HHB(2F,3CL)-O2 | (6-12) | 4% |
| 3-HBB(2F,3CL)-O2 | (6-13) | 3% |

Use Example 13

| | | |
|---|---|---|
| 5-HBF(1F,2F,8F,9F)-O2 | (1-2-5) | 3% |
| 5O-BF(1F,2F,8F,9F)-O2 | (1-1-2) | 4% |
| 2-HH-3 | (2-1) | 15% |
| 2-HH-5 | (2-1) | 3% |
| 3-HH-4 | (2-1) | 10% |
| 3-HB-O2 | (2-5) | 3% |
| 1-BB-3 | (2-8) | 9% |
| 3-HHB-1 | (3-1) | 4% |
| 3-HHB-O1 | (3-1) | 3% |
| 5-B(F)BB-2 | (3-8) | 2% |
| 3-BB(2F,3F)-O2 | (5-3) | 7% |
| 5-BB(2F,3F)-O2 | (5-3) | 4% |
| 2-HH1OB(2F,3F)-O2 | (6-5) | 15% |
| 3-HH1OB(2F,3F)-O2 | (6-5) | 18% |

Use Example 14

| | | |
|---|---|---|
| V-H1OBF(1F,2F,8F,9F)-3 | (1-2-46) | 4% |
| 2-HH-3 | (2-1) | 12% |
| 7-HB-1 | (2-5) | 11% |
| 5-HB-O2 | (2-5) | 11% |
| 5-HBB(F)B-2 | (4-5) | 7% |
| 5-HBB(F)B-3 | (4-5) | 7% |
| 3-HB(2F,3F)-O2 | (5-1) | 15% |
| 5-HB(2F,3F)-O2 | (5-1) | 16% |
| 5-HBB(2F,3F)-O2 | (6-7) | 6% |
| 3-HHB(2F,3CL)-O2 | (6-12) | 3% |
| 4-HHB(2F,3CL)-O2 | (6-12) | 3% |
| 5-HHB(2F,3CL)-O2 | (6-12) | 2% |
| 3-HH1OCro(7F,8F)-5 | (9-6) | 3% |

Use Example 15

| | | |
|---|---|---|
| 5-H1OBF(1F,2F,8F)-3 | (1-2-45) | 3% |
| 3-HH-V | (2-1) | 30% |
| 1-BB-3 | (2-8) | 8% |
| 3-HHB-1 | (3-1) | 8% |
| 5-B(F)BB-2 | (3-8) | 7% |
| 3-BB(2F,3F)-O2 | (5-3) | 12% |
| 2-HH1OB(2F,3F)-O2 | (6-5) | 18% |
| 3-HH1OB(2F,3F)-O2 | (6-5) | 14% |

Use Example 16

| | | |
|---|---|---|
| 5-H1OBF(1F,2F,8F,9F)-3 | (1-2-43) | 5% |
| 5O-BF(1F,2F,8F,9F)-3 | (1-1-7) | 5% |
| 2-HH-3 | (2-1) | 5% |
| 3-HH-V | (2-1) | 5% |
| 3-HH-V1 | (2-1) | 8% |
| 1V2-HH-1 | (2-1) | 8% |
| 1V2-HH-3 | (2-1) | 7% |
| 3-HHB-1 | (3-1) | 3% |
| 3-HHB-3 | (3-1) | 2% |
| 3-BB(2F,3F)-O2 | (5-3) | 8% |
| 5-BB(2F,3F)-O2 | (5-3) | 4% |
| 3-H1OB(2F,3F)-O2 | (5-5) | 7% |
| 3-HDhB(2F,3F)-O2 | (6-3) | 5% |
| 2-HH1OB(2F,3F)-O2 | (6-5) | 6% |
| 3-HH1OB(2F,3F)-O2 | (6-5) | 14% |
| 2-BB(2F,3F)B-3 | (7-1) | 8% |

NI = 74.0° C.; η = 25.6 mPa · s.; Δn = 0.107; Δε = −4.4.

Use Example 17

| | | |
|---|---|---|
| 5-Dh1OBF(1F,2F,8F,9F)-O2 | (1-2-50) | 4% |
| 5-HH-VFF | (2-1) | 25% |
| 2-BTB-1 | (2-10) | 12% |
| 3-HHB-1 | (3-1) | 6% |
| VFF-HHB-1 | (3-1) | 6% |
| VFF2-HHB-1 | (3-1) | 8% |
| 3-H2BTB-2 | (3-17) | 5% |
| 3-H2BTB-3 | (3-17) | 5% |
| 3-H2BTB-4 | (3-17) | 5% |
| 3-HB-C | (15-1) | 18% |
| 1V2-BEB(F,F)-C | (15-15) | 6% |

Use Example 18

| | | |
|---|---|---|
| 5-BBF(1F,2F,8F,9F)-O2 | (1-2-22) | 6% |
| 3-HH-V | (2-1) | 36% |
| 3-HH-V1 | (2-1) | 8% |
| 3-HHB-1 | (3-1) | 5% |
| V-HHB-1 | (3-1) | 4% |
| V2-BB(F)B-1 | (3-6) | 5% |
| 3-HHEH-5 | (3-13) | 5% |
| 1V2-BB-F | (12-1) | 3% |
| 3-BB(F,F)XB(F,F)-F | (13-97) | 8% |
| 3-HHBB(F,F)-F | (14-6) | 3% |
| 5-HB(F)B(F,F)XB(F,F)-F | (14-41) | 4% |
| 3-BB(F)B(F,F)XB(F,F)-F | (14-47) | 3% |
| 4-BB(F)B(F,F)XB(F,F)-F | (14-47) | 5% |
| 5-BB(F)B(F,F)XB(F,F)-F | (14-47) | 5% |

Use Example 1

| | | |
|---|---|---|
| 5-HBF(1F,2F,8F,9F)-O2 | (1-2-5) | 3% |
| 3-HH-V | (2-1) | 42% |
| 3-HH-V1 | (2-1) | 7% |
| 3-HHB-1 | (3-1) | 4% |
| V-HHB-1 | (3-1) | 5% |
| V2-BB(F)B-1 | (3-6) | 5% |
| 3-HHEH-5 | (3-13) | 3% |
| 1V2-BB-F | (12-1) | 3% |
| 3-BB(F,F)XB(F,F)-F | (13-97) | 4% |
| 3-GB(F,F)XB(F,F)-F | (13-113) | 4% |
| 3-HHBB(F,F)-F | (14-6) | 3% |
| 3-BB(F)B(F,F)XB(F,F)-F | (14-47) | 5% |
| 4-BB(F)B(F,F)XB(F,F)-F | (14-47) | 5% |
| 5-BB(F)B(F,F)XB(F,F)-F | (14-47) | 3% |
| 3-GB(F)B(F,F)XB(F,F)-F | (14-57) | 4% |

Use Example 20

| | | |
|---|---|---|
| 5O-BF(1F,2F,8F,9F)-O2 | (1-1-2) | 4% |
| 3-HH-4 | (2-1) | 6% |
| 3-HH-VFF | (2-1) | 5% |
| 3-HB-O1 | (2-5) | 15% |
| 1-BB-5 | (2-8) | 5% |
| 3-HHB-1 | (3-1) | 6% |
| V-HB(2F,3F)-O2 | (5-1) | 5% |
| 5-HB(2F,3F)-O2 | (5-1) | 12% |
| 2-HHB(2F,3F)-1 | (6-1) | 10% |
| 3-HHB(2F,3F)-1 | (6-1) | 10% |
| 3-HHB(2F,3F)-O2 | (6-1) | 11% |
| 5-HHB(2F,3F)-O2 | (6-1) | 11% |

Use Example 21

| | | |
|---|---|---|
| V-H1OBF(1F,2F,8F,9F)-3 | (1-2-46) | 3% |
| 5-H1OBF(1F,2F,8F)-3 | (1-2-45) | 3% |
| 2-HH-3 | (2-1) | 10% |
| 2-HH-5 | (2-1) | 6% |
| 7-HB-1 | (2-5) | 5% |
| 5-HB-O2 | (2-5) | 7% |
| 1-BB-3 | (2-8) | 5% |
| 5-HBB(F)B-2 | (4-5) | 10% |
| 5-HBB(F)B-3 | (4-5) | 8% |
| 3-HB(2F,3F)-O2 | (5-1) | 13% |
| 5-HB(2F,3F)-O2 | (5-1) | 10% |
| 2-H1OB(2F,3F)-O2 | (5-5) | 3% |
| 3-H1OB(2F,3F)-O2 | (5-5) | 3% |
| V-HHB(2F,3F)-O2 | (6-1) | 3% |
| V2-HHB(2F,3F)-O2 | (6-1) | 3% |
| 5-HHB(2F,3CL)-O2 | (6-12) | 2% |
| 3-HH1OCro(7F,8F)-5 | (9-6) | 6% |

Use Example 22

| | | |
|---|---|---|
| 5-H1OBF(1F,2F,8F,9F)-3 | (1-2-43) | 3% |
| 2-HH-5 | (2-1) | 3% |
| 3-HH-4 | (2-1) | 12% |
| 3-HH-5 | (2-1) | 5% |
| 3-HB-O2 | (2-5) | 13% |
| 3-HHB-1 | (3-1) | 4% |
| 3-HHB-3 | (3-1) | 3% |
| 3-HHB-O1 | (3-1) | 3% |
| 3-DhB(2F,3F)-O2 | (5-2) | 3% |
| 2-BB(2F,3F)-O2 | (5-3) | 8% |

-continued

| | | |
|---|---|---|
| 5-H2B(2F,3F)-O2 | (5-4) | 12% |
| 3-HH2B(2F,3F)-O2 | (6-4) | 4% |
| V-HBB(2F,3F)-O2 | (6-7) | 4% |
| 3-HBB(2F,3F)-O2 | (6-7) | 9% |
| 5-HBB(2F,3F)-O2 | (6-7) | 9% |
| 3-HHB(2F,3CL)-O2 | (6-12) | 5% |

NI = 81.9° C.; η = 25.2 mPa · s; Δn = 0.106; Δε = −4.4.

Use Example 23

| | | |
|---|---|---|
| 5O-BF(1F,2F,8F,9F)-3 | (1-1-7) | 6% |
| 2-HH-3 | (2-1) | 6% |
| 3-HH-V1 | (2-1) | 8% |
| 1V2-HH-1 | (2-1) | 8% |
| 1V2-HH-3 | (2-1) | 7% |
| V-HHB-1 | (3-1) | 3% |
| V2-HHB-1 | (3-1) | 3% |
| 3-HHB-1 | (3-1) | 3% |
| 3-HHB-3 | (3-1) | 2% |
| V2-BB(2F,3F)-O2 | (5-3) | 4% |
| 5-BB(2F,3F)-O2 | (5-3) | 4% |
| 3-H1OB(2F,3F)-O2 | (5-5) | 5% |
| 3-HDhB(2F,3F)-O2 | (6-3) | 7% |
| 3-HH1OB(2F,3F)-O2 | (6-5) | 19% |
| 3-dhBB(2F,3F)-O2 | (6-9) | 3% |
| 3-HchB(2F,3F)-O2 | (6-18) | 3% |
| 2-BB(2F,3F)B-3 | (7-1) | 9% |

NI = 89.3° C.; η = 24.1 mPa · s; Δn = 0.112; Δε = −4.1.

Use Example 24

| | | |
|---|---|---|
| 5-Dh1OBF(1F,2F,8F,9F)-O2 | (1-2-50) | 3% |
| 2-HH-3 | (2-1) | 14% |
| 3-HH-4 | (2-1) | 10% |
| 3-HB-O2 | (2-5) | 3% |
| 1-BB-3 | (2-8) | 10% |
| 3-HHB-1 | (3-1) | 5% |
| 3-HHB-O1 | (3-1) | 4% |
| V-HBB-2 | (3-4) | 5% |
| 5-B(F)BB-2 | (3-8) | 2% |
| 3-BB(2F,3F)-O2 | (5-3) | 9% |
| 5-BB(2F,3F)-O2 | (5-3) | 5% |
| 2-HH1OB(2F,3F)-O2 | (6-5) | 10% |
| 3-HH1OB(2F,3F)-O2 | (6-5) | 20% |

Use Example 25

| | | |
|---|---|---|
| 5-BBF(1F,2F,8F,9F)-O2 | (1-2-22) | 3% |
| 3-HH-V | (2-1) | 35% |
| 3-HH-V1 | (2-1) | 6% |
| 3-HHB-1 | (3-1) | 5% |
| V-HHB-1 | (3-1) | 4% |
| V2-BB(F)B-1 | (3-6) | 3% |
| 3-HHEH-5 | (3-13) | 4% |
| 1V2-BB-F | (12-1) | 3% |
| 3-BB(F,F)XB(F,F)-F | (13-97) | 4% |
| 3-GB(F,F)XB(F,F)-F | (13-113) | 3% |
| 3-HHBB(F,F)-F | (14-6) | 3% |
| 3-BB(F)B(F,F)XB(F,F)-F | (14-47) | 3% |
| 4-BB(F)B(F,F)XB(F,F)-F | (14-47) | 4% |
| 5-BB(F)B(F,F)XB(F,F)-F | (14-47) | 3% |
| 3-GB(F)B(F,F)XB(F,F)-F | (14-57) | 3% |
| 4-GB(F)B(F,F)XB(F,F)-F | (14-57) | 4% |
| 5-GB(F)B(F,F)XB(F,F)-F | (14-57) | 5% |
| 3-GB(F)B(F,F)XB(F,F)-F | (14-57) | 5% |

Use Example 26

| | | |
|---|---|---|
| 5-HBF(1F,2F,8F,9F)-O2 | (1-2-5) | 4% |
| 3-HH-V | (2-1) | 38% |
| 3-HH-V1 | (2-1) | 5% |
| 3-HHB-1 | (3-1) | 3% |
| V-HHB-1 | (3-1) | 4% |
| V2-BB(F)B-1 | (3-6) | 4% |
| 3-HHEH-5 | (3-13) | 4% |
| 1V2-BB-F | (12-1) | 5% |
| 3-BB(F,F)XB(F,F)-F | (13-97) | 9% |
| 3-HHBB(F,F)-F | (14-6) | 3% |
| 5-HB(F)B(F,F)XB(F,F)-F | (14-41) | 3% |
| 3-BB(F)B(F,F)XB(F,F)-F | (14-47) | 3% |
| 4-BB(F)B(F,F)XB(F,F)-F | (14-47) | 5% |
| 5-BB(F)B(F,F)XB(F,F)-F | (14-47) | 3% |
| 2-dhBB(F,F)XB(F,F)-F | (14-50) | 3% |
| 3-dhBB(F,F)XB(F,F)-F | (14-50) | 4% |

Use Example 27

| | | |
|---|---|---|
| 5O-BF(1F,2F,8F,9F)-O2 | (1-1-2) | 5% |
| 3-HH-V | (2-1) | 34% |
| 3-HH-V1 | (2-1) | 5% |
| 3-HHB-1 | (3-1) | 4% |
| V-HHB-1 | (3-1) | 5% |
| V2-BB(F)B-1 | (3-6) | 4% |
| 3-HHEH-5 | (3-13) | 3% |
| 1V2-BB-F | (12-1) | 3% |
| 3-BB(F,F)XB(F,F)-F | (13-97) | 5% |
| 3-GB(F,F)XB(F,F)-F | (13-113) | 3% |
| 3-HHBB(F,F)-F | (14-6) | 3% |
| 3-BB(F)B(F,F)XB(F,F)-F | (14-47) | 3% |
| 4-BB(F)B(F,F)XB(F,F)-F | (14-47) | 6% |
| 5-BB(F)B(F,F)XB(F,F)-F | (14-47) | 3% |
| 3-GB(F)B(F,F)XB(F,F)-F | (14-57) | 4% |
| 3-GBB(F,F)XB(F,F)-F | (14-58) | 3% |
| 4-GBB(F,F)XB(F,F)-F | (14-58) | 3% |
| 5-GBB(F,F)XB(F,F)-F | (14-58) | 4% |

Use Example 28

| | | |
|---|---|---|
| 5-B(F)BF(1F,2F,8F,9F)-O2 | (1-2-29) | 4% |
| 3-HH-V | (2-1) | 31% |
| 3-HH-V1 | (2-1) | 5% |
| 3-HHB-1 | (3-1) | 4% |
| V-HHB-1 | (3-1) | 5% |
| 3-HBB-2 | (3-4) | 5% |
| V2-BB(F)B-1 | (3-6) | 5% |
| 3-HHEH-3 | (3-13) | 3% |
| 3-HHEH-5 | (3-13) | 3% |
| 1V2-BB-F | (12-1) | 3% |
| 3-GB(F)B(F)-F | (13) | 3% |
| 3-BB(F)B(F,F)-CF3 | (13-69) | 3% |
| 3-GB(F)B(F,F)-F | (13-69) | 3% |
| 3-GB(F,F)XB(F,F)-F | (13-113) | 3% |
| 3-HBB(F,F)XB(F,F)-F | (14-38) | 3% |
| 3-BB(F)B(F,F)XB(F)-F | (14-46) | 3% |
| 3-BB(F,F)XB(F)B(F,F)-F | (14-56) | 4% |
| 3-GB(F,F)XB(F,F)B(F,F)-F | (14-57) | 5% |
| 4-GB(F)B(F,F)XB(F,F)-F | (14-57) | 3% |
| 5-GB(F)B(F,F)XB(F,F)-F | (14-57) | 2% |

NI = 76.3° C.; Δn = 0.100; Δε = 5.8.

Use Example 29

| | | |
|---|---|---|
| 5-Dh1OBF(1F,2F,8F,9F)-3 | (1-2-49) | 3% |
| 3-HH-V | (2-1) | 32% |
| 3-HH-V1 | (2-1) | 5% |
| 5-HH-V | (2-1) | 5% |
| 3-HHB-1 | (3-1) | 4% |
| V-HHB-1 | (3-1) | 5% |
| 2-BB(F)B-3 | (3-6) | 5% |
| 3-HHEH-5 | (3-13) | 3% |
| 1V2-BB-F | (12-1) | 3% |
| 3-BB(F,F)XB(F,F)-F | (13-97) | 10% |
| 3-GB(F)B(F)B(F)-F | (14) | 3% |
| 3-HHBB(F,F)-F | (14-6) | 3% |
| 3-HBBXB(F,F)-F | (14-32) | 3% |
| 5-HB(F)B(F,F)XB(F,F)-F | (14-41) | 5% |
| 3-GBB(F)B(F,F)-F | (14-55) | 3% |
| 4-GBB(F)B(F,F)-F | (14-55) | 5% |
| 3-BB(2F,3F)XB(F,F)-F | (—) | 3% |

NI = 87.0° C.; η = 21.0 mPa · s; Δn = 0.102; Δε = 4.1.

Use Example 30

| | | |
|---|---|---|
| 5-B(F)BF(1F,2F,8F,9F)-O2 | (1-2-29) | 3% |
| 3-HH-V | (2-1) | 31% |
| 3-HH-V1 | (2-1) | 7% |
| V-HH-V1 | (2-1) | 6% |
| 3-HHB-1 | (3-1) | 4% |
| V-HHB-1 | (3-1) | 5% |
| 1-BB(F)B-2V | (3-6) | 4% |
| 3-HHEBH-3 | (4-6) | 3% |
| 1V2-BB-F | (12-1) | 3% |
| 3-HHXB(F,F)-F | (13-100) | 5% |
| 3-HHXB(F,F)-CF3 | (13-100) | 3% |
| 3-GB(F,F)XB(F,F)-F | (13-113) | 4% |
| 3-GB(F)B(F,F)-F | (13-116) | 4% |
| 3-HHBB(F,F)-F | (14-6) | 3% |
| 3-BB(F,F)B(F,F)XB(F,F)-F | (14-47) | 3% |
| 4-BB(F,F)B(F,F)XB(F,F)-F | (14-47) | 5% |
| 5-BB(F)B(F,F)XB(F,F)-F | (14-47) | 3% |
| 3-GB(F)B(F,F)XB(F,F)-F | (14-57) | 4% |

NI = 89.1° C.; Δn = 0.105; Δε = 5.1.

Use Example 31

| | | |
|---|---|---|
| 5-Dh1OBF(1F,2F,8F,9F)-3 | (1-2-49) | 3% |
| 2-HH-3 | (2-1) | 21% |
| 4-HH-V | (2-1) | 9% |
| 3-HB-O2 | (2-5) | 2% |
| 1-BB-3 | (2-8) | 5% |
| 3-HHB-1 | (3-1) | 3% |
| 3-HHB-O1 | (3-1) | 3% |
| V-HBB-2 | (3-4) | 3% |
| 5-B(F)BB-2 | (3-8) | 3% |
| 2O-B(2F,3F)B(F)-O2 | (5) | 9% |
| 4O-B(2F,3F)B(F)-O2 | (5) | 6% |
| 2-HH1OB(2F,3F)-O2 | (6-5) | 12% |
| 3-HH1OB(2F,3F)-O2 | (6-5) | 13% |
| 3-HB(2F,3F)B-2 | (7) | 4% |
| V-HH2BB(2F,3F)-O2 | (—) | 4% |

NI = 77.6° C.; η = 22.9 mPa · s; Δn = 0.102; Δε = −3.3.

Use Example 32

| | | |
|---|---|---|
| 5-B(F)BF(1F,2F,8F,9F)-O2 | (1-2-29) | 4% |
| 3-HH-V | (2-1) | 25% |
| 1-BB-3 | (2-8) | 7% |
| 3-HHB-1 | (3-1) | 8% |
| 5-B(F)BB-2 | (3-8) | 5% |
| 3-BB(2F,3F)-O2 | (5-3) | 12% |
| 2O-B(2F,3F)B(F)H-3 | (6) | 6% |
| 2-HH1OB(2F,3F)-O2 | (6-5) | 15% |
| 3-HH1OB(2F,3F)-O2 | (6-5) | 12% |
| 5-HFLF4-3 | (—) | 3% |
| 3-H2BBB(2F,3F)-O2 | (—) | 3% |

NI = 84.6° C.; Δn = 0.121; Δε = −3.6.

INDUSTRIAL APPLICABILITY

A liquid crystal compound of the invention has good physical properties. A liquid crystal composition containing the compound can be widely applied to a liquid crystal display device used in a personal computer, a television and so forth.

What is claimed is:

1. A compound, represented by formula (1):

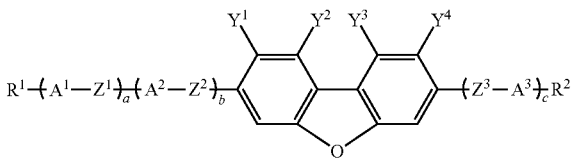

wherein, in formula (1), $R^1$ and $R^2$ are independently hydrogen or alkyl having 1 to 15 carbons, and in the alkyl, at least one —CH$_2$— may be replaced by —O—, —S—, —CO— or —SiH$_2$, and at least one —CH$_2$CH$_2$— may be replaced by —CH═CH— or —C≡C—, and in the divalent groups at least one hydrogen may be replaced by fluorine or chlorine;

wherein:
i) when $R^1$ is hydrogen, $R^2$ is alkyl having 1 to 15 carbons, and in the alkyl, at least one —CH$_2$— may be replaced by —O—, —S—, —CO— or —SiH$_2$, and at least one —CH$_2$CH$_2$— may be replaced by —CH═CH— or —C≡C—, and in the divalent groups at least one hydrogen may be replaced by fluorine or chlorine;

ii) when $R^2$ is hydrogen, $R^1$ is alkyl having 1 to 15 carbons, and in the alkyl, at least one —CH$_2$— may be replaced by —O—, —S—, —CO— or —SiH$_2$, and at least one —CH$_2$CH$_2$— may be replaced by —CH═CH— or —C≡C—, and in the divalent groups at least one hydrogen may be replaced by fluorine or chlorine;

iii) when $R^1$ is hydrogen, alkoxy having 1 to 15 carbons, or alkenyloxy having 2 to 15 carbons, $R^2$ is alkyl having 1 to 15 carbons, and in the groups at least one hydrogen may be replaced by fluorine;

iv) when $R^2$ is hydrogen, alkoxy having 1 to 15 carbons, or alkenyloxy having 2 to 15 carbons, $R^1$ is alkyl having 1 to 15 carbons, and in the groups at least one hydrogen may be replaced by fluorine;

v) when $R^1$ is hydrogen, alkenyl having 2 to 15 carbons, alkoxy having 1 to 15 carbons or alkenyloxy having 2 to 15 carbons, $R^2$ is alkenyl having 2 to 15 carbons, and in the groups at least one hydrogen may be replaced by fluorine;

vi) when $R^2$ is hydrogen, alkenyl having 2 to 15 carbons, alkoxy having 1 to 15 carbons or alkenyloxy having 2 to 15 carbons, $R^1$ is alkenyl having 2 to 15 carbons, and in the groups at least one hydrogen may be replaced by fluorine;

3. The compound according to claim 1, wherein, in formula (1), $Z^1$, $Z^2$ and $Z^3$ are independently a single bond, —(CH$_2$)$_2$—, —CH=CH—, —C≡C—, —COO—, —OCO—, —CF$_2$O—, —OCF$_2$—, —CH$_2$O—, —OCH$_2$— or —CF=CF—.

4. The compound according to claim 1, represented by any one of formulas (1-1) to (1-5):

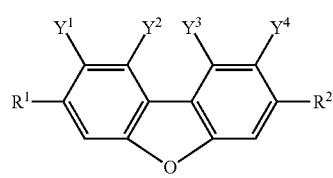
(1-1)

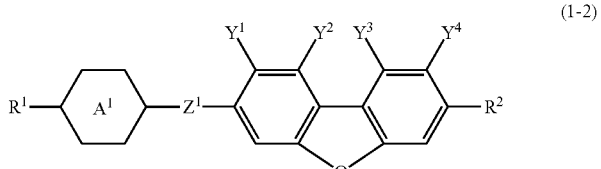
(1-2)

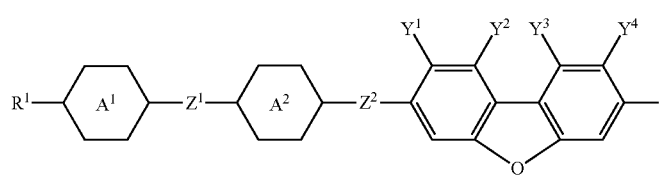
(1-3)

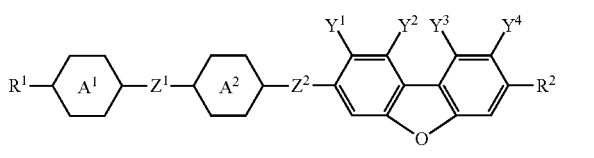
(1-4)

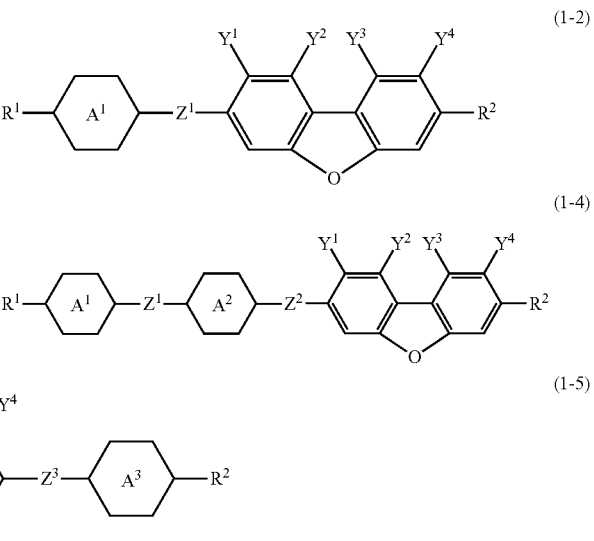
(1-5)

$A^1$, $A^2$ and $A^3$ are independently 1,2-cyclopropylene, 1,3-cyclobutylene, 1,3-cyclopentylene, 1,4-cyclohexylene, 1,4-cycloheptylene, 1,4-phenylene, decahydronaphthalene-2,6-diyl, 1,2,3,4-tetrahydronaphthalene-2,6-diyl, naphthalene-2,6-diyl, 9,10-dihydrophenanthrene-2,7-diyl, 9H-xanthene-2,6-diyl or 9H-fluorene-2,7-diyl, and in the groups, at least one —CH$_2$— may be replaced by —O—, —S—, —CO— or —SiH$_2$—, and at least one —CH$_2$CH$_2$— may be replaced by —CH=CH— or —CH=N—, and in the divalent groups, at least one hydrogen may be replaced by fluorine, chlorine, —C≡N, —CF$_3$, —CHF$_2$, —CH$_2$F, —OCF$_3$, —OCHF$_2$ or —OCH$_2$F;

$Z^1$, $Z^2$ and $Z^3$ are independently a single bond or alkylene having 1 to 6 carbons, and in the alkylene, at least one —CH$_2$— may be replaced by —O—, —S—, —CO— or —SiH$_2$—, and one or two —CH$_2$CH$_2$— may be replaced by —CH=CH— or —C≡C—, and in the divalent groups at least one hydrogen may be replaced by fluorine or chlorine;

$Y^1$, $Y^2$, $Y^3$ and $Y^4$ are independently hydrogen, fluorine, chlorine, —CF$_3$ or —CHF$_2$, and at least two of $Y^1$, $Y^2$, $Y^3$ and $Y^4$ is fluorine, chlorine, —CF$_3$ or —CHF$_2$; and a, b and c are independently 0 or 1, and a sum of a, b and c is 0 to 3.

2. The compound according to claim 1, wherein, in formula (1), $A^1$, $A^2$ and $A^3$ are independently 1,4-cyclohexylene, 1,4-cycloheptylene, 1,4-cyclohexenylene, 1,4-phenylene, 2-fluoro-1,4-phenylene, 2,3-difluoro-1,4-phenylene, tetrahydropyran-2,5-diyl, 1,3-dioxane-2,5-diyl, pyridine-2,5-diyl, pyrimidine-2,5-diyl, decahydronaphthalene-2,6-diyl, 1,2,3,4-tetrahydronaphthalene-2,6-diyl or naphthalene-2,6-diyl.

wherein, in formulas (1-1) to (1-5), $R^1$ and $R^2$ are independently hydrogen, alkyl having 1 to 10 carbons, alkenyl having 2 to 10 carbons, alkoxy having 1 to 10 carbons or alkenyloxy having 2 to 10 carbons, and in the groups, at least one hydrogen may be replaced by fluorine;

wherein:

i) when $R^1$ is hydrogen, $R^2$ is alkyl having 1 to 10 carbons, alkenyl having 2 to 10 carbons, alkoxy having 1 to 10 carbons or alkenyloxy having 2 to 10 carbons, and in the groups at least one hydrogen may be replaced by fluorine;

ii) when $R^2$ is hydrogen, $R^1$ is alkyl having 1 to 10 carbons, alkenyl having 2 to 10 carbons, alkoxy having 1 to 10 carbons or alkenyloxy having 2 to 10 carbons, and in the groups at least one hydrogen may be replaced by fluorine;

iii) when $R^1$ is hydrogen, alkoxy having 1 to 10 carbons, or alkenyloxy having 2 to 10 carbons, $R^2$ is alkyl having 1 to 10 carbons, and in the groups at least one hydrogen may be replaced by fluorine;

iv) when $R^2$ is hydrogen, alkoxy having 1 to 10 carbons, or alkenyloxy having 2 to 10 carbons, $R^1$ is alkyl having 1 to 10 carbons, and in the groups at least one hydrogen may be replaced by fluorine;

v) when $R^1$ is hydrogen, alkenyl having 2 to 10 carbons, alkoxy having 1 to 10 carbons or alkenyloxy having 2 to 10 carbons, $R^2$ is alkenyl having 2 to 10 carbons, and in the groups at least one hydrogen may be replaced by fluorine;

vi) when $R^2$ is hydrogen, alkenyl having 2 to 10 carbons, alkoxy having 1 to 10 carbons or alkenyloxy having 2 to 10 carbons, $R^1$ is alkenyl having 2 to 10 carbons, and in the groups at least one hydrogen may be replaced by fluorine;

ring $A^1$, ring $A^2$ and ring $A^3$ are independently 1,4-cyclohexylene, 1,4-cyclohexenylene, 1,4-phenylene, 2-fluoro-1,4-phenylene, 2,3-difluoro-1,4-phenylene or tetrahydropyran-2,5-diyl;

$Z^1$, $Z^2$ and $Z^3$ are independently a single bond, —(CH$_2$)$_2$—, —C≡C—, —CF$_2$O—, —OCF$_2$—, —CH$_2$O— or —OCH$_2$—; and $Y^1$, $Y^2$, $Y^3$ and $Y^4$ are independently hydrogen, fluorine, chlorine, —CF$_3$ or —CHF$_2$, and at least two of $Y^1$, $Y^2$, $Y^3$ and $Y^4$ is fluorine, chlorine, —CF$_3$ or —CHF$_2$.

5. The compound according to claim 1, represented by any one of formulas (1-6) to (1-11):

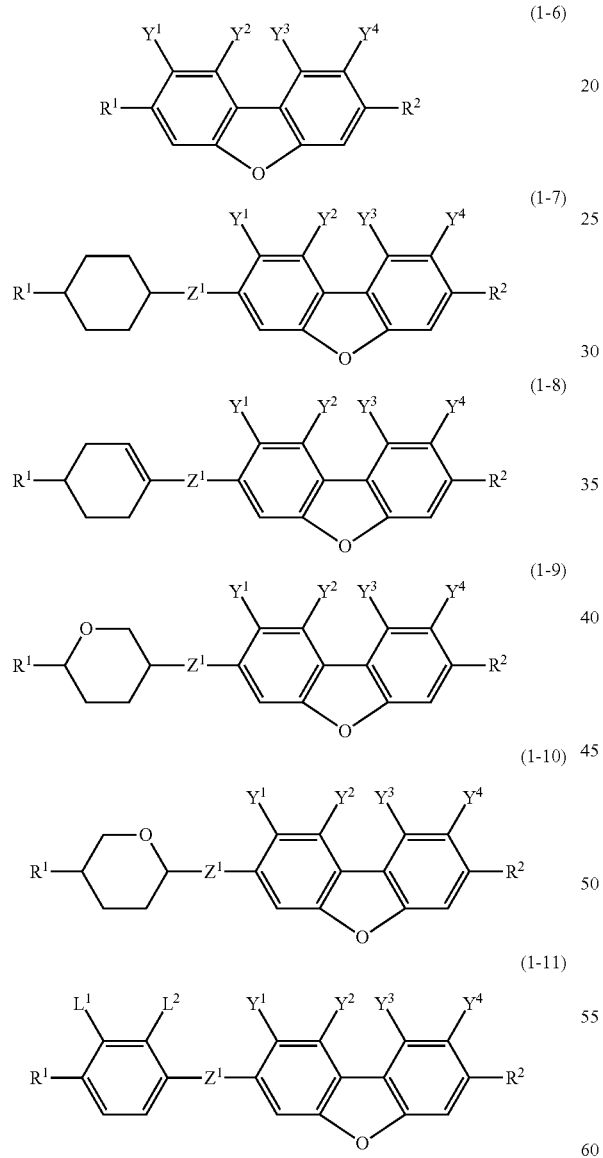

wherein, in formulas (1-6) to (1-11),
$R^1$ and $R^2$ are independently alkyl having 1 to 10 carbons, alkenyl having 2 to 10 carbons, alkoxy having 1 to 10 carbons or alkenyloxy having 2 to 10 carbons, and in the groups, at least one hydrogen may be replaced by fluorine;

wherein:
i) when $R^1$ is alkoxy having 1 to 10 carbons, or alkenyloxy having 2 to 10 carbons, $R^2$ is alkyl having 1 to 10 carbons, and in the groups at least one hydrogen may be replaced by fluorine;
ii) when $R^2$ is alkoxy having 1 to 10 carbons, or alkenyloxy having 2 to 10 carbons, $R^1$ is alkyl having 1 to 10 carbons, and in the groups at least one hydrogen may be replaced by fluorine;
iii) when $R^1$ is alkenyl having 2 to 10 carbons, alkoxy having 1 to 10 carbons or alkenyloxy having 2 to 10 carbons, $R^2$ is alkenyl having 2 to 10 carbons, and in the groups at least one hydrogen may be replaced by fluorine;
iv) when $R^2$ is alkenyl having 2 to 10 carbons, alkoxy having 1 to 10 carbons or alkenyloxy having 2 to 10 carbons, $R^1$ is alkenyl having 2 to 10 carbons, and in the groups at least one hydrogen may be replaced by fluorine;

$Z^1$ is a single bond, —(CH$_2$)$_2$—, —CH$_2$O— or —OCH$_2$—;

$Y^1$, $Y^2$, $Y^3$ and $Y^4$ are independently hydrogen or fluorine, and at least two of $Y^1$, $Y^2$, $Y^3$ and $Y^4$ is fluorine; and $L^1$ and $L^2$ are independently hydrogen or fluorine.

6. The compound according to claim 1, represented by any one of formulas (1-12) to (1-14):

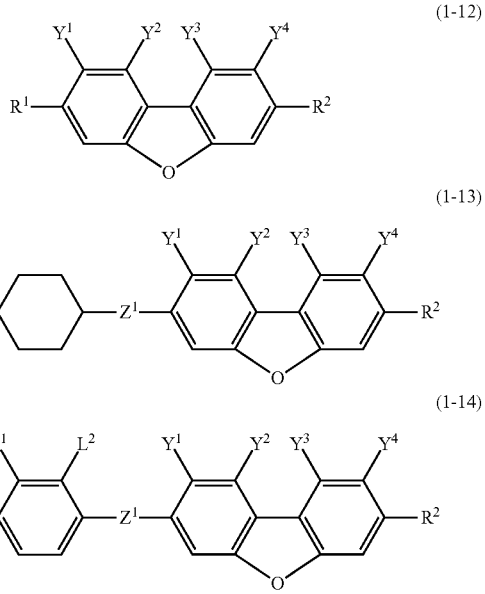

wherein, in formulas (1-12) to (1-14),
$R^1$ and $R^2$ are independently alkyl having 1 to 10 carbons, alkenyl having 2 to 10 carbons or alkoxy having 1 to 10 carbons;

wherein:
i) when $R^1$ is alkoxy having 1 to 10 carbons $R^2$ is alkyl having 1 to 10 carbons;
ii) when $R^2$ is alkoxy having 1 to 10 carbons, $R^1$ is alkyl having 1 to 10 carbons;
iii) when $R^1$ is alkenyl having 2 to 10 carbons or alkoxy having 1 to 10 carbons, $R^2$ is alkenyl having 2 to 10 carbons;
iv) when $R^2$ is alkenyl having 2 to 10 carbons or alkoxy having 1 to 10 carbons, $R^1$ is alkenyl having 2 to 10 carbons;

$Z^1$ is a single bond, —(CH$_2$)$_2$—, —CH$_2$O— or —OCH$_2$—;
$Y^1$, $Y^2$, $Y^3$ and $Y^4$ are independently hydrogen or fluorine, and at least two of $Y^1$, $Y^2$, $Y^3$ and $Y^4$ is fluorine; and
$L^1$ and $L^2$ are independently hydrogen or fluorine.
7. The compound according to claim 1, represented by any one of formulas (1-15) to (1-32):
(1-15)
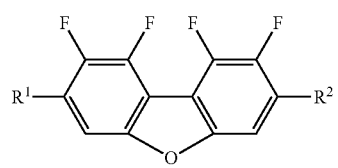
(1-16)
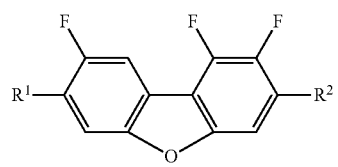
(1-17)
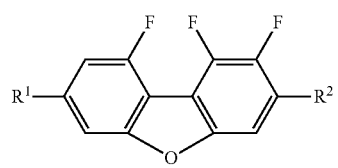
(1-18)
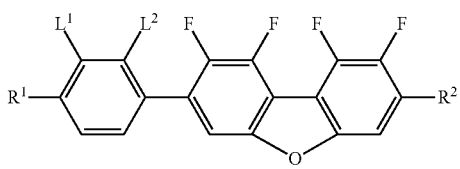
(1-19)
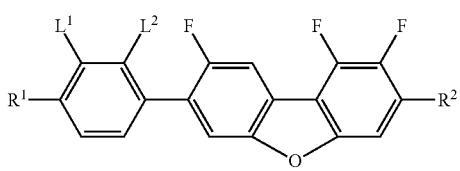
(1-20)
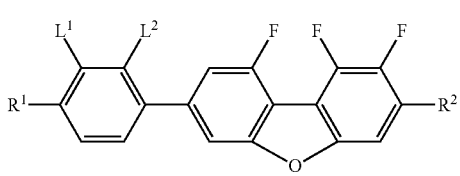
(1-21)
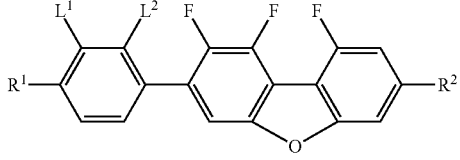
-continued
(1-22)
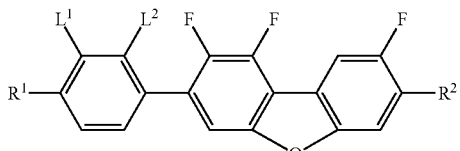
(1-23)
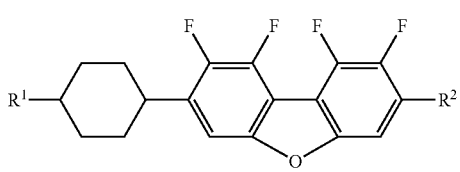
(1-24)
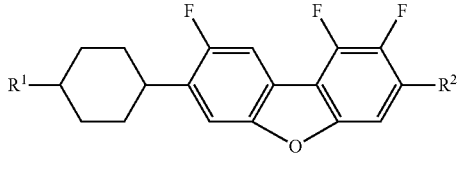
(1-25)
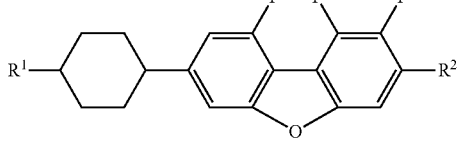
(1-26)
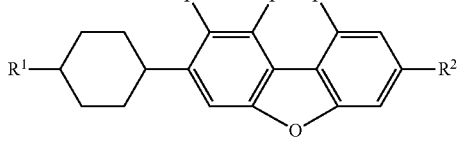
(1-27)
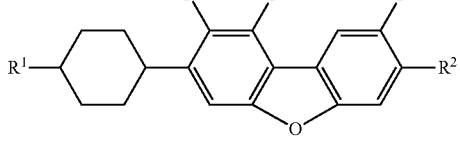
(1-28)
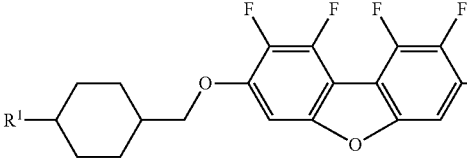
(1-29)
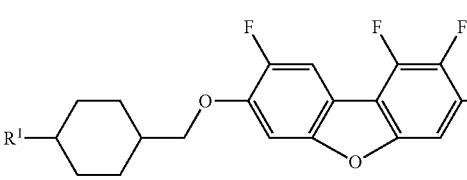
(1-30)
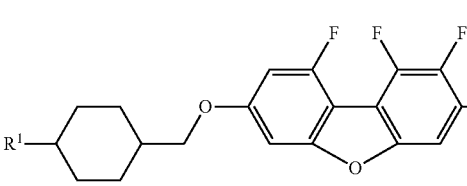

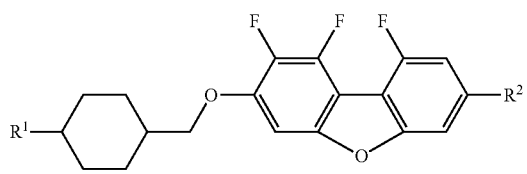
(1-31)

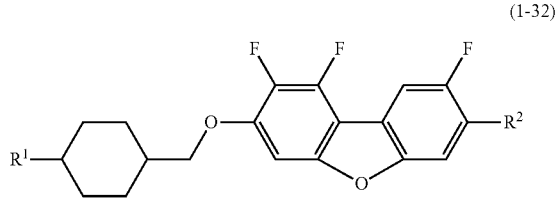
(1-32)

wherein, in formulas (1-15) to formula (1-32),
R¹ and R² are independently alkyl having 1 to 10 carbons, alkenyl having 2 to 10 carbons or alkoxy having 1 to 10 carbons; and
wherein:
i) when $R^1$ is alkoxy having 1 to 10 carbons, $R^2$ is alkyl having 1 to 10 carbons;
ii) when $R^2$ is alkoxy having 1 to 10 carbons, $R^1$ is alkyl having 1 to 10 carbons;
iii) when $R^1$ is alkenyl having 2 to 10 carbons or alkoxy having 1 to 10 carbons, $R^2$ is alkenyl having 2 to 10 carbons;
iv) when $R^2$ is alkenyl having 2 to 10 carbons or alkoxy having 1 to 10 carbons, $R^1$ is alkenyl having 2 to 10 carbons;
$L^1$ and $L^2$ are independently hydrogen or fluorine.

8. The compound according to claim 1, represented by any one of formulas (1-33) to (1-36):

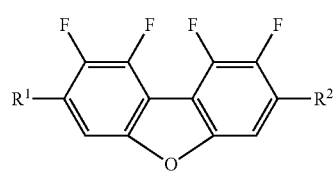
(1-33)

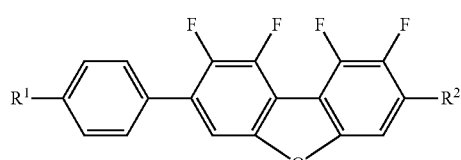
(1-34)

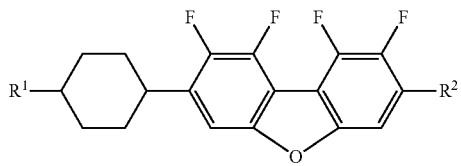
(1-35)

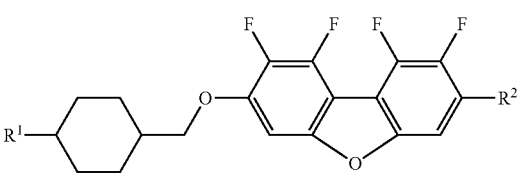
(1-36)

wherein, in formulas (1-33) to (1-36),
$R^1$ and $R^2$ are independently alkyl having 1 to 10 carbons or alkoxy 1 to 10 carbons;
wherein:
i) when $R^1$ is alkoxy having 1 to 10 carbons, $R^2$ is alkyl having 1 to 10 carbons;
ii) when $R^2$ is alkoxy having 1 to 10 carbons, $R^1$ is alkyl having 1 to 10 carbons.

9. A liquid crystal composition, containing at least one compound according to claim 1.

10. The liquid crystal composition according to claim 9, further containing at least one compound selected from the group of compounds represented by formulas (2) to (4):

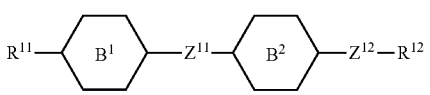
(2)

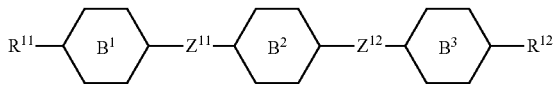
(3)

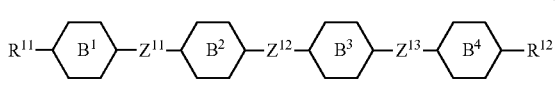
(4)

wherein, in formulas (2) to (4),
$R^{11}$ and $R^{12}$ are independently alkyl having 1 to 10 carbons or alkenyl having 2 to 10 carbons, and in the alkyl and the alkenyl, at least one —CH₂— may be replaced by —O—, and in the groups, at least one hydrogen may be replaced by fluorine;
ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and
$Z^{11}$, $Z^{12}$ and $Z^{13}$ are independently a single bond, —COO—, —CH₂CH₂—, —CH=CH— or —C≡C—.

11. The liquid crystal composition according to claim 9, further containing at least one compound selected from the group of compounds represented by formulas (5) to (11):

(5)

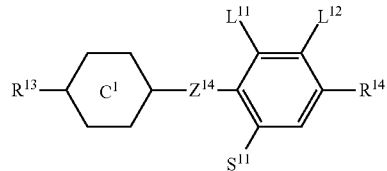

(6)

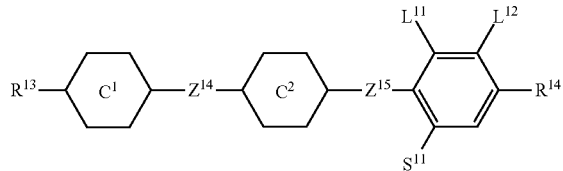

(7)

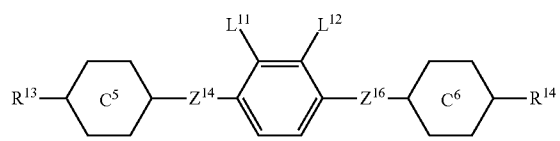

(8)

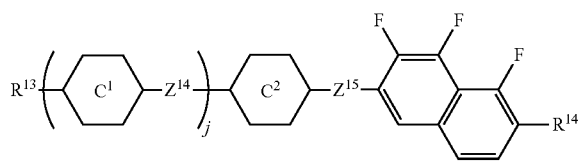

(9)

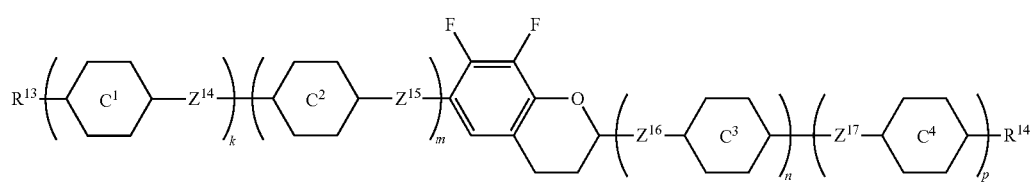

(10)

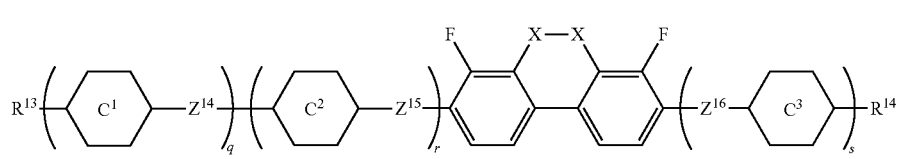

(11)

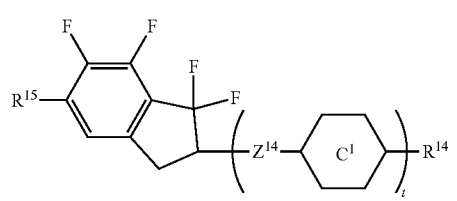

wherein, in formulas (5) to (11),
- $R^{13}$, $R^{14}$ and $R^{15}$ are independently alkyl having 1 to 10 carbons or alkenyl having 2 to 10 carbons, and in the alkyl and the alkenyl, at least one —CH$_2$— may be replaced by —O—, and in the groups, at least one hydrogen may be replaced by fluorine, and $R^{15}$ may be hydrogen or fluorine;
- ring $C^1$, ring $C^2$, ring $C^3$ and ring $C^4$ are independently 1,4-cyclohexylene, 1,4-cyclohexenylene, 1,4-phenylene, 1,4-phenylene in which at least one hydrogen may be replaced by fluorine, tetrahydropyran-2,5-diyl, or decahydronaphthalene-2,6-diyl;
- ring $C^5$ and ring $C^6$ are independently 1,4-cyclohexylene, 1,4-cyclohexenylene, 1,4-phenylene, tetrahydropyran-2,5-diyl or decahydronaphthalene-2,6-diy;
- $Z^{14}$, $Z^{15}$, $Z^{16}$ and $Z^{17}$ are independently a single bond, —COO—, —CH$_2$O—, —OCF$_2$—, —CH$_2$CH$_2$— or —OCF$_2$CH$_2$CH$_2$—;
- $L^1$ and $L^{12}$ are independently fluorine or chlorine;
- $S^{11}$ is hydrogen or methyl;
- X is —CHF— or —CF$_2$—; and
- j, k, m, n, p, q, r and s are independently 0 or 1, a sum of k, m, n and p is 1 or 2, a sum of q, r and s is 0, 1, 2 or 3, and t is 1, 2 or 3.

12. The liquid crystal composition according to claim 9, further containing at least one compound selected from the group of compounds represented by formulas (12) to (14):

(12)

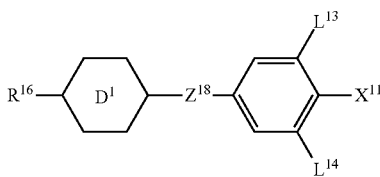

(13)

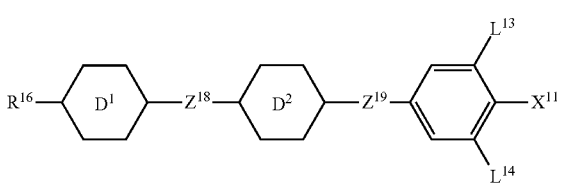

(14)

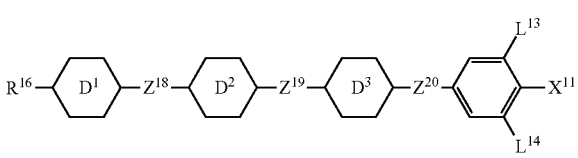

wherein, in formulas (12) to (14), $R^{16}$ is alkyl having 1 to 10 carbons or alkenyl having 2 to 10 carbons, and in the alkyl and the alkenyl, at least one —$CH_2$— may be replaced by —O—, and in the groups, at least one hydrogen may be replaced by fluorine;

$X^{11}$ is fluorine, chlorine, —$CF_3$, —$CHF_2$, —$CH_2F$, —$OCF_3$, —$OCHF_2$, —$OCF_2CHF_2$ or —$OCF_2CHFCF_3$;

ring $D^1$, ring $D^2$ and ring $D^3$ are independently 1,4-cyclohexylene, 1,4-phenylene, 1,4-phenylene in which at least one hydrogen is replaced by fluorine, tetrahydropyran-2,5-diyl, 1,3-dioxane-2,5-diyl, or pyrimidine-2,5-diyl;

$Z^{18}$, $Z^{19}$ and $Z^{20}$ are independently a single bond, —COO—, —$CH_2O$—, —$CF_2O$—, —$OCF_2$—, —$CH_2CH_2$—, —CH=CH—, —C≡C— or —$(CH_2)_4$—; and $L^{13}$ and $L^{14}$ are independently hydrogen or fluorine.

13. The liquid crystal composition according to claim 9, further containing at least one compound selected from the group of compounds represented by formula (15):

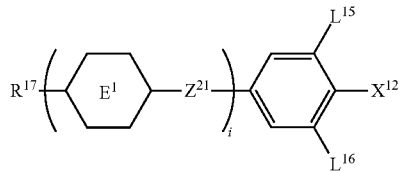

wherein, in formula (15), $R^{17}$ is alkyl having 1 to 10 carbons or alkenyl having 2 to 10 carbons, and in the alkyl and the alkenyl, at least one —$CH_2$— may be replaced by —O—, and in the groups, at least one hydrogen may be replaced by fluorine;

$X^{12}$ is —C≡N or —C≡C—C≡N;

ring $E^1$ is 1,4-cyclohexylene, 1,4-phenylene, 1,4-phenylene in which at least one hydrogen is replaced by fluorine, tetrahydropyran-2,5-diyl, 1,3-dioxane-2,5-diyl, or pyrimidine-2,5-diyl;

$Z^{21}$ is a single bond, —COO—, —$CH_2O$—, —$CF_2O$—, —$OCF_2$—, —$CH_2CH_2$— or —C≡C—;

$L^{15}$ and $L^{16}$ are independently hydrogen or fluorine; and i is 1, 2, 3 or 4.

14. A liquid crystal display device, including the liquid crystal composition according to claim 9.

* * * * *